United States Patent
Chang et al.

(10) Patent No.: US 10,010,626 B2
(45) Date of Patent: *Jul. 3, 2018

(54) MOLECULAR CONSTRUCTS WITH TARGETING AND EFFECTOR MOIETIES

(71) Applicant: Immunwork Inc., Taipei (TW)

(72) Inventors: Tse-Wen Chang, Taipei (TW); Hsing-Mao Chu, Taipei (TW); Chun-Yu Lin, Taipei (TW)

(*) Notice: Subject to any disclaimer, the term of this patent is extended or adjusted under 35 U.S.C. 154(b) by 40 days.

This patent is subject to a terminal disclaimer.

(21) Appl. No.: 14/997,827

(22) Filed: Jan. 18, 2016

(65) Prior Publication Data

US 2016/0208021 A1    Jul. 21, 2016

Related U.S. Application Data

(60) Provisional application No. 62/104,405, filed on Jan. 16, 2015, provisional application No. 62/114,427, filed on Feb. 10, 2015, provisional application No. 62/137,737, filed on Mar. 24, 2015.

(51) Int. Cl.

| | |
|---|---|
| *A61K 39/00* | (2006.01) |
| *A61K 39/44* | (2006.01) |
| *A61K 47/18* | (2017.01) |
| *A61K 47/30* | (2006.01) |
| *A61K 47/42* | (2017.01) |
| *A61K 47/48* | (2006.01) |
| *A61K 31/4745* | (2006.01) |
| *A61K 31/537* | (2006.01) |
| *A61K 31/739* | (2006.01) |
| *C07K 16/32* | (2006.01) |
| *C07K 16/18* | (2006.01) |
| *C07K 16/22* | (2006.01) |
| *C07K 16/24* | (2006.01) |
| *C07K 16/28* | (2006.01) |
| *C07K 16/46* | (2006.01) |
| *C07K 14/655* | (2006.01) |
| *C07K 14/715* | (2006.01) |
| *C07K 14/485* | (2006.01) |
| *A61K 31/397* | (2006.01) |
| *A61K 31/4709* | (2006.01) |
| *A61K 31/4545* | (2006.01) |

(52) U.S. Cl.
CPC ...... *A61K 47/48538* (2013.01); *A61K 31/397* (2013.01); *A61K 31/4545* (2013.01); *A61K 31/4709* (2013.01); *A61K 31/4745* (2013.01); *A61K 31/537* (2013.01); *A61K 31/739* (2013.01); *A61K 47/48215* (2013.01); *A61K 47/48246* (2013.01); *A61K 47/48384* (2013.01); *A61K 47/48546* (2013.01); *A61K 47/48561* (2013.01); *A61K 47/48692* (2013.01); *C07K 14/485* (2013.01); *C07K 14/655* (2013.01); *C07K 14/7151* (2013.01); *C07K 16/18* (2013.01); *C07K 16/22* (2013.01); *C07K 16/241* (2013.01); *C07K 16/244* (2013.01); *C07K 16/2803* (2013.01); *C07K 16/2809* (2013.01); *C07K 16/2818* (2013.01); *C07K 16/2863* (2013.01); *C07K 16/2875* (2013.01); *C07K 16/2887* (2013.01); *C07K 16/32* (2013.01); *C07K 16/468* (2013.01); *C07K 2317/21* (2013.01); *C07K 2317/24* (2013.01); *C07K 2317/31* (2013.01); *C07K 2317/55* (2013.01); *C07K 2317/622* (2013.01); *C07K 2317/64* (2013.01); *C07K 2317/71* (2013.01); *C07K 2317/73* (2013.01); *C07K 2317/732* (2013.01); *C07K 2317/76* (2013.01); *C07K 2319/30* (2013.01); *C07K 2319/33* (2013.01)

(58) Field of Classification Search
None
See application file for complete search history.

(56) References Cited

PUBLICATIONS

Henricks et al, Cancer Treatment Reviews, 2015, vol. 41, pp. 859-867.*
Meng, Analytical Biochemistry, 2012, vol. 421, pp. 351-361.*
Sun and Coy, Current Drug Delivery, 2011, vol. 8, pp. 2-10.*
Onori et al, International Journal of Cancer, 2009, vol. 127, pp. 43-54.*
Luster, European Journal of Nuclear medicine and Molecular Imaging, 2003, vol. 30, pp. 1371-1377.*
Brooks et al, Clinical Cancer Research, 2012, vol. 18, pp. 1855-1862.*
Lewiecki et al, Expert Opinion in Biological Therapy, 2006, vol. 6, pp. 1041-1050.*
Malik et al, Journal of Controlled Release, 2000, vol. 65, pp. 133-148. (Year: 2000).*
Marty et al (British Journal of Cancer, 2002, vol. 87, pp. 106-112). (Year: 2002).*

* cited by examiner

*Primary Examiner* — Karen A. Canella

(57) ABSTRACT

The present disclosure provides various molecular constructs having a targeting element and an effector element. Methods for treating various diseases using such molecular constructs are also disclosed.

51 Claims, 33 Drawing Sheets

MOLECULAR CONSTRUCTS WITH TARGETING AND EFFECTOR MOIETIES

CROSS-REFERENCE TO RELATED APPLICATIONS

This application relates to and claims the benefit of U.S. Provisional Application No. 62/104,405, filed Jan. 16, 2015, U.S. Provisional Application No. 62/114,427, filed Feb. 10, 2015, and U.S. Provisional Application No. 62/137,737, filed Mar. 24, 2015; the contents of the applications are incorporated herein by reference in their entirety.

BACKGROUND OF THE INVENTION

1. Field of the Invention

The present disclosure relates to the field of pharmaceuticals; more particularly, to multi-functional molecular constructs, e.g., those having targeting and effector elements for delivering the effector (e.g., therapeutic drug) to targeted sites.

2. Description of the Related Art

The continual advancement of a broad array of methodologies for screening and selecting monoclonal antibodies (mAbs) for targeted antigens has helped the development of a good number of therapeutic antibodies for many diseases that were regarded as untreatable just a few years ago. According to Therapeutic Antibody Database, approximately 2,800 antibodies have been studied or are being planned for studies in human clinical trials, and approximately 80 antibodies have been approved by governmental drug regulatory agencies for clinical uses. The large amount of data on the therapeutic effects of antibodies has provided information concerning the pharmacological mechanisms how antibodies act as therapeutics.

One major pharmacologic mechanism for antibodies acting as therapeutics is that, antibodies can neutralize or trap disease-causing mediators, which may be cytokines or immune components present in the blood circulation, interstitial space, or in the lymph nodes. The neutralizing activity inhibits the interaction of the disease-causing mediators with their receptors. It should be noted that fusion proteins of the soluble receptors or the extracellular portions of receptors of cytokines and the Fc portion of IgG, which act by neutralizing the cytokines or immune factors in a similar fashion as neutralizing antibodies, have also been developed as therapeutic agents.

Several therapeutic antibodies that have been approved for clinical applications or subjected to clinical developments mediate their pharmacologic effects by binding to receptors, thereby blocking the interaction of the receptors with their ligands. For those antibody drugs, Fc-mediated mechanisms, such as antibody-dependent cellular cytotoxicity (ADCC) and complement-mediated cytolysis (CMC), are not the intended mechanisms for the antibodies.

Some therapeutic antibodies bind to certain surface antigens on target cells and render Fc-mediated functions and other mechanisms on the target cells. The most important Fc-mediated mechanisms are antibody-dependent cellular cytotoxicity (ADCC) and complement-mediated cytolysis (CMC), which both will cause the lysis of the antibody-bound target cells. Some antibodies binding to certain cell surface antigens can induce apoptosis of the bound target cells.

Antibodies can also serve as carriers of cytotoxic molecules or other therapeutic agents without the antibodies' serving obvious therapeutic effector functions. In general, those antibodies bind to "tumor-associated" antigens on target cells, but cannot cause cell lysis by themselves. Antibodies specific for CD19 and CD22 on B lymphomas are well known. For many years, those antibodies have been explored as carriers for cytotoxic agents, including radioactive nuclides with very short half-lives, such as $^{90}Y$, $^{131}I$, and $^{177}Lu$. Some antibodies have also been studied as targeting agents for liposomes loaded with cytotoxic drugs, such as doxorubicin, paclitaxel, and amphotericin B. The field of antibody drug conjugates (ADC) has experienced an explosive phase of research and development in recent years, mainly attributing to the development of extremely cytotoxic drugs, such as auristatin, maytansine, calicheamicin, and camptothecin, and of methodologies for conjugating the cytotoxic molecules onto antibody molecules. Those ADCs have been designed to target diffusive (or liquid) tumors of the blood, lymphoid system, and bone marrow, including various types of lymphomas and leukemia, expressing one or more unique CD markers. Some ADCs are also being developed for solid tumors. A few of this new generation of antibody drug conjugates have been approved for clinical uses and many are in clinical trials.

However, in the first generation of ADCs, the cytotoxic drug molecules are linked non-selectively to cysteine or lysine residues in the antibody, thereby resulting in a heterogeneous mixture of ADCs with different numbers of drug molecules per ADC. This approach leads to some safety and efficacy issues. For example, the first FDA-approved ADC, gemtuzumab ozogamicin, for treating acute myelogenous leukemia, is now withdrawn from the market due to unacceptable toxicity.

The concept and methodology for preparing antibodies with dual specificities germinated more than three decades ago. In recent year, the advancement in recombinant antibody engineering methodologies and the drive to develop improved medicine has stimulated the development bi-specific antibodies adopting a large variety of structural configurations.

For example, the bi-valent or multivalent antibodies may contain two or more antigen-binding sites. A number of methods have been reported for preparing multivalent antibodies by covalently linking three or four Fab fragments via a connecting structure. For example, antibodies have been engineered to express tandem three or four Fab repeats.

Several methods for producing multivalent antibodies by employing synthetic crosslinkers to associate, chemically, different antibodies or binding fragments have been disclosed. One approach involves chemically cross-linking three, four, and more separately Fab fragments using different linkers. Another method to produce a construct with multiple Fabs that are assembled to one-dimensional DNA scaffold was provided. Those various multivalent Ab constructs designed for binding to target molecules differ among one another in size, half-lives, flexibility in conformation, and ability to modulate the immune system. In view of the foregoing, several reports have been made for preparing molecular constructs with a fixed number of effector elements or with two or more different kinds of functional elements (e.g., at least one targeting element and at least one effector element). However, it is often difficult to build a molecular construct with a particular combination of the targeting and effector elements either using chemical synthesis or recombinant technology. Accordingly, there exists a need in the related art to provide novel molecular platforms to build a more versatile molecule suitable for covering applications in a wide range of diseases.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

<I> Peptide Core-Based Multi-Arm Linkers

In the first aspect, the present disclosure is directed to a linker unit that has at least two different functional elements linked thereto. For example, the linker unit may have linked thereto two different effector elements, one targeting element and one effector element, or one effector element and a polyethylene glycol (PEG) chain for prolonging the circulation time of the linker unit. The present linker unit is designed to have at least two different functional groups such that the functional elements can be linked thereto by reacting with the respective functional groups. Accordingly, the present linker unit can serve as a platform for preparing a molecular construct with two or more functional elements.

According to various embodiments of the present disclosure, the linker unit comprises a center core and a plurality of linking arms. The center core is a polypeptide core comprising (1) a plurality of lysine (K) resides, in which each K residue and a next K residue are separated by a filler sequence comprising glycine (G) and serine (S) residues, and the number of K residues ranges from 2 to 15; or (2) the sequence of $(X_{aa}\text{-}K)_n$, where $X_{aa}$ is a PEGylated amino acid having 2 to 12 repeats of ethylene glycol (EG) unit, and n is an integral from 2 to 15. Optionally, the filler sequence consists of 2 to 20 amino acid residues. In various embodiments, the filler sequence may have the sequence of GS, GGS, GSG, or SEQ ID NOs: 1-16. According to some embodiments of the present disclosure, the center core comprises 2-15 units of the sequence of $G_{1\text{-}5}SK$; preferably, the center core comprises the sequence of $(GSK)_{2\text{-}15}$. Each of the linking arms is linked to the K residues of the center core via forming an amide linkage between the K residue and the linking arm. The linking arm linked to the center core has a maleimide group at its free-terminus. Also, the amino acid residue at the N- or C-terminus of the center core has an azide group or an alkyne group; alternatively or additionally, the amino acid residue at the N- or C-terminus of the center core is a cysteine (C) residue, in which the thiol group of the amino acid residue is linked with a coupling arm having an azide group, an alkyne group, a tetrazine group or a strained alkyne group at the free terminus of the coupling arm.

In some embodiments, the linking arm is a PEG chain, preferably having 2 to 20 repeats of EG units. Also, the coupling arm is a PEG chain, preferably having 2 to 12 repeats of EG units.

Regarding amino acid residues having the azide group, non-limiting examples of said amino acid residues include L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, and 6-azido-D-lysine. As to the amino acid residues having the alkyne group, illustrative examples thereof include L-homopropargylglycine (L-HPG), D-homopropargylglycine (D-HPG), and beta-homopropargylglycine (β-HPG).

When the amino acid residues at the N- or C-terminus of the center core is the cysteine residue, the strained alkyne group at the free terminus of the coupling arm may be, a cyclooctene group, such as trans-cyclooctene (TCO) group; or a cyclooctyne group, e.g. dibenzocyclooctyne (DBCO), difluorinated cyclooctyne (DIFO), bicyclononyne (BCN), and dibenzocyclooctyne (DICO) group. Alternatively, the tetrazine group at the free terminus of the coupling arm includes, but is not limited to, 1,2,3,4-tetrazine, 1,2,3,5-tetrazine, and 1,2,4,5-tetrazine, and derivatives thereof, such as, 6-methyl tetrazine.

According to various embodiments of the present disclosure, the linker unit further comprises a plurality of first elements. Each of the first elements is linked to one of the linking arms via thiol-maleimide reaction. According to various optional embodiments of the present disclosure, the first element is an effector element suitable for eliciting an intended effect (e.g., a therapeutic effect) in a subject. Alternatively, the first element may be a targeting element for directing the linker unit to the site of interest.

Still optionally, the linker unit further comprises a second element that is different from the first elements. In some embodiments, the second element has an azide or alkyne group, so that it is linked to the center core or the coupling arm by coupling with the corresponding alkyne or azide group of the center core or the coupling arm in the presence of Cu(I) as a catalyst in a reaction referred to as "Cu(I) azide-alkyne click chemistry (CuAAC) reaction." Alternatively, in some embodiments, the second element having an azide or cyclooctyne group is linked to the center core or the coupling arm by coupling with the corresponding cyclooctyne or azide group of the center core or the coupling arm via "strain-promoted azide-alkyne click chemistry (SPAAC) reaction". Still alternatively, in certain embodiments, the second element having a tetrazine or cyclooctene group is linked to the center core or the coupling arm by coupling with the corresponding cyclooctene or tetrazine group of the center core or the coupling arm via "inverse electron demand Diels-Alder (iEDDA) reaction". In optional embodiments of the present disclosure, when the first element is an effector element, then the second element may be another effector element, which works additively or synergistically with or independently of the first element; alternatively, the second element may be a targeting element or an element for improving the pharmacokinetic property of the linker unit, such as solubility, clearance, half-life, and bioavailability. In some other optional embodiments, when the first element is the targeting element, then the second element is preferably an effector element or an element for improving the pharmacokinetic property of the linker unit.

In certain embodiments, the linker unit further comprises an optional third element that is different from the first and second elements. In the case where the second element is directly linked to the center core, the other terminus (i.e., the free terminus that is not linked with the second element) of the center core is optionally a cysteine residue, which can be used to introduce an optional third element. Specifically, the thiol group of the cysteine residue is reacted with a maleimide group of a PEG chain; and the thus-linked PEG chain is designated as the coupling arm, which has a tetrazine group or a strained alkyne group at its free terminus. Accordingly, the third element is then linked to the coupling arm via iEDDA reaction. In the case where the linker unit comprises both the second and third elements, it is preferable that at least one of the first and second elements is an effector as described above, while the third element may be the element for improving the pharmacokinetic property of the linker unit. One example of the element for improving the pharmacokinetic property is a long PEG chain having a molecular weight of about 20,000 to 50,000 daltons.

<II> Uses of Peptide Core-Based Multi-Arm Linkers

The linker unit according to the first aspect of the present disclosure may find its utility in clinical medicine for the treatment of various diseases. Hence, the second aspect of the present disclosure is directed to a method for treating these diseases. According to various embodiments of the present disclosure, the method for treating a particular disease includes the step of administering to the subject in need thereof a therapeutically effective amount of the linker unit according to the above-mentioned aspect and embodiments of the present disclosure. As could be appreciated, said linker unit may be administered in a pharmaceutical formulation, which comprises a pharmaceutically-acceptable excipient suitable for the intended or desired administration route, in addition to the present linker unit.

Various illustrative combinations of the first and second elements of the present linker unit for treating some particular diseases are disclosed below for facilitating the understanding of some embodiments of the present disclosure.

According to some embodiments of the present disclosure, the present molecular construct is useful in treating an immune disorder, in which the first element is a single-chain variable fragment (scFv) specific for a cytokine or a receptor of the cytokine; or a soluble receptor of the cytokine, while the second element is an scFv specific for a tissue-associated extracellular matrix protein. In these cases, the first element is an effector element for treating one or more immune disorders, while the second element is a targeting element that facilitates the delivery of the linker unit to the disease site.

Non-limiting examples of the cytokine include tumor necrosis factor-α (TNF-α), interleukin-17 (IL-17), IL-1, IL-6, shared protein of IL-12 and IL-23, and B cell activating factor (BAFF), while non-limiting examples of the cytokine receptor is the receptor specific for IL-6 (i.e., IL-6R) or IL-17 (i.e., IL-17R). As for the soluble receptor of a cytokine, examples of which include, but are not limited to, the soluble receptor of the cytokine specific for TNF-α or IL-1. Illustrative examples of the tissue-associated extracellular matrix protein include, but are not limited to, α-aggrecan, collagen I, collagen II, collagen III, collagen V, collagen VII, collagen IX, and collagen XI.

According to some specific but illustrative examples of linker units suitable for treating psoriasis, the first element is an scFv specific for TNF-α, shared protein of IL-12 and IL-23, IL-17, or IL-17R; and the second element is an scFv specific for collagen I or collagen VII.

In some optional examples, the linker units suitable for treating immune disorders such as systemic lupus erythematosus (SLE), cutaneous lupus or Sjogren's syndrome comprises an scFv specific for BAFF as the first element and an scFv specific for collagen I or collagen VII as the second element.

For treating rheumatoid arthritis, psoriatic arthritis, or ankylosing spondylitis, the illustrative linker units comprises the first element, which is an scFv specific for TNF-α, IL-1, IL-6, shared protein of IL-12 and IL-23, IL-17, IL-6R, or IL-17R; and the second element, which is an scFv specific for collagen II, collagen IX, collagen XI, or α-aggrecan.

The linker units are also suitable for treating inflammatory bowel diseases, e.g., Crohn's disease and ulcerative colitis, among others. In these cases, the present linker unit uses an scFv specific for TNF-α as the first element, and an scFv specific for collagen III or collagen V as the second element.

Another set of diseases treatable by the present linker unit is diffused tumor, including, but not limited to, acute lymphocytic leukemia (ALL), chronic lymphocytic leukemia (CLL), acute myelogenous leukemia (AML), chronic myelogenous leukemia (CML), Hodgkin lymphoma, non-Hodgkin lymphoma, and myeloma. In these embodiments, the first element may be a targeting element such as an scFv specific for a first cell surface antigen, whereas the second element may be an effector element such as an scFv specific for a second cell surface antigen.

The first cell surface antigen suitable for use as the targeting element for treating diffused tumors includes, but is not limited to, CD5, CD19, CD20, CD22, CD23, CD27, CD30, CD33, CD34, CD37, CD38, CD43, CD72a, CD78, CD79a, CD79b, CD86, CD134, CD137, CD138, and CD319. On the other hand, non-limiting examples of the second cell surface antigen suitable for use as the effector element include CD3 and CD16a.

For the treatment of B-lymphocyte-derived lymphoma or leukemia, the illustrative first element is an scFv specific for CD5, CD19, CD20, CD22, CD23, CD30, CD37, CD79a, or CD79b, while the illustrative second element is an scFv specific for CD3 or CD16a.

To treat plasmacytoma or multiple myeloma, the illustrative first element is an scFv specific for CD38, CD78, CD138, or CD319, while the illustrative second element is an scFv specific for CD3 or CD16a.

Regarding T-cell derived lymphoma or leukemia, the illustrative first element for the treatment thereof is an scFv specific for CD5, CD30, or CD43, while the second element is an scFv specific for CD3 or CD16a.

For treating myelogenous leukemia, the illustrative first element is an scFv specific for CD33 or CD34, while the illustrative second element is an scFv specific for CD3 or CD16a.

Still another set of diseases that may be treated by the present linker unit is solid tumor, including, but not limited to, melanomas, esophageal carcinomas, gastric carcinomas, brain tumor, small cell lung cancer, non-small cell lung cancer, bladder cancer, breast cancer, pancreatic cancer, colon cancer, rectal cancer, colorectal cancer, renal cancer, hepatocellular carcinoma, ovary cancer, prostate cancer, thyroid cancer, testis cancer, and head and neck squamous cell carcinoma. Additionally, the present linker unit is also suitable for treating advanced, malignant, or metastatic solid tumors.

To construct a linker unit for treating solid tumors, the first element (i.e., the targeting element) is chosen from a peptide hormone, a growth factor, and a first scFv specific for a tumor-associated antigen; whereas the second element (i.e., the effector element) is a second scFv specific for a cell surface antigen.

For example, the peptide hormone is secretin, cholecystokinin (CCK), somatostatin, or thyroid-stimulating hormone (TSH). Regarding the growth factor, it may be the epidermal growth factor (EGF), mutant EGF, epiregulin, heparin-binding epidermal growth factor (HB-EGF), vascular endothelial growth factor A (VEGF-A), basic fibroblast growth factor (bFGF), or hepatocyte growth factor (HGF). Illustrative examples of the tumor-associated antigen include human epidermal growth factor receptor 1 (HER1), HER2, HER3, HER4, carbohydrate antigen 19-9 (CA 19-9), carbohydrate antigen 125 (CA 125), carcinoembryonic antigen (CEA), mucin 1 (MUC 1), ganglioside GD2, melanoma-associated antigen (MAGE), prostate-specific membrane antigen (PSMA), prostate stem cell antigen (PSCA), mesothelin, mucine-related Tn, Sialyl Tn, Globo H, stage-specific embryonic antigen-4 (SSEA-4), and epithelial cell adhesion molecule (EpCAM). As to the cell surface antigen, it can be CD3 or CD16a.

In some instances, the tumor-associated antigen may be shed from the solid tumor of a subject and wanders into his/her circulation system. In these cases, the present method for treating solid tumor comprises the step of, (a) subjecting the subject to a blood dialysis procedure using an antibody specific for one or more tumor-associated antigens to remove the tumor-associated antigens that are shed from the tumor and wanders into the circulation of the subject; and (b) administering the present linker unit for treating the solid tumor.

Yet another representative disease treatable by the present linker unit is osteoporosis. Illustrative linker units suitable for treating osteoporosis include a first element (in this case, an effector element) that is a first scFv specific for ligand of receptor activator of nuclear factor κB (RANKL); and a second element (or a targeting element) that is a second scFv specific for collagen I or osteonectin.

Age-related macular degeneration (AMD) is another example of the diseases treatable by the present linker unit. Illustrative linker units suitable for treating AMD include a first element of an scFv specific for VEGF-A, and a second element of a long PEG chain having a molecular weight of about 20,000 to 50,000 daltons. In this case, the first element is the effector element for treating AMD, while the second element is used to enhance the pharmacokinetic property of the linker unit.

<III> Molecular Constructs with Targeting and Effector Moieties

In the third aspect, the present disclosure is directed to a molecular construct comprising two linker units coupling to each other either directly or indirectly, in which the core of one linker unit is configured to be linked with at least one targeting element while the core of the other linker unit is configured to be linked with at least one effector element. The present molecular construct is advantageous in that the two linker units are coupled to each other via an iEDDA reaction, a SPAAC reaction, or a CuAAC reaction. This design allows for a facile synthesis of a molecular construct with a complex structure. According to the principles and spirits of the present disclosure, the two linker units respectively carrying different numbers and/or types of functional elements can be independently prepared, and then conjugated together. In this way, it becomes feasible for a skilled artisan to construct libraries of molecular constructs respectively carrying different functional elements, and then select and combine two molecular constructs (or linker units) from the libraries to generate a desired constructs, depending on the needs and/or intended applications. Moreover, the number of functional elements per linker unit may be controlled by adjusting the number of specific functional group(s) of the core.

According to one embodiment of the present disclosure, the molecular construct comprises a first linker unit and a second linker unit. Specifically, the first linker unit comprises a first center core and one or more linking arms (hereinafter, the first linking arms) and optionally a coupling arm (hereinafter, the first coupling arms) that are respectively linked to the first center core; the second linker unit comprises a second center core and one or more linking arms (hereinafter, the second linking arms) and optionally a coupling arm (hereinafter, the second coupling arm) that are respectively linked to the second center core. The first and second linker units are coupled to each other via iEDDA, SPAAC, or CuAAC reaction occurred between any of the followings: the first and second center cores, the first coupling arm and the second center core, the first and second coupling arms, or the first center core and the second coupling arm.

According to the embodiments of the present disclosure, both the first and second center cores have a plurality of amine groups. Each of the linking arms is linked to the center core via forming an amide bond therebetween, for example, between the N-hydroxysuccinimidyl (NHS) group and the amine group. After being linked to the center core, the linking arm thus has a maleimide group at the free terminus thereof. In the presence of the maleimide group, a first targeting element and a first effector element are respectively linked to the first and second linking arms via thiol-maleimide reaction.

According to some embodiments of the present disclosure, each of the linking arms is a PEG chain having 2-20 repeats of EG units. Also, each of the coupling arms is a PEG chain having 2-12 repeats of EG units.

According to various embodiments of the present disclosure, each of the first and second center cores may be a compound core or a polypeptide core. In some examples, both the first and second center cores are compounds cores of the same or different compound(s). In certain preferred embodiments, both the first and second center cores are polypeptide cores having the same or different sequence(s). Alternatively, one of the two cores is a compound core, while the other is a polypeptide core.

Non-limiting examples of the compound suitable for use as the present compound core include, benzene-1,3,5-triamine, 2-(aminomethyl)-2-methylpropane-1,3-diamine, tris (2-aminoethyl)-amine, benzene-1,2,4,5-tetraamine, 3,3',5, 5'-tetraamine-1,1'-biphenyl, tetrakis-(2-aminoethyl) methane, tetrakis(ethylamine)-hydrazine, N,N,N',N',-tetrakis-(aminoethyl)-ethylenediamine, benzene-1,2,3,4,5, 6-hexaamine, 1-N,1-N,3-N,3-N,5-N,5-N-hexakis-(methylamine)-benzene-1,3,5-triamine, 1-N,1-N,2-N,2-N,4-N,4-N,5-N,5-N-octakis-(methylamine)-benzene-1,2,4,5-triamine, and N,N-bis[(1-amino-3,3-diaminoethyl)-pentyl] methane-diamine.

In the case where the center core is a compound core, the coupling arm is linked to one of the plurality of amine groups of the center core by forming an amide bond between the coupling arm and the center core. Meanwhile, the free terminus of the coupling arm has an azide, an alkyne, a strained alkyne, or a tetrazine group.

According to some embodiments of the present disclosure, the polypeptide suitable for use as the present polypeptide core comprises a plurality of lysine (K) residues; optionally, 2 to 15 K residues. Also, each K residue and the next K residue are separated by a filler sequence comprising glycine (G) and serine (S) residues; optionally, the filler sequence consists of 2 to 20 amino acid residues. In various embodiments, the filler sequence may have the sequence of GS, GGS, GSG, or SEQ ID NOs: 1-16. In some embodiments, the polypeptide comprises 2-15 units of the sequence of $G_{1-5}SK$, for example, $(GSK)_{2-15}$. In one embodiment, the polypeptide core has the sequence of SEQ ID NOs: 17, 18, 19, 21, 22, 23, or 24.

Alternatively, the polypeptide core may comprise the sequence of $(X_{aa}$-K$)n$, where $X_{aa}$ is a PEGylated amino acid having 2 to 12 repeats of ethylene glycol (EG) unit, and n is an integral from 2 to 15. In one embodiment, the polypeptide core has the sequence of SEQ ID NO: 25 or 26.

In the case where the center core is a polypeptide core, it may comprise a cysteine residue at its N- or C-terminus. In these instances, the coupling arm is linked to the cysteine residue of the center core via the thiol-maleimide reaction. The coupling arm linked to the cysteine residue has an azide, an alkyne, a strained alkyne, or a tetrazine group at the free-terminus thereof.

The first and second linker units may be coupled via various configurations, which are described in detail below, depending on the presence or absence of the first and second coupling arms. For a linker unit having a compound core, it is preferable that it is linked with another linker unit via a coupling arm (i.e., the first or second coupling arm), while for a linker unit having a polypeptide core, the need for a coupling arm becomes optional.

When the first and second linker units respectively comprise the coupling arms, then one of the coupling arms (say, for example, the first coupling arm) has a tetrazine group at the free-terminus thereof, and the other coupling arm (in this case, the second coupling arm) has a strained alkyne group at the free-terminus thereof, such that the two linker units are coupled via the iEDDA reaction occurred between the two coupling arms (i.e., the first and second coupling arms). Preferably, the tetrazine group is 1,2,3,4-tetrazine, 1,2,3,5-tetrazine, and 1,2,4,5-tetrazine, or derivatives thereof, such as, 6-methyl tetrazine; and the strained alkyne group is TCO. The same rule also applies in the case where the free termini of both coupling arms respectively have an azide group and an alkyne group; in this instance, the two linker units are coupled via the CuAAC reaction occurred between the two coupling arms (i.e., the first and second coupling arms). Alternatively, one of the coupling arm has an azide group, and the other of the coupling arm has a strained alkyne group (preferably, DBCO, DIFO, BCN, or DICO); accordingly, the two coupling arm can be coupled via the SPAAC reaction. These configurations may occur between two linker units, where both units have either compound cores or polypeptide cores, as well as in situations where one linker unit has a compound core, while the other has a polypeptide core.

When only one linker unit has the coupling arm (as an example, the first linker unit with the first coupling arm), the center core of the other linker unit (for example, the second center core) is a polypeptide core. In this case, the first amino acid residue at the N- or C-terminus of one of the second center core is an amino acid residue having an azide group or an alkyne group. In some embodiments, the amino acid residue having the azide or alkyne group would undergo CuAAC reaction with the corresponding alkyne or azide group of the first coupling arm of the first linker unit, thereby coupling the first and second linker units. Alternatively, the first amino acid residue at the N- or C-terminus of one of the second center core is an amino acid residue having an azide group, which can be linked to the coupling arm of the first linker unit having a strained alkyne group (preferably, DBCO, DIFO, BCN, or DICO) at the free-terminus via the SPAAC reaction. This configuration may occur between two linker units, where both units have polypeptide cores, or in situations where one linker unit has a compound core, while the other has a polypeptide core.

It is also possible that the first and second linker units are coupled without the presence of any coupling arms (that is, the first and second coupling arms). In other words, the first and second coupling arms are directly linked with each other. This configuration mostly occurs between two polypeptide cores. Specifically, one of the two center cores (say, for example, the first center core) has an amino acid residue having an azide group at the N- or C-terminus thereof, while the other center core (such as the second center core) has an amino acid residue having an alkyne group at the N- or C-terminus thereof. In this way, the azide group of the first center core reacts with the alkyne group of the second center core, thereby coupling the first and second linker units.

Non-limiting examples of amino acid residues having the azide group include, L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, and 6-azido-D-lysine. Illustrative examples of amino acid residues having the alkyne group include, but are not limited to, L-homopropargylglycine (L-HPG), D-homopropargylglycine (D-HPG), and beta-homopropargylglycine (β-HPG).

According to some embodiments of the present disclosure, one of the first and second linker units of the molecular construct further comprises an additional linking arm (hereinafter, the third linking arm) linked to the first or the second linker unit.

In some embodiments, the third linking arm is configured to be linked with a long PEG chain having a molecular weight of about 20,000 to 50,000 daltons via thiol-maleimide reaction. Optionally, the third linking arm is configured to be linked with a single scFv, as either a targeting element or an effector element. In some examples, the first and second linking arms are connected with two different effector elements, and the targeting element linked to the third linking arm is an scFv specific for collagen I, collagen II, collagen III, collagen V, collagen VII, collagen IX, collagen XI, aggrecan, or osteonectin. In other examples, the first and second linking arms are connected with two different targeting elements, and the effector element linked to the third linking arm is an scFv specific for CD3 or CD16a.

In other embodiments, the present molecular construct further comprises a third linker unit. The third linker unit comprises a third center core, a linking arm (hereinafter, the third linking arm), and optionally a coupling arm (hereinafter, the third coupling arm). In this case, the third linker unit is linked to the first or the second linker unit via CuAAC reaction, iEDDA reaction, or SPAAC reaction occurred between any of the followings: the first or the second coupling arm and the third coupling arm, the first or the second center core and the third coupling arm, the first or the second coupling arm and the third center core, or the first or the second center core and the third center core.

Regarding the third linking arm of the third linker unit, it may have a maleimide group at the free terminus thereof, which is used to link a second effector element or targeting element via thiol-maleimide reaction.

As would be appreciated, the targeting/effector element (such as a drug) having an NHS group can be directly linked to the K residue of the first, second, and/or third center core via forming an amide linkage between the NHS group and the K residue without the presence of the linking arm (i.e., the first, second, or third linking arm).

According to various embodiments of the present disclosure, the first, second, and optionally, the third center core may be the same or different.

<IV> Uses of Molecular Constructs with Targeting and Effector Moieties

The molecular construct according to the third aspect of the present disclosure may find its utility in clinical medicine for the treatment of various diseases. Hence, the fourth aspect of the present disclosure is directed to a method for treating these diseases. According to various embodiments of the present disclosure, the method for treating a particular disease includes the step of administering to the subject in need thereof a molecular construct according to the third aspect of the present disclosure and embodiments thereof in a therapeutically effective amount. As could be appreciated, said molecular construct may be administered in a pharmaceutical formulation, which comprises a pharmaceutically-acceptable excipient suitable for the intended or desired administration route, in addition to the present molecular construct.

Various illustrative combinations of the first and second elements of the present molecular construct for treating some particular diseases are disclosed below for facilitating the understanding of some embodiments of the present disclosure.

In some embodiments, the first element is a single-chain variable fragment (scFv) specific for a cytokine or a receptor of the cytokine; or a soluble receptor of the cytokine, while the second element is an scFv specific for a tissue-associated extracellular matrix protein. In these cases, the first element is an effector element for treating one or more immune disorders, while the second element is a targeting element that facilitates the delivery of the molecular construct to the disease site.

Non-limiting examples of the cytokine include tumor necrosis factor-α (TNF-α), interleukin-17 (IL-17), IL-1, IL-6, shared protein of IL-12 and IL-23, and B cell activating factor (BAFF), while non-limiting examples of the cytokine receptor is the receptor specific for IL-6 (i.e., IL-6R) or IL-17 (i.e., IL-17R). As for the soluble receptor of a cytokine, examples of which include, but are not limited to, the soluble receptor of the cytokine specific for TNF-α or IL-1. Illustrative examples of the tissue-associated extracellular matrix protein include, but are not limited to, α-aggrecan, collagen I, collagen II, collagen III, collagen V, collagen VII, collagen IX, and collagen XI.

According to some specific but illustrative examples of molecular constructs suitable for treating psoriasis, the first element is an scFv specific for TNF-α, shared protein of IL-12 and IL-23, IL-17, or IL-17R; and the second element is an scFv specific for collagen I or collagen VII.

In some optional examples, the molecular constructs suitable for treating immune disorders, such as systemic lupus erythematosus (SLE), cutaneous lupus, or Sjogren's syndrome, comprise an scFv specific for BAFF as the first element and an scFv specific for collagen I or collagen VII as the second element.

For treating rheumatoid arthritis, psoriatic arthritis, or ankylosing spondylitis, the illustrative molecular constructs comprise a first element that is an scFv specific for TNF-α, IL-1, IL-6, shared protein of IL-12 and IL-23, IL-17, IL-6R, or IL-17R; and a second element that is an scFv specific for collagen II, collagen IX, collagen XI, or α-aggrecan.

The molecular constructs are also suitable for treating inflammatory bowel diseases, e.g., Crohn's disease and ulcerative colitis, among others. In these cases, the present molecular construct uses an scFv specific for TNF-α as the first element, and an scFv specific for collagen III or collagen V as the second element.

Another set of diseases treatable by the present molecular construct is diffused tumor, including, but not limited to, acute lymphocytic leukemia (ALL), chronic lymphocytic leukemia (CLL), acute myelogenous leukemia (AML), chronic myelogenous leukemia (CML), Hodgkin lymphoma, non-Hodgkin lymphoma, and myeloma. In these embodiments, the first element may be a targeting element such as an scFv specific for a first cell surface antigen, whereas the second element may be a cytotoxic drug, or an effector element such as an scFv specific for a second cell surface antigen.

The first cell surface antigen suitable for use as the targeting element for treating diffused tumor includes, but is not limited to, CD5, CD19, CD20, CD22, CD23, CD27, CD30, CD33, CD34, CD37, CD38, CD43, CD72a, CD78, CD79a, CD79b, CD86, CD134, CD137, CD138, and CD319. On the other hand, non-limiting examples of the second cell surface antigen suitable for use as the effector element include CD3 and CD16a. Alternatively, the first and second cell surface antigens are respectively CD79a and CD79b. The cytotoxic drug suitable for the treatment of diffused tumor includes, but is not limited to, auristatin, maytansine, doxorubicin, calicheamicin, and camptothecin.

For the treatment of B-lymphocyte-derived lymphoma or leukemia, the illustrative first element is an scFv specific for CD5, CD19, CD20, CD22, CD23, CD30, CD37, CD79a, or CD79b; while the illustrative second element is a cytotoxic drug, or an scFv specific for CD3 or CD16a.

To treat plasmacytoma or multiple myeloma, the illustrative first element is an scFv specific for CD38, CD78, CD138, or CD319; while the illustrative second element is a cytotoxic drug, or an scFv specific for CD3 or CD16a.

Regarding T-cell derived lymphoma or leukemia, the illustrative first element for the treatment thereof is an scFv specific for CD5, CD30, or CD43; while the second element is a cytotoxic drug, or an scFv specific for CD3 or CD16a.

For treating myelogenous leukemia, the illustrative first element is an scFv specific for CD33 or CD34; while the illustrative second element is a cytotoxic drug, or an scFv specific for CD3 or CD16a.

Still another set of diseases that may be treated by the present molecular construct is solid tumor, including, but not limited to, melanomas, esophageal carcinomas, gastric carcinomas, brain tumor, small cell lung cancer, non-small cell lung cancer, bladder cancer, breast cancer, pancreatic cancer, colon cancer, rectal cancer, colorectal cancer, renal cancer, hepatocellular carcinoma, ovary cancer, prostate cancer, thyroid cancer, testis cancer, and head and neck squamous cell carcinoma. Additionally, the present molecular construct is also suitable for treating advanced, malignant, or metastatic solid tumors.

To construct a molecular construct for treating solid tumors, the first element (i.e., the targeting element) is chosen from a peptide hormone, a first growth factor, and a first scFv specific for a tumor-associated antigen; whereas the second element (i.e., the effector element) is a cytotoxic drug, a toll-like receptor (TLR) agonist, a chelator complexed with a radioactive nuclide, a cytokine, or a second scFv specific for a second growth factor, a cell surface antigen, a hapten, or the cytokine.

For example, the peptide hormone is secretin, cholecystokinin (CCK), somatostatin, or thyroid-stimulating hormone (TSH). Regarding the first growth factor, it may be the epidermal growth factor (EGF), mutant EGF, epiregulin, heparin-binding epidermal growth factor (HB-EGF), vascular endothelial growth factor A (VEGF-A), basic fibroblast growth factor (bFGF), or hepatocyte growth factor (HGF). Illustrative examples of the tumor-associated antigen include human epidermal growth factor receptor 1 (HER1), HER2, HER3, HER4, carbohydrate antigen 19-9 (CA 19-9), carbohydrate antigen 125 (CA 125), carcinoembryonic antigen (CEA), mucin 1 (MUC 1), ganglioside GD2, melanoma-associated antigen (MAGE), prostate-specific membrane antigen (PSMA), prostate stem cell antigen (PSCA), mesothelin, mucine-related Tn, Sialyl Tn, Globo H, stage-specific embryonic antigen-4 (SSEA-4), and epithelial cell adhesion molecule (EpCAM).

As the cytotoxic drug suitable for treating diffused tumors, the cytotoxic drug used in the molecular construct for the treatment of solid tumors includes, but is not limited to, auristatin, maytansine, doxorubicin, calicheamicin, and camptothecin. Non-limiting TLR agonist includes lipopolysaccharide (LPS), monophosphoryl lipid A, motolimod, imiquimod, resiquimod, gardiquimod, CpG oligodeoxynucleotide (CpG DON), lipoteichoic acid, β-glucan, and zymosan. The chelator is selected from the group consisting of 1,4,7,10-tetraazacyclododecane-1,4,7,10-tetraacetic acid (DOTA), 1,4,7-triaza-cyclo-nonane-1,4,7-triacetic acid (NOTA), 1,4,7-triazacyclononane-1,4-diacetic acid (NODA), and diethylenetriaminepentaacetic acid (DTPA); and the radioactive nuclide is $^{111}$In, $^{131}$I, or $^{177}$Lu. As to the cytokine, it can be selected from the group consisting of IL-2, IFN-α, IFN-γ, and TNF-α. The second growth factor capable of being specifically recognized and bound by the second scFv is EGF, mutant EGF, VEGF-A, bFGF, or HGF. The cell surface antigen specifically recognized and bound by the second scFv is selected from the group consisting of CD3, CD16a, CD28, CD134, cytotoxic T-lymphocyte-associated protein 4 (CTLA-4, or CD152), programmed cell death 1 (PD-1, or CD279), and programmed cell death 1 ligand 1 (PD-L1, or CD274). The cytokine specifically recognized and bound by the second scFv is selected from the group consisting of IL-2, IFN-α, IFN-γ, and TNF-α; in these cases, the second scFv is a non-neutralizing scFv.

In some instances, some tumor-associated antigens may be shed from the solid tumor of a subject and wanders into the circulation system of the subject. In these cases, the present method for treating solid tumor comprises the step of, (a) subjecting the subject to a blood dialysis procedure using an antibody specific for one or more tumor-associated antigens to remove the tumor-associated antigens that are shed from the tumor and wander into the circulation of the subject; and (b) administering the present molecular construct for treating the solid tumor.

According to some embodiments of the present disclosure, when the second element is the second scFv specific for the hapten, then the method further comprises the step of administering to the subject an immunoregulatory effector that is tagged with the same hapten. In the embodiments, the hapten is selected from the group consisting of dinitrophenol (DNP), trinitrophenol (TNP), and a short peptide having an amino acid sequence of WADWPGPP (SEQ ID NO: 20); and the immunoregulatory effector is IFN-α, IL-2, TNF-α, and IFN-γ, and an IgG antibody specific for PD-1, PD-L1, CTLA-4, or CD3.

Yet another representative disease treatable by the present molecular construct is osteoporosis. Illustrative molecular constructs suitable for treating osteoporosis include a first element (in this case, an effector element) that is a first scFv specific for ligand of receptor activator of nuclear factor κB (RANKL); and a second element (e.g., a targeting element) that is a second scFv specific for collagen I or osteonectin.

BRIEF DESCRIPTION OF THE DRAWINGS

The present description will be better understood from the following detailed description read in light of the accompanying drawings briefly discussed below.

Figure 1A:
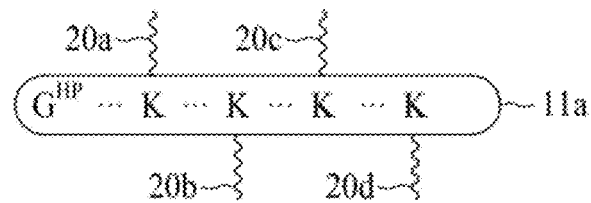
FIG. 1A to FIG. 1K are schematic diagrams illustrating linker units according to certain embodiments of the present disclosure.
Figure 1B:
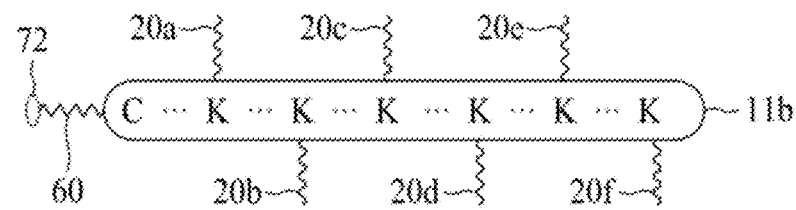
Figure 1C:
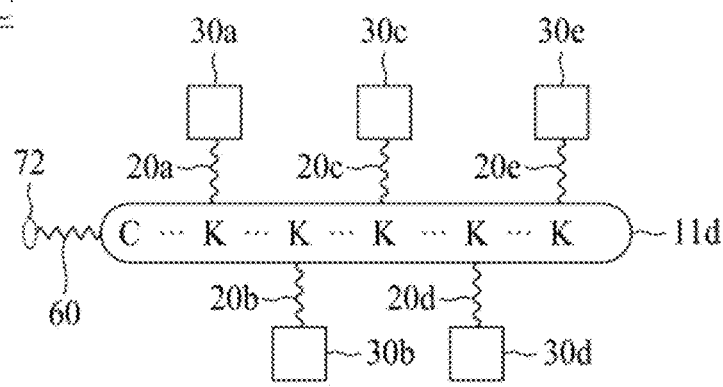

In accordance with common practice, the various described features/elements are not drawn to scale but instead are drawn to best illustrate specific features/elements relevant to the present invention. Also, like reference numerals and designations in the various drawings are used to indicate like elements/parts, where possible.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Specifically, as used herein and in the claims, the singular forms "a" and "an" include the plural reference unless the context clearly indicated otherwise. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

This present disclosure pertains generally to molecular constructs, in which each molecular construct comprises a targeting element (T) and an effector element (E), and these molecular constructs are sometimes referred to as "T-E molecules", "T-E pharmaceuticals" or "T-E drugs" in this document.

As used herein, the term "targeting element" refers to the portion of a molecular construct that directly or indirectly binds to a target of interest (e.g., a receptor on a cell surface or a protein in a tissue) thereby facilitates the transportation of the present molecular construct into the interested target. In some example, the targeting element may direct the molecular construct to the proximity of the target cell. In other cases, the targeting element specifically binds to a molecule present on the target cell surface or to a second molecule that specifically binds a molecule present on the cell surface. In some cases, the targeting element may be internalized along with the present molecular construct once it is bound to the interested target, hence is relocated into the cytosol of the target cell. A targeting element may be an antibody or a ligand for a cell surface receptor, or it may be a molecule that binds such antibody or ligand, thereby indirectly targeting the present molecular construct to the target site (e.g., the surface of the cell of choice). The localization of the effector (therapeutic agent) in the diseased site will be enhanced or favored with the present molecular constructs as compared to the therapeutic without a targeting function. The localization is a matter of degree or relative proportion; it is not meant for absolute or total localization of the effector to the diseased site.

According to the present invention, the term "effector element" refers to the portion of a molecular construct that elicits a biological activity (e.g., inducing immune responses, exerting cytotoxic effects and the like) or other functional activity (e.g., recruiting other hapten tagged therapeutic molecules), once the molecular construct is directed to its target site. The "effect" can be therapeutic or diagnostic. The effector elements encompass those that bind to cells and/or extracellular immunoregulatory factors. The effector element comprises agents such as proteins, nucleic acids, lipids, carbohydrates, glycopeptides, drug moieties (both small molecule drug and biologics), compounds, elements, and isotopes, and fragments thereof.

Although the terms, first, second, third, etc., may be used herein to describe various elements, components, regions, and/or sections, these elements (as well as components, regions, and/or sections) are not to be limited by these terms. Also, the use of such ordinal numbers does not imply a sequence or order unless clearly indicated by the context. Rather, these terms are simply used to distinguish one element from another. Thus, a first element, discussed below, could be termed a second element without departing from the teachings of the exemplary embodiments.

Here, the terms "link," "couple," and "conjugates" are used interchangeably to refer to any means of connecting two components either via direct linkage or via indirect linkage between two components.

The term "polypeptide" as used herein refers to a polymer having at least two amino acid residues. Typically, the polypeptide comprises amino acid residues ranging in length from 2 to about 200 residues; preferably, 2 to 50 residues. Where an amino acid sequence is provided herein, L-, D-, or beta amino acid versions of the sequence are also contemplated. Polypeptides also include amino acid polymers in which one or more amino acid residues are an artificial chemical analogue of a corresponding naturally occurring amino acid, as well as to naturally occurring amino acid polymers. In addition, the term applies to amino acids joined by a peptide linkage or by other, "modified linkages" (e.g., where the peptide bond is replaced by an α-ester, a β-ester, a thioamide, phosphoramide, carbomate, hydroxylate, and the like).

In certain embodiments, conservative substitutions of the amino acids comprising any of the sequences described herein are contemplated. In various embodiments, one, two, three, four, or five different residues are substituted. The term "conservative substitution" is used to reflect amino acid substitutions that do not substantially alter the activity (e.g., biological or functional activity and/or specificity) of the molecule. Typically, conservative amino acid substitutions involve substitution one amino acid for another amino acid with similar chemical properties (e.g., charge or hydrophobicity). Certain conservative substitutions include "analog substitutions" where a standard amino acid is replaced by a non-standard (e.g., rare, synthetic, etc.) amino acid differing minimally from the parental residue. Amino acid analogs are considered to be derived synthetically from the standard amino acids without sufficient change to the structure of the parent, are isomers, or are metabolite precursors.

In certain embodiments, polypeptides comprising at least 80%, preferably at least 85% or 90%, and more preferably at least 95% or 98% sequence identity with any of the sequences described herein are also contemplated.

"Percentage (%) amino acid sequence identity" with respect to the polypeptide sequences identified herein is defined as the percentage of polypeptide residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two polypeptide sequences was carried out by computer program Blastp (protein-protein BLAST) provided online by Nation Center for Biotechnology Information (NCBI). The percentage amino acid sequence identity of a given polypeptide sequence A to a given polypeptide sequence B (which can alternatively be phrased as a given polypeptide sequence A that has a certain % amino acid sequence identity to a given polypeptide sequence B) is calculated by the formula as follows:

$$X/Y \times 100\%$$

where X is the number of amino acid residues scored as identical matches by the sequence alignment program BLAST in that program's alignment of A and B, and where Y is the total number of amino acid residues in A or B, whichever is shorter.

The term "PEGylated amino acid" as used herein refers to a polyethylene glycol (PEG) chain with one amino group and one carboxyl group. Generally, the PEGylated amino acid has the formula of $NH_2-(CH_2CH_2O)_n-COOH$. In the present disclosure, the value of n ranges from 1 to 20; preferably, ranging from 2 to 12.

As used herein, the term "terminus" with respect to a polypeptide refers to an amino acid residue at the N- or C-end of the polypeptide. With regard to a polymer, the term "terminus" refers to a constitutional unit of the polymer (e.g., the polyethylene glycol of the present disclosure) that is positioned at the end of the polymeric backbone. In the present specification and claims, the term "free terminus" is used to mean the terminal amino acid residue or constitutional unit is not chemically bound to any other molecular.

The term "antigen" or "Ag" as used herein is defined as a molecule that elicits an immune response. This immune response may involve a secretory, humoral and/or cellular antigen-specific response. In the present disclosure, the term "antigen" can be any of a protein, a polypeptide (including mutants or biologically active fragments thereof), a polysaccharide, a glycoprotein, a glycolipid, a nucleic acid, or a combination thereof.

In the present specification and claims, the term "antibody" is used in the broadest sense and covers fully assembled antibodies, antibody fragments that bind with antigens, such as antigen-binding fragment (Fab/Fab'), F(ab')$_2$ fragment (having two antigen-binding Fab portions linked together by disulfide bonds), variable fragment (Fv), single chain variable fragment (scFv), bi-specific single-chain variable fragment (bi-scFv), nanobodies, unibodies and diabodies. "Antibody fragments" comprise a portion of an intact antibody, preferably the antigen-binding region or variable region of the intact antibody. Typically, an "antibody" refers to a protein consisting of one or more polypeptides substantially encoded by immunoglobulin genes or fragments of immunoglobulin genes. The well-known immunoglobulin genes include the kappa, lambda, alpha, gamma, delta, epsilon, and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. A typical immunoglobulin (antibody) structural unit is known to comprise a tetramer. Each tetramer is composed of two identical pairs of polypeptide chains, with each pair having one "light" chain (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively. According to embodiments of the present disclosure, the antibody fragment can be produced by modifying the nature antibody or by de novo synthesis using recombinant DNA methodologies. In certain embodiments of the present disclosure, the antibody and/or antibody fragment can be bispecific, and can be in various configurations. For example, bispecific antibodies may comprise two different antigen binding sites (variable regions). In various embodiments, bispecific antibodies can be produced by hybridoma technique or recombinant DNA technique. In certain embodiments, bispecific antibodies have binding specificities for at least two different epitopes.

The term "specifically binds" as used herein, refers to the ability of an antibody or an antigen-binding fragment thereof, to bind to an antigen with a dissociation constant (Kd) of no more than about $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, and/or to bind to an antigen with an affinity that is at least two-folds greater than its affinity to a nonspecific antigen.

The term "immune disorder" as used herein refers to a disorder involving deficiency of humoral immunity, deficiency of cell-mediated immunity, combined immunity deficiency, unspecified immunity deficiency, and autoimmune disease.

The term "tumor" as used herein, refers to all neoplastic cell growth and proliferation, whether malignant or benign, and all pre-cancerous and cancerous cells and tissues. In the present specification and claims, the term "tumor" comprises solid tumors and diffused tumors.

The term "solid tumor" as used herein, denotes an abnormal mass of tissue that usually does not contain cysts or liquid areas. Different types of solid tumors are named for the type of cells that form them. Examples of solid tumors include, but are not limited to, sarcomas and carcinomas. Generally, "sarcomas" are cancers arising from connective or supporting tissues such as bone or muscle. "Carcinomas" are cancers arising from glandular cells and epithelial cells, which line body tissues.

The term "diffused tumor" as used herein refers to leukemia and/or hematological malignancy that is formed from hematopoietic (blood-forming) cells and affect blood, bone marrow, or lymph nodes. The example of the diffused tumor includes, but is not limited to, acute lymphocytic leukemia (ALL), chronic lymphocytic leukemia (CLL), acute myelogenous leukemia (AML), chronic myelogenous leukemia (CML), Hodgkin lymphoma, non-Hodgkin lymphoma, and myeloma.

The term "tumor-associated antigen" (TAA) as used herein refers to any cancer antigen that is known in the art and includes antigens found on the cancer cell surface, as well as those that are shed from cancerous cell and become soluble (i.e., soluble cancer antigens). Several cell surface antigens disposed on tumors or normal cells have soluble counterparts. Such antigens include, but are not limited to those found on cancer-associated fibroblasts (CAFs), tumor endothelial cells (TEC) and tumor-associated macrophages (TAM).

The term "treatment" as used herein includes preventative (e.g., prophylactic), curative or palliative treatment; and "treating" as used herein also includes preventative (e.g., prophylactic), curative or palliative treatment. In particular, the term "treating" as used herein refers to the application or administration of the present molecular construct or a pharmaceutical composition comprising the same to a subject, who has a medical condition a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition.

The term "effective amount" as used herein refers to the quantity of the present molecular protein that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of subject being treated, the duration of the treatment, the nature of concurrent therapy (if any), and the specific formulations employed and the structure of the compounds or its derivatives. Effective amount may be expressed, for example, as the total mass of active component (e.g., in grams, milligrams or micrograms) or a ratio of mass of active component to body mass, e.g., as milligrams per kilogram (mg/kg).

The terms "application" and "administration" are used interchangeably herein to mean the application of a molecular construct or a pharmaceutical composition of the present invention to a subject in need of a treatment thereof.

The terms "subject" and "patient" are used interchangeably herein and are intended to mean an animal including the human species that is treatable by the molecular construct, pharmaceutical composition, and/or method of the present invention. The term "subject" or "patient" intended to refer to both the male and female gender unless one gender is specifically indicated. Accordingly, the term "subject" or "patient" comprises any mammal, which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human. The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammalis except human.

The present disclosure is based, at least on the construction of the T-E pharmaceuticals that can be delivered to target cells, target tissues or organs at increased proportions relative to the blood circulation, lymphoid system, and other cells, tissues or organs. When this is achieved, the therapeutic effect of the pharmaceuticals is increased, while the scope and severity of the side effects and toxicity is decreased. It is also possible that a therapeutic effector is administered at a lower dosage in the form of a T-E molecule, than in a form without a targeting component. Therefore, the therapeutic effector can be administered at lower dosages without losing potency, while lowering side effects and toxicity.

Diseases that can Benefit from Better Drug Targeting

Drugs used for many diseases can be improved for better efficacy and safety, if they can be targeted to the disease sites, i.e., if they can be localized or partitioned to the disease sites more favorably than the normal tissues or organs. Following are primary examples of diseases, in which drugs can be improved if they can be preferentially distributed to the disease sites or cells.

I Immune Disorder

According to the design of molecular constructs of the present disclosure, the diseases, conditions, and/or disorders treatable with the present method is an immune disorder; for example, an autoimmune disorder that includes, but is not limited to, psoriasis, systemic lupus erythematosus (SLE), cutaneous lupus, Sjogren's syndrome, rheumatoid arthritis, psoriatic arthritis, ankylosing spondylitis, and inflammatory bowel disease.

Most of the autoimmune diseases, such as rheumatoid arthritis, systemic lupus erythematosus, Sjögren's syndrome, psoriasis, Crohn's disease, inflammatory bowel diseases, and others affect connective tissues. Regardless of the etiological nature, whether it is environmental, genetic, epigenetic, or their combinations, the affected tissues are damaged by prolong inflammatory processes. It is rationalized in this invention that in bringing anti-inflammatory therapeutic agents, such as anti-TNF-α, anti-IL-17, anti-BAFF, anti-IL-6, anti-IL-12/IL-23, to the diseased connective tissues, the components of the extracellular matrix may be employed as target antigens. The target antigens that may be considered include the various types of collagens, laminins, elastins, fibrillins, fibronectins, and tenascins. Connective tissues fill in nearly all parts of the human body. However, due to the structural and functional requirements of the connective tissues in different locations, the types of those extracellular matrix components are different, providing excellent choices for target tissue specificity.

The advantages of choosing extracellular components over cell surface antigens for targeting the anti-inflammatory therapeutic agents are that the choices of selectivity among the various types of matrix proteins and the abundant amounts of the extracellular matrix proteins. Furthermore, because cells are not used as antigenic targets, the potential harmful effects of direct binding to cells by anti-inflammatory agents can be avoided.

I-(i) Rheumatoid Arthritis, Psoriatic Arthritis, or Ankylosing Spondylitis

Several antibodies against TNF-α, e.g., infliximab and adalimumab, and fusion proteins of TNF-α receptor and IgG.Fc (e.g. etanercept) are approved or in human clinical trials for use to treat rheumatoid arthritis, ankylosing spondylitis, and other autoimmune diseases. The extracellular portion of the receptor for interleukin-1 (IL-1), anakinra, is approved for treating rheumatoid arthritis. Antibodies against the shared p40 protein of IL-12 and IL-23, e.g., ustekinumab and briakinumab, are approved for psoriatic arthritis or in trials for rheumatoid arthritis. An antibody against IL-6 receptor (tocilizumab) is approved for rheumatoid arthritis and systemic juvenile idiopathic arthritis, and several antibodies against IL-6, e.g., sarilumab and olokizumab, are in clinical trials for treating rheumatoid arthritis. An antibody specific for IL-17 (secukinumab) is approved for psoriasis and in clinical trials for rheumatoid arthritis and ankylosing spondylitis.

While those therapeutic agents can alleviate severe symptoms better than previously available medications, they cause a range of serious side effects in some treated patients. For example, infliximab can cause serious blood disorders, like leukopenia and thrombocytopenia, serious infections, lymphoma and other solid tumors, reactivation of hepatitis B and tuberculosis, and other serious problems. Anakinra causes frequent infections, and severe side effects on the gastrointestinal and the respiratory tracts and the blood forming organs. It is important that the serious side effects of these widely used therapeutic agents be minimized, while retaining or even enhancing their therapeutic effects.

In rheumatoid arthritis, joints of the knees, fingers, toes, and other joints are affected, and in ankylosing spondylitis, joints of the spine and the sacroiliac joint of the pelvis are affected. In the diseased joints, the surface of the bones and the articular cartilage lining the bone surfaces are attacked by the inflammatory immune components in the joints. The articular cartilage in the joints is a smooth cartilage that contains an extracellular matrix. The cartilage is avascular and approximately 60% of the weight is water and the remaining content is composed of collagens and α-aggrecan, a proteoglycan, and other matrix molecules. Collagen II forms the major fibril in the cartilage. Aggrecan is the second most abundant component in the cartilage. Collagen XI is bound to the surface of the collagen II fibril helping to form fibril networks and collagen IX is associated with collagen II and collagen XI. The cartilage has a large surface and the α-aggrecan has a structure and shape like a feather. In addition to the cartilage formation, the joints have also ligaments, which connect adjacent bones, such as the cruciate ligaments, and tendons, which connect muscles to the bones. The ligaments and tendons are formed by fibrous network of collagen types I, II, and III, and elastin and fibrillins 1 and 2.

The present invention rationalizes that the antagonist for TNF-α, IL-1, and shared protein of IL-12 and IL-23 can be carried to the diseased joints by using antibody fragments, such as scFv, specific for collagen II, α-aggrecan, collagen XI or collagen IX, or alternatively, collagen I, elastin or fibrillin 1 as the targeting agent. A preferred anti-collagen II antibody is one that binds to native collagen II in the joints and does not bind to N-terminal and C-terminal propeptides, which are cleaved off during fibril assembly. A preferred anti-aggrecan antibody is one that binds to whole native α-aggrecan molecules and does not bind to fragments that are cleaved off and released into the blood circulation. By adopting the present molecular construct with scFv of anti-collagen II as targeting agent, in comparison with regular IgG against TNF-α, IL-1, and shared protein of IL-12 and IL-23, larger proportions of the present therapeutic agents can be carried to the diseased sites and less amounts of the therapeutic agents will be present in other irrelevant, normal tissues, especially, lymphoid organs, and hence fewer side effects will occur.

I-(ii) Psoriasis

Most patients with psoriasis or plaque psoriasis present inflammatory symptoms primarily in the skin and not in other tissues and organs. Psoriasis involves mainly keratinocytes in part of skin in the affected patients. A systematic administration of monoclonal antibodies anti-TNF-α, anti-IL-12/IL-23, and anti-IL-17 or anti-IL-17 receptor (anti-IL-17R) or other anti-inflammatory agents, such as anti-IL-6, causes unwanted side effects, as discussed in the preceding section. The serious adverse side effects of all these immune modulating antibodies have been well documented.

A number of membrane or extracellular proteins, such as filaggrin, collagen I, which are expressed at much higher levels in the skin tissues than most of other tissues, probably can be considered as the target proteins to shuffle therapeutic agents to the skin. Filaggrin is present in the tight junction between cells and is probably accessible by antibodies in the diseased tissue sites. While collagen I is also present in the bone matrix and many parts of the body, it is present in the dermis layer of the skin in abundant proportions.

For damping the inflammatory activity caused by the diseased keratinocytes, which manifests psoriatic symptoms, it is not necessary to deliver the anti-inflammatory antibody drugs to be in contact with the keratinocytes. The keratinocytes are in the outmost, epidermis layer of the skin; blood vessels, sweat glands, and collagen fibers are in the middle dermis layer of the skin. The inner layer is hypodermis, where adipose tissues are. The three layers of human skin together are 2-3 mm thick. If the anti-inflammatory antibodies are delivered to the dermis layer by scFv specific for collagen I, they can diffuse into the other layers. Or, the antibodies can trap inflammatory cytokines in the three layers of the skin.

Several proteins present at the dermo-epidermal junction may also be employed as targets for carrying therapeutic agents to the skin. These include type VII collagen, type XVII collagen, and laminins type 5, 6, or 10. The dermoepidermal junction is the area of tissue that joins the epidermal and dermal layers of the skin. The basal cells in the stratum basale of epidermis connect to the basement membrane by the anchoring filament of hemidesmosomes. The cells of the papillary layer of the dermis are attached to the basement membrane by anchoring fibrils, which consist of type VII collagen. Type XVII collagen, a transmembrane protein (also referred to as BP180) expressed on keratinocytes, is a structural component of hemidesmosomes, multiprotein complexes at the dermal-epidermal basement membrane zone that mediate adhesion of keratinocytes to the underlying membrane. Laminins are structural non-collagenous glycoproteins present in basement membranes. Among the many types of laminins, types 5, 6, and 10 are specific of the basal lamina present under stratified epithelia.

I-(iii) Systemic Lupus Erythematosus (SLE), Cutaneous Lupus, or Sjogren's Syndrome Systemic lupus erythematosus (SLE) is an autoimmune disease involving multiple autoantigens, such as nucleic acids, histones, and other nuclear proteins. Sjögren's syndrome is an autoimmune disease, in which the immune system attacks the exocrine glands, specifically the salivary and lacrimal glands, which produce saliva and tears, respectively, resulting the symptoms of dry eyes and dry mouth, leading to infections and various other problems. Both of these diseases occur 9 times more frequently in women than in men, especially in women of child-bearing ages 15 to 35. SLE is a systemic autoimmune connective tissue disease and affects many organs and tissues. In general, those tissues and organs, such as the heart, lungs, bladder, and kidneys, which exhibit elasticity and can expand and contract, contain collagen network. In several types of SLE, cutaneous manifestation of inflammatory symptoms is prominent.

For more than 50 years, not a single new therapeutic agent had been developed for SLE, until belimumab, a human monoclonal antibody specific for BAFF was developed and approved. However, the therapeutic effect of belimumab for SLE has been considered to be marginal. Belimumab causes a host of side effects, including more incidences of serious infections and deaths in the treatment group than the placebo group. Interestingly, in a phase II trial on Sjögren's syndrome, belimumab showed more successful results than in SLE.

In addition to BAFF, researchers have been searching other therapeutic targets for SLE. While not a single inflammatory cytokine has been identified as mainly responsible for the pathological process in SLE, the expression of a group of genes known as downstream events of type 1 interferon stimulation, which is termed "type 1 interferon signature", has been documented in many studies. The pathogenesis of SLE has been found to be associated with the activation of toll-like receptors 7 and 9 (TLR 7 and TLR9), which induce the expression of a group of genes similar to that resulting from the activation by IFN-α.

Several monoclonal antibodies specific for IFN-α, including rontalizumab, sifalimumab, and anifrolumab have been studied in clinical trials for the treatment of SLE. Since IFN-α is involved in many functions, a systemic administration of an antibody against IFN-α without localized targeting to disease sites may render serious side effects.

I-(iv) Inflammatory Bowel Disease

Anti-TNF-α (such as adalimumab) has also been approved for treating Crohn's disease and ulcerative colitis (a form of inflammatory bowel disease). However, as described in an earlier section, the administration of anti-TNF-α is associated with a range of series side effects, including severe infectious diseases and B cell lymphoma. Therefore, in treating patients with Crohn's disease or ulcerative colitis with anti-TNF-α, it will be desirable to distribute the administered anti-TNF-α in favor of the intestine and colon. It has been found collagen III and type V are relatively abundant in the connective tissues in the intestine and bowel.

II Tumor

Several classes of large numbers of therapeutic agents have been developed and experimented in animal models and in human clinical trials for the treatment of malignant tumors, including diffused and solid tumors and primary and metastatic tumors of varying clinical stages. These therapeutic agents, some of which have been approved by governmental regulatory agencies for use in patients, include (1) a large number of compounds targeting key cellular regulatory pathways or structural components, or damaging DNA or important cellular machinery, (2) antibodies specific for surface antigens of certain cell types or specific for certain tumor-associated antigens and capable of mediating apoptosis, antibody-dependent cellular cytotoxicity (ADCC), or complement-mediated cytolysis (CMC) of the targeted cells, (3) antibodies specific for certain tumor-associated antigens, which are conjugated with potent cytotoxic drugs, (4) immunoregulatory cytokines, such as interferon-α (IFN-α), interleukin-2 (IL-2), or interferon-γ (IFN-γ), which can activate the immune system in fighting against malignant cells, (5) antibodies targeting certain cell surface markers of B and T lymphocytes, e.g., anti-CD20 rituximab, (6) antibodies targeting growth factor receptors, e.g., anti-HER2/Neu trastuzumab and anti-EGFR cetuximab, (7) antibodies targeting vascular endothelial growth factor-A (VEGF-A) for inhibiting angiogenesis, e.g., bevacizumab, and (8) antibodies binding to immune checkpoints, such as PD1 (programmed cell death protein 1, CD279), e.g., nivolumab, PD-L1 (programmed cell death protein ligand 1, CD274), e.g., MPDL3280A, CTLA-4 (cytotoxic T-lymphocyte protein 4, CD152), e.g., ipilimumab, which inhibit the negative feedback of immune reactions and allow continual activation of on-going immune responses.

The usefulness of therapeutic agents for treating cancer as well as for many other diseases is limited or compromised by their toxicity, because the agents also act on some normal cells to some degrees. Therefore, many therapeutic agents have limited therapeutic windows and therefore, in order to control their toxic effects, they are administered in many of the treated patients at suboptimal doses, as far as therapeutic efficacy is concerned, which are insufficient to achieve satisfactory therapeutic effects.

The antibody-drug conjugate approach, which is being pursued actively, requires that the tumor-targeting antibodies together with the carried cytotoxic drugs be internalized by the targeted cells expressing the tumor-associated antigens, which the targeting antibodies recognize. This requirement may potentially limit the power of the current antibody-drug conjugate approach, because cells in a tumor express a tumor-associated antigen at varying densities. Those cells expressing relatively low levels may not be killed by the current antibody-drug conjugates during treatment and will grow up as the therapeutic agents are discontinued.

II-(i) Diffused Tumor

II-(i)-A Targeting Cancerous Cells Originated from Leukocytes

The cancer derived from malignantly transformed cells of the lymphoid and myeloid lineages account for a significant proportion among all cancer. Those tumors are generally diffusive and not solid. Thus, the targeting of leukocyte-derived tumors will involve the targeting of the individual tumor cells. Therefore, the identification of the expression of cell-surface antigens of the tumor cells is a key in the targeting of leukocyte-derived tumors.

Tumors derived from white blood cells (leukocytes) are generally classified into three categories: (1) leukemia found in the blood and bone marrow, (2) lymphoma found in the lymphatic system, and (3) myeloma in many parts of bone marrow and also in the blood.

Leukemia has four broad classifications: (1) acute lymphocytic leukemia (ALL), (2) chronic lymphocytic leukemia (CLL), (3) acute myelogenous leukemia (AML), and (4) chronic myelogenous leukemia (CML). However, as advanced diagnostic and analytic methods are being developed, new types of leukemia, such as B cell CLL, T cell CLL, B cell prolymphocytic leukemia, Hairy cell leukemia, and others are been defined.

Lymphomas are divided into two categories: (1) Hodgkin lymphomas and (2) non-Hodgkin lymphomas. Of the patients who have lymphomas, about 12% have Hodgkin lymphomas and the rest have non-Hodgkin lymphomas. Of the non-Hodgkin lymphomas, most are B cell-derived and there are many subtypes of B cell non-Hodgkin lymphomas. The rest of the non-Hodgkin lymphomas are T cell lymphomas.

Myeloma is derived from antibody-producing plasma cells and is also referred to as plasmacytoma. Myeloma cells are found in bone marrow and can travel in the blood circulation and establish growth in many parts of the bone and hence myeloma is also called multiple myeloma.

While leukemia, lymphomas, and myeloma are derived from myeloid, lymphoid, and plasma cells, the diagnosis of the tumor types is often very complex, involving tissue and cellular examinations with histological, immunohistological, morphological, and cellular marker analyses of the biopsied tumor samples. Since the pluripotent stem cells, the myeloid lineage, which differentiate into granulocytes (neutrophils, eosinophils, and basophils), monocytes and macrophages, and platelets, and the lymphoid lineage, which differentiate into B cells and T cells, undergo many steps of differentiation and maturation, the malignant transformation can occur at any of the differentiation stages. Furthermore, the cancerous transformation may augment and gain certain traits and reduce or lose certain traits.

The surface markers or differentiation antigens, especially those, which have been assigned a CD (cluster of differentiation) number, have become very useful and often necessary to identify the various leukocytes and immunocytes in the studies of innate and adaptive immunity. Often the identification of a cell type requires a set of markers.

For antibody-based therapeutic approaches for targeting cancer of the leukocyte origin, identification of the surface markers of a targeted tumor is very useful and powerful. However, among the patients who have been diagnosed to have the same type of tumor, the surface markers can vary over a large range in terms of density.

II-(i)-B Surface Markers on B Cell-Derived Lymphocytic Leukemia and Lymphoma

Both ALL and CLL are not solid tumors. ALL is derived from lymphoblasts, precursor B cells, precursor T cells, or B cells. ALL consists of the immunophenotypic subtypes: (1) precursor B cell acute lymphoblastic leukemia, which expresses cell surface markers associated with B cell precursors and precursor T cell acute lymphoblastic leukemia, which express markers of precursor T cells, (2) Burkitt's lymphoma, which is derived from B cells of the germinal center and express cell surface markers associated with B cells, and (3) acute biphenotypic leukemia, which express markers of both lymphoid and myeloid cells.

CLL is also referred to as B-cell CLL (B-CLL), because CLL is mostly derived from B cells. Thus, the major difference of the cellular origin between ALL and CLL is that ALL is derived from lymphoblasts, which are the common precursors of B cells and T cells and CLL is derived from B cells. All CLL cells in a patient are from monoclonal, derived original one B cell of a particular set of $V_H$ and $V_L$. The cells of CLL express CD19 and CD20, and characteristically CD5 and CD23.

Hodgkin lymphomas are characterized by the presence of Reed-Sternberg cells, which are multi-nucleated giant cells derived from B cells. There are at least four subtypes of Hodgkin lymphomas based on the morphology of Reed-Sternberg cells and the composition of reactive cell infiltrate in the lymph node biopsy specimen: (1) nodular sclerosing Hodgkin lymphoma, (2) mixed-cellularity, (3) lymphocyte-rich or lymphocytic predominance, and (4) lymphocyte depleted. It is well established that Hodgkin lymphoma is derived from mature B cells. Cells of Hodgkin lymphoma, depending on its immunophenotype, express a subset of CD15, CD20, CD30, CD79a, and CD138. Most of the cases of non-Hodgkin lymphomas are derived from B cells. There are at least 14 subtypes of B-cell non-Hodgkin lymphomas.

B lymphocytes are the source of antigen-specific antibodies and are a critical component of the adaptive immune system for the defense against infectious pathogens. However, B cells can also be pathogenic and the cause of several types of diseases. B-cell disorders are divided into undesired immunoglobulin production (autoimmune and allergic diseases) and uncontrolled proliferation (lymphomas, leukemia). B cells have proven to be effective targets for the treatment of multiple autoimmune disorders and B-lineage cancer. Many approaches pertaining to B-cell depletion for the treatment of B cell malignancies and antibody-mediated diseases have been developed with partial success or are in active experimental stages. These include therapeutic antibodies that target human B-cell surface antigens, such as CD19, CD20, CD22, CD37, CD79a/CD79b, and isotype-specific Ig receptor. Some of such antibodies can cause lysis of B cells. Some other antibodies will cause B cell lysis when the antibodies are conjugated with cytotoxic drugs.

Multiple myeloma, also referred to as plasma cell myeloma, is the second most common hematological malignancies (after non-Hodgkin lymphoma), constituting 1% of all cancers and 2% of all cancer deaths. Multiple myeloma produces large quantities of myeloma proteins and occupies bone marrow and manifests a series of symptoms, including bone pain, anemia, renal failure, infection, and neurological problems. Multiple myeloma is derived from the malignant transformation of plasma cells, which differentiate from B lymphocytes. However, cells of multiple myeloma do not express the most common B cell markers, such as CD19, CD20, and CD22.

A number of therapies and drugs have been experimented and a few have been approved for the treatment of multiple myeloma. These include corticosteroids, chemotherapies, proteasome inhibitors, and immunoregulatory compounds.

II-(i)-C Unique B Cell Antigens Igα, Igβ and migis-δ as Targets of Antibodies

Igα (CD79a)/Igβ (CD79b) is set of antigens that are expressed in association of the B cell receptor (BCR) complex on the surface of cells of the B-cell lineage. Igα/Igβ is a heterodimeric transmembrane protein, which is composed of two distinct chains Igα and Igβ stabilized by disulfide bonding. Igα/Igβ forms a complex with the BCR and generates a signal following recognition of antigen by the BCR complex. During the development of B cell maturation, Igα/Igβ is expressed in the pre-B-cell stage and is early than CD20 for the expression pattern on the B-cell lineage. Igα/Igβ has been considered as attractive target for the B cell depletion therapy in the treatment of non-Hodgkin lymphomas because Igα/Igβ is expressed on B cells and on most non-Hodgkin lymphomas.

The mIgD and mIgM are coexpressed on the surface of mature B cells and function as part of BCR. The mIgD contains a unique migis-δ peptide segment of 27 AA, which represents the extracellular portions of the membrane-anchoring segment of mIgD and is located between the CH3 domain and transmembrane segment. It has been proposed that migis-δ peptide provides an antigenic site for targeting mIgD-expressing B cells. The site is present on the mIgD-expressing B cells and not on the secreted IgD.

II-(i)-D T Cell Tumors

T lymphocyte subsets through their surface molecules and secreted factors mediate a complex network of immunoregulatory activities on humoral and cellular immune effector functions, including the production of different classes of antibodies, the secretion of various cytokines, and the generation of cytotoxic T cells and other cytolytic cells. Many autoimmune diseases are caused by the abnormal activities of T cells against self-components or cells. For example, in type-I diabetes, the insulin-producing β cells in the islets of Langerhans of pancreas are attacked and killed by autoimmune T cells. The devastating autoimmune diseases, such as systemic lupus erythematosus (SLE), multiple sclerosis, and inflammatory bowel diseases, are caused mainly by T cells. Furthermore, the rejection reaction toward organ or tissue transplants is mediated mainly by T cells.

There are also a few forms of T cell malignancy. Thus, modulating T cell activities or removing T cells has been an active area of drug discovery research. A variety of antibodies and their modified forms against T cell surface antigens, including CD3, CD4, CD8, CD25, and CD28 have been studied in animal models or human clinical trials for treating various human diseases mentioned above. Some antibodies with or without the conjugation with cytotoxic drugs can cause the lysis of the targeted T cell subsets. Some antibodies can cause anergy or an idled, inactive state of T cells without actually lysing the cells.

T lymphocytes play major roles in regulating activities of various immunocytes and various other cell types in adaptive and native immunity. In the development of therapeutic agents to target lymphocytes, fewer candidates have been successfully developed for targeting T cells than for targeting B cells. However, there have been increasing numbers of therapeutic antibodies that are being developed to target surface antigens of T cell subsets. Antibodies targeting T cell surface antigens can potentially be employed to treat malignant tumors derived from T cells. Antibodies may also be used to modulate T cell activities, either to inhibit them or to enhance them.

II-(i)-E Myelogenous Leukemia

AML is derived from myeloid stem cells or myeloid blasts, the precursors for the mature granulocytes and monocytes. Many of the subtypes of AML are caused by mutagens, which cause chromosomal translocations or loss of certain gene segments. Cells of AML derived from various differentiation stages express some subsets of surface markers of CD13, CD14, CD15, CD33, CD34, CD36, CD41, CD61, CD64, CD65, and CD11c. Cells of AML derived from the early precursor myeloid stages express CD34, which is a surface marker of pluripotent stem cells, and CD33, which is a marker of immature myeloid cells. Cells of AML derived from many myeloid differentiation stages express CD15, a marker of mature myeloid cells. CML is a clonal bone marrow stem cell disorder resulted from the malignant transformation of a stem cell or myeloid stem cell, or from the translocation of the Philadelphia chromosome.

II-(ii) Solid Tumor

II-(ii)-A Solid Tumor and Tumor-Associated Antigens

Cells of many types of tumors express certain antigens on cell surface at elevated levels compared to those on normal cells. Those antigens are referred to as tumor-associated antigens. For example, serum samples from patients with pancreatic tumors and many types of gastrointestinal cancer, including colorectal cancer, esophageal cancer, and hepatocellular carcinoma, contain CA19-9 antigen (carbohydrate antigen 19-9, a sialyl-Lewis A antigen). The cells of those tumors express CA19-9 on the extracellular matrix on cell surface. Similarly, serum samples from patients with ovarian cancer, endometrial cancer, fallopian tube cancer, and some other types of cancer have elevated CA-125 (carbohydrate antigen 125, mucin 16) and the cells of those tumors express CA125. Overexpression of cell surface associated glycoprotein mucin 1 (MUC1) is often associated with colon, breast, ovarian, lung, and pancreatic cancer.

The ganglioside GD2 is highly expressed on neuroectoderm-derived tumors and sarcomas, including neuroblastoma, retinoblastoma, melanoma, small cell lung cancer, brain tumors, osteosarcoma, rhabdomyosarcoma, Ewing's sarcoma in children and adolescents, as well as liposarcoma, fibrosarcoma, leiomyosarcoma and other soft tissue sarcoma in adults.

While mesothelin is expressed on normal mesothelial cells, it is expressed on many human cancers, mesothelioma, tumors of the pancreas, ovary, lung, and stomach, cholangiocarcinoma, and triple-negative breast cancer.

Tn antigen is a structural element on glycoproteins, in which N-acetylgalactosamine (GalNAc) is linked to serine or threonine by a glycosidic bond, i.e. as an O-glycan. Addition of single monosaccharide residues creates disaccharide antigens: the Thomsen-Friedenreich antigen (TF antigen or T antigen) is formed by substitution with galactose (Gal(b1-3)GalNAc); the sialyl-Tn antigen (STn antigen) is formed by substitution with sialic acid (Neu5Ac(a2-6)GalNAc. TN and sialy-Tn are not usually found on healthy cell surfaces, but may be found on cancer cells.

Tumor-associated antigens that have been widely studied as markers of tumors or explored as targets for immunological therapies include (1) epidermal growth factor receptors (EGFRs)—human epidermal growth factor 1 (EGFR or HER1), HER2, HER3, HER4, or their mutants; (2) glycoproteins—CA19-9 (bearing Sialyl Lewis$^A$ antigen), CA125 (bearing mucin 16 or MUC 16), cell surface-associated mucin 1 (MUC1), or carcinoembryonic antigen, melanoma-associated antigen (MAGE), prostate-specific membrane antigen (PSMA), prostate stem cell antigen (PSCA), or mesothelin; (3) mucin-related Tn or Sialyl Tn; (4) the blood group Lewis related Lewis$^Y$, Sialyl Lewis$^Y$, Sialyl Lewis$^A$, or Lewis$^X$; (5) glycosphingolipids—Globo H or stage-specific embryonic antigen-4 (SSEA-4); or (6) gangliosides—GD2, GD3, GM2, fucosyl GM1, or Neu5GcGM3.

II-(ii)-B Growth Factors, Peptide Hormones, and Cytokines as Targeting Agents for Cells Overexpressing Receptors A number of growth factors, peptide hormones and regulatory cytokines regulate important physiological processes in a human body. These substances mediate their functions through interacting with their receptors on different cell types. The most prominent are endocrine or exocrine cells in organs or compartments or organs bearing function-specific receptors, which respond to growth factors, hormones, or cytokines. For example, the exocrine cells in the pancreas bear receptors that respond to secretin, gastrin, and cholecystokinin (CCK) from duodenum and stomach during food intake and digestive process.

When malignant transformation occurs to the receptor-bearing cells, the tumorous cells maintain the expression of the receptors. In fact, in many cases, an abnormally high expression of the receptors occurs due to certain mutations in the cells, which are not necessarily in the receptors themselves. The affected cells thus become malignantly transformed. The overexpression of receptors on tumors, e.g., somatostatin receptors are strongly expressed on most neuroendocrine tumors, and the targeting of those receptors for therapeutic and diagnostic (e.g., radio-imaging) purposes have been an active area of research. Neuroendocrine tumors are generally rare, but include a long list of tumors of various cell origins, including those of gastroenteropancreatic neuroendocrine tumors, thyroid gland tumors, Merkel cell carcinoma, adrenomedullary tumors, and many others.

Examples of this line of research are numerous. The over-expression of the family of epidermal growth factor receptors (EGFRs) in breast cancer, lung cancer, colon cancer, and many other types of carcinoma is well documented. For example, monoclonal antibody trastuzumab specific for HER2/Neu receptor is broadly used for treating HER2-positive breast cancer. Cetuximab specific for EGFR is being used in treating metastatic colon cancer, metastatic non-small cell lung cancer, and head and neck cancer. Small molecular inhibitors, such as gefitinib and erlotinib, which interrupts the tyrosine kinase domain in EGFR, have also been developed for the treatment of several type of cancer.

Pancreatic cancer is one of the most vicious cancers. Among the various types of pancreatic cancers, the pancreatic (ductal or invasive) adenocarcinoma derived from the exocrine cells account for 85%, although those ductal epithelial cells account only for 10% among all cells in the pancreas. The exocrine cells express receptors for the peptide hormones, gastrin, secretin, or cholecystokinin, which are secreted by the cells in the stomach and duodenum, and respond to those hormones and secrete bicarbonate ions and digestive enzymes. The overexpressed receptors for CCK and gastrin in pancreatic cancer and many other types have also been explored as a target for radioimaging. Other hormones and receptors, which are under active investigation, are somatostatin and gastrin-releasing peptide. In such radio-imaging approaches, CCK or gastrin of their peptide analogues are coupled with chelating groups for radioactive nuclides. In the imaging procedure, the imaging agents bind to the primary or metastasized tumors containing cells expressing the receptors. Peptide hormones or their analogues carrying radionuclides, lutetium-177, yttrium-90, or indium-111, have also been experimented for treating tumors.

II-(ii)-C Immune Checkpoints as Targets

CTLA-4 is a protein receptor that down-regulates the immune system. CTLA-4 is found on the surface of T cells, and acts as an "off" switch when bound to CD80 (B7-1) or CD86 (B7-2) on the surface of antigen presenting cells. Such binding prevents the binding of those receptors by CD28, which activates the immune response. A human IgG1 antibody specific for CTLA-4, ipilimumab, has been approved for treating melanoma and in clinical studies for treating several other types of cancer. The treatment with ipilimumab has been associated with severe and potential fatal immunological side effects due to T cell activation and proliferation.

PD-1 is expressed on the surface of activated T cells. If PD-1 is blocked by its ligand, PD-L1, the T cell becomes inactive. This is a way that the body regulates the immune system to avoid an overreaction of immune responses. Many cancer cells make PD-L1 and thereby disarm the T cells and inhibit them from attacking the cancer cells. Two human antibodies against PD-1, pembrolizumab and nivolumab, have been approved for treating unresectable or metastatic melanoma, which no longer respond to other drugs, and squamous non-small cell lung cancer. An anti-PD-L1 antibody, MPDL3280A, is now in Phase II or III clinical trials for triple-negative breast cancer, metastatic non-small cell lung cancer, bladder carcinoma, and renal cell carcinoma. A large number of anti-PD-1 and anti-PD-L1 antibodies are in research or early clinical trials.

Many researchers are exploring other targets, such as OX40, CD137, and CD27 on the activated T cells and their corresponding ligands, OX40L, CD137L, and CD137 the antigen-presenting cells or tumor cells for releasing the brakes of T cell activation. Those pathways are considered to be milder in T-cell activation strength than the CTLA-4 and PD-1 pathways.

While antibodies specific for PD-1 or PD-L1 look very promising for treating several types of cancer, the current clinical development suggest that those antibodies will require the combination with chemotherapies, other antibodies, or targeted therapies. Also, the antibodies also cause a range of severe side effects. We rationalize that if the antibodies specific for immune checkpoints were carried to the targeted tumor site, better therapeutic efficacy could be achieved, and fewer side effects would occur.

II-(ii)-D Vascular Endothelial Growth Factor as Targets

Vascular endothelial growth factor A (VEGF-A) is essential for angiogenesis (blood vessel formation) as the tumor grows. The blood circulation is required for oxygen and nutrient supplies, waste disposal and many other functions. Antibodies specific for VEGF-A, such as bevacizumab specific for VEGF-A, are effective as a monotherapy or in combination with chemotherapy in treating a few forms of cancer. However, bevacizumab is associated with a range of side effects, including hypertension and heightened risk of bleeding, bowel perforation, and necrotizing fasciitis.

II-(ii)-E Immunoregulatory Cytokines as Cancer Therapeutic Agents

The immunoregulatory cytokines referred to in this invention are those that are known to be stimulatory and are major drivers in activating immune responses. These cytokines include interleukin-2 (IL-2), interferon-α (IFN-α), interferon-γ (IFN-γ), and TNF-α. Among them, IFN-α, which is a strong activator of T cells, has been approved for use in hairy-cell leukemia, AIDS-related Kaposi's sarcoma, follicular lymphoma, chronic myeloid leukemia and melanoma. However, clinical studies so far have not established major therapeutic utilities of those immunoregulatory cytokines in treating tumors, mainly because the therapeutic doses of those cytokines in systematic administrations are limited by the side effects of the cytokines. In general, cytokines act mainly in the microenvironment of the lymphoid system.

III Osteoporosis Disease

An antibody specific for RANKL (CD254), the ligand of RANK (RANK, receptor activator of nuclear factor κ B), denosumab, is approved for the treatment of osteoporosis. The development of denosumab represents a major advancement in the care for osteoporosis. However, the administration of denosumab causes common side effects, such as infections of the urinary and respiratory tracts, cataracts, constipation, rashes, and joint pain. It is hence desirable that the therapeutic agent is carried preferentially to the bone.

RANKL is a membrane protein, belonging to the tumor necrosis factor ligand family. RANKL is detected at high levels in the lung, thymus, and lymph nodes. It is also detected at low levels in the bone marrow, stomach, peripheral blood, spleen, placenta, leukocytes, heart, thyroid and skeletal muscle. Since IgG anti-RANKL, such as denosumab, can serve a therapeutic agent for osteoporosis, the molecular constructs of this invention should provide as better therapeutic agents than IgG anti-RANKL.

Another target for antibodies for the treatment of osteoporosis is sclerostin, encoded by SOST gene. The glycoprotein is produced and secreted by osteocytes and negatively regulates osteoblastic bone formation. The loss or defective mutation of SOST gene causes progressive bone thickening. A defective mutation in the SOST gene increases bone formation. Antibodies against sclerostin cause increased bone formation, bone mineral density, and stronger bones. The phase I and II clinical trials of two humanized monoclonal antibodies against sclerostin, blosozumab and romosozumab, indicated that the antibody treatment is associated with increased bone mineral density and bone formation and decreased bone resorption.

In light of the foregoing discussion, molecular platforms for constructing the T-E molecules of this invention are provided in the present disclosure. Detailed discussion relating to the structure of said molecular constructs are provided below, as well as the practical applications of each molecular construct.

Part I Peptide Core-Based Multi-Arm Linkers

The first aspect of the present disclosure pertains to a linker unit that comprises, (1) a center core that comprises 2-15 lysine (K) residues, and (2) 2-15 linking arms respectively linked to the K residues of the center core. The present center core is characterized in having or being linked with an azide group, an alkyne group, a tetrazine group, or a strained alkyne group at its N- or C-terminus.

In the preparation of the present linker unit, a PEG chain having a N-hydroxysuccinimidyl (NHS) group at one terminus and a maleimide group at the other terminus is linked to the K residue of the center core by forming an amide bond between the NHS group of the PEG chain and the amine group of the K residue. In the present disclosure, the PEG chain linked to the K residue is referred to as a linking arm, which has a maleimide group at the free-terminus thereof.

According to the embodiments of the present disclosure, the center core is a polypeptide that has 8-120 amino acid residues in length and comprises 2 to 15 lysine (K) residues, in which each K residue and the next K residue are separated by a filler sequence.

According to embodiments of the present disclosure, the filler sequence comprises glycine (G) and serine (S) residues; preferably, the filler sequence consists of 2-15 residues selected from G, S, and a combination thereof. For example, the filler sequence can be, GS,
GGS,
GSG,
GGGS (SEQ ID NO: 1),
GSGS (SEQ ID NO: 2),
GGSG (SEQ ID NO: 3),
GSGGS (SEQ ID NO: 4),
SGGSG (SEQ ID NO: 5),
GGGGS (SEQ ID NO: 6),
GGSGGS (SEQ ID NO: 7),
GGSGGSG (SEQ ID NO: 8),
SGSGGSGS (SEQ ID NO: 9),
GSGGSGSGS (SEQ ID NO: 10),
SGGSGGSGSG (SEQ ID NO: 11),
GGSGGSGGSGS (SEQ ID NO: 12),
SGGSGGSGSGGS (SEQ ID NO: 13),
GGGGSGGSGGGGS (SEQ ID NO: 14),
GGGSGSGSGSGGGS (SEQ ID NO: 15), or
SGSGGGGGSGGSGSG (SEQ ID NO: 16).

The filler sequence placed between two lysine residues may be variations of glycine and serine residues in somewhat random sequences and/or lengths. Longer fillers may be used for a polypeptide with fewer lysine residues, and shorter fillers for a polypeptide with more lysine residues. Hydrophilic amino acid residues, such as aspartic acid and histidine, may be inserted into the filler sequences together with glycine and serine. As alternatives for filler sequences made up with glycine and serine residues, filler sequences may also be adopted from flexible, soluble loops in common human serum proteins, such as albumin and immunoglobulins.

According to certain preferred embodiments of the present disclosure, the center core comprises 2-15 units of the sequence of $G_{1-5}SK$. Alternatively, the polypeptide comprises the sequence of $(GSK)_{2-15}$; that is, the polypeptide comprises at least two consecutive units of the sequence of GSK. For example, the present center core may comprises the amino acid sequence of the following, Ac-CGGSGGSGGSKGSGSK (SEQ ID NO: 17),
Ac-CGGSGGSGGSKGSGSKGSK (SEQ ID NO: 18), or
Ac-CGSKGSKGSKGSKGSKGSKGSKGSKGSK (SEQ ID NO: 19), in which Ac represents the acetyl group.

According to certain embodiments of the present disclosure, the center core is a polypeptide that comprises the sequence of $(X_{aa}\text{-}K)_n$, in which $X_{aa}$ is a PEGylated amino acid having 2 to 12 repeats of ethylene glycol (EG) unit, and n is an integral from 2 to 15.

As described above, the present center core is characterized in having or being linked with an azide group, an alkyne group, a tetrazine group, or a strained alkyne group at its N- or C-terminus. According to some embodiments of the present disclosure, the present center core comprises, at its N- or C-terminus, an amino acid residue having an azide group or an alkyne group. The amino acid residue having an azide group can be, L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, or 6-azido-D-lysine. For example, the present center core may have the sequence of, Ac-$(GSK)_{2-7}$-$(G_{2-4}S)_{1-8}$-$A^{AH}$,
Ac-$A^{AH}$-$(SG_{2-4})_{1-8}$-$(GSK)_{2-7}$,
Ac-$A^{AH}$-$(SG_{2-4})_{0-7}$-$(GSK)_{2-6}$-$(G_{2-4}S)_{1-8}$-C,
Ac-C-$(SG_{2-4})_{0-7}$-$(GSK)_{2-6}$-$(G_{2-4}S)_{1-8}$-$A^{AH}$,
Ac-K-$(Xaa_{2-12}$-$K)_{2-4}$-$Xaa_{2-12}$-$A^{AH}$,
Ac-$A^{AH}$-$Xaa_{2-12}$-K-$(Xaa_{2-12}$-$K)_{2-4}$,
Ac-$A^{AH}$-$Xaa_{2-12}$-K-$(Xaa_{2-12}$-$K)_{1-3}$-$Xaa_{2-12}$-C, or
Ac-C-$Xaa_{2-12}$-K-$(Xaa_{2-12}$-$K)_{1-3}$-$Xaa_{2-12}$-$A^{AH}$, in which Xaa is a PEGylated amino acid having specified repeats of EG unit, Ac represents the acetyl group, and $A^{AH}$ represents the AHA residue.

Exemplary amino acid having an alkyne group includes, but is not limited to, L-homopropargylglycine (L-HPG), D-homopropargylglycine (D-HPG), or beta-homopropargylglycine (β-HPG). In this case, the present center core may have the sequence of, Ac-$(GSK)_{2-7}$-$(G_{2-4}S)_{1-8}$-$G^{HP}$,
Ac-$G^{HP}$-$(SG_{2-4})_{1-8}$-$(GSK)_{2-7}$,
Ac-$G^{HP}$-$(SG_{2-4})_{0-7}$-$(GSK)_{2-6}$-$(G_{2-4}S)_{1-8}$-C,
Ac-C-$(SG_{2-4})_{0-7}$-$(GSK)_{2-6}$-$(G_{2-4}S)_{1-8}$-$G^{HP}$,
Ac-K-$(Xaa_{2-12}$-$K)_{2-4}$-$Xaa_{2-12}$-$G^{HP}$,
Ac-$G^{HP}$-$Xaa_{2-12}$-K-$(Xaa_{2-12}$-$K)_{2-4}$,
Ac-$G^{HP}$-$Xaa_{2-12}$-K-$(Xaa_{2-12}$-$K)_{1-3}$-$Xaa_{2-12}$-C, or
Ac-C-$Xaa_{2-12}$-K-$(Xaa_{2-12}$-$K)_{1-3}$-$Xaa_{2-12}$-$G^{HP}$, in which Xaa is a PEGylated amino acid having specified repeats of EG unit, Ac represents the acetyl group, and $G^{HP}$ represents the HPG residue.

It is noted that many of the amino acids containing an azide or alkyne group in their side chains and PEGylated amino acids are available commercially in t-boc (tert-butyloxycarbonyl)- or Fmoc (9-fluorenylmethyloxycarbonyl)-protected forms, which are readily applicable in solid-phase peptide synthesis.

According to some working examples of the present disclosure, the center core may comprise the sequence of, Ac-$G^{HP}$GGSGGSGGSKGSGSK (SEQ ID NO: 21),
Ac-$G^{HP}$GGSGGSGGSKGSGSKGSK (SEQ ID NO: 22),
Ac-$A^{AH}$GGSGGSGGSKGSGSKGSK (SEQ ID NO: 23),
Ac-$G^{HP}$GGSGGSGGSKGSGSKGSGSC (SEQ ID NO: 24),
Ac-C-$Xaa_2$-K-$Xaa_2$-K-$Xaa_2$-K (SEQ ID NO: 25), or
Ac-C-$Xaa_6$-K-$Xaa_6$-K-$Xaa_6$-K-$Xaa_6$-K-$Xaa_6$-K (SEQ ID NO: 26), in which Xaa is a PEGylated amino acid having specified repeats of EG unit, Ac represents the acetyl group, $A^{AH}$ represents the AHA residue, and $G^{HP}$ represents the HPG residue.

Alternatively, the present center core is linked with a coupling arm, which has a functional group (e.g., an azide group, an alkyne group, a tetrazine group, or a strained alkyne group) at the free-terminus thereof (that is, the terminus that is not linked to the center core). In these cases, the present center core comprises a cysteine residue at its N- or C-terminus. To prepare a linker unit linked with a coupling arm, a PEG chain having a maleimide group at one terminus and a functional group at the other terminus is linked to the cysteine residue of the center core via thiol-maleimide reaction occurred between the maleimide group of the PEG chain and the thiol group of the cysteine residue. In the present disclosure, the PEG chain linked to the cysteine residue of the center core is referred to as the coupling arm, which has a functional group at the free-terminus thereof.

Preferably, the coupling arm has a tetrazine group or a strained alkyne group at the free-terminus thereof. These coupling arms have 2-12 EG units. According to the embodiments of the present disclosure, the tetrazine group is 1,2,3,4-tetrazine, 1,2,3,5-tetrazine, 1,2,4,5-tetrazine, or derivatives thereof. Example of strained alkyne group includes, but is not limited to, trans-cyclooctene (TCO), dibenzocyclooctyne (DBCO), difluorinated cyclooctyne (DIFO), bicyclononyne (BCN), and dibenzocyclooctyne (DICO). According to some embodiments of the present disclosure, the tetrazine group is 6-methyl-tetrazine.

Example of the present center core linked with the coupling arm includes, but is not limited to, Ac-$(GSK)_{2-7}$-$(G_{2-4}S)_{1-8}$-C-$Xaa_{2-12}$-tetrazine,
Ac-$(GSK)_{2-7}$-$(G_{2-4}S)_{1-8}$-C-$Xaa_{2-12}$-strained alkyne,
Ac-K-$(Xaa_{2-12}$-$K)_{2-4}$-$Xaa_{2-12}$-C-$Xaa_{2-12}$-tetrazine,
Ac-K-$(Xaa_{2-12}$-$K)_{2-4}$-$Xaa_{2-12}$-C-$Xaa_{2-12}$-strained alkyne,
Tetrazine-$Xaa_{2-12}$-C(Ac)-$(SG_{2-4})_{1-8}$-$(GSK)_{2-7}$,
Strained alkyne-$Xaa_{2-12}$-C(Ac)-$(SG_{2-4})_{1-8}$-$(GSK)_{2-7}$,
Tetrazine-$Xaa_{2-12}$-C(Ac)-$Xaa_{2-12}$-K-$(Xaa_{2-12}$-$K)_{2-4}$, and
Strained alkyne-$Xaa_{2-12}$-C(Ac)-$Xaa_{2-12}$-K-$(Xaa_{2-12}$-$K)_{2-4}$.

Alternatively, the center core has an azide or alkyne group at one terminus and a coupling arm with tetrazine or strained alkyne group at the other terminus. Examples are the following:

Ac-$A^{AH}$-$(SG_{2-4})_{0-7}$-$(GSK)_{2-6}$-$(G_{2-4}S)_{1-8}$-C-$Xaa_{2-12}$-tetrazine,
Ac-$A^{AH}$-$(SG_{2-4})_{0-7}$-$(GSK)_{2-6}$-$(G_{2-4}S)_{1-8}$-C-$Xaa_{2-12}$-strained alkyne,
Tetrazine-$Xaa_{2-12}$-C(Ac)-$(SG_{2-4})_{0-7}$-$(GSK)_{2-6}$-$(G_{2-4}S)_{1-8}$-$A^{AH}$,
Strained alkyne-$Xaa_{2-12}$-C(Ac)-$(SG_{2-4})_{0-7}$-$(GSK)_{2-6}$-$(G_{2-4}S)_{1-8}$-$A^{AH}$,
Ac-$A^{AH}$-$Xaa_{2-12}$-K-$(Xaa_{2-12}$-$K)_{1-3}$-$Xaa_{2-12}$-C-$Xaa_{2-12}$-tetrazine,
Ac-$A^{AH}$-$Xaa_{2-12}$-K-$(Xaa_{2-12}$-$K)_{1-3}$-$Xaa_{2-12}$-C-$Xaa_{2-12}$-strained alkyne,
Tetrazine-$Xaa_{2-12}$-C(Ac)-$Xaa_{2-12}$-K-$(Xaa_{2-12}$-$K)_{1-3}$-$Xaa_{2-12}$-$A^{AH}$, Strained alkyne-Xaa$_{2-12}$-C(Ac)-Xaa$_{2-12}$-K-(Xaa$_{2-12}$-K)$_{1-3}$-Xaa$_{2-12}$-A$^{AH}$,
Ac-G$^{HP}$-(SG$_{2-4}$)$_{0-7}$-(GSK)$_{2-6}$-(G$_{2-4}$S)$_{1-8}$-C-Xaa$_{2-12}$-tetrazine,
Ac-G$^{HP}$-(SG$_{2-4}$)$_{0-7}$-(GSK)$_{2-6}$-(G$_{2-4}$S)$_{1-8}$-C-Xaa$_{2-12}$-strained alkyne,
Tetrazine-Xaa$_{2-12}$-C(Ac)-(SG$_{2-4}$)$_{0-7}$-(GSK)$_{2-6}$-(G$_{2-4}$S)$_{1-8}$-G$^{HP}$,
Strained alkyne-Xaa$_{2-12}$-C(AC)-(SG$_{2-4}$)$_{0-7}$-(GSK)$_{2-6}$-(G$_{2-4}$S)$_{1-8}$-G$^{HP}$,
Ac-G$^{HP}$-Xaa$_{2-12}$-K-(Xaa$_{2-12}$-K)$_{1-3}$-Xaa$_{2-12}$-C-Xaa$_{2-12}$-tetrazine,
Ac-G$^{HP}$-Xaa$_{2-12}$-K-(Xaa$_{2-12}$-K)$_{1-3}$-Xaa$_{2-12}$-C-Xaa$_{2-12}$-strained alkyne,
Tetrazine-Xaa$_{2-12}$-C(Ac)-Xaa$_{2-12}$-K-(Xaa$_{2-12}$-K)$_{1-3}$-Xaa$_{2-12}$-G$^{HP}$, and
Strained alkyne-Xaa$_{2-12}$-C(Ac)-Xaa$_{2-12}$-K-(Xaa$_{2-12}$-K)$_{1-3}$-Xaa$_{2-12}$-G$^{HP}$.

The polypeptide may also be synthesized using recombinant technology by expressing designed gene segments in bacterial or mammalian host cells. It is preferable to prepare the polypeptide as recombinant proteins if the core has high numbers of lysine residues with considerable lengths. As the length of a polypeptide increases, the number of errors increases, while the purity and/or the yield of the product decrease, if solid-phase synthesis was adopted. To produce a polypeptide in bacterial or mammalian host cells, a filler sequence ranges from a few amino acid residues to 10-20 residues may be placed between two K residues. Further, since AHA and HPG are not natural amino acids encoded by the genetic codes, the N-terminal or C-terminal residue for those recombinant polypeptides is cysteine. After the recombinant proteins are expressed and purified, the terminal cysteine residue is then reacted with short bifunctional cross-linkers, which have maleimide group at one end, which reacts with SH group of cysteine residue, and alkyne, azide, tetrazine, or strained alkyne at the other end.

The synthesis of a polypeptide using PEGylated amino acids involves fewer steps than that with regular amino acids such as glycine and serine resides. In addition, PEGylated amino acids with varying lengths (i.e., numbers of repeated ethylene glycol units) may be employed, offering flexibility for solubility and spacing between adjacent amino groups of lysine residues. Other than PEGylated amino acids, the center cores may also be constructed to comprise artificial amino acids, such as D-form amino acids, homo-amino acids, N-methyl amino acids, etc. Preferably, the PEGylated amino acids with varying lengths of polyethylene glycol (PEG) are used to construct the center core, because the PEG moieties contained in the amino acid molecules provide conformational flexibility and adequate spacing between conjugating groups, enhance aqueous solubility, and are generally weakly immunogenic. The synthesis of PEGylated amino acid-containing center core is similar to the procedures for the synthesis of regular polypeptides.

Optionally, for stability purpose, the present center core has an acetyl group to block the amino group at its N-terminus.

As could be appreciated, the number of the linking arms linked to the center core is mainly determined by the number of lysine resides comprised in the center core. Since there are at least two lysine residues comprised in the present center core, the present linker unit may comprise a plurality of linking arms.

Reference is now made to FIG. 1A. As illustrated, the linker unit 10A comprises a center core 11*a* comprising one HPG ($G^{HP}$) residue and four lysine (K) residues respectively separated by filler sequences (denoted by the dots throughout the drawings). The filler sequences between the HPG residue and K residue or between any two K residues may comprise the same or different amino acid sequences. In this example, four linking arms 20*a*-20*d* are linked to the lysine residues by forming an amide linkage between the NHS group and the amine group of the lysine residue, respectively. As could be appreciated, certain features discussed above regarding the linker unit 10A or any other following linker units are common to other linker units disclosed herein, and hence some or all of these features are also applicable in the following examples, unless it is contradictory to the context of a specific embodiment. However, for the sake of brevity, these common features may not be explicitly repeated below.

FIG. 1B provides a linker unit 10B according to another embodiment of the present disclosure. The center core 11*b* comprises one cysteine (C) residue and six lysine (K) residues respectively separated by the filler sequences. In this example, the linker unit 10B comprises six linking arms 20*a*-20*f* that are respectively linked to the lysine residues. According to the embodiments of the present disclosure, the linking arm is a PEG chain having 2-20 repeats of EG units.

Unlike the linker unit 10A of FIG. 1A, the linker unit 10B further comprises a coupling arm 60. As discussed above, a PEG chain having a maleimide group at one end and a functional group at the other end is used to form the coupling arm 60. In this way, the coupling arm 60 is linked to the cysteine residue of the center core 11*b* via thiol-maleimide reaction. In this example, the functional group at the free terminus of the coupling arm 60 is a tetrazine group 72. According to the embodiments of the present disclosure, the coupling arm is a PEG chain having 2-12 repeats of EG units.

When the release of effector elements at the targeted site is required, a cleavable bond can be installed in the linking arm. Such a bond is cleaved by acid/alkaline hydrolysis, reduction/oxidation, or enzymes. One embodiment of a class of cleavable PEG chains that can be used to form the coupling arm is NHS-$PEG_{2-20}$-S—S-maleimide, where S—S is a disulfide bond that can be slowly reduced, while the NHS group is used for conjugating with the amine group of the center core, thereby linking the PEG chain onto the center core. The maleimide group at the free terminus of the linking arm may be substituted by an azide, alkyne, tetrazine, or strained alkyne group.

According to certain embodiments of the present disclosure, the linking arm that is linked to the K residue of the center core has a maleimide group at its free terminus. In this way, a functional element (such as, a targeting element or an effector element) having a thiol group may react with the maleimide group of the linking arm via the thiol-maleimide reaction so that the functional element is linked to the linking arm. For the sake of illustration, the functional elements linked to the linking arms are referred to as the first elements. As could be appreciated, the number of the first elements carried by the present linker unit depends on the number of K residues of the center core (and thus, the number of the linking arms). Accordingly, one of ordinary skill in the art may adjust the number of the first elements of the linker unit as necessary, for example, to achieve the desired targeting or therapeutic effect.

An example of a linker unit 10C having the first elements is illustrated FIG. 1C. Other than the features disused hereafter, FIG. 1C is quite similar to FIG. 1B. First, there are five K residues in the center core 11*d*, and accordingly, five linking arms 20*a*-20*e* are linked thereto, respectively. Second, the linker unit 10C has five first elements 30a-30e linked to each of the linking arms 20a-20e. As disused below, the optional tetrazine group 72 allows for the conjugation with an additional functional element, another molecular construct (see, Part III below).

In order to increase the intended or desired effect (e.g., the therapeutic effect), the present linker unit may further comprise a second element in addition to the first element. For example, the second element can be either a targeting element or an effector element. In optional embodiments of the present disclosure, the first element is an effector element, while the second element may be another effector element, which works additively or synergistically with or independently of the first element. Still optionally, the first and second elements exhibit different properties; for example, the first element is a targeting element, and the second element is an effector element, and vice versa. Alternatively, the first element is an effector element, and the second element is an element capable of improving the pharmacokinetic property of the linker unit, such as solubility, clearance, half-life, and bioavailability.

According to one embodiment of the present disclosure, the first element is the targeting element that renders the present linker unit specifically target to a lesion site, the second element is the effector element that elicits a therapeutic effect once the present linker unit is delivered to the lesion site. For example, in the treatment of diffused tumor, the present linker unit may comprise a plurality of targeting elements as the first elements and one effector element as the second element. In this case, the targeting element specifically targets the cell surface antigen expressed on the diffused tumor (e.g., CD5, CD19, CD20, CD22, CD23, CD30, CD37, CD79a, or CD79b); while the effector element (e.g., the antibody fragment specific for CD3 or CD16a) recruits T cells or NK cells to kill the tumor cells.

According to an alternative embodiment of the present disclosure, the first element is the effector element and the second element is the targeting element. For example, in the treatment of autoimmune disease, the present linker unit may comprise one targeting element that specifically targets the tissue-associated extracellular matrix protein (e.g., α-aggrecan, collagen I, collagen II, collagen III, collagen V, collagen VII, collagen IX, and collagen XI) and a plurality of effector elements that produce an therapeutic effect on the lesion site.

Structurally, the second element is linked to the azide, alkyne, tetrazine, or strained alkyne group at the N- or C-terminus of the center core. Specifically, the second element may be optionally conjugated with a short PEG chain (preferably having 2-12 repeats of EG units) and then linked to the N- or C-terminal amino acid residue having an azide group or an alkyne group (e.g., AHA residue or HPG residue). Alternatively, the second element may be optionally conjugated with the short PEG chain and then linked to the coupling arm of the center core.

According to some embodiments of the present disclosure, the center core comprises an amino acid having an azide group (e.g., the AHA residue) at its N- or C-terminus; and accordingly, a second element having an alkyne group is linked to the N- or C-terminus of the center core via the CuAAC reaction. According to other embodiments of the present disclosure, the center core comprises an amino acid having an alkyne group (e.g., the HPG residue) at its N- or C-terminus; and a second element having an azide group is thus capable of being linked to the N- or C-terminus of the center core via the "Copper(I)-catalyzed alkyne-azide cycloaddition (CuAAC)" reaction (or the "click" reaction for short) as exemplified in Scheme 1.

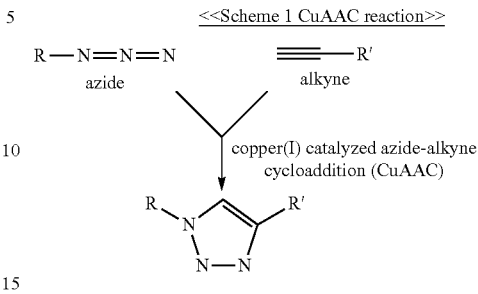

The CuAAC reaction yields 1,5-disubstituted 1,2,3-triazole. The reaction between alkyne and azide is very selective and there are no alkyne and azide groups in natural biomolecules. Furthermore, the reaction is quick and pH-insensitive. It has been suggested that instead of using copper (I), such as cuprous bromide or cuprous iodide, for catalyzing the click reaction, it is better to use a mixture of copper (II) and a reducing agent, such as sodium ascorbate to produce copper (I) in situ in the reaction mixture. Alternatively, the second element can be linked to the N- or C-terminus of the present center core via a copper-free reaction, in which pentamethylcyclopentadienyl ruthenium chloride complex is used as the catalyst to catalyze the azide-alkyne cycloaddition.

Figure 1D:
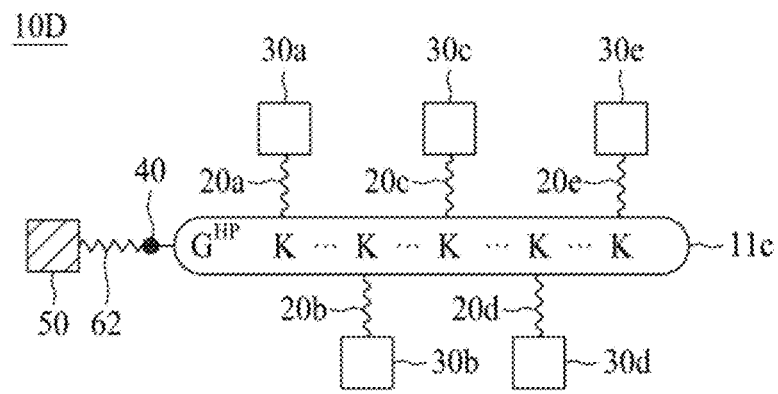

FIG. 1D provides an example of the present linker unit 10D carrying a plurality of first elements and one second element. In this example, the center core 11c comprises one HPG ($G^{HP}$) residue and five lysine (K) residues. Five linking arms 20a-20e are respectively linked to the five K residues of the center core 11c; and five first elements 30a-30e are respectively linked to said five linking arms 20a-20e via the thiol-maleimide reaction. In addition to the first elements, the linker unit 10D further comprises one second element 50 that is linked to one end of a short PEG chain 62. Before being conjugated with the center core 11c, the other end of the short PEG chain 62 has an azide group. In this way, the azide group may reacted with the HPG residue that having an alkyne group via CuAAC reaction, so that the second element 50 is linked to the center core 11c. The solid dot 40 depicted in FIG. 1D represents the chemical bond resulted from the CuAAC reaction occurred between the HPG residue and the azide group.

Alternatively, the second element is linked to the center core via a coupling arm. According to certain embodiments of the present disclosure, the coupling arm has a tetrazine group, which can be efficiently linked to a second element having a TCO group via the inverse electron demand Diels-Alder (iEDDA) reaction (see, scheme 2). According to other embodiments of the present disclosure, the coupling arm has a TCO group, which is capable of being linked to a second element having a tetrazine group via the iEDDA reaction. In the iEDDA reaction, the strained cyclooctenes that possess a remarkably decreased activation energy in contrast to terminal alkynes is employed, and thus eliminate the need of an exogenous catalyst.

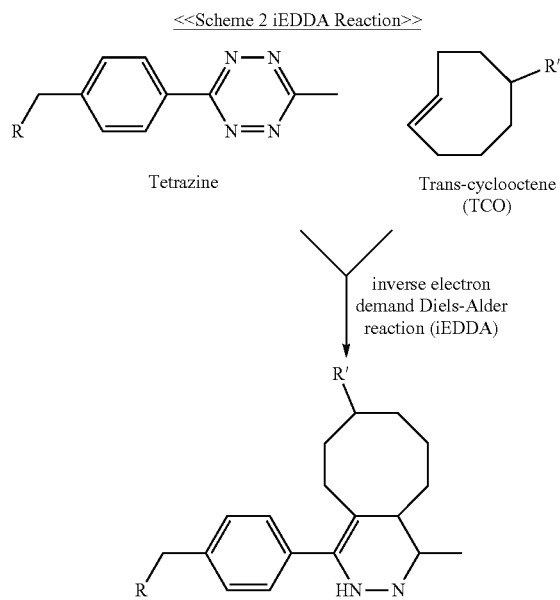

<<Scheme 2 iEDDA Reaction>>

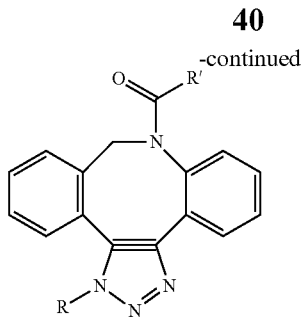

Figure 1E:
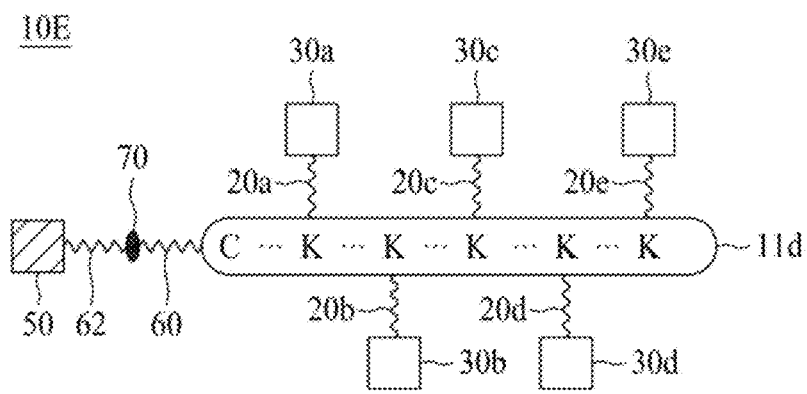

Reference is now made to FIG. 1E, in which the center core 11d of the linker unit 10E comprises a terminal cysteine (C) residue and five lysine (K) residues. As depicted in FIG. 1E, five linking arms 20a-20e are respectively linked to the five K residue of the center core 11d, and then five first elements 30a-30e are respectively linked to the five linking arms 20a-20e via thiol-maleimide reactions. The cysteine residue is linked to the coupling arm 60, which, before being conjugated with the second element, comprises a tetrazine group or a TCO group at its free-terminus. In this example, a second element 50 linked with a short PEG chain 62 having a corresponding TCO or tetrazine group can be linked to the coupling arm 60 via the iEDDA reaction. The ellipse 70 as depicted in FIG. 1E represents the chemical bond resulted from the iEDDA reaction occurred between the coupling arm 60 and the short PEG chain 62.

According to other embodiments of the present disclosure, before the conjugation with a second element, the coupling arm has an azide group. As such, the coupling arm can be linked to the second element having a strained alkyne group (e.g., the DBCO, DIFO, BCN, or DICO group) at the free-terminus of a short PEG chain via SPAAC reaction (see, scheme 3), and vice versa.

<<Scheme 3 SPAAC reaction>>

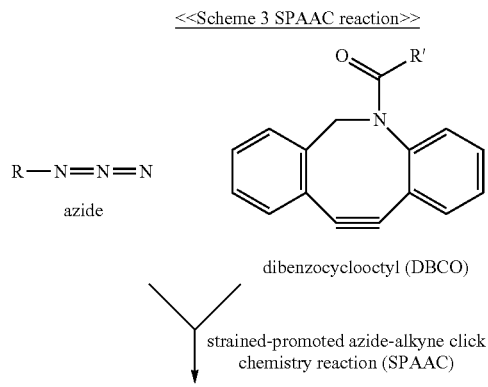

Figure 1F:
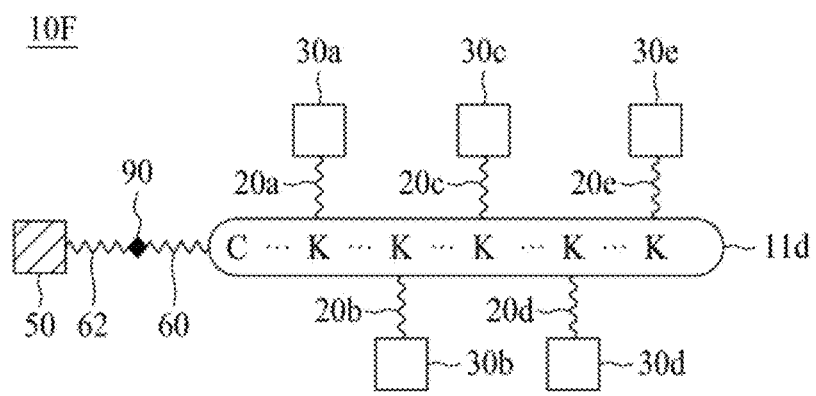

Reference is now made to FIG. 1F, in which the linker unit 10F has a structure similar to the linker unit 10E of FIG. 1E, except that the coupling arm 60 comprises an azide or a strained alkyne group (e.g., the DBCO, DIFO, BCN, or DICO group), instead of the tetrazine or TCO group. Accordingly, the second element 50 linked with a short PEG chain 62 may have a corresponding strained alkyne (e.g., DBCO, DIFO, BCN, or DICO) or azide group, so that it can be linked to the coupling arm 60 via the SPAAC reaction. The diamond 90 as depicted in FIG. 1F represents the chemical bond resulted from the SPAAC reaction occurred between the coupling arm 60 and the short PEG chain 62.

<<Scheme 4 Preparation of linker unit linked with two different scFvs via linking arm and C-terminal amino acid residue>>

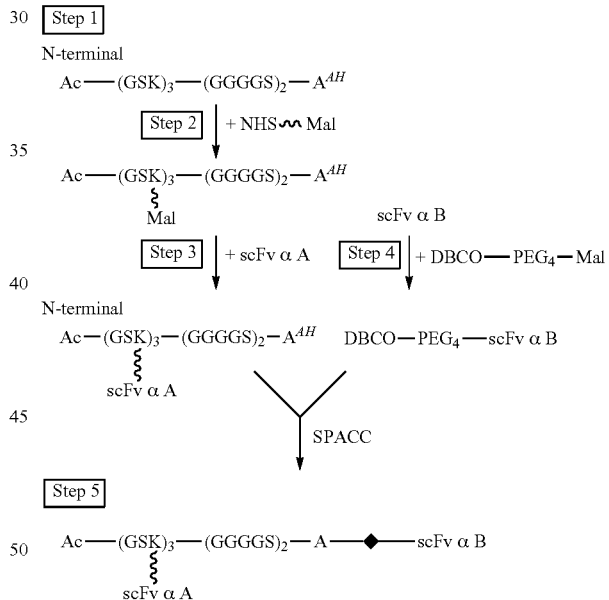

Scheme 4 is an exemplary illustration of the process of preparing the present linker unit. In step 1, the center core having the amino acid sequence of $(GSK)_3(GGGGS)_2A^{AH}$ (SEQ ID NO: 46) is prepared. In step 2, three linking arms are respectively linked to the lysine (K) residues of the center core via forming an amide bond between the NHS group and the amine group; the linking arm linked to the center core has a maleimide (Mal) group at the free-terminus thereof. In step 3, three anti-A antigen scFvs (scFv α A) as the first element are respectively linked to the linking arms via the thiol-maleimide reaction. Meanwhile, in step 4, one anti-B antigen scFv (scFv α B) as the second element is linked with a short PEG chain that has 4 repeats of EG units and a DBCO group at the free terminus. Finally, in step 5, the second element is linked to the AHA residue of the center core via the SPAAC reaction.

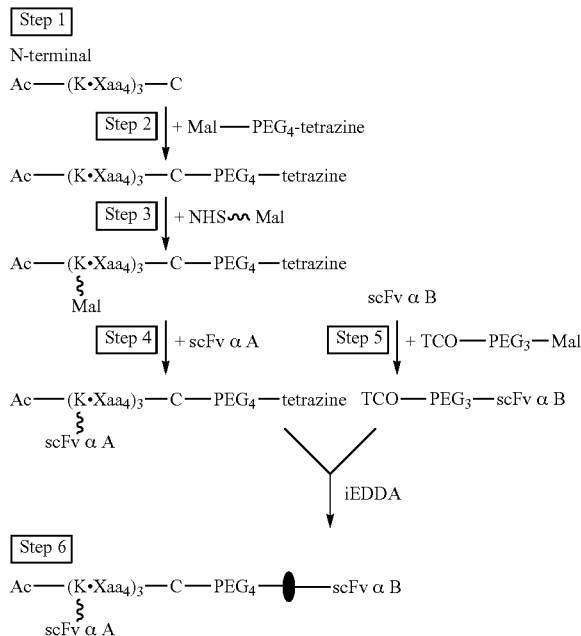

<<Scheme 5 Preparation of linker unit linked with two different scFvs via linking arm and coupling arm>>

Scheme 5 illustrates another example of the process for preparing the present linker unit. In step 1, the center core comprising the amino acid sequence of $(K\text{-}Xaa)_3$ and a cysteine residue at the C-terminus thereof is prepared. In step 2, a PEG chain (as the coupling arm) that has the maleimide (Mal) group at one terminus and a tetrazine group at the other terminus is linked to the cysteine residue via the thiol-maleimide reaction. Then, in step 3, three linking arm are respectively linked to the lysine (K) residues of the center core. Next, three anti-A antigen scFvs (scFv α A) as the first elements are respectively linked to the linking arms via the thiol-maleimide reaction as described in step 4. Meanwhile, in step 5, one anti-B antigen scFv (scFv α B) as the second element is linked with a short PEG chain that has 3 repeats of EG units and a TCO group at the free terminus. Finally, in step 6, the second element is linked to the coupling arm via the iEDDA reaction.

PEGylation is a process, in which a PEG chain is attached or linked to a molecule (e.g., a drug or a protein). It is known that PEGylation imparts several significant pharmacological advantages over the unmodified form, such as improved solubility, increased stability, extended circulating life, and decreased proteolytic degradation. According to one embodiment of the present disclosure, the second element is a PEG chain, which has a molecular weight of about 20,000 to 50,000 daltons.

Figure 1G:
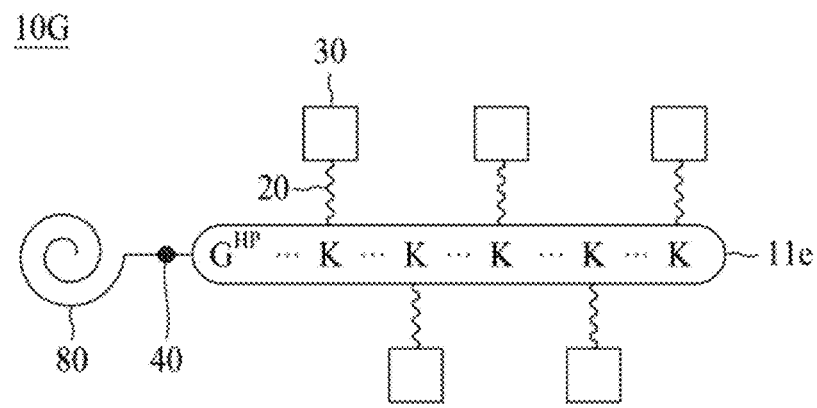

FIG. 1G provides an alternative example of the present linker unit (linker unit 10G), in which five first elements 30 are respectively linked to the lysine residues via the linking arms 20, and the HPG ($G^{HP}$) residue of the center core 11e is linked with a PEG chain 80 via the CuAAC reaction. The solid dot 40 depicted in FIG. 1G represents the chemical bond resulted from the CuAAC reaction occurred between the AHA residue and the PEG chain 80.

Figure 1H:
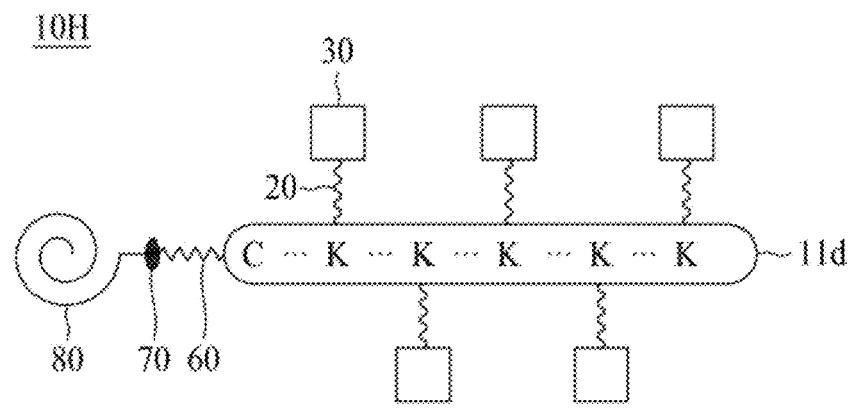

FIG. 1H provides another example of the present disclosure, in which the N-terminus of the center core 11d is a cysteine residue that is linked to a coupling arm 60. A PEG chain 80 can be efficiently linked to the coupling arm 60 via the iEDDA reaction. The ellipse 70 of the linker unit 10H represents the chemical bond resulted from the iEDDA reaction occurred between the coupling arm 60 and the PEG chain 80.

Figure 1I:
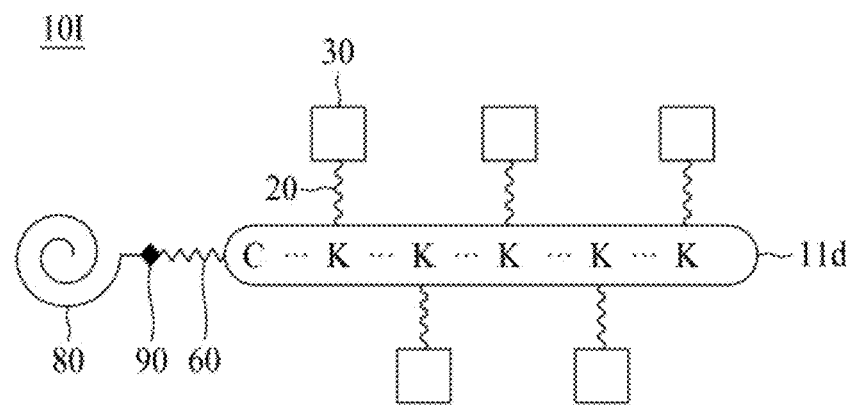

FIG. 1I provides an alternative example of the present linker unit, in which the linker unit 10I has a structure similar to the linker unit 10H of FIG. 1H, except that the PEG chain 80 is linked to the coupling arm 60 via the SPAAC reaction. The diamond 90 depicted in FIG. 1I represents the chemical bond resulted from the SPAAC reaction occurred between the coupling arm 60 and the PEG chain 80.

According to some embodiments of the present disclosure, in addition to the first and second elements, the present linker unit further comprises a third element. In this case, one of the N- and C-terminus of the center core is an amino acid having an azide group or an alkyne group, while the other of the N- and C-terminus of the center core is a cysteine residue. The lysine residues of the center core are respectively linked with the linking arms, each of which has a maleimide group at its free terminus; whereas the cysteine residue of the center core is linked with the coupling arm, which has a tetrazine group or a strained alkyne group at its free terminus. As described above, the first element is therefore linked to the linking arm via the thiol-maleimide reaction, and the second element is linked to the coupling arm via the iEDDA reaction. Further, a third element is linked to the terminal amino acid having an azide group or an alkyne group via the CuAAC reaction or SPAAC reaction.

Optionally, the first, second, and third elements are different. According to one embodiment of the present disclosure, the linker unit may have two different kinds of targeting elements and one kind of effector element, two different kinds of effector elements and one kind of targeting element, or one kind of targeting element, one kind of effector element, and one element capable of improving the pharmacokinetic property of the linker unit, such as solubility, clearance, half-life, and bioavailability.

Figure 1J:
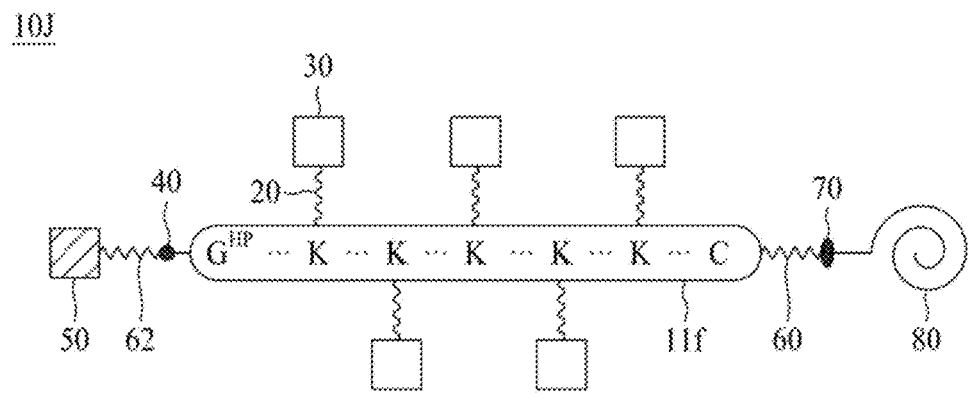

Reference is now made to the linker unit 10J of FIG. 1J, in which the center core 11f has an HPG ($G^{HP}$) residue at the N-terminus thereof and a cysteine residue at the C-terminus thereof. The linking arms 20 and the coupling arm 60 are respectively linked to the lysine (K) residues and the cysteine (C) residue of the center core 11f. Further, five first elements 30 are respectively linked to the five linking arms 20, the second element (i.e., the PEG chain) 80 is linked to the coupling arm 60, and the third element 50 is linked to the HPG residue via the short PEG chain 62. The solid dot 40 indicated the chemical bond resulted from the CuAAC reaction occurred between the HPG residue and the short PEG chain 62; while the ellipse 70 represents the chemical bond resulted from the iEDDA reaction occurred between the coupling arm 60 and the PEG chain 80.

Figure 1K:
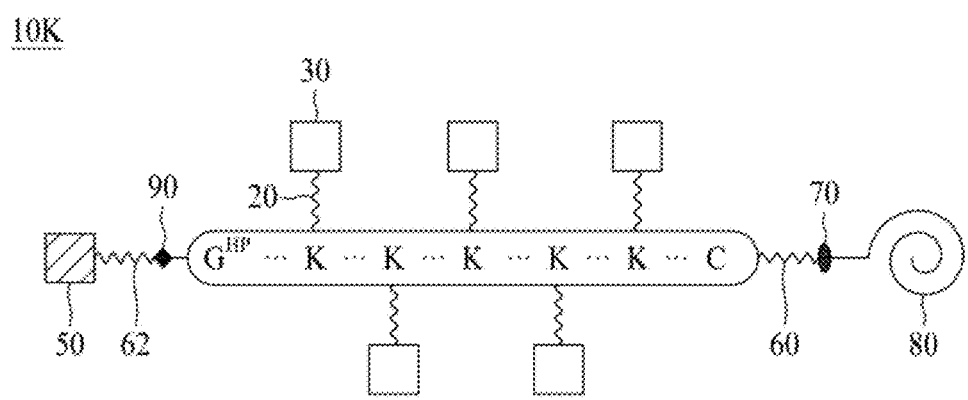

FIG. 1K provides another embodiment of the present disclosure, in which the linker unit 10K has the similar structure with the linker unit 10J of FIG. 1J, except that the short PEG chain 62 is linked with the HPG residue via the SPAAC reaction, instead of the iEDDA reaction. The diamond 90 in FIG. 1K represents the chemical bond resulted from the SPAAC reaction occurred between the short PEG chain 62 and the HPG residue.

In the preferred embodiments of this disclosure, the linking arms have a maleimide group in the free terminus for conjugating with first elements having the sulfhydryl group via the thiol-maleimide reaction. Also, there is one cysteine residue or an amino acid residue with an azide or alkyne group at a terminus of the peptide core for attaching a coupling arm for linking a second element.

It is conceivable for those skilled in the arts that variations may be made. A conjugating group, other than maleimide, such as azide, alkyne, tetrazine, or strained alkyne may be used for the free terminus of the linking arms, for linking with first elements with a CuAAC, iEDDA, or SPAAC reaction. Also the cysteine residue (or an amino acid residue with an azide or alkyne group) of the peptide core needs not to be at the N- or C-terminus. Furthermore, two or more of such residues may be incorporated in the peptide core to attach multiple coupling arms for linking a plurality of second elements.

Part II Uses of Peptide Core-Based Multi-Arm Linkers

Compared with previously known therapeutic constructs, the present linker unit discussed in Part I is advantageous in two points:

(1) The number of the functional elements may be adjusted in accordance with the needs and/or applications. The present linker unit may comprise two elements (i.e., the first and second elements) or three elements (i.e., the first, second, and third elements) in accordance with the requirements of the application (e.g., the disease being treated, the route of administration of the present linker unit, and the binding avidity and/or affinity of the antibody carried by the present linker unit). For example, when the present linker unit is directly delivered into the tissue/organ (e.g., the treatment of eye), one element acting as the effector element may be enough, thus would eliminate the need of a second element acting as the targeting element. However, when the present linker unit is delivered peripherally (e.g., oral, enteral, nasal, topical, transmucosal, intramuscular, intravenous, or intraperitoneal injection), it may be necessary for the present linker unit to simultaneously comprise a targeting element that specifically targets the present linker unit to the lesion site; and an effector element that exhibits a therapeutic effect on the lesion site. For the purpose of increasing the targeting or treatment efficacy or increasing the stability of the present linker unit, a third element (e.g., a second targeting element, a second effector element, or a PEG chain) may be further included in the present linker unit.

(2) The first element is provided in the form of a bundle. As described in Part I of the present disclosure, the number of the first element may vary with the number of lysine residue comprised in the center core. If the number of lysine residue in the center core ranges from 2 to 15, then at least two first elements may be comprised in each linker unit. Thus, instead of providing one single molecule (e.g., cytotoxic drug and antibody) as traditional therapeutic construct or method may render, the present linker unit is capable of providing more functional elements (either as targeting elements or as effector elements) at one time, thereby greatly improves the therapeutic effect.

In certain therapeutic applications, it is desirable to have a single copy of a targeting or effector element. For example, in using an scFv for targeting an extracellular matrix protein for delivering a bundle of scFv for neutralizing a pro-inflammatory cytokine, a single copy of the scFv specific for the extracellular protein is desirable, so that unwanted effects due to overly tight binding may be avoided. In another example, in using scFv specific for CD3 or CD16a to recruit T cells or NK cells to kill targeted tumor cells bound by a bundle of scFv specific for a tumor-associated antigen on the tumor cells, a single copy of the scFv specific for CD3 or CD16a is desirable, so that unwanted effects due to cross-linking of the CD3 or CD16a may be avoided. In still another example, it is desirable to have only one copy of long-chain PEG for enhancing pharmacokinetic properties. Two or more long PEG chains may cause tangling and affect the binding properties of the targeting or effector elements.

Based on the advantages listed above, the second aspect of the present disclosure pertains to a use of the present linker unit. Specifically, the present disclosure provides a method for treating different diseases (including immune disorder, diffused tumor, solid tumor, osteoporosis disease, and age-related macular degeneration), in which the method comprising administering a subject in need thereof a therapeutically effective amount of the present linker unit.

A first set of diseases treatable by the present linker unit is the immune disorder. Illustrative linker units suitable for treating immune disorders include a first element that is an antibody fragment specific for a pro-inflammatory cytokine or a receptor of the cytokine; or a soluble receptor specific for the cytokine; and a second element that is an antibody fragment specific to the tissue specific extracellular matrix protein.

According to one embodiment, the present linker unit suitable for treating psoriasis comprises a first element of an scFv specific for TNF-α, shared protein of IL-12 and IL-23, IL-17, or the receptor of IL-17; and a second element of an scFv specific for collagen I or collagen VII.

According to another embodiment, the present linker unit suitable for treating systemic lupus erythematosus (SLE), cutaneous lupus, or Sjogren's syndrome comprises an scFv specific for BAFF as the first element; and an scFv specific for collagen I or collagen VII as the second element.

Some skin diseases, such as atopic dermatitis, pemphigus vulgaris, and several types of urticaria, which have obvious inflammatory manifestation in the skin, are not treated with antibodies targeting specific TNF-α, shared protein of IL-12 and IL-23, IL-17, or BAFF, because those antibodies are not found to be sufficiently efficacious. It is rational to expect that if those anti-inflammatory antibodies are distributed favorable to the skin, they may be able to treat those skin diseases.

According to still another embodiment, the present linker unit is used to treat rheumatoid arthritis, psoriatic arthritis, or ankylosing spondylitis. In the embodiment, the first element is an scFv specific for TNF-α, IL-1, IL-6, shared protein of IL-12 and IL-23, IL-17, IL-6R, or IL-17R; and the second element is an scFv specific for collagen II, collagen IX, collagen XI, or α-aggrecan.

According to further another embodiment, the present linker unit suitable for treating inflammatory bowel disease (e.g., Crohn's disease and ulcerative colitis) comprises an scFv specific for TNF-α as the first element; and an scFv specific for collagen III or collagen V as the second element.

In the treatment of diffused tumor (for example, acute lymphocytic leukemia (ALL), chronic lymphocytic leukemia (CLL), acute myelogenous leukemia (AML), chronic myelogenous leukemia (CML), Hodgkin lymphoma, non-Hodgkin lymphoma, and myeloma), the first element of the present linker unit is the antibody fragment specific for the cell surface antigen associated with and/or overexpressed on the diffused tumor; and the second element of the present linker unit is the antibody fragment specific for the cell surface antigen CD3 or CD16a. According to the embodiments of the present disclosure, the cell surface antigen associated with and/or overexpressed on the diffused tumor is CD5, CD19, CD20, CD22, CD23, CD27, CD30, CD33, CD34, CD37, CD38, CD43, CD72a, CD78, CD79a, CD79b, CD86, CD134, CD137, CD138, or CD319.

For treating B-lymphocyte-derived lymphoma or leukemia, the first element is an scFv specific for CD5, CD19, CD20, CD22, CD23, CD30, CD37, CD79a, or CD79b; and the second element is an scFv specific for CD3 or CD16a.

In the treatment of plasmacytoma or multiple myeloma, the first element is an scFv specific for CD38, CD78, CD138, or CD319; and the second element is an scFv specific for CD3 or CD16a.

To treat T-cell derived lymphoma or leukemia, the first element is an scFv specific for CD5, CD30, or CD43; and the second element is an scFv specific for CD3 or CD16a.

As to the treatment of myelogenous leukemia, the first element is an scFv specific for CD33 or CD34; and the second element is an scFv specific for CD3 or CD16a.

Another set of diseases treatable by the present linker unit is solid tumors, which can be melanomas, esophageal carcinomas, gastric carcinomas, brain tumor, small cell lung cancer, non-small cell lung cancer, bladder cancer, breast cancer, pancreatic cancer, colon cancer, rectal cancer, colorectal cancer, renal cancer, hepatocellular carcinoma, ovary cancer, prostate cancer, thyroid cancer, testis cancer, or head and neck squamous cell carcinoma. According to the embodiment of the present disclosure, the first element of the present linker unit is a peptide hormone, a growth factor, or an scFv specific for a tumor-associated antigen; and the second element is an scFv specific for the cell surface antigen CD3 or CD16a.

According to the embodiments of the present disclosure, the peptide hormone is secretin, cholecystokinin (CCK), somatostatin, or thyroid-stimulating hormone (TSH).

In the embodiments of the present disclosure, the growth factor is selected from the group consisting of epidermal growth factor (EGF), mutant EGF, epiregulin, heparin-binding epidermal growth factor (HB-EGF), vascular endothelial growth factor A (VEGF-A), basic fibroblast growth factor (bFGF), and hepatocyte growth factor (HGF).

According to one embodiment, the tumor-associated antigen is selected from the group consisting of human epidermal growth factor receptor (HER1), HER2, HER3, HER4, carbohydrate antigen 19-9 (CA 19-9), carbohydrate antigen 125 (CA 125), carcinoembryonic antigen (CEA), mucin 1 (MUC 1), ganglioside GD2, melanoma-associated antigen (MAGE), prostate-specific membrane antigen (PSMA), prostate stem cell antigen (PSCA), mesothelin, mucine-related Tn, Sialyl Tn, Globo H, stage-specific embryonic antigen-4 (SSEA-4), and epithelial cell adhesion molecule (EpCAM).

In some instances, some tumor-associated antigen may be shed from the solid tumor of a subject and wanders into the circulation system of the subject. In these cases, the present method for treating solid tumor comprises the step of, (a) subjecting the subject to a blood dialysis procedure using an antibody specific for one or more tumor-associated antigens to remove the tumor-associated antigens that are shed from the tumor and wanders into the circulation of the subject; and (b) administering the present linker unit for treating the solid tumor.

For the purpose of treating osteoporosis disease, the first element of the present disclosure is an scFv specific for ligand of receptor activator of nuclear factor κB (RANKL); and the second element of the present disclosure is a second scFv specific for collagen I or osteonectin.

According to the embodiments of the present disclosure, the present linker unit is useful in treating age-related macular degeneration (AMD), in which the first element of the present linker unit is an scFv specific for VEGF-A; and the second element of the present disclosure is a long PEG chain having a molecular weight of about 20,000 to 50,000 daltons.

Part III Molecular Constructs with Targeting and Effector Moieties

Another aspect of the present disclosure pertains to a molecular construct comprising at least two linker units. In addition to the peptide core-based multi-arm linker units discussed above in Part I of the present disclosure, the molecular construct may also use a linker unit with a compound core (see, below) as one or both of its linker units. According to certain embodiments of the present disclosure, at least one of the linker units of the present molecular construct comprises the polypeptide core. Preferably, at least two linker units of the present molecular construct comprise the polypeptide cores. More preferably, all the linker units of present molecular construct respectively comprise the polypeptide cores.

III-(i) Linker Units with a Compound Core

In addition to the linker unit described in part I of the present disclosure, also disclosed herein is another linker unit that employs a compound, instead of the polypeptide, as the center core. Specifically, the compound is benzene-1,3, 5-triamine, 2-(aminomethyl)-2-methylpropane-1,3-diamine, tris(2-aminoethyl)amine, benzene-1,2,4,5-tetraamine, 3,3',5, 5'-tetraamine-1,1'-biphenyl, tetrakis(2-aminoethyl)methane, tetrakis-(ethylamine)hydrazine, N,N,N',N',-tetrakis(aminoethyl)ethylenediamine, benzene-1,2,3,4,5,6-hexaamine, 1-N, 1-N,3-N,3-N,5-N,5-N-hexakis(methylamine)-benzene-1,3,5-triamine, 1-N,1-N,2-N,2-N,4-N,4-N,5-N,5-N,-octakis (methylamine)-benzene-1,2,4,5-triamine, benzene-1,2,3,4, 5,6-hexaamine, or N,N-bis[(1-amino-3,3-diaminoethyl) pentyl]-methanediamine. Each of these compounds has 3 or more amine groups in identical or symmetrical configuration. Therefore, when one of the amine groups of a compound is conjugated with a coupling arm, all of the molecules of the compound have the same configuration.

Similar to the mechanism of linkage described in Part I of the present disclosure, each compound listed above comprises a plurality of amine groups, and thus, a plurality of PEG chains having NHS groups can be linked to the compound via forming an amine linkage between the amine group and the NHS group; the thus-linked PEG chain is designated as linking arm, which has a maleimide group at the free-terminus thereof. Meanwhile, at least one of the amine groups of the compound core is linked to another PEG chain, which has an NHS group at one end, and a functional group (e.g., an azide, alkyne, tetrazine, or strained alkyne group) at the other end; the thus-linked PEG chain is designated as coupling arm, which has a functional group at the free-terminus thereof.

Accordingly, two different elements can be respectively linked to the linking arm and/or coupling arm via the thiol-maleimide reaction (the linkage between the element and the linking arm) and the CuAAC reaction, SPAAC reaction or the iEDDA reaction (the linkage between the element and the coupling arm).

According to some embodiments of the present disclosure, the linking arm is a PEG chain having 2-20 repeats of EG units; and the coupling arm is a PEG chain having 2-12 repeats of EG unit. In one embodiment, both the linking and coupling arms have 12 repeats of EG unit, in which one terminus of the coupling arm is an NHS group, and the other terminus of the coupling arm is an alkyne group.

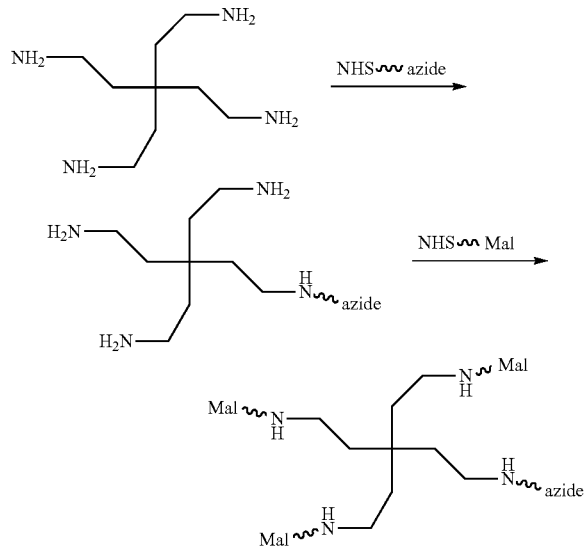

Schemes 6 and 7 respectively depict the linkages between the center core, and the linking arm and the coupling arm, in which NHS represents NHS ester, Mal represents maleimide group, azide represents azide group, and alkyne represents alkyne group.

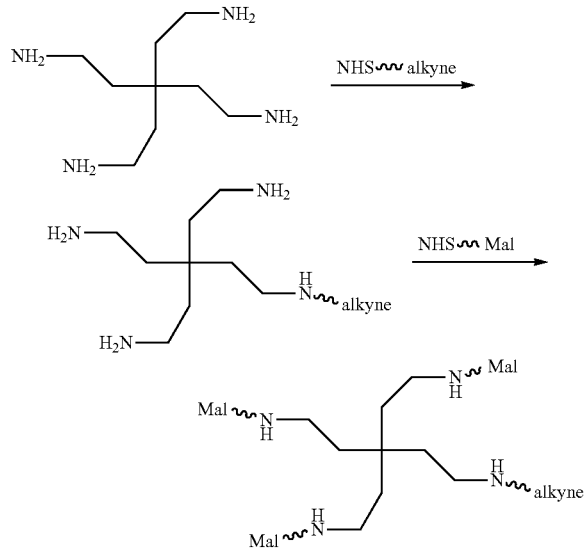

The requirement of having multiple $NH_2$ groups exist in a symmetrical and identical orientation in the compound serving as the center core is for the following reason: when one of the $NH_2$ group is used for connecting a bifunctional linker arm with N-hydroxysuccinimidyl (NHS) ester group and alkyne, azide, tetrazine, or strained alkyne group, the product, namely, a core with a coupling arm having alkyne, azide, tetrazine or strained alkyne, is homogeneous and may be purified. Such a product can then be used to produce multi-arm linker units with all other $NH_2$ groups connected to linking arms with maleimide or other coupling groups at the other ends. If a compound with multiple $NH_2$ groups in non-symmetrical orientations, the product with one bifunctional linking arm/coupling arms is not homogeneous.

Some of those symmetrical compounds can further be modified to provide center cores with more linking arms/coupling arms. For example, tetrakis(2-aminoethyl)methane, which can be synthesized from common compounds or obtained commercially, may be used as a core for constructing linker units with four linking arms/coupling arms. Tetrakis(2-aminoethyl)methane can react with bis(sulfosuccinimidyl)suberate to yield a condensed product of two tetrakis (2-aminoethyl)methane molecules, which can be used as a core for constructing linker units having six linking arms/coupling arms. The linker units, respectively having 3 linking arms/coupling arms, 4 linking arms/coupling arms and 6 linking arms/coupling arms, can fulfill most of the need for constructing targeting/effector molecules with joint-linker configuration.

As would be appreciated, the numbers of the linking arm and/or the coupling arm and the element linked thereto may vary with the number of amine groups comprised in the center core. In some preferred embodiments, the numbers of the linking arm/coupling arm and the corresponding linking element linked thereto ranges from about 1-7.

Figure 2:
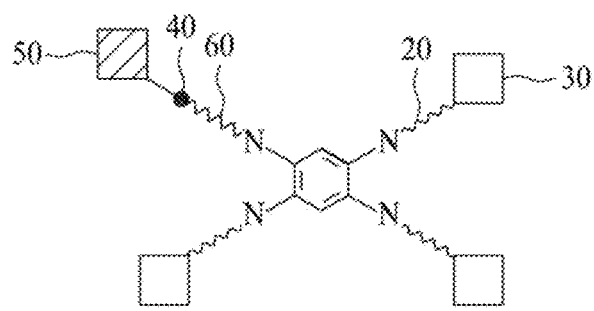
FIG. 2 is a schematic diagram illustrating a linker unit having a compound core.

Reference is now made to FIG. 2, in which benzene-1,2,4,5-tetraamine having 4 amine groups is depicted. Three of the amine groups are respectively linked to the linking arms 20, and one of the amine group is linked to the coupling arm 60, which has an azide group at its free-terminus. Three first elements 30 are then respectively linked to the three linking arms 20 via the thiol-maleimide reactions, and one second element 50 is linked to the coupling arm 60 via the CuAAC reaction. The solid dot 40 as depicted in FIG. 2 represents the chemical bond resulted from the CuAAC reaction occurred between the coupling arm 60 and the second element 50.

III-(ii) Molecular Construct with Joint-Linker Configuration

According to some embodiments of the present disclosure, the molecular construct comprises two linker units, and the linker units are coupled to each other via either the CuAAC reaction (using copper or pentamethylcyclopentadienyl ruthenium chloride complex as catalyst), the SPAAC reaction, or the iEDDA reaction. In the embodiments, one of the linker units is linked with a plurality of first elements, which act as the targeting elements, and the other of the linker units is linked with a plurality of second elements, which act as the effector elements.

According to other embodiments of the present disclosure, the molecular construct comprises three linker units, in which the first and second linker units are coupled to each other via the iEDDA reaction, and then, the third linker unit is coupled to the first or second linker unit via the CuAAC reaction. Alternatively, the first and second linker units are coupled to each other via the iEDDA reaction, and the third linker unit is coupled to the first or second linker unit via the SPAAC reaction. In the embodiments, the first, second, and third linker units respectively carry a plurality of first, second, and third elements, in which the first, second, and third elements are different. According to one embodiment, two of the three elements (i.e., the first, second, and third elements) are targeting elements, and one of the three elements is an effector element. According to another embodiment, two of the three elements are effector elements, and one of the three elements is a targeting element. According to still another embodiment, one of the three elements is a targeting element, another of the three elements is an effector element, and the other of the three elements is an element capable of improving the pharmacokinetic property of the molecular construct, such as solubility, clearance, half-life, and bioavailability.

Figure 3A:
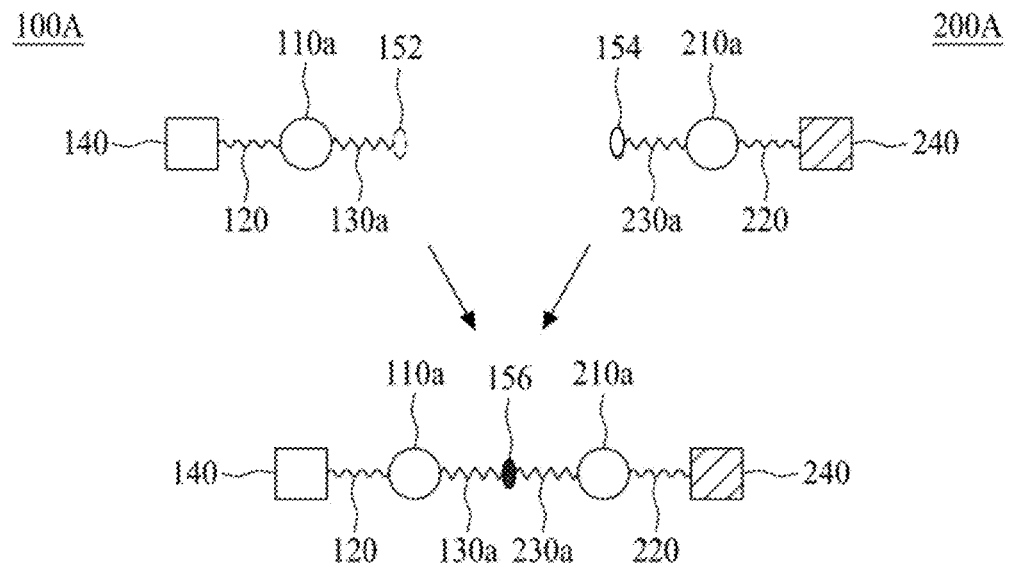
FIG. 3A to FIG. 3D are schematic diagrams illustrating T-E molecular constructs according to some embodiments of the present disclosure.

Reference is first made to FIGS. 3A-3D, which respectively depict the linkage between the two linker units. FIG. 3A depicts a molecular construct comprising two linker units (100A, 200A), which are coupled to each other via the iEDDA reaction. The first linker unit 100A comprises a first center core 110a, a linking arm 120 (as the first linking arm), and a coupling arm 130a (as the first coupling arm), in which the linking and coupling arms are respectively linked to the first center core 110a at one ends. Similarly, the second linker unit 200A comprises a second center core 210a, a linking arm 220 (as the second linking arm), and a coupling arm 230a (as the second coupling arm), in which the linking and coupling arms are respectively linked to the second center core 210a at one ends. One of the coupling arms 130a, 230a has a tetrazine group at its free terminus, while the other of the coupling arms 130a, 230a has a TCO group. Specifically, if the coupling arm 130a has a tetrazine group 152 at its free terminus (i.e., the terminus not connected to the first center core 110a), then the coupling arm 230a would have a TCO group 154 at its free terminus (i.e., the terminus not connected to the second center core 210a), and vice versa. Accordingly, the two linker units (100A, 200A) are coupled to each other via the iEDDA reaction occurred between the respective free ends of the coupling arms 130a, 230a. The ellipse 156 as depicted in FIG. 3A represents the chemical bond resulted from the iEDDA reaction occurred between the coupling arms 130a, 230a.

In the depicted embodiment, each of the linking arms 120, 220 has a maleimide group at its free terminus. Accordingly, a first targeting element 140 and a first effector element 240, each has a thiol group are respectively linked to the linking arms 120, 220 via the thiol-maleimide reaction.

According to one embodiment, both the first and second center cores 110a, 210a depicted in FIG. 3A are polypeptide cores. According to another embodiment, both the first and second center cores 110a, 210a depicted in FIG. 3A are compound cores. According to still another embodiment, one of the first and second center cores 110a, 210a depicted in FIG. 3A is a polypeptide core, while the other of the first and second center cores 110a, 210a depicted in FIG. 3A is a compound core.

Figure 3B:
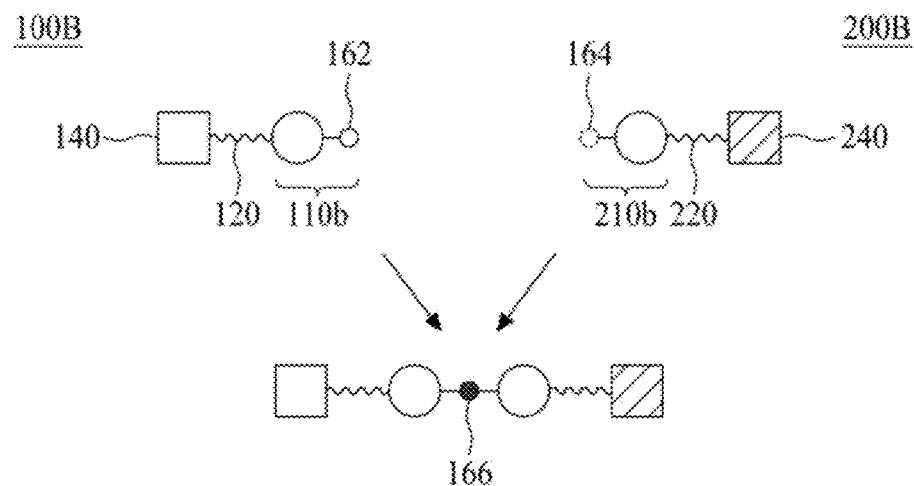

FIG. 3B provides an alternative embodiment of the present disclosure, in which both the first and second center cores 110b, 210b are polypeptide cores, and are respectively linked to a first targeting element 140 and a first effector element 240 via the linking arms 120, 220. The unique feature in this embodiment is that, one of the center cores 110b, 210b comprises an amino acid residue having an azide group (e.g., the AHA residue) at it N- or C-terminus, while the other of the center cores 110b, 210b comprises an amino acid residue having an alkyne group (e.g., the HPG residue) at it N- or C-terminus, such configuration allows the center cores 110a, 210a to be directly linked to each other, that is, without connecting through any coupling arms as that depicted in FIG. 3A. Specifically, if the center core 110b comprises the amino acid residue having the azide group 162 at its N- or C-terminus, then the center core 210b would comprises the amino acid residue having the alkyne group 164 at its N- or C-terminus, and vice versa. Accordingly, the linker units 100B, 200B can couple together directly via the CuAAC reaction occurred between the N- or C-terminal amino acid residues of the center cores 110b, 210b. The solid dot 166 as depicted in FIG. 3B represents the chemical bond formed between the N- or C-terminal amino acid residues.

Figure 3C:
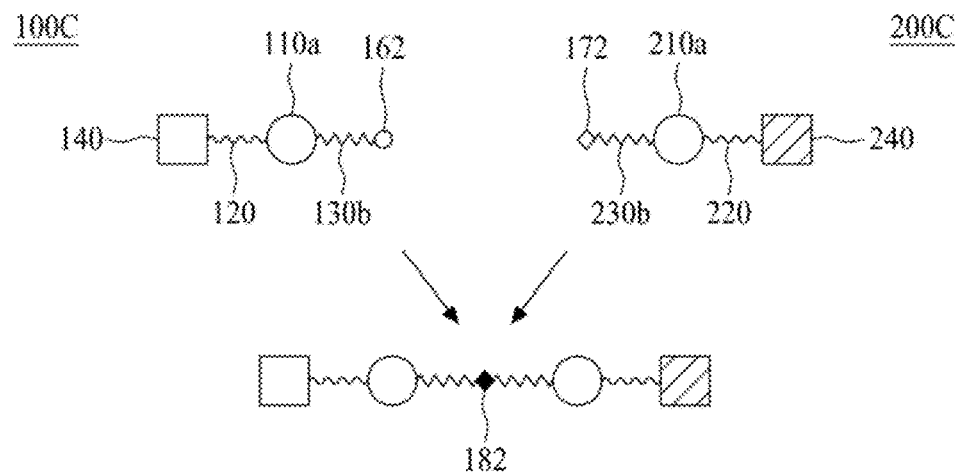

FIG. 3C is another embodiment of the present disclosure. The linker units 100C, 200C have the similar structures as the linker units 100A, 200A, except that the coupling arms 130b, 230b respectively have an azide group 162 and a DBCO group 172, instead of the azide group 152 and the alkyne group 154 as depicted in the linker units 100A, 200A of FIG. 3A. Specifically, the center core 110a is linked with a coupling arm 130b (as the first coupling arm) having an azide group 162 at its free-terminus; and the center core 210a is linked with a coupling arm 230b (as the second coupling arm) having a DBCO group 172 at its free-terminus. The linker units 100C, 200C are then coupled together via the SPAAC reaction occurred between the coupling arms 130b, 230b; and forming the chemical bond 182, depicted as a diamond.

In one embodiment, both the first and second center cores 110a, 210a depicted in FIG. 3C are polypeptide cores. In another embodiment, both the first and second center cores 110a, 210a depicted in FIG. 3C are compound cores. In still another embodiment, one of the first and second center cores 110a, 210a depicted in FIG. 3C is a polypeptide core, while the other of the first and second center cores 110a, 210a depicted in FIG. 3C is a compound core.

Figure 3D:
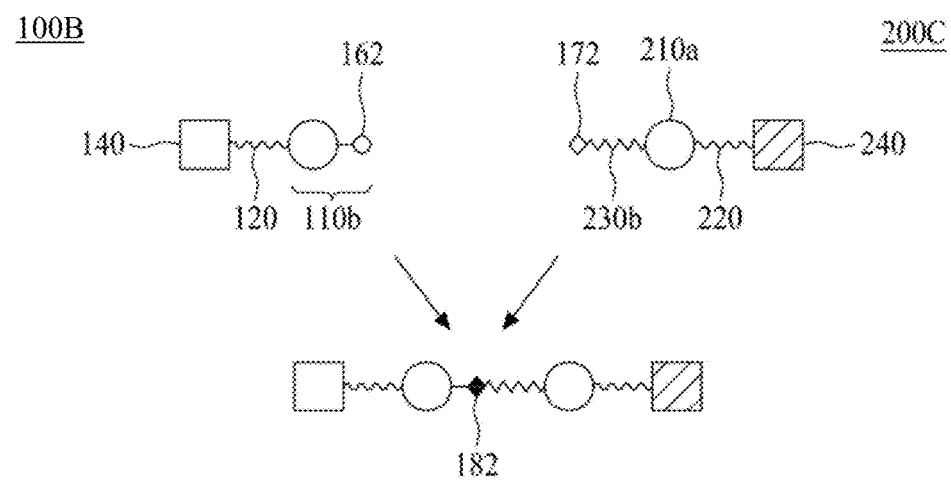

As would be appreciated, two linker units can be coupled to each other via the CuAAC reaction occurred between the center core and the coupling arm. Reference is now made to FIG. 3D, in which the center core 110b comprises a N- or C-terminal amino acid residue that has an azide group 162 (e.g., the AHA residue), and the center core 210a is linked with a coupling arm 230b having a TCO group 172 at its free-terminus. Accordingly, the linker units 100B and 200C can be coupled together via the SPAAC reaction occurred between the center core 110b and the coupling arm 230b; and forming the chemical bond 182.

According to one embodiment, the linker units 100B, 200C depicted in FIG. 3D respectively comprise polypeptide cores. According to another embodiment, the center core 100B depicted in FIG. 3D is a polypeptide core, while the center core 200C depicted in FIG. 3D is a compound core.

Alternatively, a linker unit that comprises a N- or C-terminal amino acid residue having an alkyne group (e.g., the HPG residue), and a linker unit comprising the coupling arm with an azide group at its free-terminus can be coupled together via the azide-alkyne cycloaddition occurred between the center core and the coupling arm.

Compared with other therapeutic construct, the present molecular construct is advantageous in at least the three following aspects:

(1) the linker unit comprising a specified number and/or type of targeting/effector element can be prepared independently, then proceed to be coupled together via the CuAAC reaction, the iEDDA reaction, or the SPAAC reaction;

(2) the number and kind of the targeting and/or effector elements may vary in accordance with the requirements of application (e.g., the disease being treating, and the binding avidity and/or affinity of the targeting and/or effector element). The combination of the targeting and effector elements may be adjusted according to specific needs and/or applications. Each of the present targeting and effector elements may vary with such factors like particular condition being treated, the physical condition of the patient, and/or the type of disease being treated. The clinical practitioner may combine the most suitable targeting element and the most suitable effector element so as to achieve the best therapeutic effect. According to embodiments of the present disclosure, the targeting element may be a growth factor, a peptide hormone, a cytokine, or an antibody fragment; and the effector element may be an immunomodulant, a chelator complexed with a radioactive nuclide, a cytotoxic drug, a cytokine, a soluble receptor, or an antibody fragment; and (3) compared with other coupling reactions, the CuAAC reaction, the iEDDA reaction, or the SPAAC reaction is more efficient in terms of coupling any two linker units.

Figure 4:
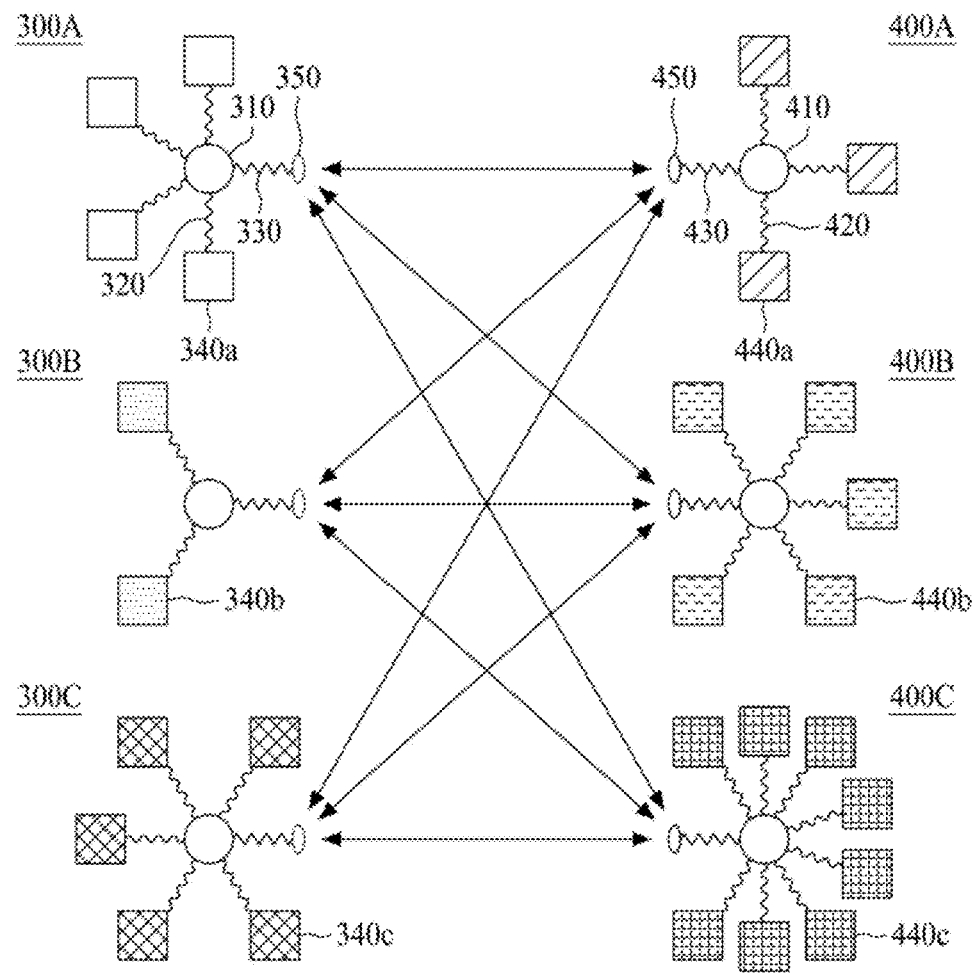
FIG. 4 is a schematic diagram that illustrates libraries for constructing molecular constructs according to some embodiments of the present disclosure.

Reference is now made to FIG. 4, in which six libraries are illustrated, and are prepared independently. In this embodiment, Libraries 1-6 respectively comprise a plurality of linker units 300A, 300B, 300C, 400A, 400B, and 400C that are linked with functional elements. Each linker units 300A, 300B, and 300C are similar in structures; in which each of the linker units 300A, 300B, and 300C comprises one center core 310, one coupling arm 330 linked thereto and has a tetrazine group 350 at its free terminus, and a specified number of the linking arm 320. For instance, Linker unit 300A comprises four linking arms 320, and accordingly, four targeting elements 340a can be respectively linked to the four linking arms 320. Similarly, two targeting elements 340b and five targeting elements 340c can be respectively linked to the linker units 300B and 300C. The targeting elements 340a, 340b, and 340c can be the same or different. As to the linker units 400A, 400B and 400C, each of these linker units comprises one center core 410, one coupling arm 430 linked thereto and has a strained alkyne group 450 at its free terminus, and a specified number of the linking arm 420. As depicted, three effector elements 440a, five effector elements 440b, and eight effector elements 440c can be respectively linked to the linker units 400A, 400B and 400C. The effector elements 440a, 440b, and 440c can be the same or different. The Libraries 1-6 may be prepared independently. One skilled artisan may select the first linker unit from Libraries 1, 2 and 3, and the second linker unit from Libraries 4, 5, and 6, then proceed to couple the first and second linker units via the iEDDA reaction occurred between the tetrazine group 350 and the strained alkyne group 450 so as to produce the molecular construct with the specified number of targeting and effector elements.

Figure 5A:
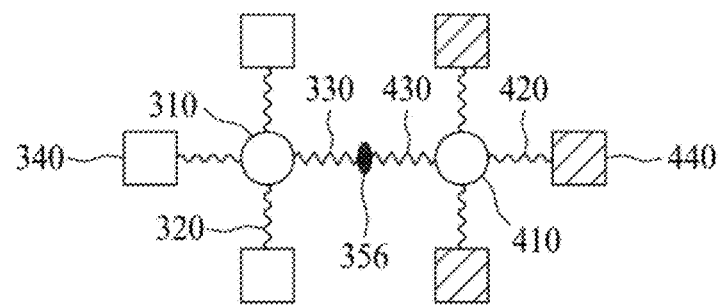
FIG. 5A and FIG. 5B are schematic diagrams that illustrate molecular constructs according to some embodiments of the present disclosure.

Based on the library concept, the present molecular construct can be produced with different configurations depending on the libraries selected. FIG. 5A provides an example of the present molecular construct, in which each of the first and second center cores (310, 410) is linked with three linking arms (320, 420) and one coupling arm (330, 430). Three first targeting elements 340 are respectively linked to the linking arms 320; and three first effector elements 440 are respectively linked to the linking arms 420. The two linker units are coupled to each other via the iEDDA reaction occurred between two coupling arms 330, 430, and forming the chemical bond 356. By this configuration, equal numbers of multiple targeting and/or effector elements may be carried in one molecular construct.

Figure 5B:
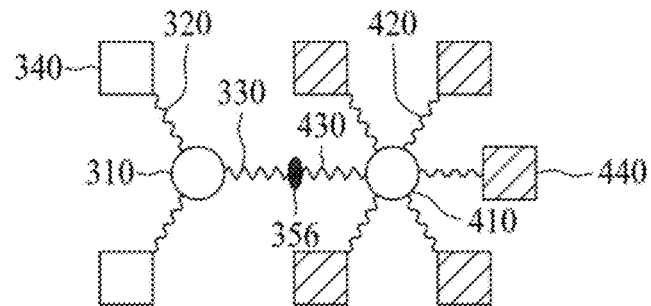

FIG. 5B provides another example of the present molecular construct, in which the first and second center cores respectively contain different numbers of amine groups (e.g., lysine residues), and accordingly, the molecular construct contains non-equal numbers of targeting and effector elements. In the depicted example, the first center core 310 is linked to one coupling arm 330, and two linking arms 320. The second center core 410 is linked to one coupling arm 430, and five linking arms 420. Accordingly, two targeting elements 340 are respectively linked to the linking arms 320; and five effector elements 440 are respectively linked to the linking arms 420. The ellipse 356 in FIG. 5B represents the linkage between two coupling arms 330, 430.

In optional embodiments, the present molecular construct may further comprise a relatively long PEG chain connected to either the first or second center core, so that the present molecular construct may be segregated further away from the reticuloendothelial system and attains a longer half-life after being administered to a subject. In the case where a protein is modified by a PEG chain so as to improve its pharmacokinetic properties and/or to decrease immunogenicity, PEG up to 20,000-50,000 daltons, is preferred. Accordingly, in one preferred embodiment of the present invention, linking arms of relatively shorter lengths are used to connect the targeting and effector elements, while a PEG chain of 20,000 to 50,000 daltons is connected to any of the linker units with the purpose of increasing in vivo half-life of the present molecular construct.

In some embodiments, multiple scFv fragments are used as the targeting and/or effector elements to construct the present molecular construct. The targeting element/effector element pharmaceuticals based on molecular constructs comprising scFv fragments should have longer in vivo half-lives than individual antibody fragments. For some clinical applications, such as using anti-TNF-α and anti-IL-12/IL-23 in the treatment of rheumatoid arthritis, anti-RANKL in the treatment of osteoporosis, and anti-VEGF-A in the treatment of the eye disease of age-related macular degeneration, much extended half-lives of the pharmaceuticals are desired, so as to eliminate the need of frequent administration of the drugs. For the molecular constructs used in those applications, PEG chains that are 20,000 to 50,000 daltons by weight, may be used as the linking arms to link the scFv fragments that serve as targeting or effector elements. PEGs of these lengths have been used to modify a large number of therapeutic proteins to increase their half-lives.

Figure 6:
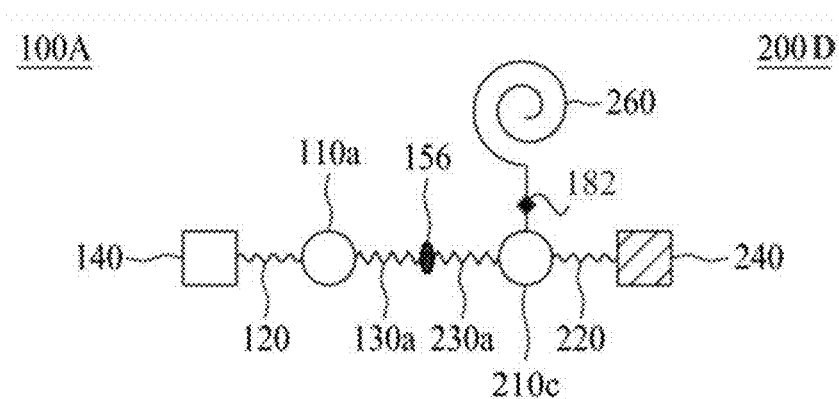
FIG. 6 is a schematic diagram that illustrates a molecular construct according to some embodiments of the present disclosure.

According to some embodiments of the present disclosure, the linker unit may comprise two linking arms respectively linked to the different functional elements. Reference is now made to FIG. 6, in which the molecular construct comprises two linker units 100A and 200D. The first and second functional elements 140, 240 (one serves as the targeting element, and the other serves as the effector element) are respectively linked to the first center core 110a and the second center core 210c via the linking arms 120, 220; and the two center cores 110a, 210c are coupled to each other via the iEDDA reaction occurred between the coupling arms 130a, 230a, in which the ellipse 156 represents the chemical bond forming therebetween. In addition to the functional element 240, the second center core 210c is further linked to a PEG chain 260. Specifically, the second center core 210c comprises an AHA residue, which can be reacted with and linked to the PEG chain 260 having a strained alkyne group via the SPAAC reaction, in which the diamond 182 represents the chemical bond forming from the SPAAC reaction. Depending on the intended and desired use, the third element can be a second targeting element, a second effector element, or an element capable of improving the pharmaceutical property of the molecular construct. According to one embodiment of the present disclosure, the PEG chain 260 has a molecular weight about 20,000 to 50,000 daltons.

Based on the concept, a linker unit may comprise a plurality of linking arms, which can be linked to a plurality of functional elements. For example, a linker unit may comprises 5-12 linking arms, which can be linked to 5-12 functional elements. This is especially useful when the functional elements are small molecules, such as cytotoxic drugs or toll-like receptor agonists. The linker unit carrying multiple molecules of a cytotoxic drug is herein referred to as a drug bundle.

Further, the polypeptide cores can be employed to prepare the molecular construct comprising three linker units. Accordingly, another aspect of the present disclosure is directed to a molecular construct comprising three linker units. Among the three linker units, two of them may be connected to each other via the iEDDA reaction, while the third linker unit is connected to any of the two linker units by the SPAAC reaction or CuAAC reaction. The rationale for constructing a multi-linker unit (e.g., three linker units) is that two different sets of targeting elements or two different sets of effector elements can be incorporated therein.

Figure 7A:
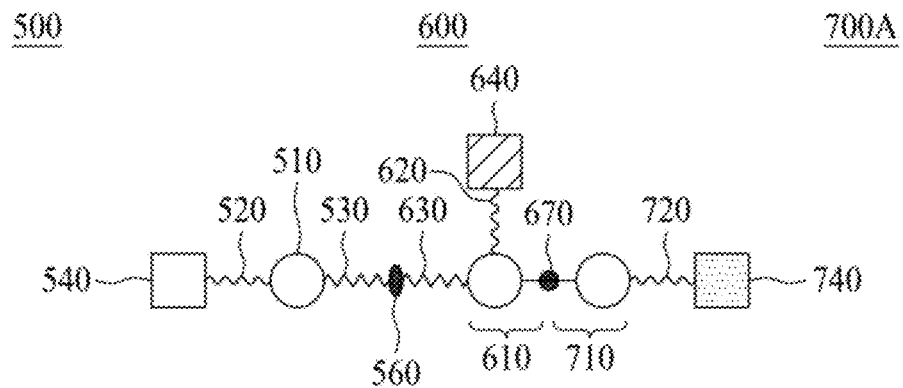
FIG. 7A and FIG. 7B are schematic diagrams illustrating molecular constructs according to various embodiments of the present disclosure.

Reference is now made to FIG. 7A, in which the molecular construct comprises three linker units (500, 600, 700A). The linker units 500, 600, 700A respectively comprise a center core (510, 610, 710), and an linking arm (520, 620, 720) with a functional element (540, 640, 740) linked thereto. The linker unit 600 is characterized in comprising a cysteine residue at one of its N- or C-terminus that is linked with a coupling arm 630; and an amino acid residue having an azide or alkyne group at the other of its N- or C-terminus. Before being conjugated, one of the coupling arms 530, 630 has a tetrazine group at its free terminus, and the other of the coupling arms 530, 630 has a strained alkyne group at its free terminus. Accordingly, the linker units 500, 600 can be coupled to each other via the iEDDA reaction occurred between the coupling arms 530, 630 as the linkage manner described in FIG. 3A. As to the linkage of the linker unit 700A, when the N- or C-terminal amino acid residue of the center core 610 has an azide group (e.g., the AHA residue), the center core 710 comprises an amino acid having an alkyne group (e.g., the HPG residue) at its N- or C-terminus; or, when the N- or C-terminal amino acid residue of the center core 610 has an alkyne group (e.g., the HPG residue), then the center core 710 comprises an amino acid having an azide group (e.g., the AHA residue) at its N- or C-terminus. Thus, as the linkage manner described in FIG. 3B, the linker units 600, 700A can be directly coupled to each other via the CuAAC reaction occurred between the N- or C-terminal amino acid residues of the center cores 610, 710 without the presence of the coupling arms. The ellipse 560 and the solid dot 670 in FIG. 7A respectively represent the chemical bonds resulted from the iEDDA reaction and the CuAAC reaction.

Figure 7B:
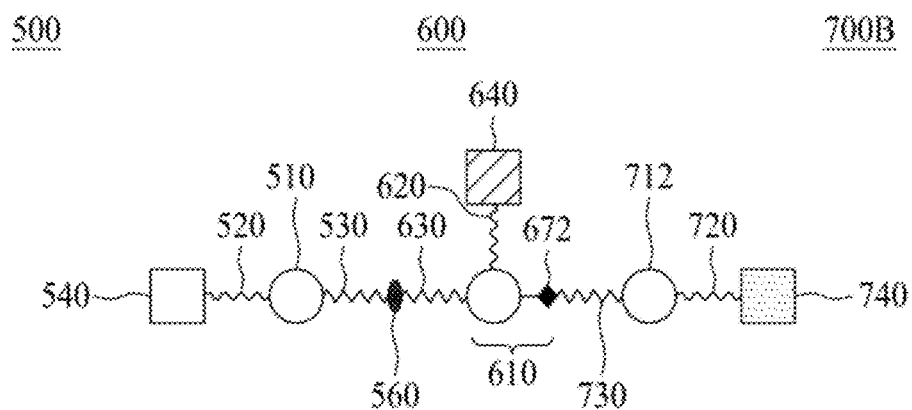

Alternatively, two of the three linker units may be connected to each other via the iEDDA reaction, while the third linker unit is connected to any of the two linker units by the SPAAC reaction. Reference is now made to FIG. 7B, in which the linker units 500, 600 are coupled together via the iEDDA reaction as described in FIG. 7A, whereas the linker unit 700B is linked to the linker unit 600 via the SPAAC reaction occurred between the center core 610 and the coupling arm 730. The diamond 672 in FIG. 7B represents the chemical bond resulted from the SPAAC reaction.

As would be appreciated, the numbers of the functional elements 540, 640, 740 respectively linked to the linker units 500, 600, and 700A or 700B may differ depending on the intended use. With the library concept depicted in FIG. 4, the linker units respectively carrying different numbers and/or types of functional elements can be prepared separately as different libraries, and one skilled artisan may select and combine the desired linker units from the libraries in accordance with the various applications.

Basically, the coupling arm of the present molecular construct described in above aspects and/or embodiments of the present disclosure that has an azide, alkyne, tetrazine, or strained alkyne group at the terminus is designed as a PEG chain having 2-12 repeats of EG units. The linking arm is designed as a PEG chain having 2-20 repeats of EG units.

Adopting a polypeptide as the center core provides versatility in the present molecular construct, in which multiple copies or types of targeting/effector elements may be present in one construct, accordingly, enhanced specificity of drug delivery and potency in the intended target sites are achieved. A large number of configurations can be adopted by employing the molecular construct comprising multiple linker units. A few examples are: a first linker unit carrying three scFvs targeting elements, and a second linker unit carrying 5 cytotoxic drugs; a first linker unit carrying three scFvs targeting elements, and a second linker unit carrying three scFvs effector elements; a first linker unit carrying two scFvs of the first set targeting elements, a second linker unit carrying two scFvs of the second set targeting elements, and a third linker unit carrying 5 cytotoxic drugs; a first linker unit carrying 2 bi-scFv targeting elements, and a second linker unit carrying two scFvs effector elements; or a first linker unit carrying three scFvs targeting elements, a second linker unit carrying two scFvs effector elements plus a linking arm attached with a long PEG of 20,000-50,000 daltons for the purpose of increasing pharmacokinetic properties.

In some embodiments of this invention, a bi-functional PEG acting as a linking arm is used to link the antigen-binding fragments of antibodies, which serve as targeting or effector elements, to the amine groups located in the polypeptide core. Each PEG may have NHS group at one end and maleimide group at the other end. The NHS group may couple with amine group in the polypeptide core, while the maleimide group may couple with sulfhydryl group of a cysteine residue of an scFv, bi-scFv, or Fab fragment of an antibody. The scFv and bi-scFv are engineered to have a polypeptide linker with terminal cysteine residue at the C-terminal. Fab may be derived from a whole IgG by pepsin cleavage, and the free sulfhydryl groups are derived from the inter-chain disulfide bond by a mild reduction reaction.

Schemes 8-12 provide several working example respectively depicting the coupling and preparation of specified linker units.

Scheme 8 is a schematic diagram depicting the preparation of the present molecular construct in accordance with one embodiment of the present disclosure, in which NHS represents NHS ester, Mal represents maleimide group, $A^{AH}$ represents L-azidohomoalanine (AHA) residue, $G^{HP}$ represents homopropargylglycine (HPG) residue, Ac represents acetyl group, and scFv represents a single-chain variable fragment. In step 1, the first center core having the amino acid sequence of $(GSK)_3(GGGGS)_2A^{AH}$ (SEQ ID NO: 46); and the second center core having the amino acid sequence of $(GSK)_5(GGGGS)_2G^{HP}$ (SEQ ID NO: 47), are respectively prepared. For the purpose of stabilizing the polypeptide, the N-terminuses of the first and second center cores are respectively modified with an acetyl group. In step 2, the linking arms are respectively linked to the lysine residues in the first and second center cores via forming an amide linkage there between; the linking arm linked to the center core has a maleimide group at the free-terminus. In step 3, the first targeting element (i.e., the antibody) having a thiol group (e.g., a cysteine residue) is linked to the linking arm linked with the first center core via the thiol-maleimide reaction; similarly, the effector element (i.e., the drug) having a thiol group is linked to the linking arm linked with the second center core via the thiol-maleimide reaction. In step 4, the two linker units are coupled via a CuAAC reaction occurred between the AHA and HPG residues.

<<Scheme 8 Coupling of linker units via C-terminal amino acid residues>>

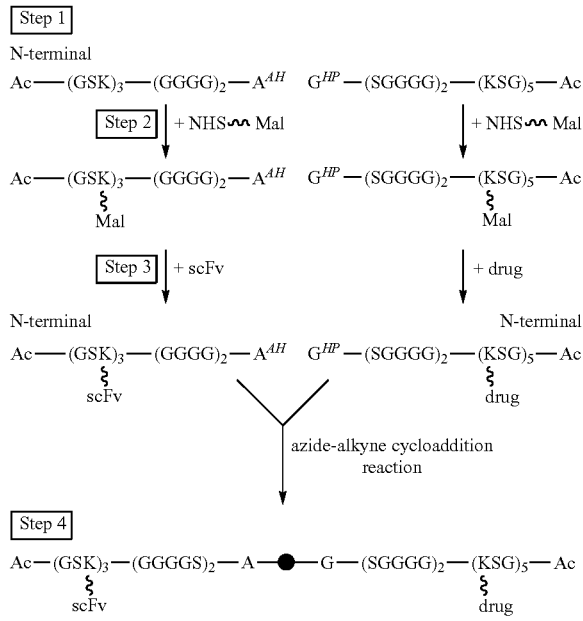

Optionally, the targeting/effector element can be linked to the center core in an alternative method. Scheme 9 is a scheme illustrating the coupling of the effector element with the polypeptide core, in which the linking arm is first linked to the center core having the amino acid sequence of $A^{AH}(SGGGG)_2(KSG)_5$ (SEQ ID NO: 48), and then the effector element (i.e., the drug) is linked to the linking arm via the thiol-maleimide reaction. In the alternative method of scheme 10, the effector element (i.e., the drug) is coupled to the linking arm so as to produce a linking arm-effector conjugate (i.e., PEG-drug); next, the linking arm-effector conjugate is linked to the center core having the amino acid sequence of $A^{AH}(SGGGG)_2(KSG)_5$ (SEQ ID NO: 48) via forming an amide linkage between the lysine residues and the NHS esters.

<<Scheme 9 Method of coupling of effector element with polypeptide core through linking to linking arms>>

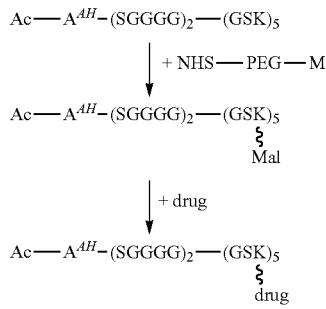

<<Scheme 10 Alternative method of coupling of effector element with polypeptide core by first conjugating with PEG chain and then linking to amino groups of lysine residues>>

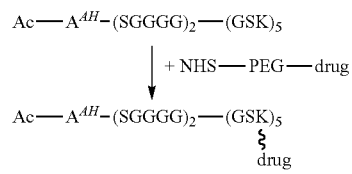

Alternatively, the linking arms for the joint-linker configuration may also be used to link bispecific scFv, which act as targeting elements or effector elements. These configurations will increase the specificity of targeting and/or the potency of the effector mechanisms.

<<Scheme 11 Preparation of molecular construct via iEDDA reaction occurred between coupling arms>>

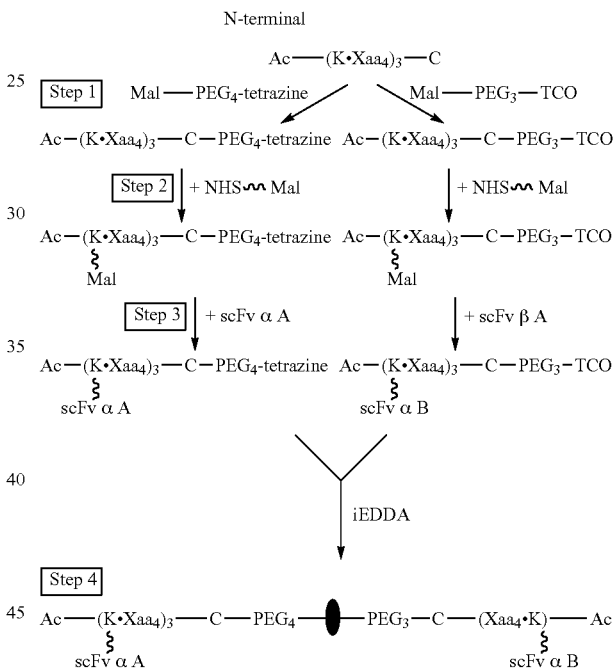

Scheme 11 provides an example of preparing the present molecular construct, which comprises two linker units; both linker units comprises the amino acid sequence of $(K-Xaa_4)_3$ and a cysteine (C) residue at the C-terminus thereof. In step 1, two coupling arms are respectively linked to the C residues of the linker units, in which one of the coupling arms has a maleimide (Mal) group at one terminus and a tetrazine group at the other terminus, while the other coupling arm has a Mal group at one terminus and a TCO group at the other terminus. In step 2, the linking arms are respectively linked to the lysine (K) residues via forming the amide bond between the linking arm and the K residue. Then, in step 3, three anti-A antigen scFvs (scFv α A) and three anti-B antigen scFvs (scFv α B) are respectively linked to the linking arms of the linker units via the thiol-maleimide reaction. Finally, in step 4, the two linker unit are coupled to each other via the iEDDA reaction occurred between the tetrazine and TCO group.

<<Scheme 12 Preparation of molecular construct having three linker units with three functional elements>>

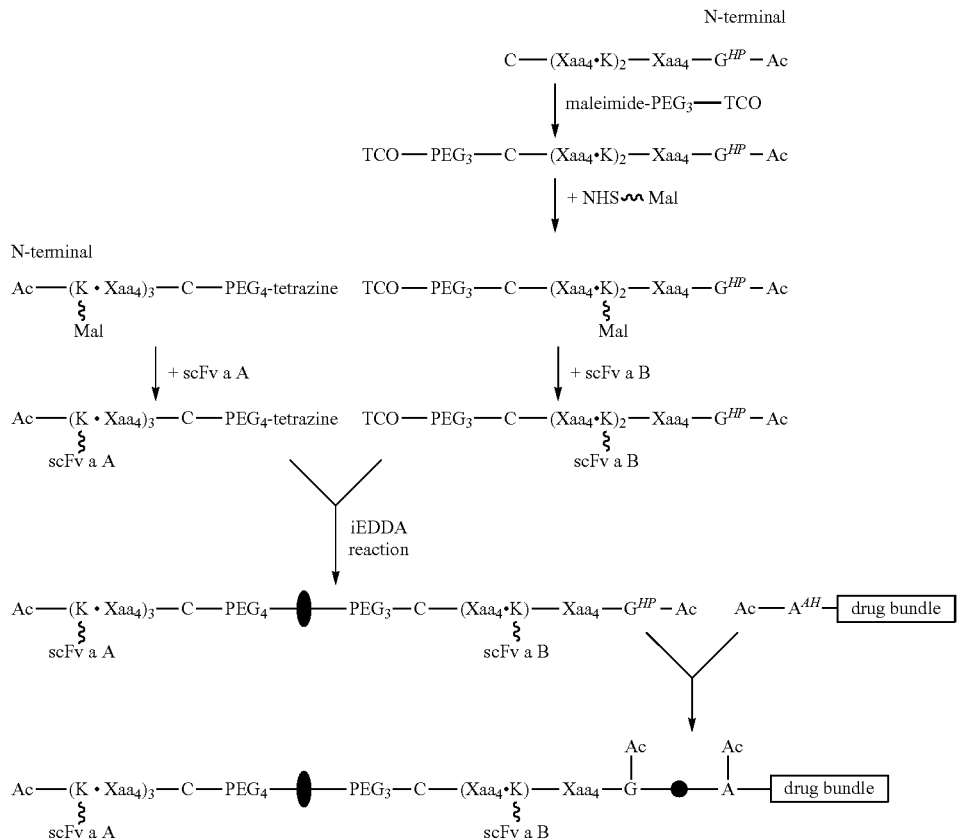

Scheme 12 provides an example of preparing a molecular construct comprising three linker units, in which two linker units respectively linked with the scFv α A and scFv α B are coupled to each other via the iEDDA reaction as described in Scheme 11 and a third linker unit couples with the second linker unit via a CuAAC reaction. In this example, the third linker unit is a drug bundle. However, this reaction scheme can be applied to a third linker unit with other elements, such as scFv. In the present example, the center linker unit (that is, the second linker unit) comprises an HPG ($G^{HP}$) residue at its N-terminus, and accordingly, a drug bundle conjugated with an AHA ($A^{AH}$) residue can be linked to the second linker unit via the CuAAC reaction occurred between the HPG and AHA residues. Alternatively, the center linker unit may comprise an AHA residue at its N or C-terminus, and can couple with a third linker unit carrying a coupling arm with a DBCO or another strained alkyne group via a SPAAC reaction. The thus-formed molecular construct in scheme 12 has three functional elements: scFv α A, scFv α B, and drug molecule. The molecular constructs with three linker units can carry three sets of scFv, of which two sets as targeting elements and one set as effector elements, or one set as targeting elements and two sets as effector elements.

When the targeting and effector elements are all scFv, and linking arms of 600 daltons (12 EG units) are used, a molecular construct with a total of six scFvs has a molecular weight of about 170,000 daltons. A molecular construct with seven scFvs has a molecular weight of about 200,000 daltons, and a molecular construct with eight scFvs has a molecular weight of about 230,000 daltons. Most of the molecular constructs of this invention have molecular weights smaller than 200,000 daltons, and a few molecular constructs have molecular weights in 200,000-250,000 daltons.

When four different sets of scFv are to be carried in one molecular construct, it is preferable to have one linker unit carrying a joined single-chain, bi-specific scFv (bi-scFv), such as scFv1-scFv2 (e.g., specific for HER2 and HER3), and the other two linker units each carrying one scFv (i.e., scFv3 and scFv4 respectively). There are two ways to construct bi-specific scFv1-scFv2. In the "tandem" configuration, $V_L1$-$V_H1$-$V_L2$-$V_H2$ or $V_H1$-$V_L1$-$V_H2$-$V_L2$ is arranged; in the "diabody" configuration, $V_L2$-$V_L1$-$V_H1$-$V_H2$ or $V_H2$-$V_H1$-$V_L1$-$V_L2$ is arranged. Proper polypeptide linkers with GGGGS (SEQ ID NO: 6) repeats or other sequences are placed between the immunoglobulin domains.

In our experience, a peptide or a PEG linker, which contain maleimide and azide groups may become polymerized upon long-term storage, due to the automatic coupling reaction between the maleimide and azide groups. Therefore, it is preferable that each linker unit is prepared freshly and independently, and processed to connecting the targeting or effector elements onto the linker units, and the coupling of the linker units through click reaction without delay. An alternative preferred embodiment is that the targeting elements and effector elements are both conjugated to linker units with alkyne groups, and the alkyne group in one of the linker units is then converted to azide with a short homo-bifunctional linker with azide at both ends. The linker units, one with alkyne and the other with azide, are then coupled via a click reaction.

The preferred linking arms for this invention are PEG. The length of the linking arms is important for several considerations. It should be long enough to allow flexibility of the linked scFv or other types of functional elements to reach targeted antigenic sites on targeted cell surface without steric constraints; yet not long enough to cause intra-molecular and inter-molecular tangling of the linking arms and their linked scFv fragments or functional elements, or to unnecessarily increase the size of the whole molecular construct for hindering tissue penetration. Linking arms that are too long may also fail to pull antigen molecules to form compacted clusters, if such clusters are required to initiate signal-transducing process for apoptosis or other cellular effects. The optimal length of linking arms for different types of combinations of targeted antigens and their binding agents may be determined by any skilled artisan in the related field without undue experimentation. In our experience with CD20 as a target antigen and anti-CD20 (rituximab) Fab in a 4-arm PEG linker, a PEG arm of about 1,000-1,200 daltons (about 25-30 ethylene glycol units) is effective in causing apoptosis. Therefore, PEG linkers of 100 to 1,000 daltons are suitable for the purpose of the present invention. A linking arm of NHS-(PEG)$_{12}$-Maleimide (approximately 500 daltons) is preferred in a number of molecular construct of this invention. A fully stretched (PEG)$_{12}$ has a length of 40-50 Å.

Applicable linking arms and coupling arms are not limited to PEG chains. Peptides comprising glycine, serine and other amino acid hydrophilic residues, and polysaccharides, and other biocompatible linear polymers, which are modified to contain NHS and maleimide groups, can be used.

For certain therapeutic applications, it is desirable that the effector elements in the molecular constructs of this disclosure be released from the linking arms, so that they can get into cells in the targeted site, including cells bound by the targeting elements or surrounding cells, to cause pharmacological effects. In those cases, a cleavable bond is engineered in the linking arm. Cleavable bonds, which are susceptible for cleavage by hydrolysis, acid exposure, reduction, and enzymes, have been developed. For example, peptide segments susceptible to matrix metalloproteinases, which are present in inflammatory tissues, have been used in constructing therapeutic constructs. One embodiment of the present invention is to use PEG linkers with S—S bond adjacent to the maleimide group (NHS-PEG$_{2-12}$-S—S-maleimide), wherein S—S is a disulfide bond, which can be slowly reduced.

According to some embodiments of the present disclosure, the targeting element described in above-mentioned embodiments is selected from the group consisting of a growth factor, a peptide hormone, a cytokine, and an antibody; and the effector element is an immunomodulant, a chelator complexed with a radioactive nuclide, a cytotoxic drug, a cytokine, a soluble receptor, or an antibody.

In the embodiments, the antibody is in the form of an antigen-binding fragment (Fab), a variable fragment (Fv), a single-chain variable fragment (scFv), a single domain antibody (sdAb), or a bi-specific single-chain variable fragment (bi-scFv). According to one embodiment, the bi-scFv is a bi-specific tandem scFv or a bi-specific diabody scFv.

In order to retain diffusing ability of the molecular constructs, a molecular size smaller than 250,000 daltons is preferred. Thus, scFv fragments are preferred for most of the embodiments. At the DNA level, genes are constructed so that the $V_L$ and $V_H$ are linked as a single polypeptide in either order ($V_L$-$V_H$ or $V_H$-$V_L$) by a peptide linker of 10-25 amino acid residues with glycine and serine being the major residues. At the C-terminal, a short stretch with glycine and serine and a terminal residue cysteine is engineered. Recombinant scFv and bi-scFv can be produced in bacteria, such as *E. coli* and *Pseudomonas putida*, in yeast, such as *Pichia pastoris*, or in mammalian cells, such as CHO and HEK293 cell lines.

The inventors' laboratory have produced a large number of IgG antibodies, Fab, scFv and various antibody fragments, Fc-based proteins, and other recombinant antibodies in HEK293 and CHO cell lines for experimentation in in vitro systems and in animal models. Our laboratory has also developed cell lines for producing antibodies for human clinical trials. The HEK293 transient expression system can be conveniently employed to produce up to 1 g of IgG or antibody fragments using a few flasks of 1-2 liters in the research laboratory. The scFv fragments to be used in the molecular constructs of this invention generally do not have a carbohydrate modification, and carbohydrate modification is not required for the binding activity of the scFv to their antigenic targets. Furthermore, only one disulfide bond and one terminal cysteine are present in the scFv fragment. Therefore, small-scale bacterial expression systems have been developed as a manufacturing alternative for producing scFv. With *E. coli*, expression systems for recovering scFv in intracellular inclusion bodies, in periplasm, and in secreted form have been employed. The scFv can be purified in most cases with an affinity column with Protein L, which interacts with $V_H$ of most κ light chain, or in other cases with ion-exchange columns.

The examples of this invention based on the joint-linker platform employ mainly scFv and Fab as the targeting and/or effector elements. However, specific binding molecules may also be screened from large libraries of binding molecules based on sdAb or other antibody fragments. Libraries of binding molecules, which are not based on immunoglobulin domains but resemble antibodies in having specific binding affinities to selected target molecules, include (1) aptamers, which are oligonucleotides or short peptides selected for binding to target molecules, (2) fynomers, which are small binding proteins derived from the human Fyn SH3 domain, (3) affimers, which are binding proteins derived from the cysteine protein inhibitor family of cystatins, and (4) DARPins (designed ankyrin repeat proteins), which are genetically engineered proteins with structures derived from the natural ankyrin proteins and consist of 3, 4, or 5 repeat motifs of these proteins. These antibody-mimetics have molecular weights of about 10K to 20K daltons.

Cytokines, growth factors, peptide hormone or their natural fragments or synthetic analogues may also be used as targeting or effector elements. Small molecule drugs, such as cytotoxic drugs (such as auristatin, maytansine, doxorubicin, calicheamicin, and camptothecin) and immunostimulatory drugs (e.g. motolimod, imiquimod, resiquimod, and gardiquimod) may also be linked as effector elements and carried to diseased target cells or tissues. CpG oligonucleotides, lipopolysaccharides derived from certain Gram-negative bacteria and glucans (such as zymosan and β-D-glucan) derived from fungi of especially *Aspergillus* and *Agaricus* species have strong immunostimulatory activities and can also be employed as effector elements. Most of those immunostimulatory substances bind to toll-like receptors on various immunocytes and hence activate the immune system.

In some embodiments of the present disclosure, at least one of the targeting element and the effector element of the present molecular construct is the antibody fragment specific for the cell surface antigen. Specifically, when the targeting element is the antibody fragment specific for the cell surface antigen, the present construct is capable of specifically targeting to the cell/tissue/organ with the cell surface antigen expressed thereon. As for the cell surface antigen-specific antibody that employed as the effector element of the present construct, it may either activate or inhibit the signaling transduction pathway via binding with the cell surface antigen, and accordingly, regulate the growth/survival/function of the cell/tissue/organ with the cell surface antigen expressed thereon. According to the embodiments, the cell surface antigen may be selected from the group consisting of, ligand of receptor activator of nuclear factor κB (RANKL), CD3, CD4, CD5, CD7, CD8, CD10, CD11c, CD13, CD14, CD15, CD16a, CD19, CD20, CD22, CD23, CD25, CD27, CD28, CD30, CD33, CD34, CD36, CD37, CD38, CD41, CD43, CD52, CD56, CD61, CD64, CD65, CD74, CD78, CD79a, CD79b, CD80, CD86, CD134, CD137, CD138, CD319, cytotoxic T-lymphocyte-associated protein 4 (CTLA-4, or CD152), programmed cell death 1 (PD-1, or CD279), and programmed cell death 1 ligand 1 (PD-L1, or CD274). According to one working example, the present molecular construct is useful in treating diffused tumors, in which the targeting element is an antibody fragment specific for CD19, CD20, CD38 or CD138; and the effector element is an antibody fragment specific for CD3 or CD16a. According to another working example, the present molecular construct is useful in treating solid tumors, in which the effector element is an antibody fragment specific for PD1. According to still another working example, the present molecular construct is useful in treating diffused tumors, in which the targeting element is an antibody fragment specific for CD79a; and the effector element is an antibody fragment specific for CD79b. According to still another working example, the present molecular construct is useful in treating diffused tumors, and the targeting element is an antibody fragment specific for CD79b; and the effector element is an antibody fragment specific for CD79a.

In some embodiments of the present disclosure, the targeting element of the present molecular construct is the antibody fragment specific for the tumor-associated antigen, which is selected from the group consisting of human epidermal growth factor receptor 1 (HER1), human epidermal growth factor receptor 2 (HER2), human epidermal growth factor receptor 3 (HER3), human epidermal growth factor receptor (HER4), carbohydrate antigen 19-9 (CA 19-9), carbohydrate antigen 125 (CA 125), mucin 1 (MUC 1), ganglioside GD2, ganglioside GD3, ganglioside GM2, fucosyl GM1, Neu5GcGM3, melanoma-associated antigen (MAGE), prostate-specific membrane antigen (PSMA), prostate stem cell antigen (PSCA), mesothelin, mucine-related Tn, Sialyl Tn, Lewis$^Y$, Sialyl Lewis$^Y$, Lewis$^A$, Lewis$^x$, heparin-binding epidermal growth factor (HB-EGF), Globo H, stage-specific embryonic antigen-4 (SSEA-4), and transferring receptor. According to one working example, the present molecular construct is useful in treating the breast tumor/cancer, in which the targeting element is an antibody fragment specific for HER1 or HER2. According to another working example, the present molecular construct is useful in treating the prostate tumor/cancer, in which the targeting element is an antibody fragment specific for PSMA.

In some embodiments of the present disclosure, the targeting element of the present molecular construct is the antibody fragment specific for the tissue specific extracellular matrix protein, which is osteonectin, α-aggrecan, collagen I, collagen II, collagen III, collagen V, collagen VII, collagen IX, or collagen XI. According to one working example, the present molecular construct is useful in treating rheumatoid arthritis, in which the targeting element is an antibody fragment specific for collagen IX. According to another working example, the present molecular construct is useful in treating psoriasis, in which the targeting element is an antibody fragment specific for collagen VII. According to still another working example, the present molecular construct is useful in treating ankylosing spondylitis, in which the targeting element is an antibody fragment specific for α-aggrecan.

In some embodiments of the present disclosure, at least one of the targeting element and the effector element of the present disclosure is the cytokine. In other embodiments of the present disclosure, at least one of the targeting element and the effector element of the present disclosure is the antibody fragment specific for the cytokine. In the embodiments, the cytokine is B cell activating factor (BAFF), interleukin-1 (IL-1), IL-2, IL-6, shared protein of IL-12 and IL-23, IL-17, interferon-α (IFN-α), IFN-β, interferon-γ (IFN-γ), tumor necrosis factor-α (TNF-α), or transforming growth factor-β (TGF-β). Specifically, when the targeting element is the cytokine (e.g., TGF-β), the present molecular construct is capable of specifically targeting to the receptor-expressing cell/tissue/organ (e.g., tumor cell with the TGF-β receptor expressed thereon). In the case of the cytokine that serves as the effector element of the present molecular construct, it may activate the cytokine-associated signaling transduction pathway via binding with the cytokine receptor, and accordingly, generate the therapeutic effect (e.g., IFN-α as the effector element that binds to IFN-α receptor and produce the pro-inflammatory or anti-tumor effect). As for the effector element being an antibody fragment specific for the cytokine, it may capture and neutralize the cytokine, and thus, inhibit the cytokine-associated signaling transduction pathway (e.g., the antibody neutralizing IL-6 and inhibit IL-6 associated inflammation). According to one working example, the present molecular construct is useful in treating autoimmune diseases, in which the effector element is an antibody fragment specific for TNF-α or IL-17. According to another working example, the present molecular construct is useful in treating solid tumors, in which the effector element is IFN-γ or IL-2. According to still another working example, the present molecular construct is useful in treating solid tumors, in which the effector element is a non-neutralizing antibody fragment specific for IFN-α or IL-2. According to further another working example, the present molecular construct is useful in treating autoimmune diseases, in which the effector element is an antibody fragment specific for BAFF.

According to some embodiments of the present disclosure, the soluble receptor is specific for TNF-α or IL-1. In the embodiments, the soluble receptor is used to capture and neutralize the cytokine without triggering the associated signaling transduction pathway.

In some embodiments of the present disclosure, the targeting element of the present molecular construct is the growth factor. In other embodiments of the present disclosure, at least one of the targeting element and the effector element of the present disclosure is the antibody fragment specific for the growth factor. In the embodiments, the growth factor is selected from the group consisting of epidermal growth factor (EGF), mutant EGF, epiregulin, heparin-binding epidermal growth factor (HB-EGF), vascular endothelial growth factor A (VEGF-A), basic fibroblast growth factor (bFGF), and hepatocyte growth factor (HGF). With similar concept as described above, when the targeting element is the growth factor (e.g., EGF), the present molecular construct is capable of specifically targeting to the receptor-expressing cell/tissue/organ (e.g., tumor cell with the EGF receptor expressed thereon). In the case of the effector element being an antibody fragment specific for the growth factor (e.g., VEGF-A), it may capture and neutralize the growth factor-associated signaling transduction pathway (e.g., VEGF-A-induced angiogenesis). According to one working example, the present molecular construct is useful in treating solid tumors, in which the effector element is an antibody fragment specific for VEGF-A.

In some embodiments of the present disclosure, the targeting element of the present molecular construct is the peptide hormone. In other embodiments of the present disclosure, at least one of the targeting element and the effector element of the present molecular construct is the antibody fragment specific for the peptide hormone. In the embodiments, the peptide hormone is selected from the group consisting of secretin, cholecystokinin (CCK), gastrin, gastrin-releasing polypeptide, glucagon-like polypeptide 1 (GLP-1), neuromedin, adrenocorticotropic hormone (ACTH), thyroid-stimulating hormone (TSH), gonadotropin-releasing hormone (GnRH), and somatostatin. According to one working example, the present molecular construct is useful in treating solid tumors, in which the targeting element is CCK or somatostatin.

In some embodiments of the present disclosure, the effector element of the present molecular construct is the antibody fragment specific for the hapten, which is selected from the group consisting of dinitrophenol (DNP), trinitrophenol (TNP), dansyl, penicillin, p-aminobenzoic acid, and a short peptide having an amino acid sequence of SEQ ID NO: 20. Specifically, when the effector element is the antibody fragment specific for the hapten, it may be used with an immunoregulatory effector that is tagged with the same hapten.

In some embodiments of the present disclosure, the effector element of the present molecular construct is the immunomodulant. According to the embodiments, the immunomodulant is a toll-like receptor agonist. In the embodiments, the toll-like receptor agonist is selected from the group consisting of lipoteichoic acid, glucan, motolimod, imiquimod, resiquimod, gardiquimod, CpG oligodeoxynucleotide (CpG DON), lipopolysaccharide (LPS), monophosphoryl lipid A, and zymosan. According to one working example, the present molecular construct is useful in treating solid tumors, in which the effector element is LPS or imiquimod.

In some embodiments of the present disclosure, the effector element of the present molecular construct is the cytotoxic drug, which is selected from the group consisting of auristatin, maytansine, doxorubicin, calicheamicin, and camptothecin.

According to some embodiments of the present disclosure, the radioactive nuclide is $^{111}$In, $^{131}$I, or $^{177}$Lu. According to other embodiments of the present disclosure, the chelator is selected from the group consisting of 1,4,7,10-tetraazacyclododecane-1,4,7,10-tetraacetic acid (DOTA), 1,4,7-triazacyclononane-1,4,7-triacetic acid (NOTA), 1,4,7-triazacyclononane-1,4-diacetic acid (NODA), and diethylenetriaminepentaacetic acid (DTPA). In one working example, the radioactive nuclide is $^{90}$Y or $^{111}$In, and the chelator is DOTA. In another working example, the radioactive nuclide is $^{111}$In, and the chelator is NOTA. In still another working example, the radioactive nuclide is $^{111}$In, and the chelator is NODA. In further another working example, the radioactive nuclide is $^{90}$Y, $^{111}$In, or $^{177}$Lu, and the chelator is DTPA.

In many molecular constructs of this invention, the preferred targeting or effector elements are Fab, Fv, single-chain Fv (scFv), single-domain antibody (sdAb), or other antigen-binding fragments of antibodies. For the scFv, a polypeptide linker with a sequence of $(GGGGS)_{2-5}$ is placed between $V_L$ and $V_H$, or between $V_H$ and $V_L$. Other sequences of flexible nature and without a rigid secondary structure, such as the linking sequences between CH1 and CH2 domains and CH2 and CH3 domains of some human immunoglobulin isotypes, may also be used. A polypeptide linker of $(GGGGS)_{1-3}$ and a terminal cysteine residue is configured at the C-terminal of the scFv or other antibody fragment, or a growth factor, hormone, or cytokine. The sulfhydryl group is for conjugating with a maleimide group at the end of the linking arms extending from a linker unit.

The antibody drug conjugate (ADC) approach, which has been pursued very actively in recent years, has an underlined rationale of bringing a payload of a cytotoxic drug to the target cells. However, in a typical ADC approach using reduced sulfhydryl groups of inter-chain disulfide bonds, in particular those in the hinge region of antibody molecules, the drug/antibody ratios (DAR) are usually variable and exhibit a distribution of 1-8 among the drug-conjugated antibody molecules. It is also known that for a typical ADC, an average DAR above 4 or 5 may cause instability and hence aggregation or precipitation problems on the antibody molecules. In a typical ADC construct, the targeting part is limited to two Fab or Fv antigen-binding fragments. In the present invention, the targeting element can accommodate growth factors, cytokines, hormones, in addition to various antibody fragments, and the effector element can accommodate a broad array of effector elements, including small molecular drugs, such as cytotoxic drugs, toll-like receptor agonists, chelators for radioactive nuclides, and proteins, such as scFv for various immune factors, cells, and/or cytokines. In the molecular construct of the present invention, the specificity of targeting is enhanced by adjusting the number of a particular targeting element and/or including two different sets of targeting elements.

The linker unit comprising cytotoxic drug payload can be prepared separately and then conjugating with different IgG antibodies for the preparation of antibody-drug conjugates. In one set of preferred embodiments, a linker unit with any of the followings: 3 or more cytotoxic drugs, 2 or more toll-like receptor agonists (e.g., LPS molecules), 2 or more chelators for radioactive nuclides (which is also referred to as bundles of cytotoxic drugs, LPS molecules, or chelators), can be conjugated to each of the two C-termini of CH3 domains of IgG molecules specific for certain target antigens. These bundles of cytotoxic drugs, LPS molecules, and chelators may be supplied to academic and industrial laboratories producing antibody drug conjugates for laboratory tests, clinical trials, or commercial distribution.

According to the embodiments of the present disclosure, there is ample flexibility in the numbers of targeting elements and effector elements that can be installed, allowing higher targeting specificity and effector activity. The linker units for a targeting element and for an effector element can be prepared separately before joining. In preparing ADCs, the bundles of cytotoxic drugs, LPS molecules, chelators for radioactive nuclides, or other small molecules can be prepared separately without exposing the antibodies to harsh chemical conditions. In using this approach, the drug to antibody ratios (DAR) can be better controlled than if the drugs are conjugated directly onto antibody molecules. The adoption of the joint-linker platform can accommodate the preparation of various targeting/effector pharmaceutical molecules. Another advantage is that IgG.Fc is not contained in the molecular constructs and can minimize potential Fc-mediated effects, such as complement-mediated activation, when such effects are not desired.

Part IV Uses of Molecular Constructs with Targeting and Effector Moieties

Many of those immunotherapeutic antibodies for treating tumors and the anti-inflammatory antibodies for treating autoimmune diseases are acting on the immune system. While the anticipated pharmacologic effect is to activate the immune system or suppress immune activities at the targeted tumor sites or diseased sites, the effect of the administered antibodies causes immunological enhancing or suppressing effects systemically, which results in a wide range of side effects. Therefore, an overriding principle of this invention is to carry the therapeutic effectors to the disease sites (e.g., a tumor, an inflammation site and the like) while minimizing an overall systemic immune-enhancing or immunosuppressing effect.

The present molecular construct, as discussed in Part III, above, possesses both the targeting and effector elements; hence, drug molecules carried by the effector element are directed to the intended target site by the targeting element. Accordingly, target treatment of any disease, condition, and/or disorder may be achieved by proper selection of the targeting and effector elements. Accordingly, another aspect of the present invention is directed to uses of the present molecular constructs (including those with the joint-linker configuration and the Fc-based ones) in the treatment of various diseases, conditions, and/or disorders. Suitable diseases, conditions and/or disorders that may be treated by the present methods include autoimmune diseases (rheumatoid arthritis, psoriasis, SLE, Sjögren's syndrome, and Crohn's disease), osteoporosis, diffusive tumors (various types of lymphomas and leukemia), solid tumors, and dry and wet age-related macular degeneration. Specifically, each of these methods comprises administering to the subject or patient a therapeutically effective amount of the molecular construct according to any of the above-mentioned aspect/embodiments.

The targeting elements involved in constructing the targeting/effector pharmaceuticals for treating the above diseases include scFv specific for (1) collagen I, collagen II, collagen III, collagen V, collagen VII, collagen IX, collagen XI, α-aggrecan, osteonectin, and some other components of extracellular matrix in joints, skin, or bone, (2) CD19, CD20, CD22, CD30, CD52, CD79a, CD79b, CD38, CD56, CD74, CD78, CD138, CD319, CD5, CD4, CD7, CD8, CD13, CD14, CD15, CD33, CD34, CD36, CD37, CD41, CD61, CD64, CD65, CD11c and other surface antigens of cells of lymphoid and myeloid lineages and of plasma cells, (3) EGFR, HER2/Neu, HER3, TN, Globo H, GD-2, CA125, CA19-9, and CEA overly expressed on solid tumors. The targeting elements may also be antibodies of hormones, growth factors, or cytokines, in which receptors of hormones, growth factors, or cytokines are expressed on tumor cells or other diseased cells. Noted that many autoimmune diseases are diseases of the connective tissues, and hence various collagen types can serve as target antigens for shuffling targeting/effector pharmaceuticals to the targeted connective tissues.

The selections of effector elements for the T-E pharmaceuticals of this invention covers a broad range of molecules, including (1) scFv specific for inflammatory cytokines (such as TNF-α, shared protein of IL-12 and IL-23, IL-17, IL-1, IL-6, BAFF), (2) scFv specific for RANKL, (3) scFv for CD3; and CD16a, expressed on T cells and NK cells, (4) scFv specific for PD-1, PD-L1, CTLA-4 and other immune checkpoints, (5) immunoenhancing cytokines (IFN-α, IFN-γ, IL-2, TNF-α), (6) cytotoxic molecules, (7) TLR agonists (LPS, motolimod, imiquimod, resiquimod, gardiquimod, CpG oligonucleotides, β-glucan, zymosan), and (9) chelating agents complexed with radioactive nuclides.

This invention rationalizes that the requirement for the strength of binding of targeting element to the targeted molecules is not uniformly same. For targeting a tumor-associated antigen on the surface of targeted tumor cells, e.g., with scFv specific for CD19, CD38, HER2/Neu, EGFR, CA125, it is generally desirable that the binding avidity of the targeting element to the targeted tumor-associated antigen is high. In such way, the specific binding to the targeted cells, in relative to other cells not expressing the antigens, will be enhanced. Furthermore, when the binding affinity and avidity is high, the targeting/effector pharmaceuticals can still bind to those target cells expressing relatively low densities of the targeted antigens. As a result, the payloads of effector elements, such as a payload of cytotoxic drugs, or immune-enhancing effector elements, have enhanced chances to exhibit their effector functions.

For shuffling anti-inflammatory agents, such as anti-TNF-α, anti-IL-17, anti-IL12/IL23, and anti-BAFF to the diseased joints, skin, or bowl, it is not necessary that the targeting element binds to the targeted antigens in the extracellular matrix in the diseased sites, e.g., scFv specific for collagen II, collagen IX, collagen VII, collagen I, or osteonectin, too tightly. It is possible that if the binding is too strong, it will elicit unwanted immune functions or affect the integrity of the extracellular matrix. It is anticipated that the abundance of the extracellular protein can sequester the therapeutic molecules with the targeting moieties; even the avidity of the targeting moieties in binding their targeted molecules is not high. An equilibrium state of the on-and-off binding of the targeting element of the T-E pharmaceutical will bring about a raised local concentration of the T-E pharmaceuticals.

This invention rationalizes that for the targeting with scFv specific for collagen II, collagen I, collagen VII, collagen IX, or osteonectin, the avidity is not too high. In preferred embodiments, if the targeting IgG antibody has an affinity constant, $Kd<1\times10^{-9}$, in binding to the target antigen, only one scFv is incorporated to the pharmaceutical, and for two scFvs to be employed in the pharmaceutical, the affinity of the targeting IgG antibody binding to the target antigen should be lower, $1\times10^{-8}>Kd>1\times10^{-9}$. To achieve increased specificity in targeting anti-TNF-α to the joints, anti-IL17 or anti-BAFF to the skin, two targeting elements each with a different binding antigen can be adopted. This will enhance the binding to the aimed target tissue over normal tissues or cells, which express one of the two target antigens.

IV-(i) Immune Disorder

The molecular constructs used for treating autoimmune diseases are designed based on the rationale that if antibodies specific for pro-inflammatory cytokines are carried to the diseased tissues affected by those pro-inflammatory cytokines, the therapeutic efficacy will be enhanced and the side effects decreased. Cytokines, unlike hormones, generally do not circulate in the blood stream and act on remote target cells. Cells of the lymph nodes emigrate via the efferent lymph vessel and enter the lymphatic circulation. The products of lymphocytes do not get out the lymph nodes moving upstream against the blood flow coming into the nodes. In fact, administered antibodies can enter lymph nodes via the blood circulation. However, most of the cytokine molecules do not get out of the lymph nodes via blood circulation. The cytokines secreted by the local lymph nodes act on cells in the microenvironment of the lymph nodes. Therefore, if antibodies targeting pro-inflammatory cytokines are channeled to some degrees to the diseased inflammatory tissues, less of the antibodies will go to the lymph nodes, and hence side effects will be decreased, and more of the antibodies will go to the diseased tissue and therapeutic efficacy can be enhanced.

Using antibody against TNF-α for example, in applying such molecular constructs or pharmaceuticals comprising the same, using the molecular construct with scFv specific for collagen II as the targeting element and scFv specific for TNF-α as the effector element, an amount of the present molecular construct carrying excess amount of effector element (i.e., scFv specific for TNF-α with an amount that exceeds the total amount of TNF-α in the blood circulation) is administered. While a small amount of the therapeutic agent is neutralized by TNF-α in the blood, the remaining amount will be favorably localized to the tissues (including joints) where collagen II is abundant. Like many cytokines (also referred as interleukins or lymphokines), TNF-α acts mainly in the microenvironment of the immune system. It has a very short half-life, about 1 hour and there is a minute amount of it in the blood circulation. The administered anti-TNF-α of this invention will not be mainly present in lymphoid system and neutralize the TNF-α in the lymphoid system. Therefore, the side effects of anti-TNF-α in causing serious infections should be decreased.

In one embodiment, the present method is useful in treating autoimmunity, in which the first targeting element is an scFv specific for α-aggrecan, collagen I, collagen II, collagen III, collagen V, collagen VII, collagen IX, or collagen XI; and the first effector element is an scFv specific for TNF-α, IL-17, IL-1, IL-6, shared protein of IL-12 and IL-23, BAFF, the receptor of IL-6 (IL-6R), or the receptor of IL-17 (IL-17R); or the soluble receptor of TNF-α or IL-1.

IV-(i)-A Psoriasis

A preferred set of the present inventions is to construct molecular constructs with scFv specific for type I collagen and type VII collagen as the targeting elements and scFv specific for TNF-α, shared protein of IL-12 and IL-23, or IL-17 as the effector elements. In one embodiment of the present disclosure, the various T-E molecules based on the "joint-linker" configuration contain scFv specific for collagen I and/or collagen VII as the targeting elements and scFv specific for IL-17 as the effector elements.

In one preferred embodiment, the present method is employed to treat psoriasis, in which the first targeting element is an scFv specific for collagen I, or collagen VII; and the first effector element is an scFv specific for TNF-α, shared protein of IL-12 and IL-23, IL-17, or IL-17R.

IV-(i)-B SLE, Cutaneous Lupus, or Sjogren's Syndrome

In the present invention, scFv of antibodies specific for BAFF or IFN-α are to be carried to the skin by targeting elements, scFv specific for collagen I and collagen VII. In one embodiment of the present disclosure, the various T-E molecules based on the "joint-linker" configuration contain scFv specific for collagen I and/or collagen VII as the targeting elements and scFv specific for BAFF as the effector elements.

In another preferred embodiment, the present method is suitable for the treatment of SLE, cutaneous lupus, or Sjogren's syndrome, in which the first targeting element is an scFv specific for collagen I or collagen VII; and the first effector element is an scFv specific for BAFF.

IV-(i)-C Rheumatoid Arthritis, Psoriatic Arthritis, or Ankylosing Spondylitis

In still another preferred embodiment, the disease treated by the present method is rheumatoid arthritis, psoriatic arthritis, or ankylosing spondylitis, in which the first targeting element is an scFv specific for collagen II, collagen IX, collagen XI, or α-aggrecan; and the first effector element is an scFv specific for TNF-α, IL-1, IL-6, shared protein of IL-12 and IL-23, IL-17, IL-6R or IL-17R.

IV-(i)-D Inflammatory Bowel Disease

It has been found that the collagen types I, III and V are abundant in the intestine and colon. It is rationalized that since collagen I is widely distributed in various tissues, it is preferable to use scFv specific for collagen III or collagen V as the targeting elements to carry scFv specific for TNF-α to the intestine and colon in patients with Crohn's disease or ulcerative colitis. In one embodiment of the present disclosure, the various T-E molecules based on the "joint-linker" configuration contain scFv specific for collagen III and/or collagen V as the targeting elements and scFv specific for TNF-α as the effector elements.

In further another preferred embodiment, the present method may be used to treat inflammatory bowel disease, in which the first targeting element is an scFv specific for collagen III or collagen V; and the first effector element is an scFv specific for TNF-α. According to the embodiment, the inflammatory bowel disease is Crohn's disease or ulcerative colitis.

IV-(ii) Tumor

The present invention rationalizes that a preferred drug targeting approach has two folds of considerations. One is to increase the avidity and specificity of the targeting agents, so that target cells expressing relatively low antigen densities are still bound by the targeting agents. Secondly, the therapeutic agents are brought to diseased tumor tissue, without requiring that the therapeutic agents be internalized into the cells that express a particular tumor-associated antigen. Examples of such therapeutic agents are scFv, which recruit T cells and NK cells for mediating cytolytic effects on the targeted cells. Another set of examples of such therapeutic agents are toll-like receptor agonists, such as LPS molecules, and scFv specific for immune checkpoints, such as scFv specific for PD-1, PD-L1, and CTLA-4, which elicit immune response in the local sites. Still another set of examples is bundles of chelating agents complexed with radioactive nuclides. With many of those therapeutic agents, cytolytic effects on the diseased cells and bystander cells can be elicited in the tissue sites regardless of the levels of tumor-associated antigen expressed by the tumor cells.

The present invention thus embodies a number of remedies to increase the relative localization of therapeutic agents in the targeted site. Such a rationalization about specific delivery of therapeutic agents to diseased sites is not limited to therapeutic agents targeting cancer but also therapeutic agents targeting tissues affected by other diseases. The target-specific delivery needs not to be absolute. In other words, it is not necessary that all administered drug molecules be delivered to the intended diseased site. As long as the delivery to the diseased target is enhanced, as compared to the same drugs without a targeting element, the therapeutic effects of the drug should be increased and the side effects decreased.

IV-(ii)-A Diffused Tumor

A preferred set of embodiments of T-E pharmaceuticals of the present invention is the employment of cytotoxic drug bundles in the joint-linker configuration. The potent cytotoxic drugs include auristatin, maytansine, doxorubicin, calicheamicin, camptothecin, and others. A preferred embodiment is that 5-10 cytotoxic molecules are carried in a linker unit. For comparison, a typical IgG antibody drug conjugates currently approved or under clinical development carry two Fab fragments for targeting and 3 or 4 molecules on the average of a cytotoxic drug for rendering lysis of the target cells. In a molecular construct of this invention, it contains 3-5 scFv specific for a target antigen as the targeting element and 5-10 cytotoxic molecules as the effector element. Both the targeting specificity and pharmacological effects can be much enhanced in comparison with the typical antibody drug conjugate approach. Furthermore, two sets of scFv for two different antigens on target cells can be employed as the targeting elements, enhancing the specificity of targeting and the uptake or internalization of the bound antibody drug conjugates by the targeted cells. In the molecular constructs of this invention, the cytotoxic molecules are conjugated through a PEG or peptide linking arms to increase solubility. The linker unit with the cytotoxic drug payload is prepared separately before the coupling with the linker unit conjugated with the targeting elements. In such an approach, the solubility of the linker unit and the entire molecular constructs should not pose a problem.

The molecular constructs described in this section bear a larger binding avidity in binding to the surface antigen of targeted cells but also a larger toxic drug payload than typical antibody drug conjugates that have been approved for clinical uses or are in clinical trials. The inclusion of bundles of cytotoxic drug payload essentially amplifies the potency of the molecular constructs and therefore can increase the specificity of the targeting therapeutic agents. It is anticipated that those therapeutic agents can be administered at a lower dose and can achieve an enhanced therapeutic efficacy and reduced toxicity in treating diffusive and solid tumors. This approach is not only suitable for different types of lymphoma and leukemia derived from B cells, T cells, and other leukocytes but also applicable for tumors that bear cell surface molecules for antibody targeting, such as tumors bearing an antigen belonging to the human epidermal growth factor receptor (EGFR) family, which are often overexpressed on many tumors.

The scFv fragments of anti-CD3 antibodies may also be conjugated to linker units as effector elements for those T-E molecules designed to target tumorous cells. The incorporation of scFv specific for CD3 helps the recruitment of T cells and the attachment of tumor target cells with cytotoxic T cells. The binding by scFv of anti-CD3 induces the activation of T cells, which results in the lysis of the contacted or bridged target cells. There are numerous examples, where the bi-specific antibodies combining anti-CD3 with antibody fragments specific for antigens, such as CD20, CD30, and EGFR, can efficiently lyse target cells expressing those antigens.

The above description has specified a number of effector mechanisms that can be employed in molecular constructs that enlist targeting functions. Those effector mechanisms include cytotoxic drug payloads and scFv specific for CD3 or CD16a. The assortment of effectors for B cell-derived tumors, T cell-derived tumors, and some other types of leukemia, some of which are in diffusive forms, is different from that for solid tumors. For example, immune-enhancing agents, such as LPS, can be incorporated as the effector element in a molecular construct for targeting solid tumors. The potent immune enhancing IgG and anti-CD28 may be applied and recruited to local tumor sites for stimulating immune activities. Those potent immune enhancers are not applicable as therapeutic effectors for treating various types of leukemia and diffusive tumors.

For achieving the effect of apoptosis, a binding agent must be able to cross-link and cluster the targeted cell surface molecule, such as B-cell receptors or CD20, effectively. We rationalize that the cross-linking of the surface molecules should achieve a "centrally-focused" cluster of cross-linked molecules, rather than a large number of small aggregates on the targeted cell surface. We further rationalize that a number of factors will affect a binding agent in achieving its apoptotic effect. The multiple valence of a binding agent can enhance the cross-linking ability. However, if the binding arms are too many, it will increase the size of the binding agent and affect its ability to penetrate into tissues. The binding agent should effectively bind to the targeted cell surface on a planar surface of a cell. Therefore, the binding arms, such as PEG-scFv, have a certain degree of flexibility and can reach to the targeted antigenic sites without steric constraints. On the other hand, if the binding arms are too long, the cross-linking and clustering effects may not be optimal, or the binding arms reach to cell surface molecules on an adjacent cell. We also rationalize that if sufficient linking arms are in a multi-arm linker unit, the Fab or scFv fragments can provide more flexibility than whole IgG or F(ab')$_2$.

The preferred embodiments in this invention have adopted the above rationales. While our invented methodologies are applicable for antibodies specific for various antigens on various types of cells, our examples employ antibodies specific for the B cells and for the antigens on those cells, namely, CD20, CD79a/CD79b (also known as Igα/β), and immunoglobulin isotype-specific antigenic epitopes, referred to as migis-α and migis-β, which are represented by the exterior segments of the membrane-anchor peptides extending from the C-termini of the membrane-bound immunoglobulin chains of α and δ.

CD20 is a transmembrane protein that has provided as a therapeutic target for the treatment of B cell malignancies. CD20 is expressed by over 95% of B lymphocytes throughout their differentiation and maturation pathway, from the pre-B cell stage to the terminally differentiated plasma cells, but is absent on the hematopoietic stem cells. CD20 is believed to exist predominantly as a tetramer on the cell surface. Until now, the most widely used B cell-targeting antibody drug is rituximab, which is a chimeric IgG1 monoclonal antibody directed against CD20. Accumulating data indicate that rituximab is effective only for about 50% of the patients with B cell lymphoma. Anti-CD20 antibodies, which are approved for clinical uses or in human clinical trials, include chimeric "C2B8" monoclonal antibody (rituximab), monoclonal antibody 1F5, and chimeric 2H7 antibody.

Antibodies specific for other B cell surface antigens, such as CD19 and CD22, generally do not cause lytic effects on B cell-derived tumor cells. We rationalize that it will be effective to employ scFv specific for a B cell surface antigen, such as CD19, in combination with scFv specific for CD20, to increase the binding specificity and avidity and to result in cell lysis of the targeted cells. In such an application, scFv specific for CD20 can be considered as a targeting element and an effector element. A large number of CD markers on B cells probably can be combined with CD20 under such a rationale, as long as there is some level of CD20 present on the intended target B tumors. In one embodiment of the present disclosure, the various T-E molecules based on the "joint-linker" configuration contain scFv specific for CD20 and CD19 as the targeting elements and scFv specific for CD3 or CD16a, and bundles of cytotoxic drugs as the effector elements.

While there are considerable heterogeneities among multiple myeloma in terms of surface antigen expression, a systematic profiling of the surface markers for individual patients can provide targeting strategies. In recent years, a number of antibody drug conjugates or bispecific antibodies targeting a few CD markers, such as CD38, CD138, CD78, and CD319, and other surface antigens are under development. We rationalize that if the avidity of the targeting antibodies and the effector mechanisms can be enhanced, the treatments can be much more specific and effective. The preferred embodiments of this invention in the treatment of multiple myeloma are molecular constructs employing 3 or more scFv of one or two antibodies specific for CD38, CD78, CD138, or CD319 as the targeting element and a drug payload with 5-10 cytotoxic drug molecules as the effector element. Other effector elements, such as scFv specific for CD3 or CD16a may also be employed. In one embodiment of the present disclosure, the various T-E molecules based on the "joint-linker" configuration contain scFv specific for CD38 and CD138 as the targeting elements and scFv specific for CD3 or CD16a, and bundles of cytotoxic drugs as the effector elements.

In order that a targeted protein on a cell surface can be effectively cross-linked to form a large cluster, the protein must possess two or more antigenic sites for the binding agent to bind (without the help of a secondary cross-linking agent). For example, because each Igα/Igβ-BCR complex has only one copy of Igα and one copy of Igβ, a binding agent with even multiple copies of Fab or scFv specific for Igα or Igβ cannot induce productive cross-linking of Igα/Igβ-BCR to form a cluster. In other words, a 4-arm multi-arm linker with 4 Fabs (or scFv) specific for Igα will at best form many small units of 4 BCRs, but cannot form larger cross-linked complexes. Therefore, for cross-linking Igα/β-BCR, a 4-6-arm linker should have 2-three scFvs specific for Igα conjugated onto one linker unit and 2-three scFvs specific for Igβ conjugated onto the other linker unit. Alternatively, a 4-arm linker with scFv specific for Igα and a 4-arm linker with scFv specific for Igβ are administered in combination to a patient.

According to some embodiments of the present disclosure T-E molecules, which resemble those designed for treating B-cell derived tumors are designed. For those constructs, scFv specific for CD markers of T cells are employed as targeting elements and the effector elements are the same as those for targeting B cell tumors. This invention also pertains to the development of molecular constructs based on fragments of anti-CD3 antibodies for causing T cell anergy or dysfunction partially without inducing T cell activation and cytokine storm. Such constructs can then be used for treating T cell-mediated autoimmune diseases, including type-I diabetes, SLE, multiple sclerosis, inflammatory bowel diseases, etc. As will be discussed in later sections, in molecular constructs with various scFv specific for tumor-associated antigens as the targeting element, scFv specific for CD3 can also be used as the effector element for recruiting T cells for the elimination of the targeted tumor cells.

According to some embodiments of the present disclosure T-E molecules, which resemble those designed for treating B-cell derived tumors are designed. For those constructs, scFv specific for CD markers of myeloid lineage cells are employed as targeting elements and the effector elements are the same as those for targeting B cell tumors.

According to other embodiments of the present disclosure, the disease treatable with the present method is a tumor, including a diffused tumor or a solid tumor. In these embodiments, the diffused tumor can be acute lymphocytic leukemia (ALL), chronic lymphocytic leukemia (CLL), acute myelogenous leukemia (AML), chronic myelogenous leukemia (CML), Hodgkin lymphoma, non-Hodgkin lymphoma, or myeloma.

In one embodiment of the present disclosure, the present method is useful in treating the diffused tumor, in which the first targeting element is an scFv specific for CD4, CD5, CD7, CD8, CD10, CD11c, CD13, CD14, CD15, CD19, CD20, CD22, CD23, CD30, CD33, CD34, CD36, CD37, CD38, CD41, CD43, CD56, CD61, CD64, CD65, CD74, CD78, CD79a, CD79b, CD80, CD138, or CD319; and the first effector element is a cytotoxic drug, or an scFv specific for CD3 or CD16a. In another embodiment of the present disclosure, one of the first targeting element and the first effector element is an scFv specific for CD79a; and the other of the first targeting element and the first effector element is an scFv specific for CD79b. Optionally, the cytotoxic drug is selected from the group consisting of auristatin, maytansine, doxorubicin, calicheamicin, and camptothecin.

In one preferred embodiment, the present method is employed to treat B-lymphocyte-derived lymphoma or leukemia, in which the first targeting element is an scFv specific for CD5, CD19, CD20, CD22, CD23, CD30, CD37, CD79a, or CD79b; and the first effector element is the cytotoxic drug, or an scFv specific for CD3 or CD16a.

In another preferred embodiment, the present method is employed in the treatment of B-lymphocyte-derived lymphoma or leukemia, in which one of the first targeting element and the first effector element is an scFv specific for CD79a; and the other of the first targeting element and the first effector element is an scFv specific for CD79b.

In still another preferred embodiment, the disease treated by the present method is plasmacytoma or multiple myeloma, in which the first targeting element is an scFv specific for CD38, CD78, CD138, or CD319; and the first effector element is a cytotoxic drug, or an scFv specific for CD3 or CD16a.

In further another preferred embodiment, the present method possesses an effect on T-cell derived lymphoma or leukemia, in which the first targeting element is an scFv specific for CD5, CD30, or CD43; and the first effector element is a cytotoxic drug, or an scFv specific for CD3 or CD16a.

In one preferred embodiment, the present method is used to treat myelogenous leukemia, in which the first targeting element is an scFv specific for CD33 or CD34; and the first effector element is a cytotoxic drug, or an scFv specific for CD3 or CD16a.

IV-(ii)-B Solid Tumor

The present invention pertains to multi-arm linkers conjugated with antibody fragments specific for the tumor-associated antigens listed above. Many antibodies specific for tumor-associated antigens, such as anti-HER2/NEU (trastuzumab), anti-CA19-9 (derived from clone 1116-NS-19-9), anti-CA125 (derived from clone OC125), anti-GD2 (ch14.18 monoclonal antibody), and anti-Globo H (clone VK9) are readily available for application. The present invention pertains to the employment of scFv or bi-scFv of antibodies specific for those tumor-associated antigens in conjunction with multi-arm linkers for carrying therapeutic agents to tumor sites.

In some embodiments of the present invention, T-E molecules in the "joint-linker" configurations are designed to conjugate multiple copies of a ligand, a growth factor, cytokine or hormone, and one or more copies of a therapeutic agent to the tumor site, where the diseased cells express the receptors to which the ligand binds. Such a drug delivery approach will enhance specificity and hence will enable higher therapeutic effects and lower side effects than simply applying the therapeutic agents.

Ligands suitable for such an approach include epidermal growth factor (EGF) and its mutants, epiregulin, heparin-binding epidermal growth factor (HB-EGF), vascular endothelial growth factor A (VEGF-A), basic fibroblast growth factors (FGF), hepatocyte growth factors (HGF), gastrin, CCK, secretin, gastrin-releasing peptide, glucagon-like peptide 1 (GLP-1), neuromedin, thyroid-stimulating hormone (TSH, or thyrotropin), adrenocorticotropic hormone (ACTH), gonadotropin-releasing hormone (GnRH) and somatostatin.

There are at least four types of VEGF's (VEGF-A, VEGF-B, VEGF-C and VEGF-D). Among them, VEGF-A is involved in the angiogenesis of endothelial cells of blood vessels. VEGF-A can bind to both VEGF receptors 1 and 2 (VEGFR1 and VEGFR2). It has been found that when the Ser2-Asp3 of EGF at the N-terminal is mutated to Trp2-Val3 or Trp2-Arg3, the mutated EGF can bind to not only HER1, but also HER2 and HER3 (Stortelers C. et al., Biochemistry 41:8732-8741, 2002). Thus, the targeting with EGF(W2V3), EGF(W2R3), or VEGF-A can reach broader scope of tumor target cells than antibodies specific for the EGF or VEGF-A receptors.

The sizes of most of those peptides or proteins are relatively small: EGF, 53 a.a., somatostatin, 14 and 28 a.a., secretin, 27 a.a., gastrin, 14-34 a.a., CCK, 8-58 a.a., gastrin-releasing peptide, 27a.a., GLP-1, 37 a.a., the receptor-binding β chain of thyroid stimulating hormone, 118 a.a., neuromedin, 10 a.a., ACTH, 39 a.a., and GnRH, 10 a.a. VEGF-A is a dimer with two peptides of 120-188 a.a. in length. In the radioimaging studies, truncated segments of the hormones or factors or artificially designed peptides have been shown to retain comparable or even stronger binding to their respective receptors. For example, an octapeptide has been designed for the imaging of tumors expressing somatostatin receptors.

Some products of bacteria, viruses, and other microorganisms can elicit strong immune response. For example, super antigens, such as staphylococcal enterotoxins, can activate a significant portion of T cells by binding to the MHC class II antigen and T cell receptor at the same time. A large variety of microbial products can bind to toll-like receptors (TLRs) and activate a broad range of immune activities.

Three TLR agonists have been approved by FDA for treatment certain cancer and infectious diseases. Bacillus Calmette-Guérin, which activates TLR2 and TLR4, has long been used as a vaccine against tuberculosis. It is now approved for use in immunotherapy of in situ bladder carcinoma. Imiquimod, a small imidazoquinoline originally developed as a topical antiviral agent, which also binds to TLR7, is approved for actinic keratosis, and superficial basal cell carcinoma. Monophosphoryl lipid A, a derivative of lipopolysaccharide (LPS) from *Salmonella minnesota*, which binds to TLR2 and TLR4, is approved as an adjuvant for a vaccine against papilloma virus, which causes most cases of cervical carcinoma.

Other TLR agonists that have been studied as potential therapeutic immunostimulatory substances include (1) glucans, include β-D-glucans derived from the cell wall of certain fungi, especially *Aspergillus* and *Agaricus* species, and zymosan derived from the cell wall of certain fungi, such as the yeast *Saccharomyces cerevisiae*, which bind to TLR2 and other receptors of immunocytes, (2) motolimod, a small molecule, which binds to TLR8, (3) imiquimod as explained above, and (4) CpG oligodeoxynucleotides (CpG DON), short single-stranded synthetic DNA molecules containing a C followed by a G nucleotide, which binds to TLR9. Those TLR binding agents generally activate dendritic cells, macrophages, natural killer cells, neutrophils, and other immune cells of the native immunity and elicit the production of a large array of inflammatory cytokines, which augment the adaptive immunity. The native and the adaptive immunity act in synergy in the removal of the pathologic elements.

LPS derived from Gram-negative bacteria, also referred to as endotoxin or exogenous pyrogen, is a very strong stimulator of the immune system. LPS binds to CD14/TLR4/MD2 receptor complex on monocytes, dendritic cells, and macrophages, elicits strong responses of the innate immune system, and induces production of inflammatory cytokines. In humans, LPS at 1 μg/kg can induce shock and is a powerful immunostimulatory agent. Systemic administration of unmodified LPS can potentially be very risky.

The present invention rationalize if LPS can be tied to a carrier and carried to tumor site, it can elicit in situ powerful local immune response, cause the release of inflammatory cytokines, increase vascular permeability, and recruit various effector cells to the site. This may help lyse the tumor cells in the inflamed tissue. Since cells in a tumor express tumor-associated antigens at varying density, the present approach elicits immune activities to all cells in a tumor site regardless of the cells' densities of tumor-associated antigens.

This invention rationalizes that the powerful inflammatory activity of the LPS will be largely limited to the targeted tumor site. Accordingly, a preferred embodiment is that three scFvs specific for a tumor-associated antigen are conjugated to one linker unit as the targeting element and 2-3 LPS or monophosphoryl lipid A molecules are conjugated to the other linker unit as the effector element. Additionally, two sets of scFv specific for two tumor-associated antigens may be separately conjugated to two linker units, which are then joined to form the targeting element.

It is demonstrated that LPS can be conjugated to a protein via a linker. The methodology involves the activation of LPS with 1-cyano-4-dimethylaminopyridinium tetrafluoroborate (CDAP) and the coupling with a primary amino group of a protein. The experiment also shows that LPS is conjugated to the protein preserving 70% of its endotoxic activity. The conjugation of LPS to a linker unit of this invention can be achieved by following a similar procedure. Activation of the hydroxyl groups in the carbohydrate element of LPS can be performed by the treatment with CDAP under a mild condition in an aqueous solution. Subsequently, the CDAP-activated LPS is reacted with a $NH_2$—SH cross linker and then with the maleimide groups of the linking arms of a linker unit.

The present invention rationalizes that if therapeutic agents can be localized more specifically to diseased sites, larger therapeutic windows can be obtained, and more therapeutic effects can be achieved, and fewer side effects will be caused. In the present invention, T-E molecules are designed for carrying scFv specific for immune checkpoints, such as cytotoxic T-lymphocyte-associated protein 4, or CTLA-4 (CD152), programmed cell death 1, or PD-1 (CD279), and programmed cell death 1 ligand 1, or PD-L1

(CD274 or B7-H1), as effector elements for liberating immunological mechanisms to destroy cancerous cells.

The present invention rationalizes that if those cytokines are recruited to tumor sites, they can elicit strong immune activities or inflammatory activities locally, which then leads to the elimination of the tumors. Therefore, the present invention employs the multi-arm linkers for conjugating scFv or bi-scFv specific for immunoregulatory cytokines rather than the immunoregulatory cytokines themselves. The rationale is to use the scFv to recruit the immunoregulatory cytokines, which are already present in the body and circulating in the blood, and to concentrate them in the tumor site. The cytokine-specific scFv used in these molecular constructs do not neutralize the activities of the cytokines. The scFv also do not have very high binding affinity for the cytokines. For those individual scFv fragments, Kd in the range of $1-5 \times 10^{-8}$ is adequate. In this preferred embodiment, each of the scFv can potentially recruit multiple molecules of an immunoregulatory cytokine, rendering increased therapeutic effects.

Some tumors have two overexpressed tumor-associated markers, e.g., CA19-9 and CCK/gastrin receptors on some gastrointestinal and neuroendocrine tumors, or Globo H and HER2/Neu on some breast tumors. The present invention rationalizes that by employing two guiding mechanisms, each carrying a different effector agent, e.g., one with a cytotoxic drug payload and the other with LPS, the combined therapeutic effects will be stronger and the side effects will be smaller. In a preferred therapeutic modality, the molecular conjugate with LPS, anti-PD-1, anti-PD-L1, anti-CTLA-4, anti-TNF-α, anti-IFN-γ, or anti-IFN-α, is applied first, so that an "in-situ" inflammation or immune activation is induced, permitting increased vascular permeability. If the local inflammation or immune activation cannot lead to the complete cytolytic effects on the tumor or diseased cells, a subsequent administration of a molecular construct carrying cytotoxic drug payload can augment the cytolytic effects on the cells bearing the targeted tumor-associated antigen.

The therapeutic effectors that can be carried to the targeted solid tumor site by the targeting components include the following: (1) cytotoxic drugs, which kill the bound cells; (2) anti-CD16a or anti-CD3, which induces ADCC or cytotoxic activities; (3) LPS or other TLR agonists, anti-IL-2, anti-TNF-α, anti-IFN-γ, or anti-IFN-α, which activate immune activities; (4) anti-PD1, anti-PD-L1, anti-CTLA4, or other immune checkpoint inhibitors, which liberate immune checkpoints and depress inhibitory feedback activities. The therapeutic aim of these agents is to cause the lysis of the tumor cells bearing receptors for the ligand.

As examples, various T-E molecules in joint-linker configuration incorporate scFv specific for HER2/Neu alone or in combination with scFv specific for HER1 as targeting elements and a cytotoxic drug, LPS, or scFv specific for CD3, CD16a, PD1, or VEGF-A as effector elements. Various T-E molecules in joint-linker configuration incorporate scFv specific for GD2 alone or in combination with scFv specific for Globo H as targeting elements and a cytotoxic drug, LPS, or scFv specific for CD3, CD16a, PD1, or VEGF-A as effector elements. Various T-E molecules in joint-linker configuration incorporate cholecystokinin (CCK) alone or in combination with somatostatin as targeting elements and a cytotoxic drug, LPS, or scFv specific for CD3, CD16a, PD1, or VEGF-A as effector elements. Several T-E molecules in joint-linker configuration incorporate scFv specific for prostate-specific membrane antigen (PSMA) as the targeting elements and scFv specific, but non-neutralizing for IL-2, TNF-α, IFN-α, or IFN-γ as the effector elements.

In a previous section, the employment of growth factors, peptide hormone, or cytokines as targeting elements in molecular constructs based on multi-arm linker units was elucidated and the preferred embodiments were described. Those non-immunoglobulin peptides or proteins can also be configured into IgG-like molecular constructs or 2-chain IgG.Fc fusion proteins. Specifically, growth factors, such as EGF or its mutant, epiregulin, HB-EGF, VEGF-A, FGF, HGF, gastrin, CCK, secretin, gastrin-releasing peptide, GLP-1, neuromedin, the β-chain of TSH, ACTH, GnRH, or somatostatin, can be incorporated as targeting elements. Tumors derived from cells expressing receptors of those growth factors or hormones often express those receptors. In one embodiment of the present disclosure, the molecular constructs enlist EGF as a targeting element in IgG.Fc fusion protein configurations. The effector elements include linker units containing cytotoxic molecules or LPS molecules, which are conjugated to the C-terminal peptide linkers. The effectors may also be scFv specific for CD3, CD16a, PD-1, or VEGF-A. Immunoregulatory cytokines, such as IFN-α, TNF-α, IL-2, and IFN-γ, can be incorporated as effector elements. The scFv or immunoregulatory cytokine can be expressed as part of the recombinant peptide chain.

The invention also pertains to a preferred embodiment of T-E molecules that incorporate scFv specific for tumor-associated antigens as targeting elements and scFv specific for haptens as effector elements. Such haptens include dinitrophenol (DNP), trinitrophenol (TNP), dansyl group, penicillin, p-aminobenzoic acid, or short peptides derived from proteins of human cells, viruses, or bacteria, for which antibodies are already available. For example, a peptide WADWPGPP (SEQ ID NO: 49) of 8 amino acid residues, which is located in the CεmX domain of membrane-bound IgE on human B lymphocytes is unique in sequence in the entire protein database, is not physically accessible by antibodies on the B cell surface. When a T-E molecule of this design is administered to a patient with a tumor expressing the tumor-associated antigen the drug aims to target, the T-E molecule binds to the tumor cells and serves as the base in the tumor site to recruit subsequently administered immunoregulatory antibodies, cytokines, or other proteins, which are tagged with the hapten.

The hapten tagged on the therapeutic molecule can be engineered via a peptide linker, such as GGGGS (SEQ ID NO: 6) or (GGGGS)$_2$ (SEQ ID NO: 6), at the C-terminal end of antibodies, such as IgG antibodies specific for PD-1, PD-L1, CTLA-4, VEGF-A, CD3, CD28, or immunoregulatory cytokines, such as IL-2, TNF-α, INF-α, or INF-γ. The peptide linker and the peptide hapten can be expressed as part of an integral recombinant protein. Bundles of cytotoxic drug payload based on a linker unit may also be tagged with the hapten through a linking arm and be recruited to the tumor site. This treatment strategy will increase the relative distribution of the therapeutic agents in favor of the tumor site and achieve enhanced therapeutic effects and decreased toxicity and side effects.

IgG specific for CD3 or CD28 are extremely powerful T cell activators. A systemic application of these antibodies can cause massive cytokine storms. However, if the activation of T cells by anti-CD3 or anti-CD28 antibodies can be administered at much reduced quantities and be concentrated to tumor tissues, their induced effects may be very effective in inducing local immune activities and inflammation and recruiting various immunocytes to counter tumor cells. Thus, a preferred embodiment of the present invention is to tag these antibodies with a hapten. The tagged anti-CD3 or CD28 is then administered at very minute quantities.

Certain tumor-associated antigens, such as CA19-9, CA125, and carcinoembryonic antigen (CEA), are shed from tumor cells and are present in the blood circulation. The detection and measurements of those antigens in serum samples have become routine assays for the preliminary detection of tumors in people undergoing physical health examination. The assays have also been used to monitor the efficacy of therapy and tumor status post treatments. While tumor-associated antigens of other types in serum are not assayed routinely, they are also known to be present in the blood circulation in varying quantities.

The keys in achieving therapeutic purposes for drug-conjugated tumor-targeting pharmaceuticals is that the therapeutic agents are specifically brought to the targeted tumor sites and that minimal quantities of the toxic therapeutic agents are trapped by other molecules and tissues. The present invention also pertains to the clearance of circulating tumor-associated antigens, such as CA19-9, CA125, or CEA, when such tumor-associated antigens are the antigenic targets of the targeting elements of the T-E pharmaceuticals of this invention. The clearance of the tumor-associated antigen in the blood can be performed by passing the patient's plasma through affinity columns packed with resins conjugated with the antibodies specific for the intended tumor-associated antigens in a blood dialysis procedure, prior to the application of the pharmaceuticals of this invention specific for the targeted tumor-associated antigens.

There are several potential mechanisms that cause the lysis of a target cell upon the binding of an antibody to a cell surface antigen on the target cell. These mechanisms include apoptosis, antibody-dependent cellular cytotoxicity (ADCC), and complement-mediated cytolysis (CMC). The relative importance of these three mechanisms may depend on the targeted antigens and the antibodies binding to the antigens. In the case of targeting Igα or Igβ by antibodies for causing B cell lysis, IgG antibodies specific for Igα or Igβ do not cause effective lysis, suggesting that the antibodies fail to elicit all three lytic mechanisms. The antibodies do not cross-link Igα or Igβ effectively to cause apoptosis, as explained in an earlier section above. They also seem to fail mediate effective ADCC and CMC. A research group is therefore developing a toxin-conjugated anti-10 effectively to cause apoptosis. It is also likely that antibodies specific for tumor associated antigens of peptidoglycan or mucin nature cannot induce internalization of the antibodies and their carried cytotoxic drugs.

The present invention also pertains to the new treatment modality of sequential administrations of a PEG-modified binding agent and a drug-conjugated anti-PEG antibody. The PEG-modified binding agents include protein therapeutics that are conjugated with PEG to improve pharmacokinetic properties and the multi-arm linker-based therapeutics, which employ PEG linking arms, of this invention. In cases when the PEG-modified binding agents do not lead to effective cytolytic mechanisms of the targeted cells, due to low density of the targeted surface antigen, insufficient cross-linking, inability to induce apoptosis, or other reasons, the cytolytic effect is enhanced or induced by the use of drug-conjugated anti-PEG IgG or F(ab')$_2$. Multiple molecules of anti-PEG IgG or F(ab')$_2$ can bind to each strand of PEG and multiple molecules of a cytotoxic drug can be carried by each anti-PEG IgG or F(ab')$_2$ molecule. The use of the divalent anti-PEG IgG or F(ab')$_2$ can cause cross-linking of the complexes of targeted surface antigen and the PEG-linked binding agent. The binding by divalent anti-PEG IgG or F(ab')$_2$ can cause the aggregation of the large complexes (targeted surface antigen plus PEG-linked binding agent plus drug-conjugated divalent anti-PEG IgG or F(ab')$_2$ and lead to the internalization of such complexes by the target cells. The internalized drug will then cause the cytolysis of the targeted cells. The treatment strategy should be effective in combination with the use of the molecular constructs for targeting tumor-associated antigens.

Such a strategy enables enhanced binding and specificity of the tumor-targeting binders, amplification by the anti-PEG antibody binding, and hence a larger and more specific drug payload. The drug-conjugated anti-PEG IgG can be prepared by engineering the IgG by installing a (GGGGS)$_2$ (SEQ ID NO: 6) linker and a cysteine residue at the C-termini of the γ heavy chains and conjugating to the two sulfhydryl groups with two linker units of cytotoxic dug payloads, each with 3-5 molecules of a cytotoxic drug.

The present invention also pertains to the new treatment modality of sequential administrations of PEG-linked antigen-binding fragments of antibodies specific for a tumor associated antigen, such as CEA, Globo H, or SSEA4, and an LPS-conjugated anti-PEG antibody. The use of LPS-conjugated anti-PEG IgG or F(ab')$_2$ elicits strong immune response in the targeted tumor site. For example, a 4-arm PEG linker conjugated with 4 scFv fragments is first administered to a patient with cancer expressing Globo H or SSEA4, followed with a lapse of time, by an LPS-conjugated anti-PEG IgG or F(ab')$_2$.

In certain embodiments of the present disclosure, the present method is useful for treating the solid tumor.

In the embodiment, the first targeting element is a peptide hormone, a growth factor, or an antibody fragment specific for a tumor-associated antigen; and the first effector element is a cytotoxic drug, a toll-like receptor agonist, a chelator complexed with a radioactive nuclide, a cytokine, or an antibody fragment specific for a growth factor, a cell surface antigen, a hapten, or a cytokine.

According to some optional embodiments of the present disclosure, when the effector element is the antibody specific for the hapten, the method further comprises the step of administering to the subject an immunoregulatory effector that is tagged with the same hapten, prior to the administration of the present molecular construct.

According to one example, the solid tumor treatable by the present method may be melanomas, esophageal carcinomas, gastric carcinomas, brain tumor, small cell lung cancer, non-small cell lung cancer, bladder cancer, breast cancer, pancreatic cancer, colon cancer, rectal cancer, colorectal cancer, renal cancer, hepatocellular carcinoma, ovary cancer, prostate cancer, thyroid cancer, testis cancer, or head and neck squamous cell carcinoma.

According to another example, the tumor-associated antigen is selected from the group consisting of human epidermal growth factor receptor 1 (HER1), human epidermal growth factor receptor 2 (HER2), human epidermal growth factor receptor 3 (HER3), human epidermal growth factor receptor 4 (HER4), carbohydrate antigen 19-9 (CA 19-9), carbohydrate antigen 125 (CA 125), mucin 1 (MUC 1), ganglioside GD2, ganglioside GD3, ganglioside GM2, fucosyl GM1, Neu5GcGM3, melanoma-associated antigen (MAGE), prostate-specific membrane antigen (PSMA), prostate stem cell antigen (PSCA), mesothelin, mucine-related Tn, Sialyl Tn, Lewis$^Y$, Sialyl Lewis$^Y$, Lewis$^A$, Lewis$^x$, heparin-binding epidermal growth factor (HB-EGF), Globo H, and stage-specific embryonic antigen-4 (SSEA-4).

According to still another example, the peptide hormone is selected from the group consisting of secretin, gastrin, cholecystokinin (CCK), gastrin-releasing polypeptide, glucagon-like polypeptide 1 (GLP-1), neuromedin, thyroid-stimulating hormone (TSH), adrenocorticotropic hormone (ACTH), gonadotropin-releasing hormone (GnRH), and somatostatin.

According to still another example, the growth factor is selected from the group consisting of epidermal growth factor (EGF), mutant EGF, epiregulin, heparin-binding epidermal growth factor (HB-EGF), vascular endothelial growth factor A (VEGF-A), basic fibroblast growth factor (bFGF), and hepatocyte growth factor (HGF). In one working example, the first targeting element is EGF, mutant EGF, HB-EGF, VEGF-A, bFGF, or HGF. In another working example, the first effector element is an scFv specific for EGF, mutant EGF, VEGF-A, bFGF, or HGF.

In one example, the cell surface antigen is PD-1, PD-L1, CTLA-4, CD3, CD16a, CD28, or CD134.

In another example, the hapten is dinitrophenol (DNP), trinitrophenol (TNP), dansyl, penicillin, p-aminobenzoic acid, or a short peptide having an amino acid sequence of SEQ ID NO: 20.

In still another example, the cytokine is IL-2, IL-10, IL-12, IFN-α, IFN-γ, TGF-β, or TNF-α. According to one embodiment, the first effector element is a non-neutralizing scFv specific for the cytokine selected from the group consisting of IL-2, IFN-α, IFN-γ, and TNF-α.

As would be appreciated, the cytotoxic drug exhibiting a cytotoxic effect on tumor cell can be anti-estrogens (e.g., tamoxifen, raloxifene, and megestrol), LHRH agonists (e.g., goscrclin and leuprolide), anti-androgens (e.g., flutamide and bicalutamide), photodynamic therapies (e.g., vertoporfin, phthalocyanine, photosensitizer Pc4, and demethoxy-hypocrellin A), nitrogen mustards (e.g., cyclophosphamide, ifosfamide, trofosfamide, chlorambucil, estramustine, and melphalan), nitrosoureas (e.g., carmustine and lomustine), alkylsulphonates (e.g., busulfan and treosulfan), triazenes (e.g., dacarbazine, temozolomide), platinum containing compounds (e.g., cisplatin, carboplatin, oxaliplatin), vinca alkaloids (e.g., vincristine, vinblastine, vindesine, and vinorelbine), taxoids (e.g., paclitaxel, docetaxeal, and taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonucleotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, idarubicin, epirubicin, pirarubicin, zorubicin, mitoxantrone), MDR inhibitors (e.g., verapamil), $Ca^{2+}$ ATPase inhibitors (e.g., thapsigargin), imatinib, thalidomide, lenalidomide, tyrosine kinase inhibitors (e.g., axitinib, bosutinib, cediranib, dasatinib, erlotinib, gefitinib, imatinib, lapatinib, lestaurtinib, neratinib, nilotinib, semaxanib, sunitinib, toceranib, vandetanib, vatalanib, rituximab, nilotinib, sorafenib, everolimus, temsirolimus, proteasome inhibitors (e.g., bortezomib), mTOR inhibitors (e.g., rapamycin, temsirolimus, everolimus, and ridaforolimus), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, or hexamethyl melamine. According to one specific embodiment of the present disclosure, the cytotoxic drug is auristatin, maytansine, doxorubicin, calicheamicin, or camptothecin.

According to the embodiment, the toll-like receptor agonist is lipoteichoic acid, glucan, motolimod, imiquimod, resiquimod, gardiquimod, CpG oligodeoxynucleotide (CpG DON), lipopolysaccharide (LPS), monophosphoryl lipid A, or zymosan.

IV-(iii) Osteoporosis Disease

In the extracellular matrix network of the bone, the major tissue-specific protein is osteonectin, also referred to as secreted protein acidic and rich in cysteine (SPARC). Collagen I is a dominant protein in the bone matrix, although it is also present in the connective tissue lining the skin.

In treating osteoporosis, a set of the present inventions is to construct T-E molecules with scFv specific for osteonectin and/or collagen I as the targeting elements and scFv specific for RANKL or sclerostin as the effector elements. We rationalize that if anti-RANKL or anti-sclerostin antibodies can be preferentially localized in the bone, the dosage can be decreased, and the therapeutic efficacy increased. In one embodiment of the present disclosure, the various T-E molecules based on the "joint-linker" configuration contain scFv specific for osteonectin (SPARC) and collagen I as the targeting elements and scFv specific for RANKL as the effector elements.

According to certain embodiments of the present disclosure, the present method is useful in treating osteoporosis disease, in which the first targeting element is an scFv specific for collagen I or osteonectin; and the first effector element is an scFv specific for ligand of receptor activator of nuclear factor κB (RANKL).

EXPERIMENTAL EXAMPLES

Example 1: Synthesis of Peptide 1 (SEQ ID NO: 17), Peptide 2 (SEQ ID NO: 18), and Peptide 3 (SEQ ID NO: 19) as Peptide Cores, and Conjugation of SH Group of Cysteine Residue with Maleimide-PEG$_3$-Transcyclooctene (TCO) as Conjugating Arm Peptides 1 to 3 were synthesized by solid-phase peptide synthesis method and purified with reverse phase high-performance liquid chromatography (HPLC) using Shimadzu Nexera-i LC-2040C 3D HPLC system to 95% purity. The reverse phase HPLC used a Kromasil 100-5C18 column (250 mm×4.6 mm; 5 μm), with a mobile phase of acetonitrile and 0.1% trifluoroacetic acid, a linear gradient of 10% to 45% acetonitrile over 15 minutes, at a flow rate of 1.0 mL/min and a column temperature of 25° C.

Figure 8:
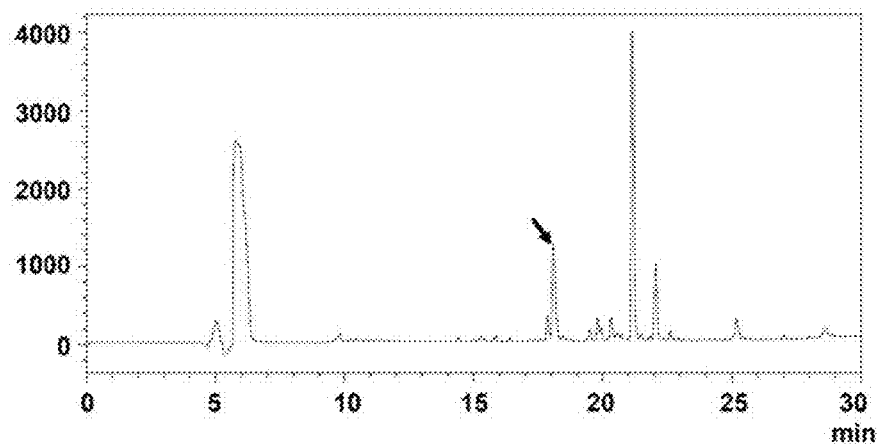
FIG. 8 shows the reverse phase HPLC elution profile for the purification of TCO-peptide 2. Peptide 2 is SEQ ID NO:18.

The purified peptide was dissolved in 100 mM sodium phosphate buffer (pH 7.0) containing 50 mM NaCl and 5 mM EDTA at a final concentration of 2 mM. The dissolved peptide was reduced by 1 mM tris(2-carboxyethyl)phosphine (TCEP) at 25° C. for 2 hours. For conjugating the SH group of the cysteine residue with maleimide-PEG$_3$-TCO (Conju-probe Inc., San Diego, USA) to create a functional linking group TCO, the peptide and maleimide-PEG$_3$-TCO were mixed at a 1/10 ratio and incubated at pH 7.0 and 25° C. for 24 hours. TCO-conjugated peptides were purified by reverse phase HPLC on a Supelco C18 column (250 mm×10 mm; 5 µm), using a mobile phase of acetonitrile and 0.1% trifluoroacetic acid, a linear gradient of 0% to 100% acetonitrile over 30 minutes, at a flow rate of 1.0 mL/min and a column temperature of 25° C. FIG. 8 shows the reverse phase HPLC elution profile for the purification of TCO-peptide 2; with the peak of the TCO-peptide 2 being indicated with an arrow.

The identification of the three synthesized TCO-peptides (illustrated below) was carried out by mass spectrometry MALDI-TOF. Mass spectrometry analyses were performed by Mass Core Facility of Institute of Molecular Biology (IMB), Academia Sinica, Taipei, Taiwan. Measurements were performed on a Bruker Autoflex III MALDI-TOF/TOF mass spectrometer (Bruker Daltonics, Bremen, Germany).

The present TCO-peptide 1, as illustrated below, had a molecular weight (m.w.) of 1807.0 daltons.

(SEQ ID NO: 17)

The present TCO-peptide 2, as illustrated below, had a m.w. of 2078.9 daltons.

(SEQ ID NO: 18)

The present TCO-peptide 3, as illustrated below, had a m.w. of 3380.8 daltons.

(SEQ ID NO: 19)

Example 2: Synthesis of Peptides 1 and 2 as Peptide Cores, and Conjugation of SH Group of Cysteine Residue with Maleimide-PEG$_4$-Tetrazine as Conjugating Arm Peptides 1 and 2 were prepared as in Example 1, and then dissolved in 100 mM sodium phosphate buffer (pH 7.0) containing 50 mM NaCl and 5 mM EDTA at 2 mM final concentration. The dissolved peptide was reduced by 1 mM TCEP at 25° C. for 2 hours. For conjugating the SH group of cysteine residue with maleimide-PEG$_4$-tetrazine (Conjuprobe Inc.) to create a functional linking group tetrazine, the peptide and maleimide-PEG$_4$-tetrazine were mixed at a 1/5 ratio and incubated at pH 7.0 and 4° C. for 24 hours. Tetrazine-conjugated peptides were purified by reverse phase HPLC on a Supelco C18 column (250 mm×10 mm; 5 µm), using a mobile phase of acetonitrile and 0.1% trifluoroacetic acid, a linear gradient of 0% to 100% acetonitrile over 30 minutes, at a flow rate of 1.0 mL/min and a column temperature of 25° C. The identification of said two synthesized tetrazine-peptides was carried out by mass spectrometry MALDI-TOF set forth in the preceding Example.

The present tetrazine-peptide 1, as illustrated below, had a m.w. of 1912.7 daltons.

(SEQ ID NO: 17)

The present tetrazine-peptide 2, as illustrated below, had a m.w. of 2185.2 daltons.

(SEQ ID NO: 18)

Example 3: Synthesis of Peptides 1 and 2 as Peptide Cores, and Conjugation of SH Group of Cysteine Residue with Maleimide-PEG$_5$-DBCO as Conjugating Arm Peptides 1 and 2 were prepared as in the earlier Example. The peptide was dissolved in 100 mM sodium phosphate buffer (pH 7.0) containing 50 mM NaCl and 5 mM EDTA at 2 mM final concentration. The dissolved peptide was reduced by 1 mM TCEP at 25° C. for 2 hours. For conjugating the SH group of cysteine residue with dibenzylcyclooctyne (DBCO) to create a functional linking group of DBCO, the peptide and maleimide-PEG$_5$-DBCO (Conjuprobe Inc.) were mixed at a 1/5 ratio and incubated at pH 7.0 and the room temperature for 24 hours. DBCO-conjugated peptides were purified by reverse phase HPLC on a Supelco C18 column (250 mm×10 mm; 5 µm), using a mobile phase of acetonitrile and 0.1% trifluoroacetic acid, a linear gradient of 0% to 100% acetonitrile over 30 minutes, at a flow rate of 1.0 mL/min and a column temperature of 25° C. The identification of the two synthesized DBCO-peptides was carried out by mass spectrometry MALDI-TOF.

The present DBCO-peptide 1, as illustrated below, had a m.w. of 1941.8 daltons.

(SEQ ID NO: 17)

The present DBCO-peptide 2, as illustrated below, had a m.w. of 2213.9 daltons.

(SEQ ID NO: 18)

Example 4: Synthesis of Peptide 4 (SEQ ID NO: 21), Peptide 5 (SEQ ID NO: 22), and Peptide 6 (SEQ ID NO: 23) as Peptide Cores Peptides 4 to 6 were synthesized by solid-phase peptide synthesis method, and then purified by reverse phase HPLC to 95% purity. The unnatural amino acids, homopropagylglycine ($G^{HP}$) and azidohomoalanine ($A^{AH}$) contained an alkyne and an azide group, respectively. The reverse phase HPLC used a Supelco C18 column (250 mm×4.6 mm; 5 µm), with a mobile phase of acetonitrile and 0.1% trifluoroacetic acid, a linear gradient of 2% to 90% acetonitrile over 30 minutes, at a flow rate of 1.0 mL/min and a column temperature of 25° C.

The identification of said three synthesized peptides was carried out by mass spectrometry MALDI-TOF. The present peptide 4 (Ac-$G^{HP}$GGSGGSGGSKGSGSK; SEQ ID NO: 21) had a molecular weight of 1317.0 daltons; the present peptide 5 (Ac-$G^{HP}$GGSGGSGGSKGSGSKGSK; SEQ ID NO: 22) had a m.w. of 1589.9 daltons; while the present peptide 6 (Ac-$A^{AH}$GGSGGSGGSKGSGSKGSK; SEQ ID NO: 23) had a m.w. of 1634.66 daltons.

Example 5: Synthesis of Peptide 7 (SEQ ID NO: 24) as Peptide Core and Conjugation of SH Group of Cysteine Residue with Maleimide-PEG$_3$-TCO or Maleimide-PEG$_4$-Tetrazine as Conjugating Arm Peptide 7 (Ac-$G^{HP}$GGSGGSGGSKGSGSKGSGSC; SEQ ID NO: 24) was synthesized, and the conjugation of the crosslinkers was performed as described in above examples. The synthesized TCO-peptide 7 and tetrazine-peptide 7 were examined using MALDI-TOF.

The present TCO-peptide 7, as illustrated below, had a m.w. of 1736.78 daltons.
Ac-$G^{HP}$-GGSGGSGGSKGSGSKGSGSC-PEG$_3$-TCO (SEQ ID NO: 24)

The present tetrazine-peptide 7, as illustrated below, had a m.w. of 1820.62 daltons.
Ac-$G^{HP}$-GGSGGSGGSKGSGSKGSGSC-PEG$_3$-Tetrazine (SEQ ID NO: 24)

Example 6: Synthesis of Peptide 8 (SEQ ID NO: 25) as Peptide Core, and Conjugation of SH Group of Cysteine Residue with Maleimide-PEG$_3$-TCO, Maleimide-PEG$_4$-Tetrazine or Maleimide-PEG$_5$-DBCO as Conjugating Arm Peptide 8 (Ac-C-Xaa-K-Xaa-K-Xaa-K; wherein Xaa was a PEGylated amino acid with 2 EG units; SEQ ID NO: 25) was synthesized by solid-phase peptide synthesis method and then purified using reverse phase HPLC to 95% purity. The reversed phase HPLC was conducted using a Kromasil 100-5C18 column (250 mm×4.6 mm; 5 µm), with a mobile phase of water and 0.1% TFA, a linear gradient of 10% to 40% acetonitrile over 12 minutes, at a flow rate of 1.0 mL/min and a column temperature of 25° C.

The identification of the synthesized peptide 8 was carried out by mass spectrometry ESI-MS. High resolution and high mass accuracy experiments were done on a LTQ Orbitrap XL ETD mass spectrometer (Thermo Fisher Scientific, San Jose, Calif.) equipped with standard ESI ion source. Mass ESI-TOF analyses were performed by GRC Mass Core Facility of Genomics Research Center, Academia Sinica, Taipei, Taiwan. The sample of the synthesized peptide showed a strong molecular ion at 981.9, corresponding to $[M-H]^-$, indicating that the actual molecular weight of the PEGylated peptide was 983.0 daltons.

The conjugation of the crosslinkers was performed as described in above examples, and mass spectrometry ESI-MS was used to examine the products (illustrated below, in which the Xaa$_2$ denotes a PEGylated amino acid with two EG units).

The present TCO-peptide 8, as illustrated below, had a m.w. of 1478.87 daltons.
TCO-PEG$_3$-C-(Xaa$_2$-K)$_3$ The present tetrazine-peptide 8, as illustrated below, had a m.w. of 1584.92 daltons.
Tetrazine-PEG$_4$-C-(Xaa$_2$-K)$_3$ The present DBCO-peptide 8, as illustrated below, had a m.w. of 1613.8 daltons
DBCO-PEG$_5$-C-(Xaa$_2$-K)$_3$ Example 7: Synthesis of Peptide 9 (SEQ ID NO: 26) as Peptide Core, and Conjugation of SH Group of Cysteine Residue with Maleimide-PEG$_3$-TCO as Conjugating Arm Peptide 9 (Ac-C-Xaa-K-Xaa-K-Xaa-K-Xaa-K-Xaa-K; wherein Xaa was a PEGylated amino acid with 6 EG units; SEQ ID NO: 26) was prepared as set forth in an earlier Example. The identification of the synthesized peptide 9 was carried out by mass spectrometry ESI-MS. The sample of the synthesized peptide showed a strong molecular ion at 828.0, corresponding to $[M+3H]^{3+}$, indicating that the actual molecular weight of the PEGylated peptide was 2480.7 daltons.

The conjugation of the crosslinker was performed as set forth in above examples, and then examined with mass spectrometry ESI-MS. The present TCO-peptide 9, as illustrated below, had a m.w. of 2975 daltons.
TCO-PEG$_3$-C-(Xaa$_6$-K)$_5$ Example 8: Synthesis of Linker Unit by Conjugating NHS-PEG$_{12}$-Maleimide to NH$_2$ Groups of TCO-Peptides 1 and 2

Figure 9:
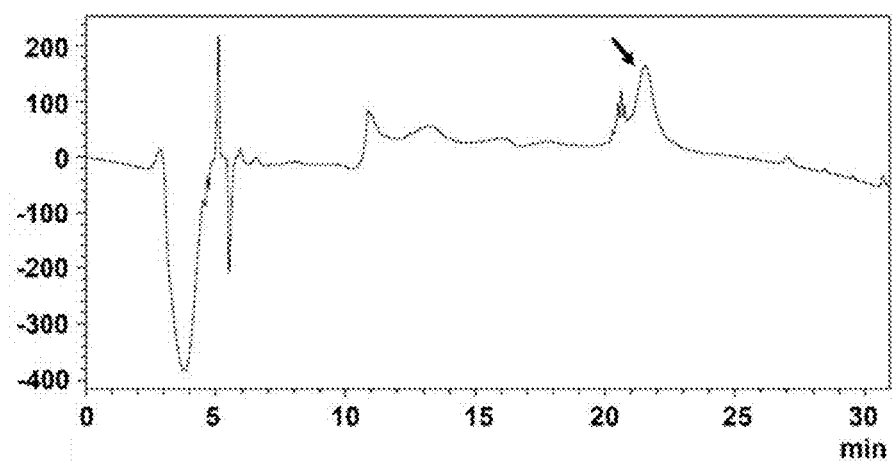
FIG. 9 shows the reverse phase HPLC profile for the purification of $PEG_{12}$-maleimide-conjugated TCO-peptide 2.

Two linking arms of PEG$_{12}$-maleimide were attached to the peptide core TCO-peptide 1; while three linking arms of PEG$_{12}$-maleimide were attached to the peptide core TCO-peptide 2. The crosslinker, NHS-PEG$_{12}$-maleimide (succinimidyl-[(N-maleimido-propionamido)-dodecaethyleneglycol] ester), was purchased from Thermo Fisher Scientific Inc. (Waltham, USA). The conjugation procedure was performed per the manufacturer's instruction; the peptide with lysine residues was dissolved in the conjugation buffer, phosphate buffered saline (PBS, pH 7.5) at 100 mM. NHS-PEG$_{12}$-maleimide crosslinker was added to the dissolved peptide at 1 mM final concentration (20-fold molar excess over 0.1 mM peptide solution). The reaction mixtures were incubated for 18 hours at room temperature. PEG$_{12}$-maleimide-conjugated TCO-peptide 1 and peptide 2 were purified by reverse phase HPLC on a Supelco C18 column (250 mm×4.6 mm; 5 µm), using a mobile phase of acetonitrile and 0.1% trifluoroacetic acid, a linear gradient of 0% to 100% acetonitrile over 30 minutes, at a flow rate of 1.0 mL/min and a column temperature of 25° C. FIG. 9 shows the reverse phase HPLC profile for the purification of PEG$_{12}$-maleimide-conjugated TCO-peptide 2, with the peak being indicated with an arrow.

The identification of the PEG$_{12}$-maleimide-conjugated TCO-peptide 1 and peptide 2 was carried out by mass spectrometry MALDI-TOF.

The present PEG$_{12}$-maleimide-conjugated TCO-peptide 1, as illustrated below, was a peptide core-based linker unit carrying one coupling arm with a TCO group and two PEG linking arms with maleimide groups. The result of mass spectrometry MALDI-TOF indicated that the present molecular construct had a m.w. of 3330.7 daltons.

(SEQ ID NO: 17)

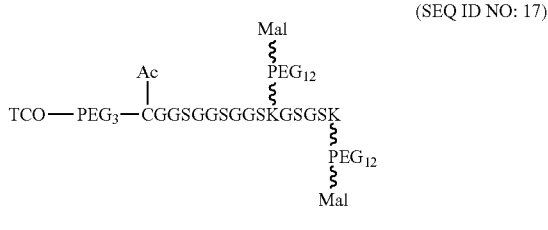

Figure 10:
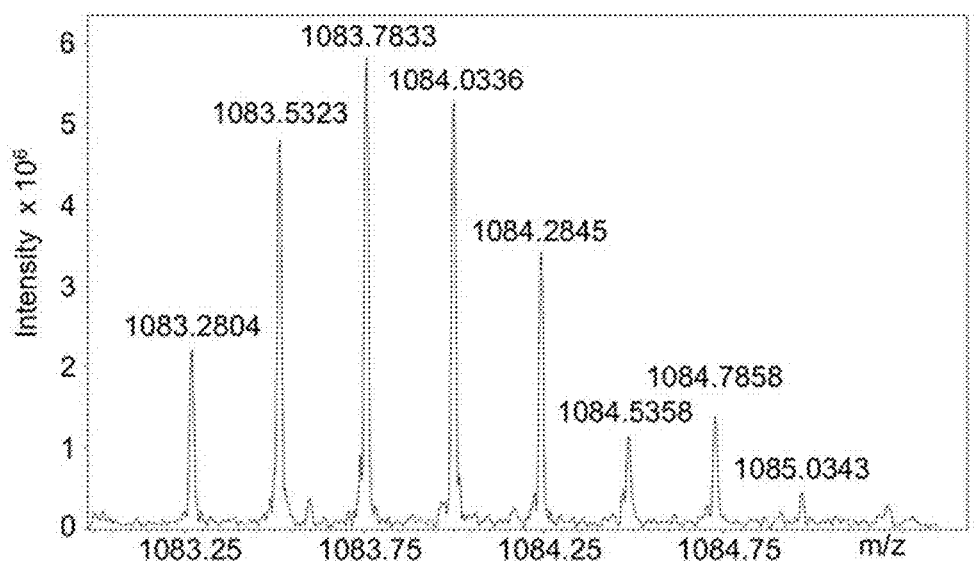
FIG. 10 shows the mass spectrometry MALDI-TOF result of $PEG_{12}$-maleimide-conjugated TCO-peptide 2.

The present PEG$_{12}$-maleimide-conjugated TCO-peptide 2, as illustrated below, was a peptide core-based linker unit carrying one coupling arm with a TCO group and three PEG linking arms with maleimide groups. FIG. 10 shows the mass spectrometry MALDI-TOF result, indicating that the present molecular construct had a m.w. of 4332 daltons; (ESI-TOF) m/z (z=4): [M+4H]$^+$; calculated for $C_{185}H_{313}N_{31}O_{83}S_1$ 1083.7829; found 1083.7833), corresponding to [M+Na]$^+$.

(SEQ ID NO: 18)

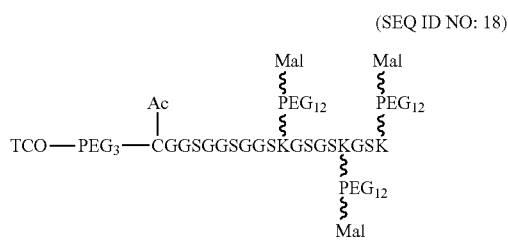

Example 9: Synthesis of Linker Unit by Conjugating NHS-PEG$_{12}$-Maleimide to NH$_2$ Groups of Tetrazine-Peptide 2 and DBCO-Peptide 1

Three linking arms of PEG$_{12}$-maleimide were attached to tetrazine-peptide 2, while two linking arms were attached to DBCO-peptide 1. The conjugation of NHS-PEG$_{12}$-maleimide to the NH$_2$ groups of the lysine residues of the peptide cores was performed as described in the earlier Examples, and the products were identified using mass spectrometry MALDI-TOF.

Figure 11A:
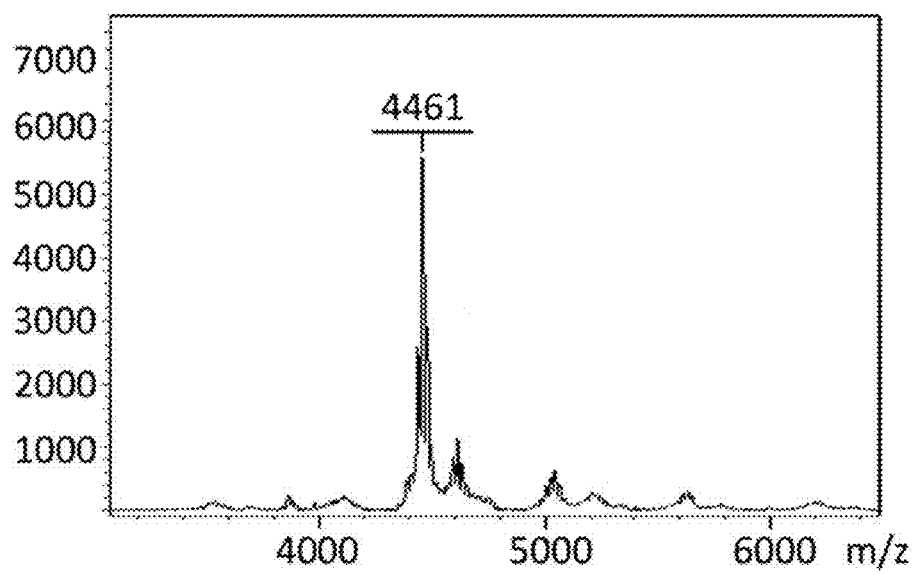
FIGS. 11A and 11B respectively show the mass spectrometry MALDI-TOF result of $PEG_{12}$-maleimide-conjugated tetrazine-peptide 2 and DBCO-peptide 2.

As illustrated below, the present PEG$_{12}$-maleimide-conjugated tetrazine-peptide 2 carried one coupling arm with a tetrazine group and three PEG linking arms with maleimide groups. FIG. 11A shows the mass spectrometry MALDI-TOF result, indicating that the construct had a m.w. of 4461 daltons.

(SEQ ID NO: 18)

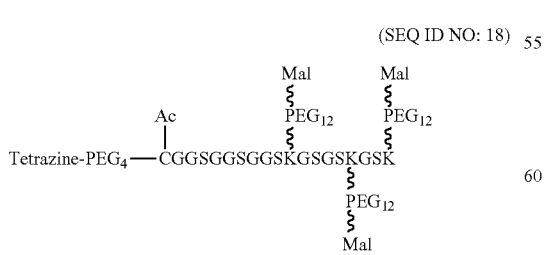

Figure 11B:
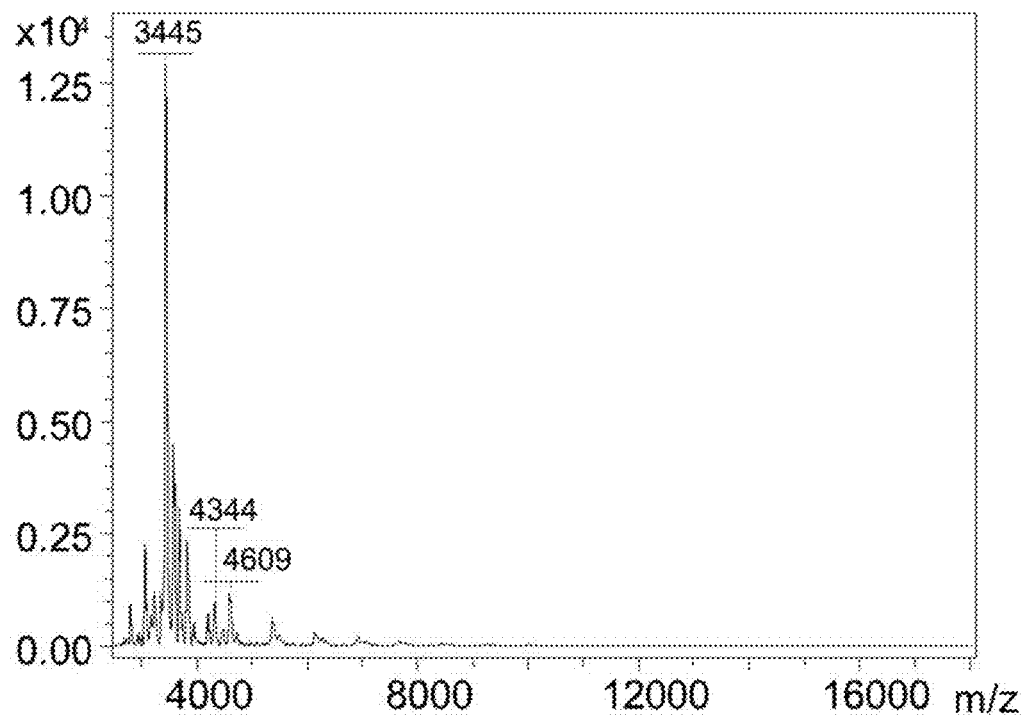

As illustrated below, the present PEG$_{12}$-maleimide-conjugated DBCO-peptide 1 carried one linking arm with a DBCO group and two PEG linking arms with maleimide groups. FIG. 11B shows the mass spectrometry MALDI-TOF result, indicating that the construct had a m.w. of 3445 daltons.

(SEQ ID NO: 17)

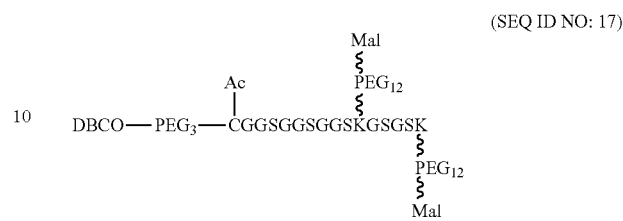

Example 10: Synthesis of Linker Unit by Conjugating NHS-PEG$_{12}$-Maleimide to NH$_2$ Groups of Peptides 4 to 6

Two linking arms of PEG$_{12}$-maleimide were attached to the peptide 4; while three linking arms of PEG$_{12}$-maleimide were attached to the peptide 5 and peptide 6. The conjugation of NHS-PEG$_{12}$-maleimide to the NH$_2$ groups of the lysine residues of the peptide cores was performed as in the earlier Example, and the products were identified using mass spectrometry MALDI-TOF.

The present PEG$_{12}$-maleimide-conjugated peptide 4, as illustrated below, had a m.w. of 2817.3 daltons; it was a peptide core-based linker unit carrying one alkyne group and two PEG linking arms with maleimide groups.

(SEQ ID NO: 21)

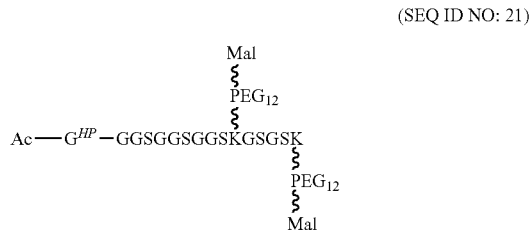

The present PEG$_{12}$-maleimide-conjugated peptide 5 (illustrated below) had a m.w. of 3839.2 daltons; it was a peptide core-based linker unit carrying one alkyne group and three PEG linking arms with maleimide groups.

(SEQ ID NO: 22)

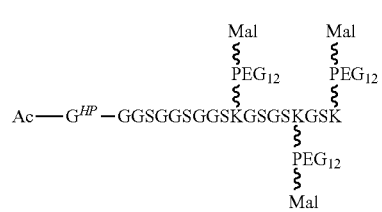

PEG$_{12}$-maleimide-conjugated peptide 6 (illustrated below) had a m.w. of 3811.5 daltons; it was a peptide core-based linker unit carrying one azide group and three PEG linking arms with maleimide groups.

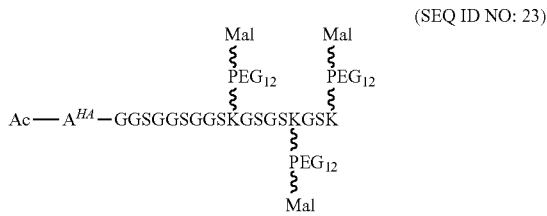

(SEQ ID NO: 23)

Example 11: Synthesis of Linker Unit by Conjugating NHS-PEG$_{12}$-Maleimide to NH$_2$ Groups of TCO-Peptide 7 and Tetrazine-Peptide 7

Two linking arms of PEG$_{12}$-maleimide were attached to a peptide core, the peptide 7 from the preceding Examples. The conjugation of NHS-PEG$_{12}$-maleimide to the NH$_2$ groups of the lysine residues of the peptide core was performed as described above, and the identification was carried out by mass spectrometry MALDI-TOF.

The present PEG$_{12}$-maleimide-conjugated TCO-peptide 7, as illustrated below, had a m.w. of 3237.63 daltons; it was a peptide core-based linker unit carrying one an alkyne group, one coupling arm with a TCO group, and two PEG linking arms with maleimide groups.

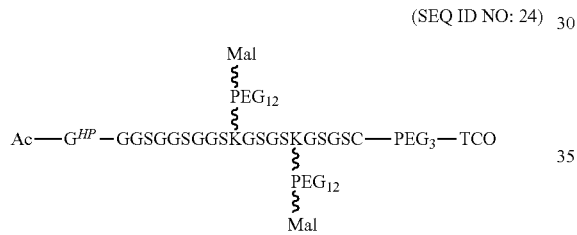

(SEQ ID NO: 24)

The present PEG$_{12}$-maleimide-conjugated tetrazine-peptide 7, as illustrated below, had a m.w. of 3342.98 daltons; it was a peptide core-based linker unit carrying one alkyne group, one coupling arm with a tetrazine group, and two PEG linking arms with maleimide groups.

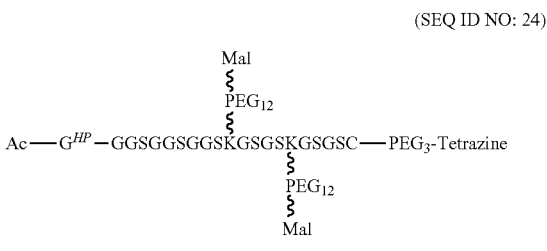

(SEQ ID NO: 24)

Example 12: Synthesis of Linker Unit by Conjugating NHS-PEG$_{12}$-Maleimide to NH$_2$ Groups of TCO-Peptide 8 and Tetrazine-Peptide 8

Three linking arms of PEG$_{12}$-maleimide were attached to the peptide cores, TCO-peptide 8 and tetrazine-peptide 8. The conjugation of NHS-PEG$_{12}$-maleimide to the NH$_2$ groups of the lysine residues of the peptide core was performed as in Example 8, and the identification was carried out by mass spectrometry MALDI-TOF.

The present PEG$_{12}$-maleimide-conjugated TCO-peptide 8 (illustrated below) had a m.w. of 3774.9 daltons; it was a linker unit based on PEGylated amino acid and lysine; it carried one coupling arm with a TCO group and three PEG linking arms with maleimide groups.

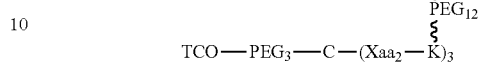

Figure 12:
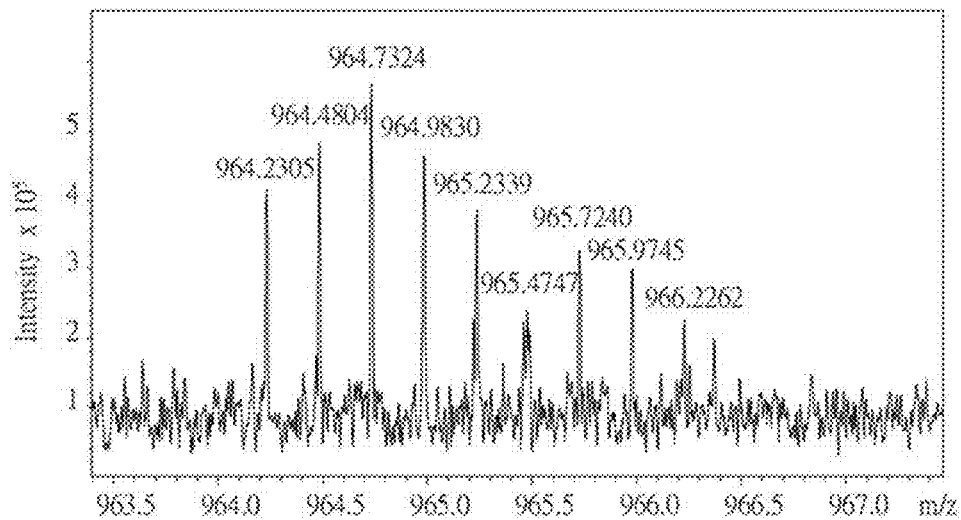
FIG. 12 shows the mass spectrometry ESI-TOF result of $PEG_{12}$-maleimide-conjugated tetrazine-peptide 8.

The present PEG$_{12}$-maleimide-conjugated tetrazine-peptide 8 (illustrated below) had a m.w. of 3856.94 daltons (FIG. 12; (ESI-TOF) m/z (z=4): [M+4H]$^+$ Calculated for $C_{171}H_{287}N_{23}O_{71}S_1H_3Na$ 964.7363; Found 964.7324); it was a linker unit based on PEGylated amino acid and lysine; it carried one coupling arm with a tetrazine group and three PEG linking arms with maleimide groups.

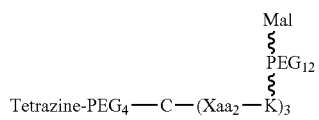

Example 13: Synthesis of Linker Unit by Conjugating NHS-PEG$_6$-Maleimide to NH$_2$ Groups of TCO-Peptide 9

Five linking arms of PEG$_6$-maleimide were attached to the peptide cores, TCO-peptide 9. The conjugation of NHS-PEG$_6$-maleimide to the NH$_2$ groups of the lysine residues of the peptide core was performed as in Example 8, the identification was carried out by mass spectrometry MALDI-TOF.

Figure 13:
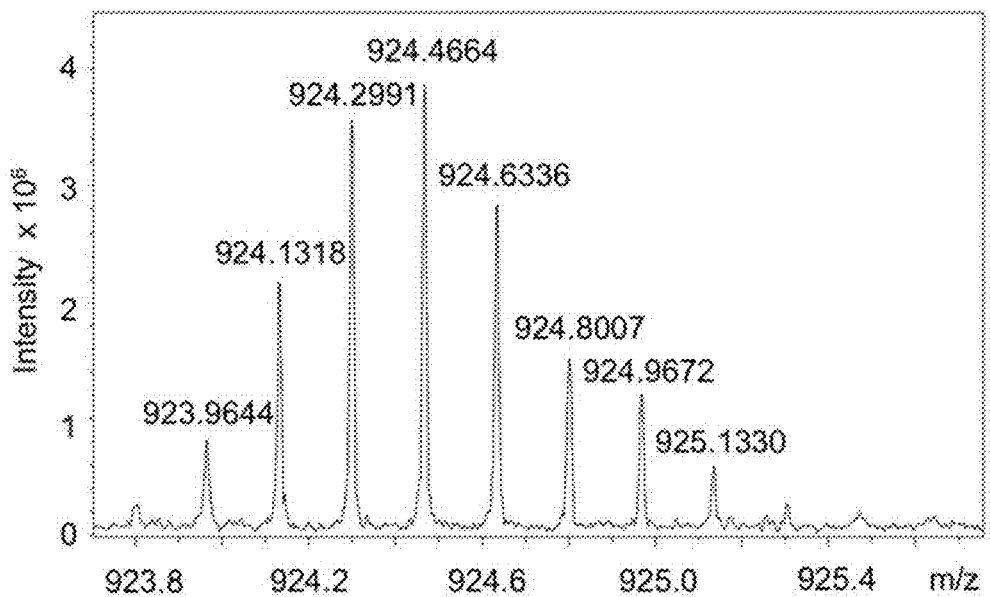
FIG. 13 shows the mass spectrometry ESI-TOF result of $PEG_6$-maleimide-conjugated TCO-peptide 9.

PEG$_6$-maleimide-conjugated TCO-peptide 9 (illustrated below) had a m.w. of 5543.78 daltons (FIG. 13; (ESI-TOF) m/z (z=6): [M+6H]$^+$ Calculated for $C_{244}H_{421}N_{29}O_{101}S_1Na$ 924.297; Found 924.299); it was a linker unit based on PEGylated amino acid and lysine; it carried one coupling arm with a TCO group and five PEG linking arms with maleimide groups.

$$TCO-PEG_3-C-(Xaa_6-\overset{\overset{\displaystyle Mal}{|}\\ \overset{\displaystyle PEG_6}{|}}{K})_5$$

Example 14: Synthesis of Linker Unit with 1,3,5-Triaminobenzene Conjugated with 1 NHS-PEG$_{12}$-Alkyne Linking Arm and 2 NHS-PEG$_{12}$-Maleimide Linking Arms 1,3,5-triaminobenzene was purchased from BOC Sciences, Creative Dynamics Inc., NY, USA, and NHS-PEG$_{12}$-alkyne linking arm and NHS-PEG$_{12}$-maleimide from Thermo Fisher Scientific Inc. Waltham, Mass., USA. The conjugation of the linking arms employed a two-step procedure as shown in scheme 13.

<<Scheme 13 Two-step synthesis of 1,3,5-triaminobenzene conjugated with one NHS—PEG$_{12}$-alkyne linking arm and two NHS—PEG$_{12}$-maleimide linking arms>>

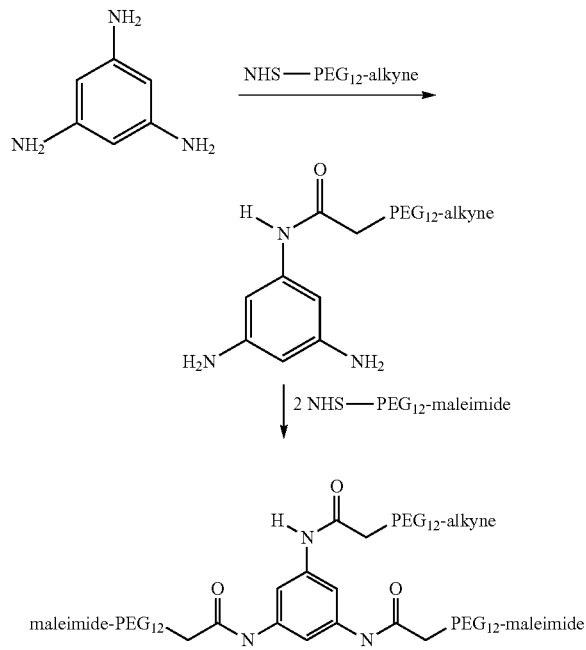

In step (i), 1,3,5-triaminobenzene was dissolved in the conjugation buffer (phosphate buffered saline, PBS, pH7.2) at 1 mM and NHS-PEG$_{12}$-alkyne crosslinker was added to 1,3,5-triaminobenzene solution at 1 mM final concentration (1:1 molar ratio). Thereafter, 4 µl of the 250 mM NHS-PEG$_{12}$-alkyne stock solution was added to 1 ml of 1,3,5-triaminobenzene solution. The reaction mixtures were incubated for 1 hour at room temperature. In step (ii), NHS-PEG$_{12}$-maleimide crosslinker was added to the incubated solution in the step (i) at 10 mM final concentration (1:30 molar ratio). Next, 30 µl of the 250 mM NHS-PEG$_{12}$-maleimide stock solution was added to 125 µl of incubated solution; then 845 µl of the conjugation buffer was added to make the final solution 1 ml. The reaction mixtures were incubated for 2 hours at room temperature.

Figure 14:
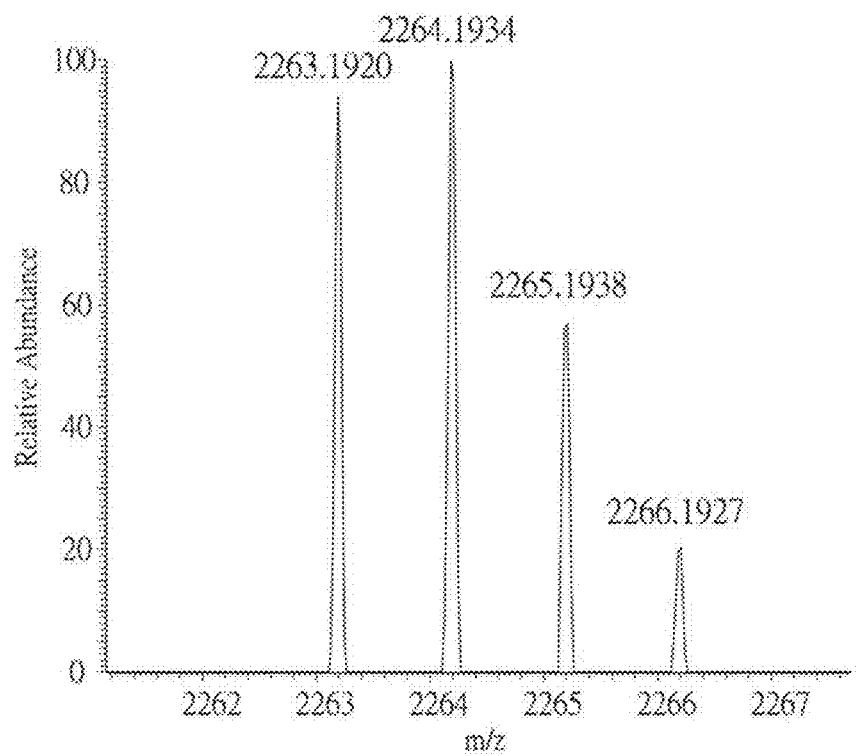
FIG. 14 shows the mass spectrometry ESI-TOF result of 1,3,5-triaminobenzene conjugated with one $NHS-PEG_{12}$-alkyne coupling arm and two $NHS-PEG_{12}$-maleimide linking arms.

The product, 1,3,5-triaminobenzene conjugated with one NHS-PEG$_{12}$-alkyne coupling arm and two NHS-PEG$_{12}$-maleimide linking arms, was purified by subjecting the reaction mixture through reverse phase HPLC column and collecting the fractions containing the linker unit. The product was analyzed by mass spectroscopy ESI (FIG. 14). The data showed (ESI-TOF) m/z: [M+H]$^+$—calculated for $C_{104}H_{108}N_7O_{46}$ 2263.1955; found 2263.1920. The three isotopic peaks were also visible in the MS spectrum at 2264.1934, 2265.1938 and 2266.1927, corresponding to [M+H+1]$^+$, [M+H+2]$^+$ and [M+H+3]$^+$.

Example 15: Conjugation of Five DM1-SMCC Molecules to TCO-Peptide 9

Figure 15:
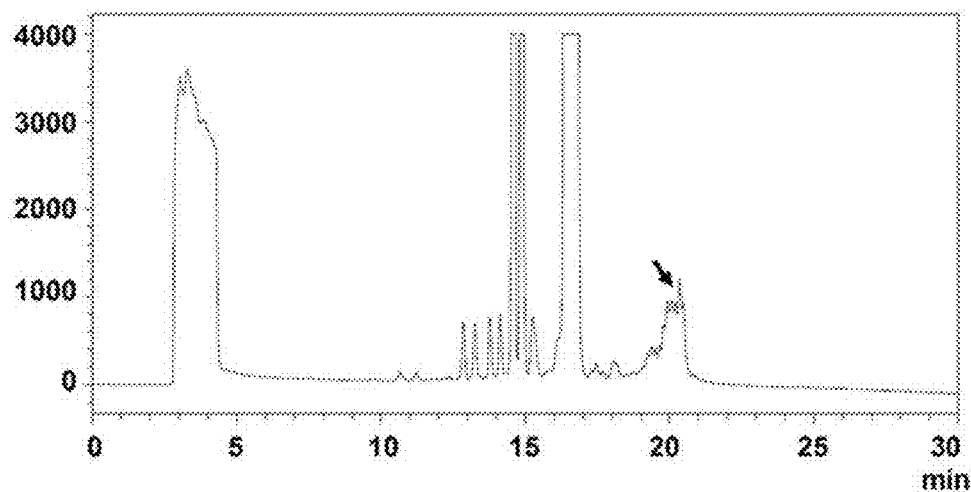
FIG. 15 shows the reverse phase HPLC profile for the purification of TCO-peptide 9 with 5 DM1-SMCC molecules.
Figure 16:
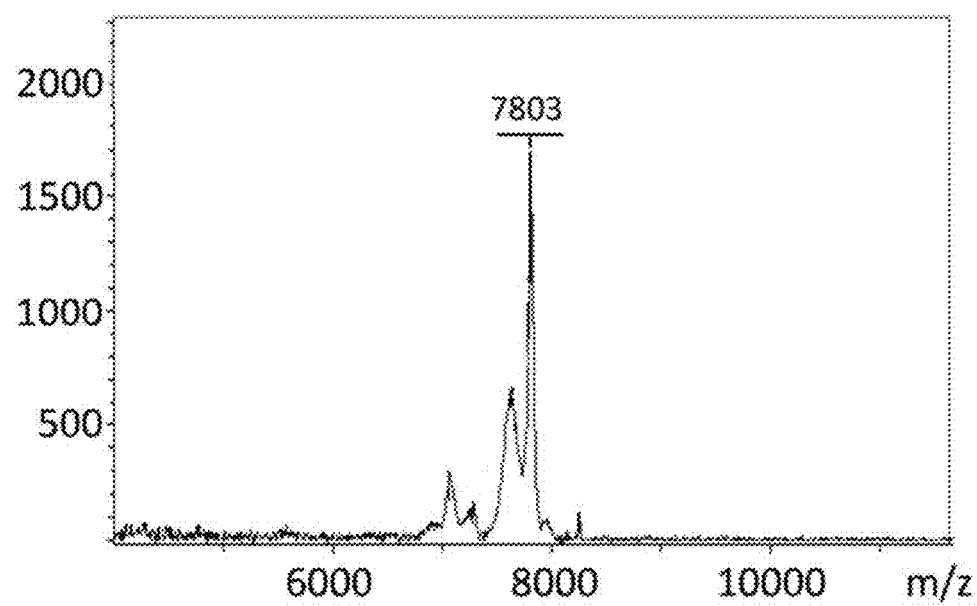
FIG. 16 shows the mass spectrometry result of TCO-peptide 9 with 5 DM1-SMCC molecules.

DM1-SMCC, which was N$_2$'-Deacetyl-N$_2$'-(3-mercapto-1-oxopropyl)-maytansine (DM1) modified by a linker, succinimidyl-4-(N-maleimido-methyl) cyclohexan-1-carboxylate (SMCC), was purchased from ALB Technology Inc., Hong Kong, China. TCO-peptide 9 with free amine groups was dissolved in 100 mM sodium phosphate buffered at pH 7.5. DM1-SMCC was added to the TCO-peptide 9 solution at 1 mM final concentration (25-fold molar excess over the 0.04 mM TCO-peptide 9 solution) by adding 4 µl of the 250 mM DM1-SMCC solution per milliliter of NH$_2$-containing TCO-peptide 9 solution. The reaction mixtures were incubated for 24 hours at room temperature. The reaction product was separated by HPLC and then lyophilized. The TCO-peptide 9 with five DM1-SMCC molecules was purified by reverse phase HPLC on a Supelco C18 column (250 mm×4.6 mm; 5 µm), using a mobile phase of acetonitrile and 0.1% trifluoroacetic acid, a linear gradient of 30% to 100% acetonitrile over 30 minutes, at a flow rate of 1.0 mL/min and a column temperature of 25° C. FIG. 15 shows the reverse phase HPLC profile for the purification of TCO-peptide 9 with five DM1-SMCC molecules (also referred to as a drug bundle); the peak being indicated with an arrow. The mass spectroscopic analysis of the thus-synthesized drug bundle, as provided in FIG. 16, indicated that the molecular construct had a m.w. of 7803 daltons.

The present drug bundle, as illustrated below, was composed of a linker unit with a free TCO functional group and a set of five DM1 molecules as effector elements.

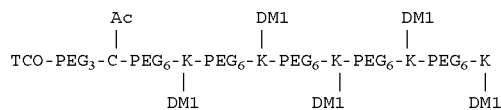

Example 16: Conjugation of LPS Molecules to TCO-Peptide 1

LPS from *Salmonella enterica* sv. Minnesota (Cat No. L2137, Sigma) was chromatographically purified on the Superdex 200 10/300 Tricon column (HR, GE Healthcare) in an ÄKTA Explorer FPLC system. The elution buffer, 50 mM HEPES, pH7.5, was used. The sample was injected and eluted isocratically at 0.5 mL/min and collected in 1-mL fractions. The fractions containing LPS were then dialyzed against MilliQ water using a 3500 MWCO membrane at 4° C. overnight. The dialyzed LPS were lyophilized for subsequent conjugation.

Before the conjugation, the purified LPS was activated as follows. An amount of 1 ml of 2 mg/ml of an aqueous LPS solution was vortexed for 3 min and sonicated for 15 min at 25° C. Then, 1 ml of 4.5 mM sodium deoxycholate (NaDC) was added; 100 µl of 2.5 mM EDTA solution was added. The mixture was stirred for 30 minutes at 37° C., sonicated for 15 minutes, and stirred for another 30 minutes at 37° C. 40 µl of 100 mg/ml 1-cyano-4-dimethylaminopyridinium tetrafluoroborate (CDAP) in acetonitrile was added. After 30 seconds, 40 µl of 0.2M aqueous triethylamine (TEA) was added. The mixture was kept at 25° C. for further 150 seconds with stirring to allow activation of LPS by CDAP.

Figure 17:
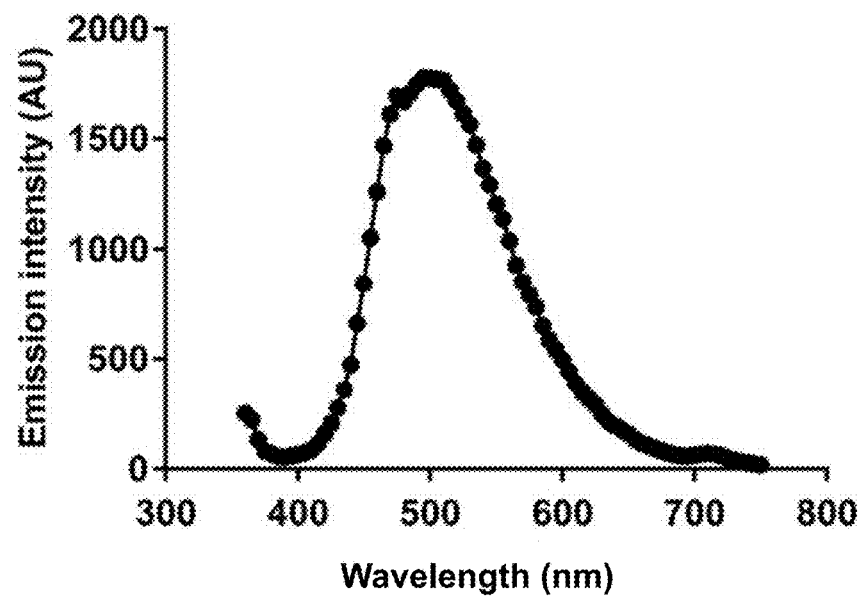
FIG. 17 shows that LPS, upon the reaction with dansyl hydrazine, exhibited an emission maximum at 495 nm in fluorescence spectrophotometric analysis.

LPS derived from *Salmonella enterica* sv. Minnesota was reacted with dansyl hydrazine to introduce a hydrazine group for subsequent coupling with amine group on a linker unit. Briefly, 1 ml of 2.0 mg/ml dansyl hydrazine in 0.1 M sodium borate buffer, pH 9.3, was added to the CDAP-activated LPS. The mixture was left to react overnight in the dark at 25° C. under stirring. The reaction was quenched by adding 100 μl of ethanolamine. The unreacted dansyl hydrazine was removed by dialysis against Milli-Q water using a 3,500 MWCO dialysis membrane for 24 hours at 4° C. in the dark. The sample was characterized using fluorescence spectroscopy by measuring the emission spectra under the excitation at 325 nm. FIG. 17 shows that LPS, upon the reaction with dansyl hydrazine, exhibited an emission maximum at 495 nm in fluorescence spectrophotometric analysis.

The identification of the purified LPS and the dansyl-activated LPS was carried out by mass spectrometry MALDI-TOF. The purified LPS had a m.w. of 3143 daltons; the dansyl-activated LPS had a m.w. of 3651 daltons, indicating one LPS conjugated with two dansyl hydrazine molecules; one dansyl hydrazine molecule had a m.w. of 265 daltons.

The conjugation of LPS molecules to the $NH_2$ groups of the lysine residues of TCO-peptide 1 was performed. Briefly, 0.67 mole of the dansyl-activated LPS was mixed with 0.067 mole of TCO-peptide 1 in 0.1 M sodium bicarbonate buffer, pH 9.5, at room temperature overnight.

The present drug bundle, as illustrated below, was composed of a linker unit with a free TCO functional group and a set of two LPS molecules as effector elements.

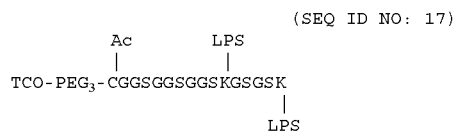

(SEQ ID NO: 17)

The present drug bundle, as illustrated below, was composed of a linker unit with a free TCO functional group and a set of five imiquimod molecules as effector elements.

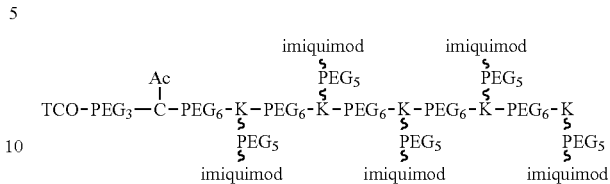

Example 18: Conjugation of DOTA-NHS to TCO-Peptide 9

DOTA-NHS (1,4,7,10-tetraazacyclododecane-1,4,7,10-tetraacetic acid N-hydroxy-succinimide ester) was purchased from Macrocyclics, Inc. Dallas, USA. Conjugation of DOTA-NHS to TCO-peptide 9 employed a two-step procedure as illustrated in Scheme 14. In the first step, TCO-peptide 9 was dissolved in the conjugation buffer (phosphate buffered saline, PBS, with 5 mM EDTA pH 7.0) at 1 mM. The reaction mixtures were incubated for overnight at room temperature. In the second step, the DOTA-NHS ester was added to the incubated solution at 100 mM final concentration (1:100 molar ratio or 1:20 equivalent ratio). Since the DOTA-NHS ester was acidic because of containing TFA, the pH of the solution was adjusted to 8.0 in order to activate the NHS ester-$NH_2$ coupling reaction. The reaction mixtures were incubated overnight at room temperature.

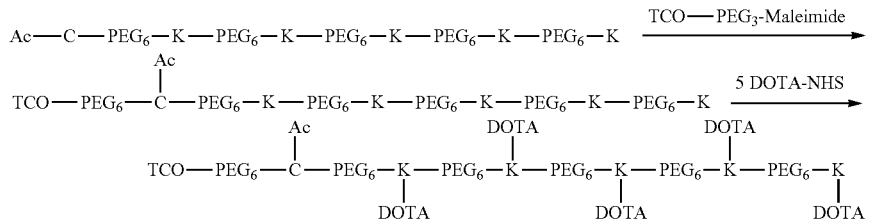

Scheme 14 Two-step procedure for conjugation of DOTA-NHS to TCO-peptide 9

Example 17: Conjugation of a Imiquimod Molecule with NHS-PEG6-Maleimide-Conjugated TCO-Peptide 9

Figure 18:
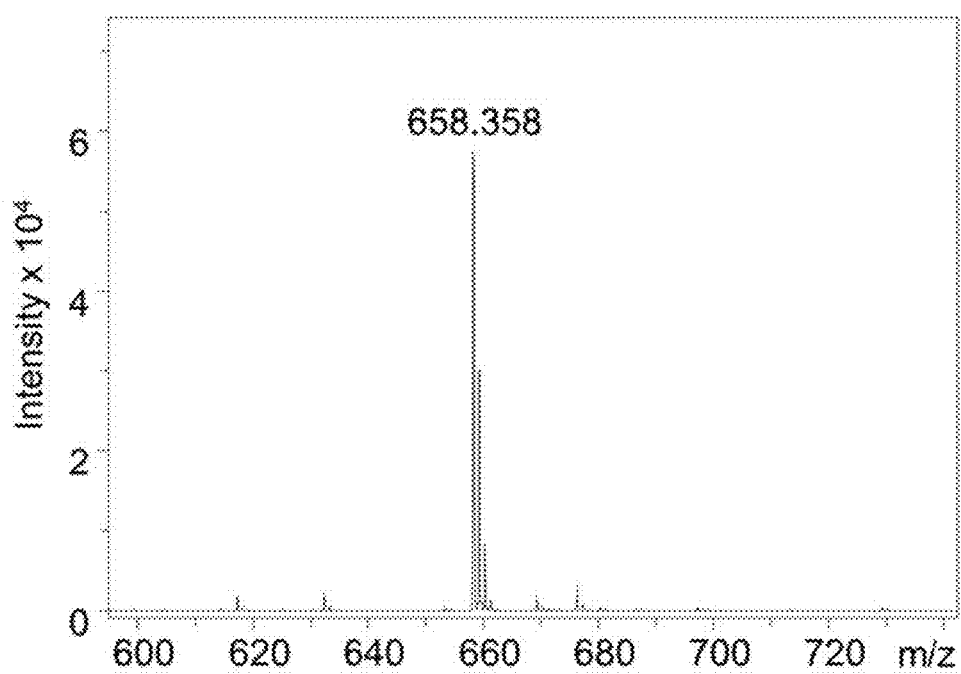
FIG. 18 shows mass spectrometric analysis of $PEG_5$-NHS conjugated with imiquimod.

The $NH_2$ group of the imiquimod molecule was reacted with a homo-bifunctional crosslinker, NHS-PEG5-NHS (Conju-probe Inc.) at a 1:3.5 molar ratio. Mass spectrometric analysis shows that PEG5-NHS conjugated with imiquimod had a m.w. of 658.36 daltons (FIG. 18).

The product, imiquimod-PEG5-NHS, was purified by HPLC to remove the excess, unreacted crosslinkers. TCO-peptide 9 and imiquimod-PEG5-NHS were then mixed in 100 mM sodium phosphate buffer at pH 7.5 at 25° C. for 18 hours. Mass spectrometric analysis shows that the drug bundle with imiquimod had a m.w. of 5135 daltons.

Figure 19A:
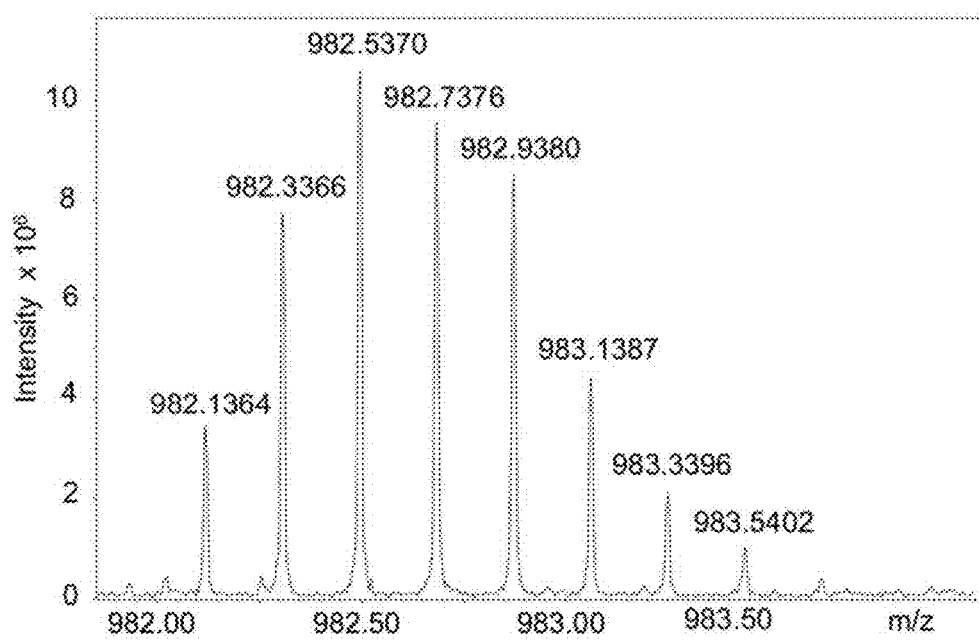
FIG. 19A shows mass spectrometry ESI-TOF result of DOTA-conjugated TCO-peptide 9.
Figure 19B:
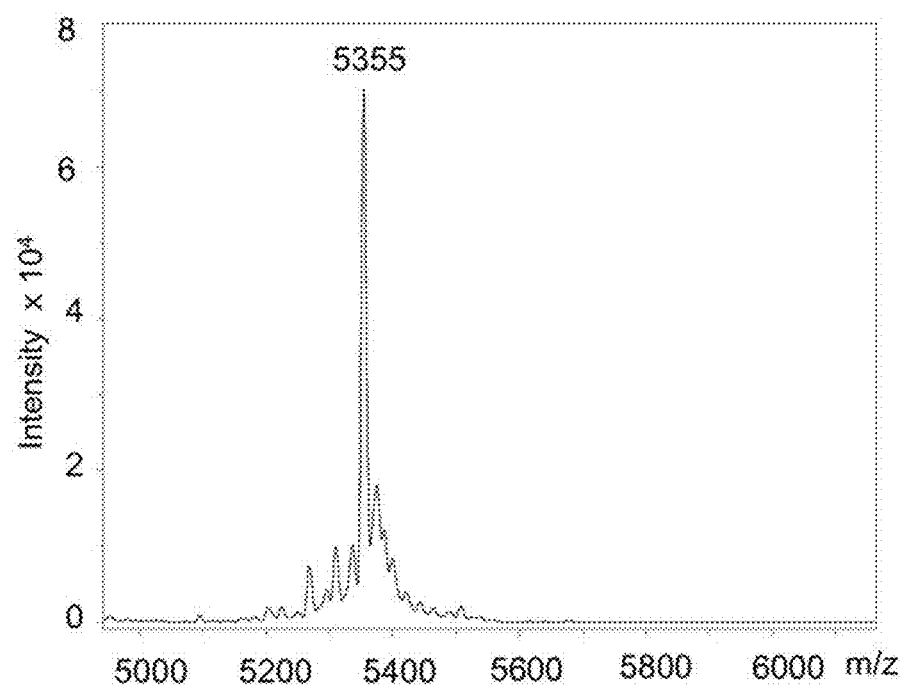
FIG. 19B shows the mass spectrometric result of $Y^{3+}$-chelated, DOTA-conjugated TCO-peptide 9.

According to the data in FIG. 19A, the present molecular construct had a m.w. of 4907.685; (ESI-TOF) m/z (z=5): $[M+3H]^+$; calculated for $C_{214}H_{38}N_{39}O_{86}S_1$ 982.5358; found 982.5370.

Example 19: Chelation of Yttrium Atoms by DOTA-Conjugated Linker Unit Based on TCO-Peptide 9

Scheme 15 shows the chelation of five $Y^{3+}$ ions by DOTA-conjugated TCO-peptide 9. Herein, $Y(NO_3)_3$ solution was added to the reaction mixtures at a 1:100 molar ratio, incubated for 2 hours at room temperature. Free DOTA-NHS and $Y^{3+}$ ions were removed from reaction mixtures by using NAP-10 Sephadex G-25 column.

<<Scheme 15 Chelation of Yttrium atom by DOTA-conjugated TCO-peptide 9>>
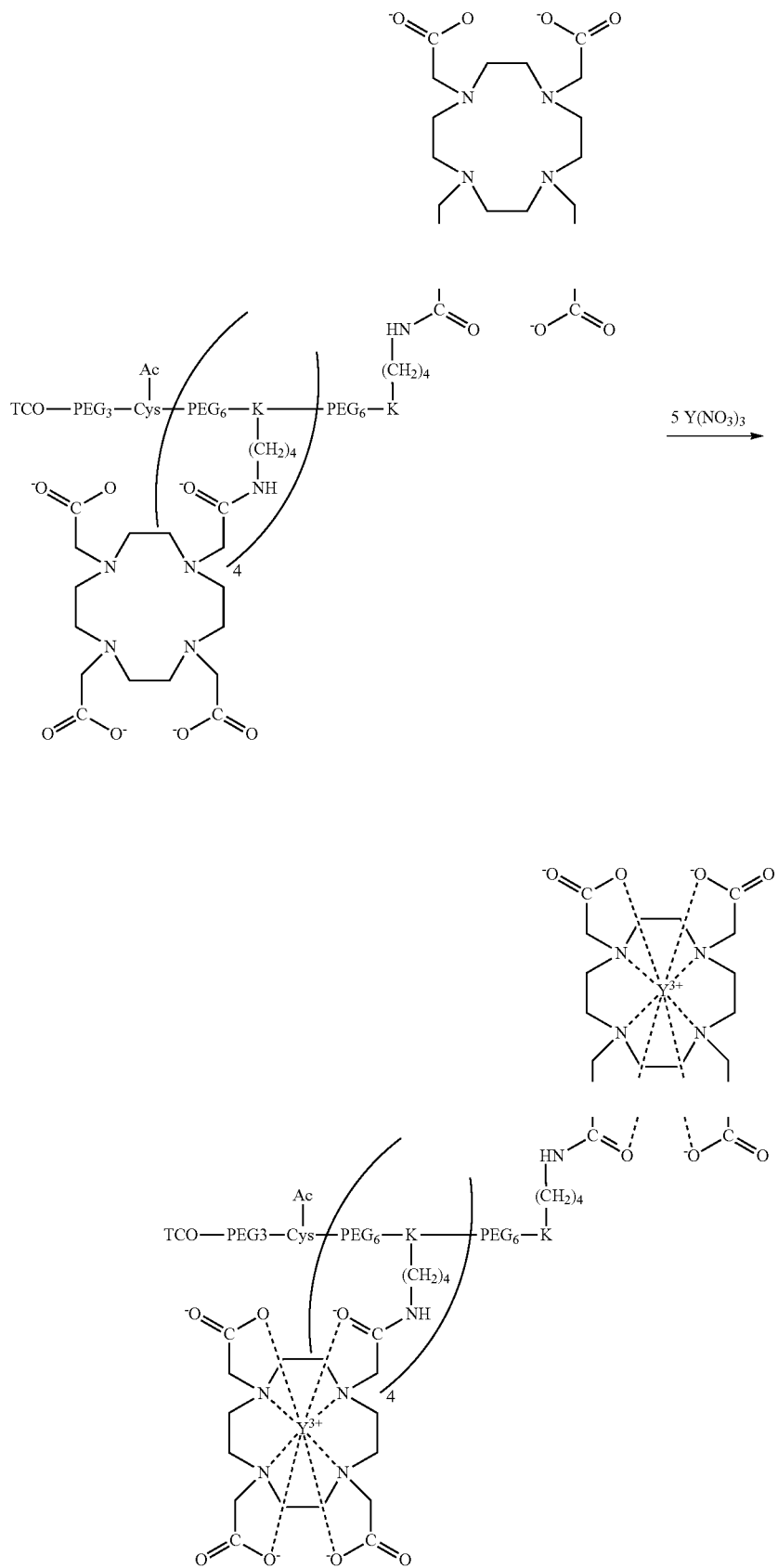

DOTA-conjugated TCO-peptide 9 with bound $Y^{3+}$ ions was analyzed by mass spectroscopy MALDI-TOF. Mass spectrometric analysis shows that the sample of DOTA-conjugated TCO-peptide 9 with bound $Y^{3+}$ ions had a m.w. of 5355 daltons (FIG. 196).

Illustrated below is the present drug bundle, which was composed of a linker unit with a free TCO functional group and a set of five DOTA groups respectively chelating an $Y^{3+}$ ion as effector elements.

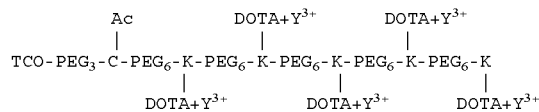

Example 20: Isolation of $V_H$ and $V_L$ Sequences from Hybridoma Cell Lines Producing Monoclonal Antibodies Respectively Specific for Human CD79a, CD79b, and Collagen VII for the Preparation of scFv Mouse B cell hybridoma 24C10 producing anti-CD79a antibody and hybridoma 1F10 producing anti-CD79b antibody were generated in our laboratory employing standard hybridoma methodology. The mouse hybridoma line LH7.2 specific for human collagen VII was a gift from Prof. Irene M. Leigh, University of Dundee, U. K. Poly(A)+RNA was reverse-transcribed with a SuperScript III RT-PCR system (Invitrogen, Carlsbad, USA), and the first strand cDNA was synthesized. To determine the sequence of variable region of 24C10, 1F10, and LH7.2, cDNA of $V_H$ and $V_L$ were amplified by PCR using a set of DNA primers provided by Ig-primer Sets (Novagen, Madison, USA) according to the manufacturer's instructions. The sequences of $V_H$ and $V_L$ for all clones were determined.

The cDNA sequences of $V_H$ and of $V_L$ of mouse anti-human CD79a monoclonal antibody clone 24C10 are indicated in SEQ ID NO: 27 and SEQ ID NO: 28, respectively; the cDNA sequences of $V_H$ and of VdL of mouse anti-human CD79b monoclonal antibody clone 1F10 are indicated in SEQ ID NO: 29 and SEQ ID NO: 30, respectively; the cDNA sequences of $V_H$ and of $V_L$ of mouse anti-human collagen VII monoclonal antibody clone LH7.2 are indicated in SEQ ID NO: 31 and SEQ ID NO: 32, respectively.

Example 21: Preparation of scFv Specific for Human CD79b or Collagen VII

To produce the scFv of anti-CD79b antibody 1F10 (SEQ ID NO: 33) and scFv of anti-human collagen VII antibody LH7.2 (SEQ ID NO: 34), DNA sequences encoding $V_L$-GSTSGSGKPGSGEGSTKG (i.e., SEQ ID NO: 50)-$V_H$-(GGGGS)$_2$ (i.e., SEQ ID NO: 6)-C were synthesized. A flexible linker (GGGGS)$_2$ (SEQ ID NO: 6) and a cysteine residue were installed at the C-terminus of the scFv, so that the modified scFv could be subsequently linked to the maleimide group of linking arms in various linker units of this invention.

Figure 20A:
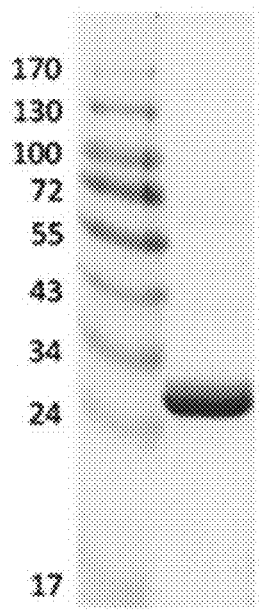
FIGS. 20A and 20B respectively show SDS-PAGE and ELISA analysis of purified scFv proteins of anti-CD79b antibody 1F10.
Figure 20B:
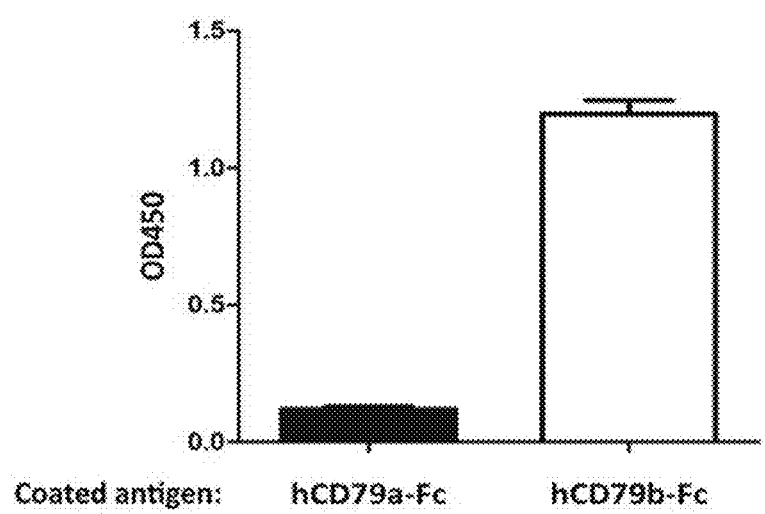
Figure 20C:
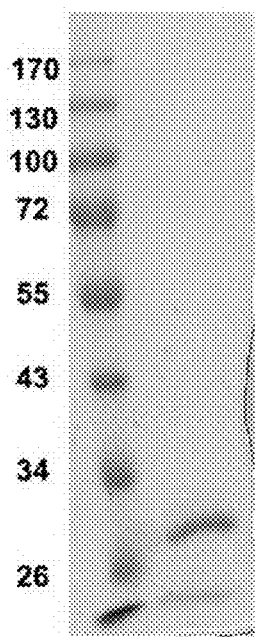
FIG. 20C and FIG. 20D respectively show SDS-PAGE and ELISA analysis of purified scFv proteins of anti-collagen VII antibody LH7.2.
Figure 20D:
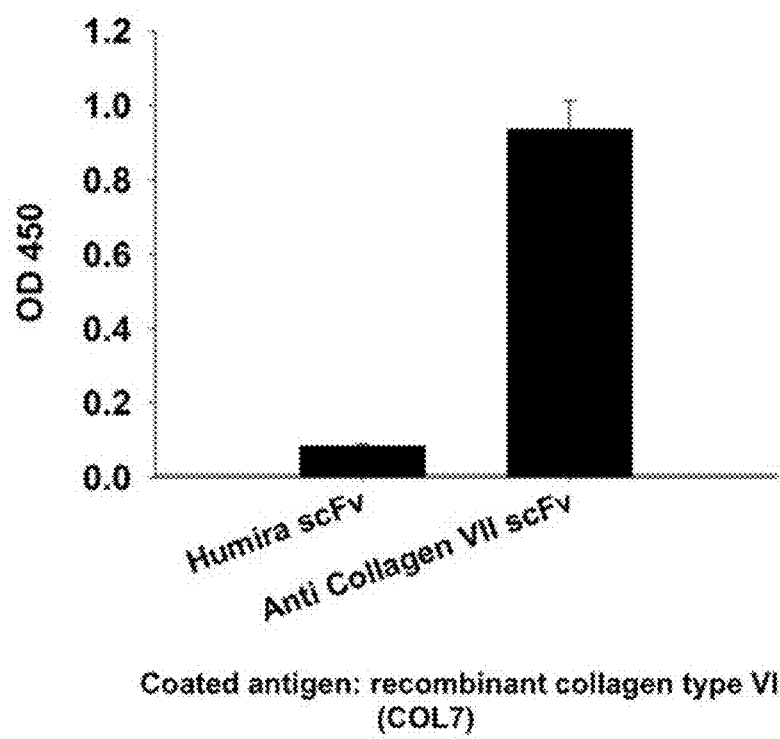

The scFv-encoding sequence was placed in pG1K expression cassette. Expi293F cells were seeded at a density of $2.0 \times 10^6$ viable cells/ml in Expi293F expression medium and maintained for 18-24 hours prior to transfection to ensure that cells were actively dividing at the time of transfection. On the day of transfection, $7.5 \times 10^8$ cells in 255 ml medium in a 2-liter Erlenmeyer shaker flask were transfected by ExpiFectamine™ 293 transfection reagent. The transfected cells were incubated at 37° C. for 16 to 18 hours post-transfection in an orbital shaker (125 rpm) and the cells were added ExpiFectamine™ 293 transfection enhancer 1 and enhancer 2 to the shaker flask, and incubated for another 6 days. Culture supernatants were harvested and scFv proteins in the media were purified using Protein L affinity chromatography. FIGS. 20A and 20B respectively showed SDS-PAGE and ELISA analysis of purified scFv proteins of anti-CD79b antibody 1F10. FIG. 20C and FIG. 20D respectively showed SDS-PAGE and ELISA analysis of purified scFv proteins of anti-collagen VII antibody LH7.2.

Example 22: Production of scFv of Trastuzumab, Rituximab, Centuximab, Nivolumab, Ipilimumab, Ranibizumab, Adalimumab, and Mutated Teplizumab by HEK293 Overexpression System The scFv derived from those antibodies were designed to contain a flexible linker of (GGGGS)$_2$ (SEQ ID NO: 6) and a terminal cysteine residue at the C-terminus. The cysteine residue provides a sulfhydryl group for conjugation with maleimide group present at the free ends of linking arms in various linker units. To produce the scFv of trastuzumab, rituximab, centuximab, nivolumab, ipilimumab, ranibizumab, adalimumab, and a mutated teplizumab, we used the $V_H$ and $V_L$ DNA sequences of those humanized antibodies without further codon optimization. DNA sequences encoding $V_L$-GSTSGSGKPGSGEGSTKG (i.e., SEQ ID NO: 50)-$V_H$-(GGGGS)$_2$ (i.e., SEQ ID NO: 6)-C were synthesized. The teplizumab antibody molecule contains a cysteine residue in CDR3 of $V_H$, which interferes with SH-maleimide conjugation explained above. We therefore prepared a mutated teplizumab substituting the cysteine residue with a serine residue. The amino acid sequences of the scFv of trastuzumab, rituximab, centuximab, nivolumab, ipilimumab, ranibizumab, adalimumab, and the mutated teplizumab, prepared for the experiments of this invention are set forth in SEQ ID NOs: 35 to 42, respectively.

For preparing scFv proteins using mammalian expression systems, we used the overexpression system based on Expi293F™ cell line for preparing 10-500 mg of scFv for experimentation. The yields were sufficient for preparing various constructs involving a specific scFv for in vitro tests and rodent animal models. The system employed Expi-Fectamine™ 293 transfection kit (Life Technologies, Carlsbad, USA) consisting of the Expi293F™ cell line, the cationic lipid-based ExpiFectamine™ 293 Reagent and ExpiFectamine™ 293 transfection Enhancers 1 and 2, and the medium (Gibco, New York, USA).

Figure 21A:
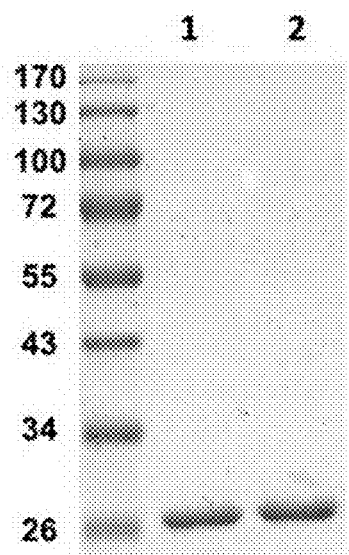
FIG. 21A shows SDS-PAGE analysis of purified scFv of trastuzumab and adalimumab.
Figure 21B:
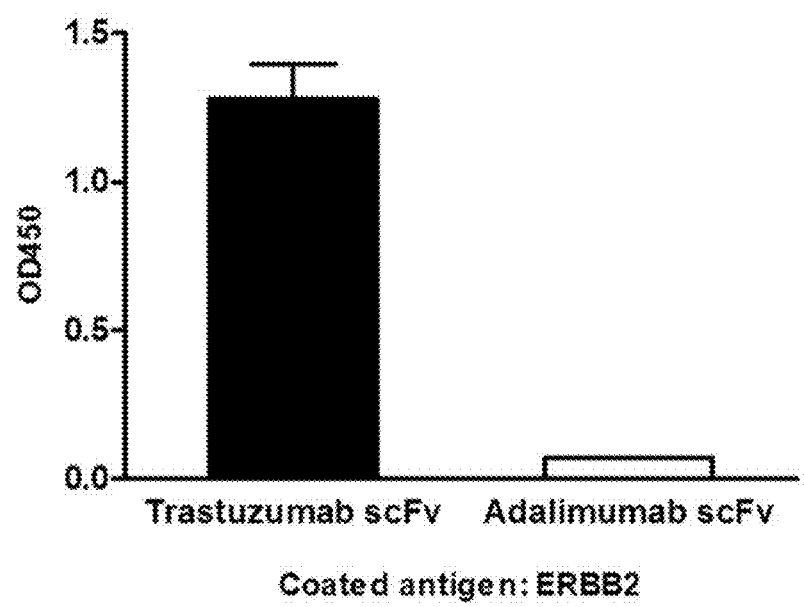
FIGS. 21B and 21C respectively show ELISA analyses of purified scFv of trastuzumab and adalimumab.
Figure 21C:
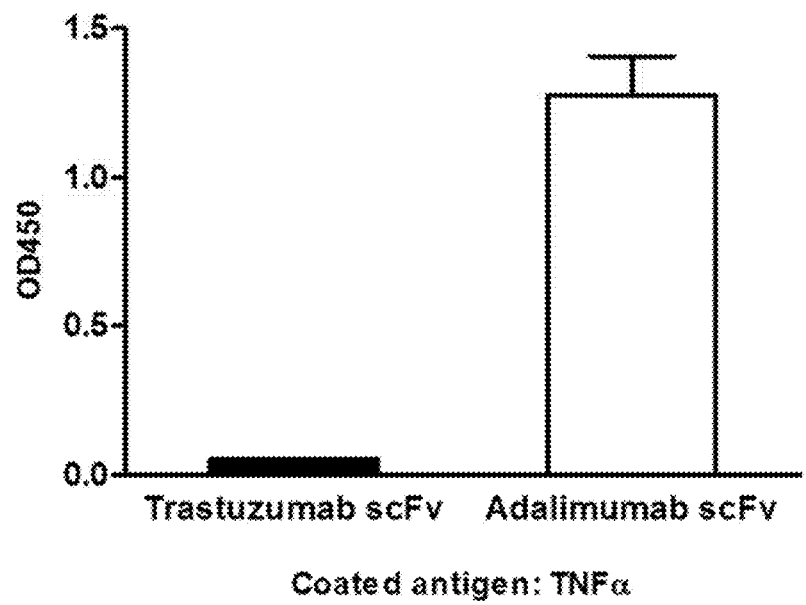
Figure 21D:
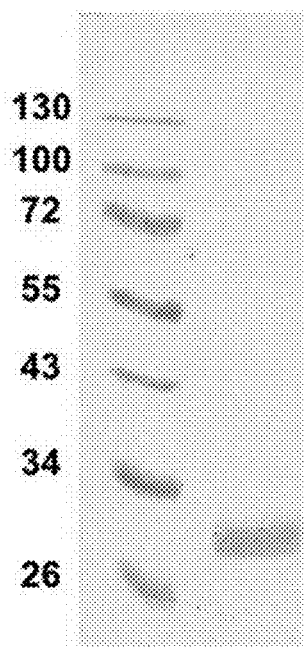
FIGS. 21D and 21E respectively show SDS-PAGE and ELISA analyses of purified scFv of centuximab.
Figure 21E:
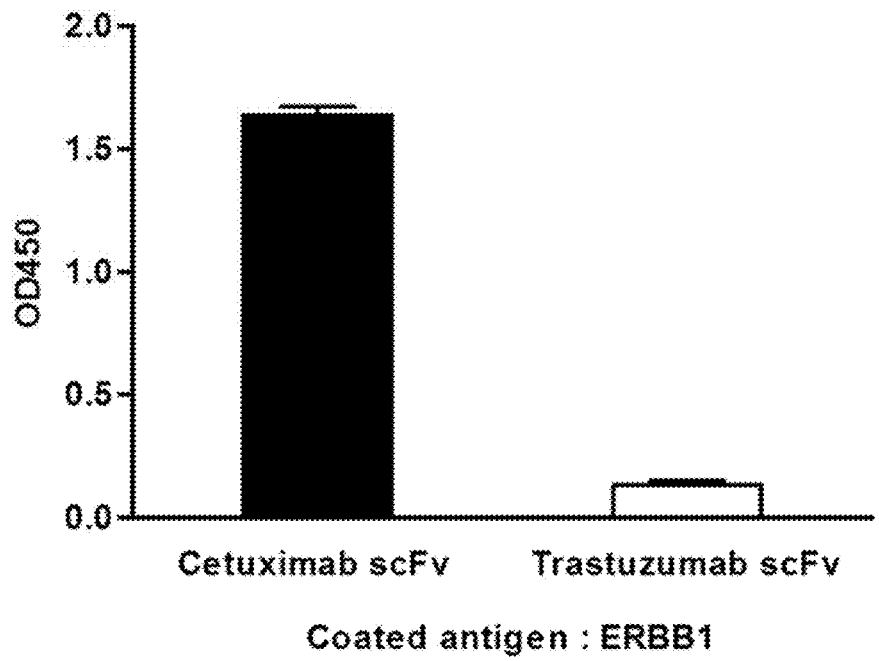

The scFv-encoding sequence was placed in pG1K expression cassette. Expi293F cells were seeded at a density of $2.0 \times 10^6$ viable cells/ml in Expi293F expression medium and maintained for 18 to 24 hours prior to transfection to ensure that the cells were actively dividing at the time of transfection. On the day of transfection, $7.5 \times 10^8$ cells in 255 ml medium in a 2-liter Erlenmeyer shaker flask were transfected by ExpiFectamine™ 293 transfection reagent. The transfected cells were incubated at 37° C. for 16 to 18 hours post-transfection in an orbital shaker (125 rpm) and the cells were added ExpiFectamine™ 293 transfection enhancer 1 and enhancer 2 to the shaker flask, and incubated for another 5 to 6 days. Culture supernatants were harvested and scFv proteins in the media were purified using Protein L affinity chromatography. In our experience with adalimumab and trastuzumab scFv proteins, over 300 mg of purified scFv could be obtained from the 1 liter culture. FIG. 21A shows SDS-PAGE (10%) analysis of purified scFv of trastuzumab (lane 1) and adalimumab (lane 2), while FIGS. 21B and 21C respectively showed ELISA analyses of purified scFv of trastuzumab and adalimumab. FIGS. 21D and 21E respectively showed SDS-PAGE and ELISA analyses of purified scFv of centuximab, in which the trastuzumab scFv (anti-HER2 scFv) was used as a negative control.

Example 23: Production of scFv of Adalimumab by an Yeast *Pichia* Expression System The intended scFv constructs were the same as in the preceding Example, while the signal peptides used were different.

DNA sequence of scFv of adalimumab was synthesized and subcloned using primers (forward 5'-GTATCTCTCGA-GAAAAGAGATATTCAGATGACGCAATCCCC-3' (SEQ ID NO: 43) and reverse 5'-GTATCTGCGGCCGCT-TAACAGGAGCCACCGCCAC-3' (SEQ ID NO: 44)) containing XhoI and NotI restriction sites into pPICZα expression vector, in which the Kex2 signal peptide allowed for extracellular secretion of scFv of adalimumab. The expression plasmid was then transformed into *Pichia pastoris* by electroporation. To screen for high yield clones, ELISA was performed to measure the expression levels of scFv of adalimumab. Out of 480 transformants, five were selected for further protein induction and examination by SDS-PAGE. The clone scFv_1-A2 was selected for subsequent large-scale fermentation.

The high-yield clone scFv_1-A2 was inoculated in 100 mL of buffered glycerol-complex medium (BMGY, containing 1% yeast extract, 2% peptone, 100 mM $K_3PO_4$, 1.34 YNB, 0.4 mg/L biotin and 1% glycerol, pH 6.0) and cultured at 30° C., 200 rpm for 24 hours. On the next day, the culture was changed to a fermentation condition maintaining at 30° C., 30% of dissolved oxygen and pH 6.0. After being fermented for 24 hours, nitrogen source (YE, peptone) and methanol (0.5%, v/v) was added to induce protein expression. The culture supernatant was harvested for protein purification.

Figure 22A:
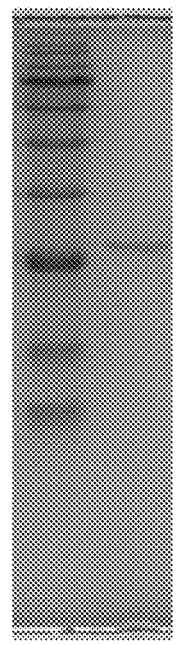
FIG. 22A shows SDS-PAGE analysis of the purified scFv of adalimumab.
Figure 22B:
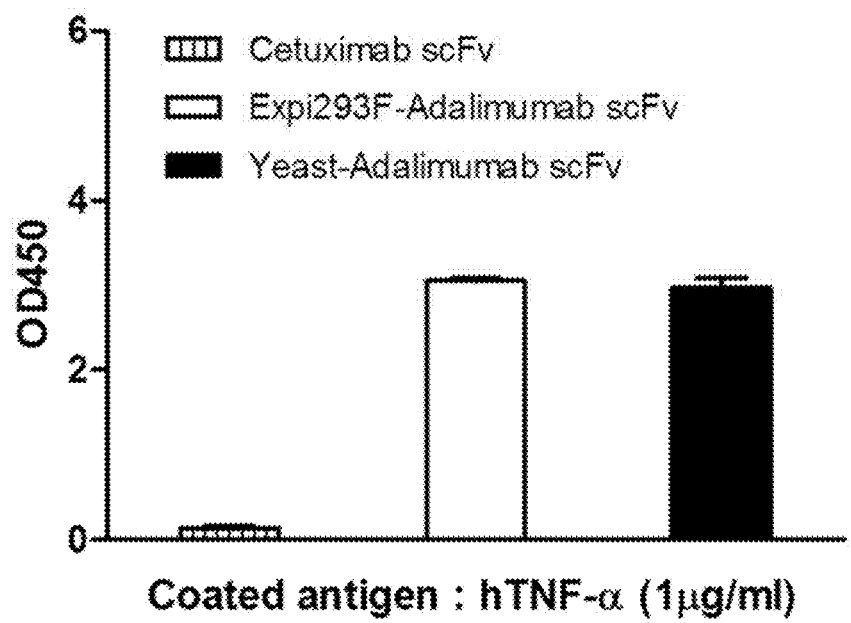
FIG. 22B shows ELISA analysis of the purified scFvs of adalimumab.

A mass spectrometric analysis showed that the scFv had a m. w. of 27296.28 daltons. FIG. 22A shows SDS-PAGE analysis of the purified scFv of adalimumab, and FIG. 22B shows ELISA analysis of the purified scFvs of adalimumab. The size of the scFv was as expected and the yeast-produced scFv of adalimumab bound to human TNF-α equally well as Expi-293F-produced scFv of adalimumab.

Example 24: Preparation of CCK Analogue

The peptide analogue of CCK (CGGGGSDY($SO_4H$)L(N)GWL(N)DF-$NH_2$; SEQ ID NO: 45) was designed to be composed of an 8-amino acid segment of CCK with three unusual amino acid residues and a consecutive N-terminal extension of six amino acid residues (CGGGGS) with a cysteine residue at the terminal. The tyrosine residue (Y) was sulfated at its OH group on the aromatic ring and L(N) was a norleucine residue. The cysteine residue provided an SH group for conjugation with PEG-maleimide linking arms of the linker unit according to the present disclosure. The peptide was custom-synthesized by Kelowna Inc., Taipei, Taiwan.

Example 25: Preparation of TCO- and DBCO-scFv Specific for CD3

The DNA sequence encoding SEQ ID NO: 42 was synthesized and expressed as in the above Examples. The sequences of $V_L$ and $V_H$ of scFv specific for CD3 were those of $V_L$ and $V_H$ of mutated Teplizumab. For the conjugation with Mal-$PEG_3$-TCO and Mal-$PEG_5$-DBCO (Conju-probe, Inc.), the cysteine residue at the C-terminal end of the purified scFv of the mutated teplizumab was reduced by incubating 5 mM DTT at room temperature for 4 hours with gentle shaking. The buffer of reduced anti-CD3 scFv was exchanged to sodium phosphate buffer (100 mM sodium phosphate, pH7.0, 50 mM NaCl, and 5 mM EDTA) by using NAP-10 Sephadex G-25 column. After the reduction reaction and buffer exchange, conjugation was conducted overnight at room temperature in a reaction molar ratio of 1:1 ([Mal-$PEG_3$-TCO or Mal-$PEG_5$-DBCO:[scFv]]. The excess crosslinker was removed by a desalting column and the TCO-conjugated and DBCO-conjugated scFv products were analyzed.

Figure 23A:
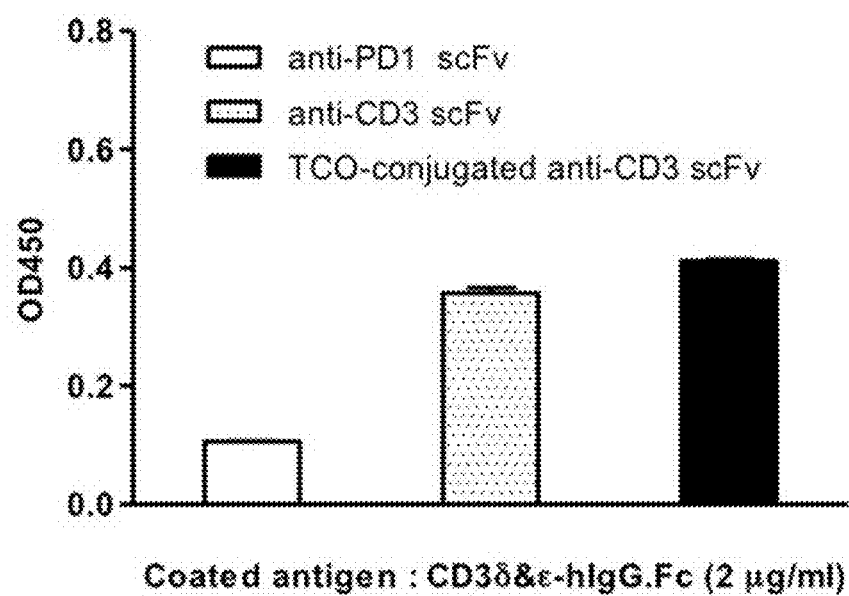
FIG. 23A and FIG. 23B show, respectively, the ELISA analysis of TCO-conjugated scFv and DBCO-conjugated scFv specific for CD3.
Figure 23B:
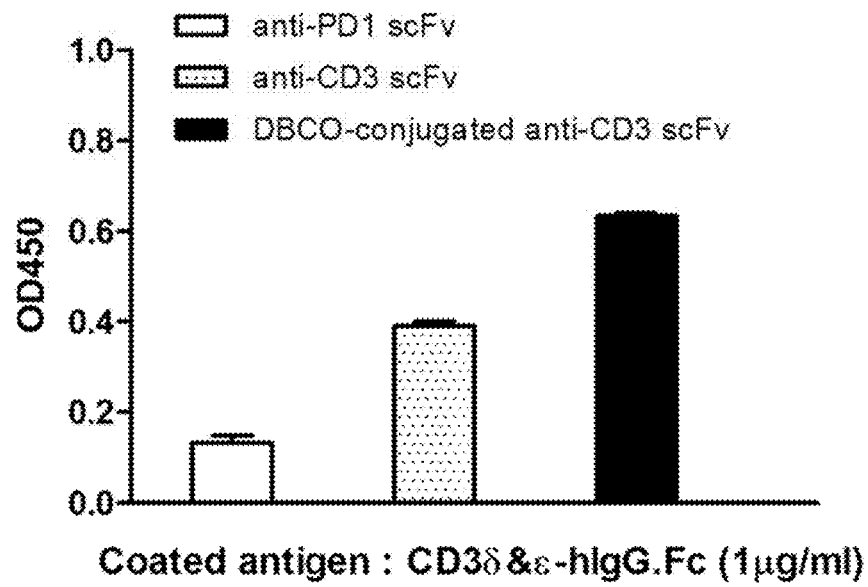

The results of mass spectroscopy MALDI-TOF analysis indicated that the sample of TCO-conjugated scFv specific for CD3 had a m.w. of 28053 daltons; while the sample of DBCO-conjugated scFv specific for CD3 had a m.w. of 28178 daltons. The purity of TCO-conjugated scFvs specific for CD3 was identified through Coomassie staining of 12% SDS-PAGE (data not shown). FIG. 23A and FIG. 23B show, respectively, the ELISA analysis of TCO-conjugated scFv and DBCO-conjugated scFv specific for CD3, in which anti-PD1 scFv and anti-CD3 scFv were used as a negative control and positive control, respectively. According to the ELISA results, both TCO-conjugated scFv and DBCO-conjugated scFv specific for CD3 bound to CD3-Fc-fusion protein.

Example 26: Conjugation of Three scFvs Specific for CD79b to Three $PEG_{12}$-Maleimide Linking Arms Based on Tetrazine-Peptide 2

This example aimed to demonstrate that three scFvs could be conjugated to the three $PEG_{12}$-maleimide linking arms based on tetrazine-peptide 2. Prior to conjugation with the tetrazine-peptide 2 that had three $PEG_{12}$-maleimide linking arms, 1F10 scFv was incubated with DTT at a molar ratio of 2:1 ([DTT]:[scFv]) at 25° C. for 4 hours with gentle shaking to keep its C-terminal cysteine in reduced form. Subsequently, the buffer of reduced 1F10 scFv was exchanged to maleimide-SH coupling reaction buffer (100 mM sodium phosphate, pH 7.0, 50 mM NaCl and 5 mM EDTA) by using an NAP-10 Sephadex G-25 column (GE Healthcare). After the reduction and buffer exchange, the conjugation to the tetrazine-peptide 2 having three $PEG_{12}$-maleimide linking arms was conducted overnight at 4° C. at a molar ratio of 1:4 ([linker]:[Protein]).

Example 27: Purification of the Targeting Linker Unit Containing Three scFvs Specific for CD79b Linked to the Three $PEG_{12}$-Maleimide Linking Arms Based on Tetrazine-Peptide 2

Figure 24A:
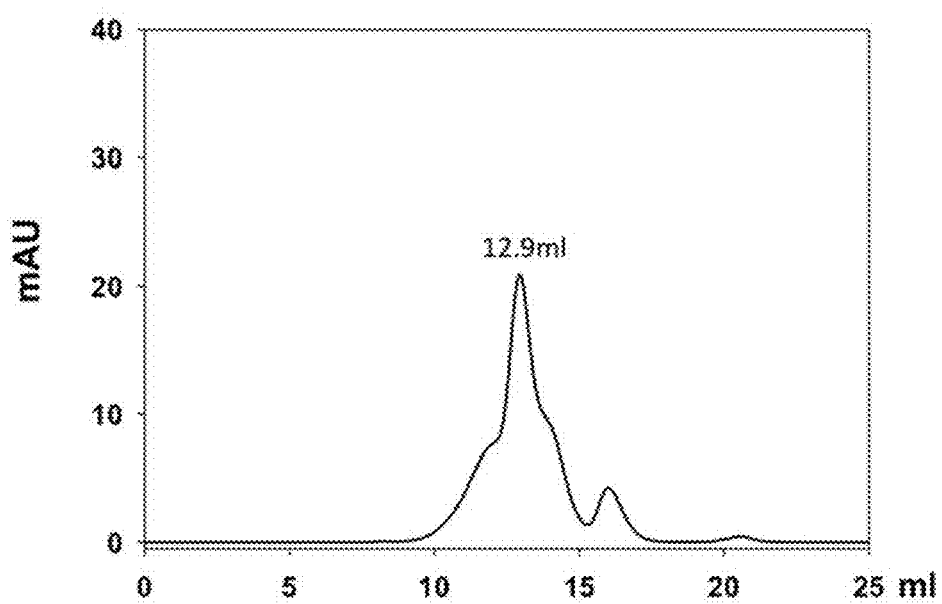
FIG. 24A is the FPLC elution profile on a synthesized linker unit composed of a free tetrazine functional group and a set of three scFvs specific for human CD79b.
Figure 24B:
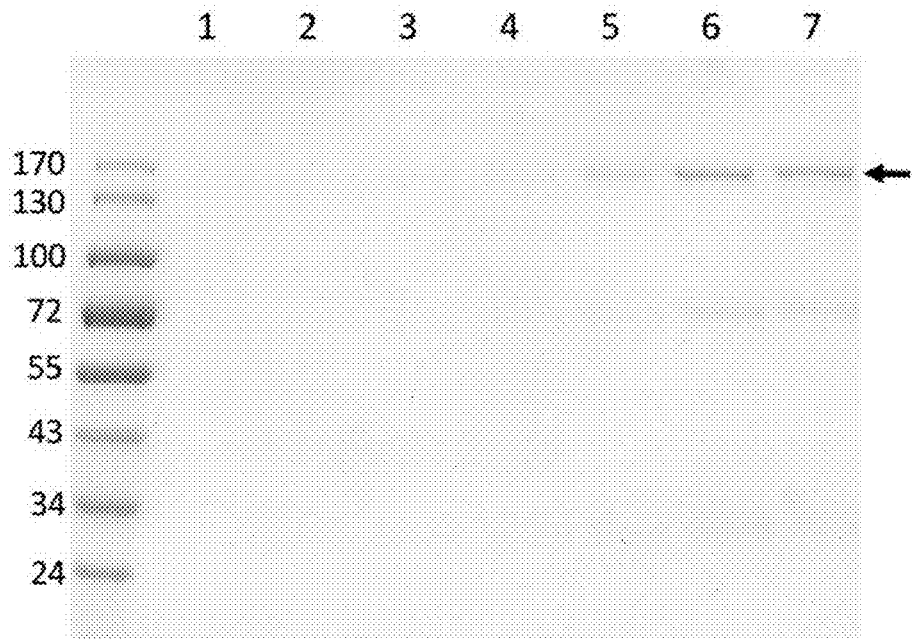
FIG. 24B shows the SDS-PAGE analysis result.

The reaction mixture of the preceding example was applied to a size exclusion chromatography column S75. The $PEG_{12}$-maleimide-conjugated tetrazine-peptide 2 conjugated with three scFvs specific for CD79b was separated from the free scFv, free $PEG_{12}$-maleimide-conjugated tetrazine-peptide 2 and the $PEG_{12}$-maleimide-conjugated tetrazine-peptide 2 conjugated with 1 and two scFvs specific for CD79b by size exclusion chromatography column S75. FIG. 24A was the FPLC elution profile on a synthesized targeting linker unit composed of a linker unit with a free tetrazine functional group and a set of three scFvs specific for human CD79b as targeting elements. The product (i.e., the PEG$_{12}$-maleimide-conjugated tetrazine-peptide 2 having a free tetrazine functional group and being conjugated with a set of three scFvs specific for CD79b) was purified in the elution fractions and shown in lane 5 to 7 of the 10% SDS-PAGE analysis shown in FIG. 24B.

Figure 24C:
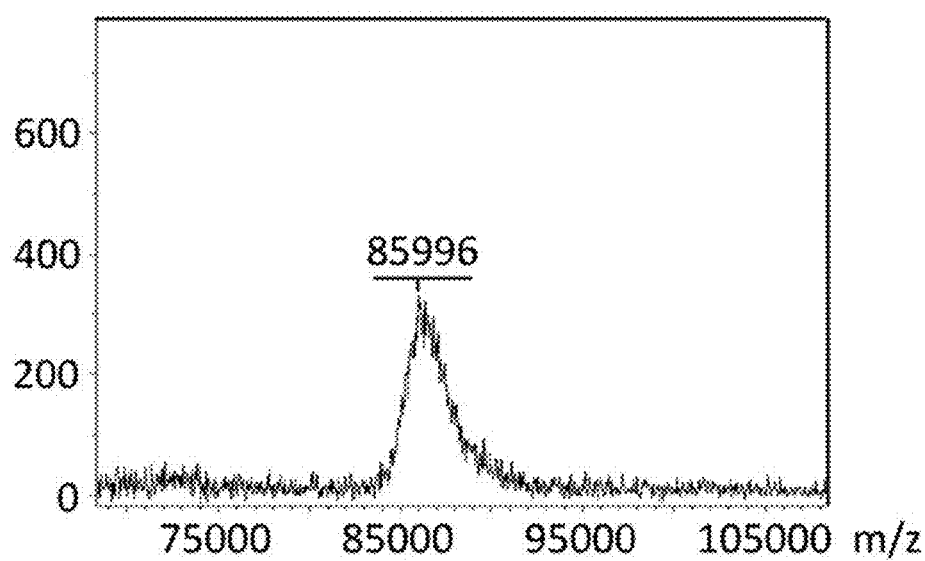
FIG. 24C shows the mass spectrometry MALDI-TOF result.

Example 28: Analysis of Targeting Linker Unit Containing Three scFvs Specific for CD79b Linked to the Three PEG$_{12}$-Maleimide Linking Arms Based on Tetrazine-Peptide 2 by Mass Spectrometry MALDI-TOF The sample of the targeting linker unit of three scFvs specific for CD79b linked to the three PEG$_{12}$-maleimide linking arms based on tetrazine-peptide 2 was confirmed by using mass spectrometry MALDI-TOF. The median of experimental molecular weight was consistent with the median of theoretical molecular weight of three 1F10 scFv conjugated to tetrazine-peptide 2 with three PEG$_{12}$-maleimide linking arms. According to the mass spectrometric profile in FIG. 24C, the present targeting linker unit had the median molecular weight of 85996 daltons. Illustrated below is the present targeting linker unit that was composed of a linker unit with a free tetrazine functional group and a set of three scFvs specific for human CD79b as targeting elements.

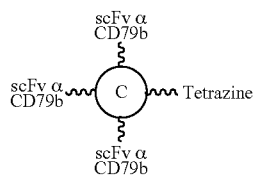

Figure 25A:
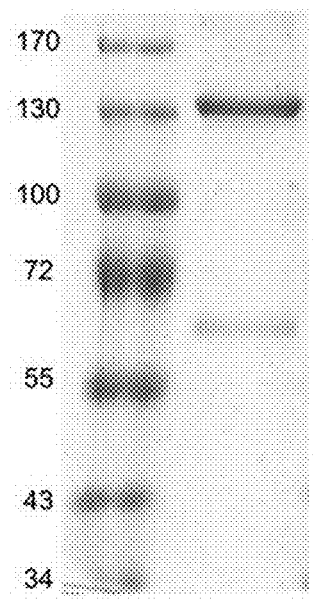
FIG. 25A and FIG. 25B respectively show the SDS-PAGE and mass spectrometry analysis result of tetrazine-peptide 2 conjugated with three scFvs specific for HER2/neu.
Figure 25B:
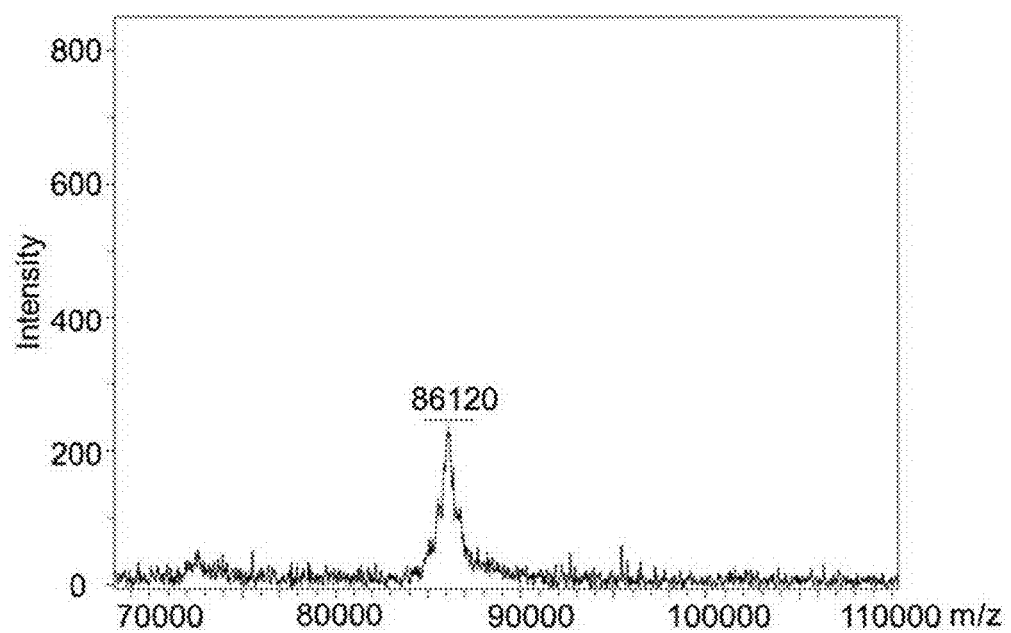

Example 29: Preparation of Targeting Linker Unit Based on Tetrazine-Peptide 2 with Three scFvs Specific for HER2/Neu The conjugation of scFv to the linker unit of prepared in an earlier Example and the purification and analysis of the product were the same as described in the preceding Examples. FIG. 25A shows the SDS-PAGE analysis of the synthesized product, indicating that the preparation was relatively pure. However, molecules with substantial PEG component generally migrate slowly in SDS-PAGE than proteins with the same molecular weight. FIG. 25B shows the mass spectrometric analysis, indicating that the purified linker unit had a m.w. of 86120 daltons. Illustrated below is the present targeting linker unit, which was composed of a linker unit with one free tetrazine functional group and a set of three scFvs specific for human HER2/neu as targeting elements.

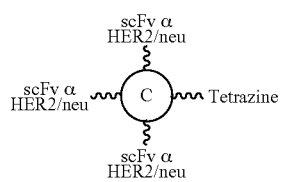

Example 30: Preparation of Effector Linker Units Based on TCO-Peptide 2 with Three scFvs Specific for TNF-α or PD-1

The conjugation of scFv to the linker unit prepared and the purification and analysis of the product were the same as the preceding Examples.

Figure 25C:
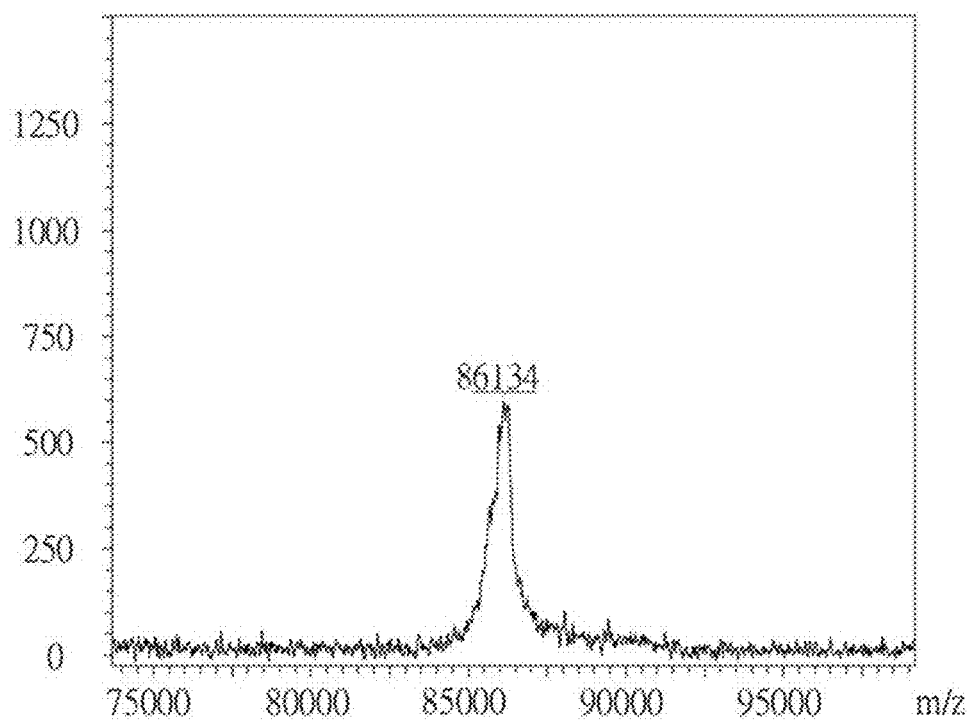
FIG. 25C shows the mass spectrometry result of TCO-peptide 2 conjugated with three scFvs specific for TNF-.

Shown in FIG. 25C was the mass spectrometric analysis of the present effector linker unit that was composed of a linker unit with a free TCO functional group and a set of three scFv specific for human TNF-α as effector elements (illustrated below). As indicated in FIG. 25C, this effector linker unit had a molecular weight of 86134 daltons.

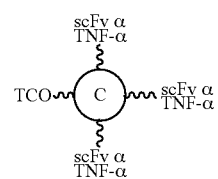

Figure 25D:
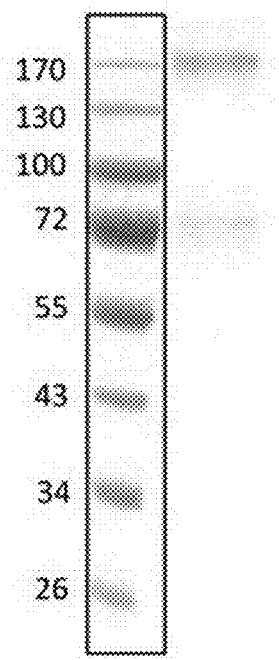
FIGS. 25D and 25E respectively show the SDS-PAGE and mass spectrometry analysis of TCO-peptide 2 conjugated with three scFvs specific for PD-1.
Figure 25E:
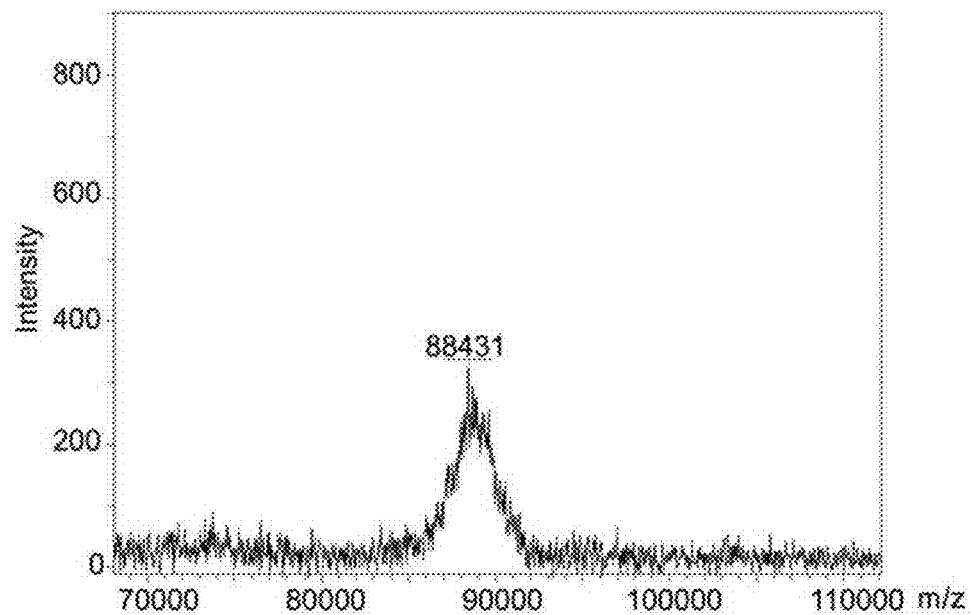

FIG. 25D and FIG. 25E respectively showed SDS-PAGE and mass spectrometric analyses of another effector linker unit that had one free TCO functional group and a set of three scFvs specific for human PD-1 as effector elements (illustrated below). As indicated in FIG. 25E, this effector linker unit had a molecular weight of 88431 daltons.

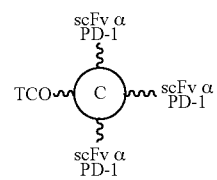

Figure 26:
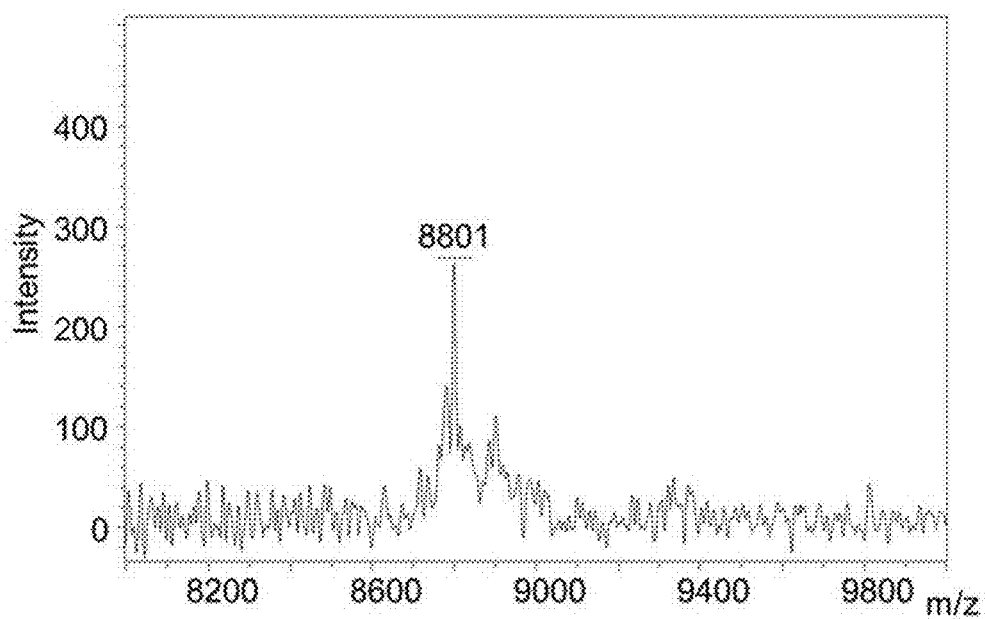
FIG. 26 shows mass spectrometry analysis result of tetrazine-peptide 2 conjugated with 3 CCK peptides.

Example 31: Preparation of Targeting Linker Unit Based on Tetrazine-Peptide 2 with Three CCK Peptide Molecules The CCK peptide was prepared in an earlier Example. The conjugation of the peptide to the 3-arm linker was performed as described in the preceding Examples. Mass spectrometric analysis showed that the linker unit with three CCK peptides had a m.w. of 8801 daltons (FIG. 26). Specifically, this targeting linker unit was composed of a linker unit with a free tetrazine functional group and a set of three CCK peptides as targeting elements.

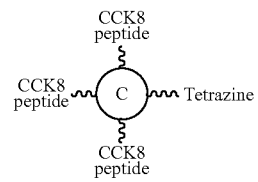

Example 32: Preparation of Targeting Linker Unit Based on TCO-Peptide 7 with Two scFvs Specific for CD20

In this example, a linker unit with two functional groups for conjugating with different linker units was prepared. This targeting linker unit served as the center linker unit in a molecular construct with three linker units, which comprised two targeting linker units and one effector linker unit. In our design, the two targeting linker units were joined via iEDDA reaction between the tetrazine and TCO groups, while the center linker unit and the effector linker unit were joined via CuAAC reaction between the alkyne and azide groups.

Figure 27:
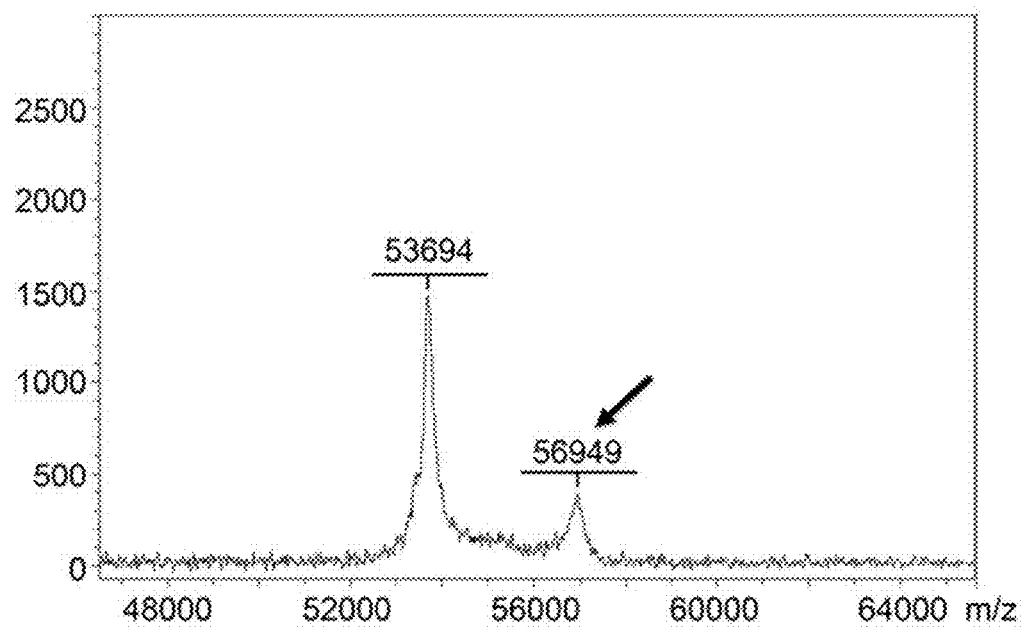
FIG. 27 shows mass spectrometry analysis result of TCO-peptide 7 conjugated with two scFvs specific for CD20.

The conjugation of scFvs to the linker unit prepared in an earlier Example and the purification and analysis of the product were the same as described in preceding Examples. The resultant targeting linker-unit (illustrated below) was composed of a linker-unit with a free TCO functional group, a free alkyne group, and a set of two scFvs specific for human CD20 as targeting elements. The mass spectrometric analysis provided in FIG. 27 indicated that such targeting linker unit had m.w. of 56949 daltons (indicated with an arrow).

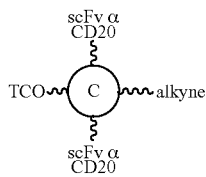

Example 33: Conjugation of Two scFvs Specific for VEGF-A to Linker Unit with One Free TCO Group and Two PEG Linking Arms with Maleimide Groups The conjugation of scFv to the linker unit prepared in an earlier Example and the purification and analysis of the product were the same as described in preceding Examples.

Figure 28:
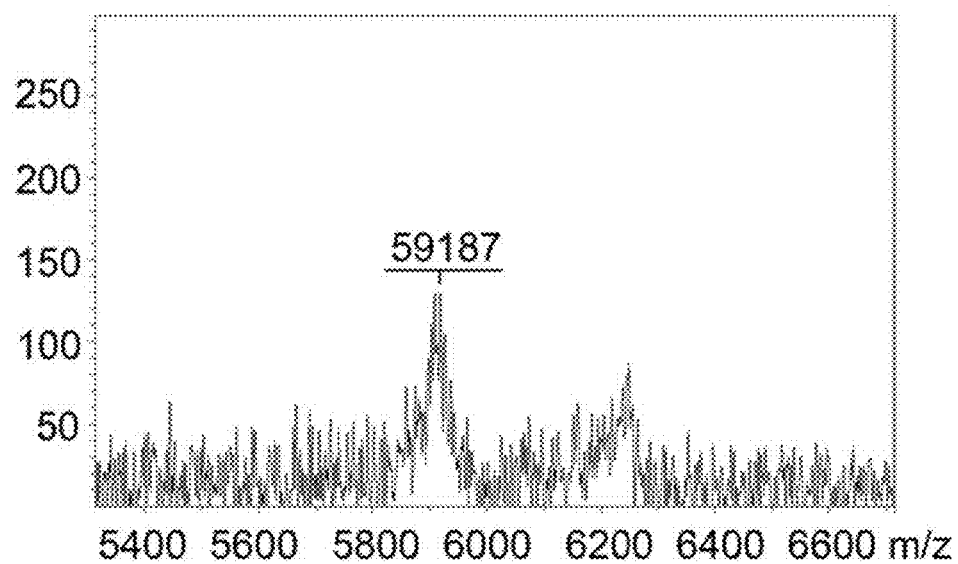
FIG. 28 shows mass spectrometry analysis result of TCO-peptide 1 conjugated with two scFvs specific for VEGF-A.

Illustrated below is the resultant linker unit, an effector linker-unit being composed of a linker unit with a free TCO functional group and a set of two scFvs specific for human VEGF-A as effector elements. The mass spectrometric analysis indicated that this linker unit had a m.w. of 59187 daltons (FIG. 28).

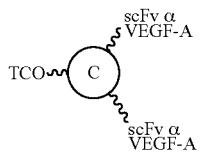

Figure 29A:
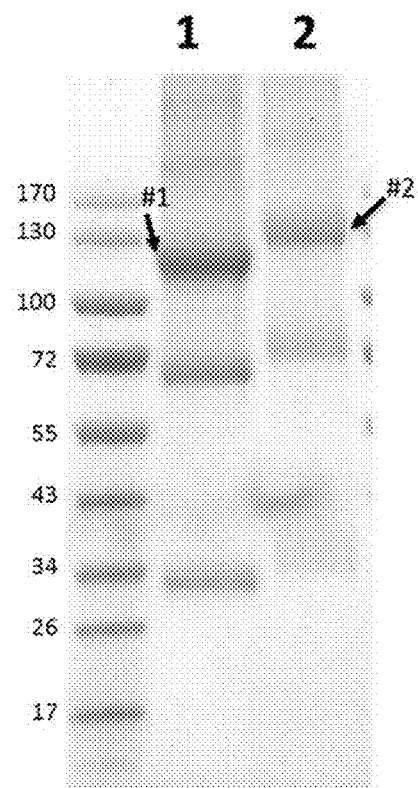
FIGS. 29A and 29B respectively show the SDS-PAGE and mass spectrometric analyses of a molecular construct with a targeting linker unit with three scFvs specific for CD79b and a drug bundle with five DM1 molecules.
Figure 29B:
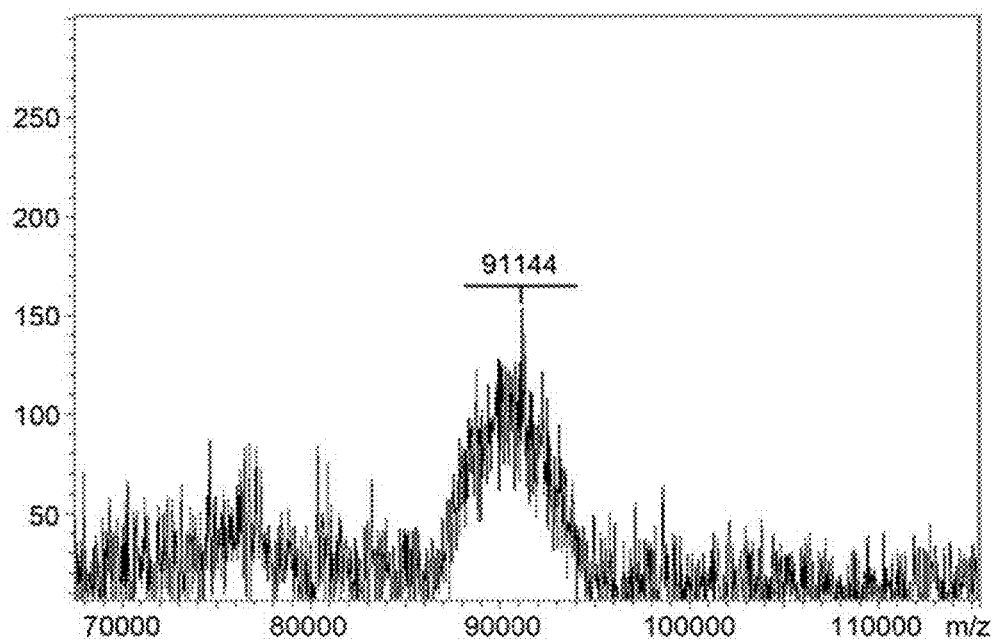
Figure 30:
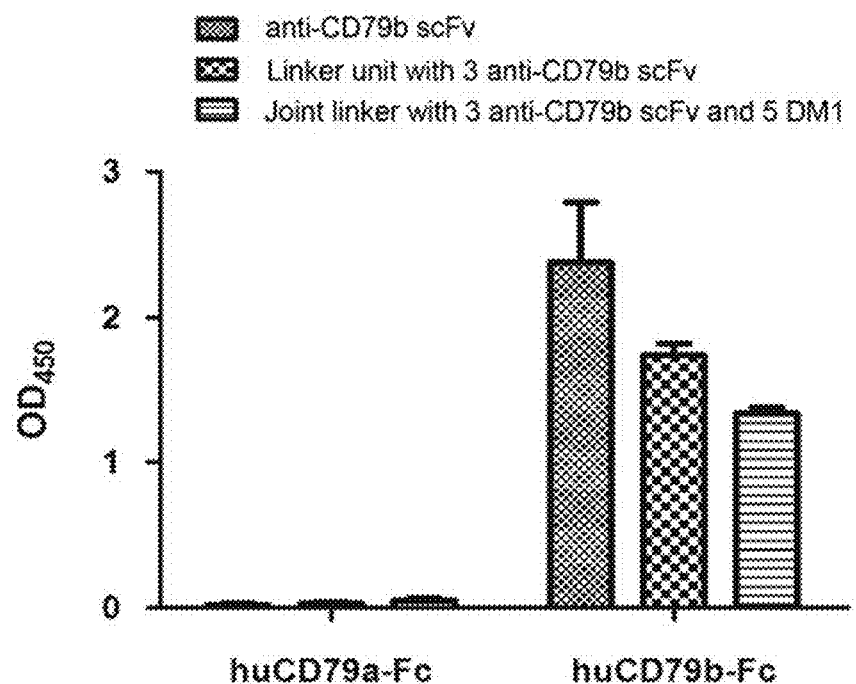
FIG. 30 shows the ELISA analyses of a molecular construct with a targeting linker unit with three scFvs specific for CD79b and a drug bundle with five DM1 molecules.

Example 34: Preparation of Joint-Linker Molecular Construct Composed of Targeting Linker Unit with Three scFvs Specific for CD79b and Effector Linker Unit with 5 DM1 Molecules In this example, a joint-linker molecular construct with three scFvs specific for CD79b and a drug bundle of PEG-(SMCC-DM1)$_5$ was constructed. The molecular construct was made by a TCO-tetrazine iEDDA reaction as described in the preceding Examples. The product, as illustrated below, was a joint-linker molecular construct with three scFvs specific for CD79b and one drug bundle having five DM1 molecules. FIG. 29A, FIG. 29B, and FIG. 30 respectively showed the SDS-PAGE, mass spectrometric (indicating a molecular weight of 91144 daltons), and ELISA analyses of the present joint-linker molecular construct. Arrow #1 was a linker unit with three scFvs of anti-CD79b; Arrow 2 was a joint-linker molecular construct with three scFvs of anti-CD79b and a drug bundle with five DM1 molecules. The ELISA results showed that the linker unit with three scFvs of anti-CD79b and the joint-linker molecular construct with three scFvs of anti-CD79b and a drug bundle of five DM1 molecules bound specifically to CD79b-Fc fusion protein.

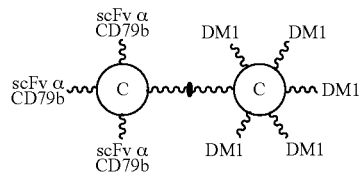

Figure 31:
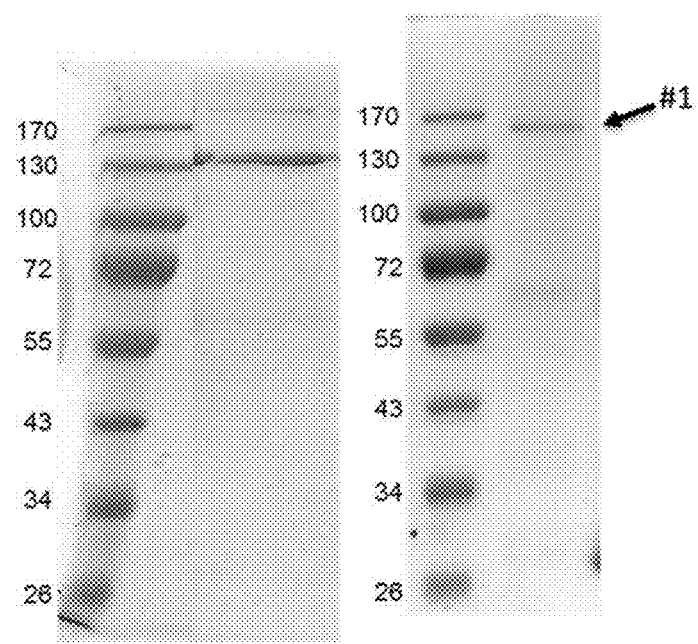
FIG. 31 shows the SDS-PAGE analyses of a molecular construct with a targeting linker unit with three scFvs specific for HER2/neu and a drug bundle with five DM1 molecules.

Example 35: Preparation of Joint-Linker Molecular Construct Composed of Targeting Linker Unit with Three scFvs Specific for HER2/Neu and Effector Linker Unit with Five DM1 Molecules In this example, a joint-linker molecular construct (illustrated below) with three scFvs specific for HER2/neu and a drug bundle having five DM1 molecules. FIG. 31 shows SDS-PAGE analysis of this product. The SDS-PAGE pattern of the linker unit with three scFvs of anti-HER2/neu (without the drug bundle) was placed on the left side for comparison. The conjugation with a drug bundle of five DM1 molecules had made the molecular construct larger.

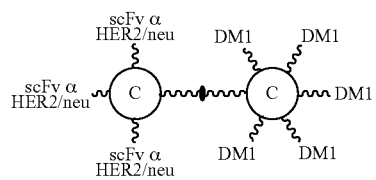

Figure 32:
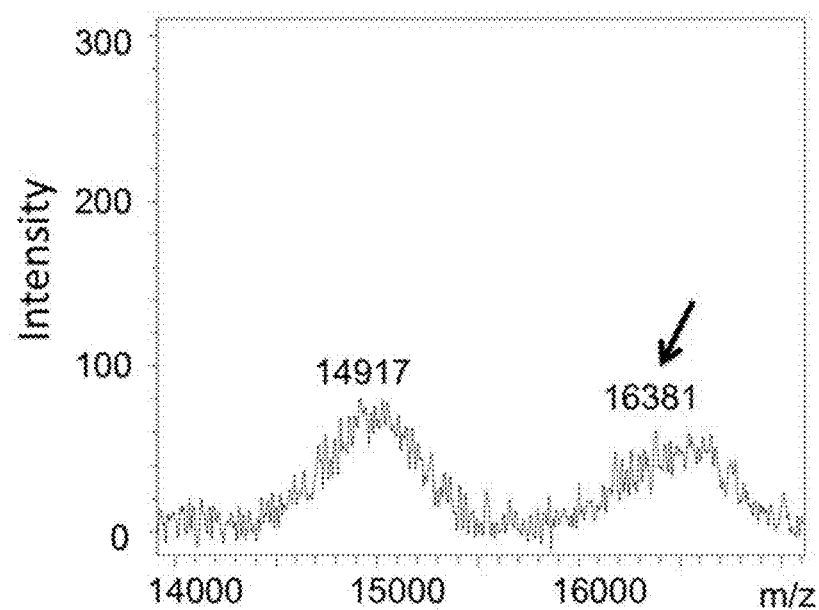
FIG. 32 shows the mass spectrometric analysis of a molecular construct with a targeting linker unit with three CCK8 peptides and a drug bundle with five DM1 molecules.

Example 36: Preparation of Joint-Linker Molecular Construct Composed of Targeting Linker Unit with Three Molecules of CCK8 Analogue and Effector Linker Unit with Five DM1 Molecules In this example, a targeting linker unit with three CCK peptide analogue molecules and one free tetrazine group and an effector linker unit (a drug bundle) with five DM1 molecules and one free TCO group were coupled via an iEDDA reaction as set forth in the preceding Example. Illustrated below was the resultant joint-linker molecular constructs that had three CCK8 peptides and one drug bundle having five DM1 molecules. FIG. 32 shows the mass spectrometric analysis of the molecular construct, indicating a m.w. of 16381 daltons.

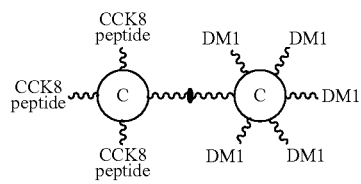

Figure 33:
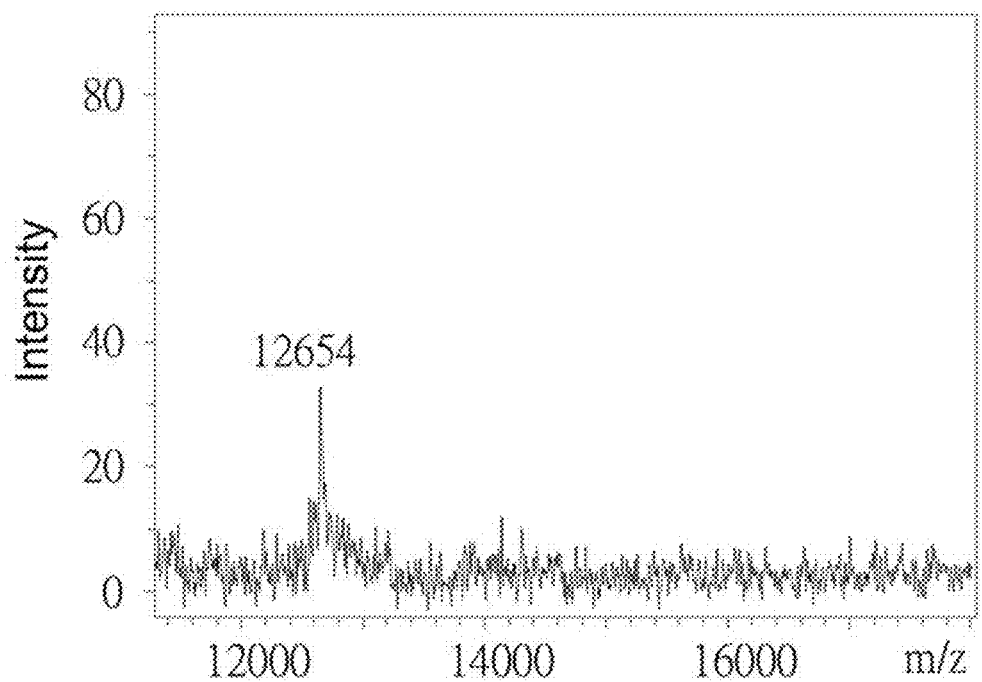
FIG. 33 shows the mass spectrometric analysis of a molecular construct with a targeting linker unit with three CCK8 peptides and a drug bundle with five DOTA groups.

Example 37: Preparation of Joint-Linker Molecular Construct Composed of Targeting Linker Unit with Three Molecules of CCK8 Analogue and Effector Linker Unit with Five DOTA Chelating Groups In this example, a targeting linker unit with three CCK peptide analogue molecules and one free tetrazine group, and an effector linker unit (a drug bundle) with five DOTA groups and chelated $Y^{+3}$ and one free TCO group were coupled via an iEDDA reaction as set forth in the preceding Example. Illustrated below was the resultant joint-linker molecular construct that had three CCK8 peptides and one drug bundle having five DOTA groups and chelated $Y^{+3}$. FIG. 33 shows the mass spectrometric analysis of the molecular construct, indicating a m.w. of 12654 daltons.

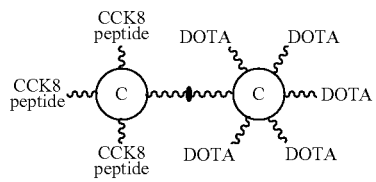

Example 38: Preparation of Joint-Linker Molecular Construct Composed of Targeting Linker Unit with Three scFvs Specific for HER2/Neu and Effector Linker Unit with Three scFvs Specific for CTLA-4

In this example, a targeting linker unit with three scFvs specific for HER2/neu and one free tetrazine group and an effector linker unit with three scFvs specific for CTLA-4 and one free TCO group were coupled via iEDDA reaction as performed in the preceding Examples. The resultant joint-linker molecular construct, as illustrated below, had three scFvs specific for HER2/neu and three scFvs specific for CTLA-4. In SDS-PAGE anlaysis of the reaction mixture, a band of about 230 kDa. in size was observed.

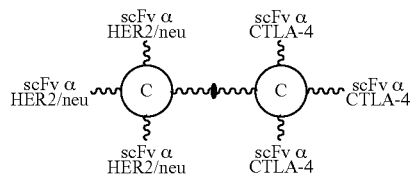

Figure 34:
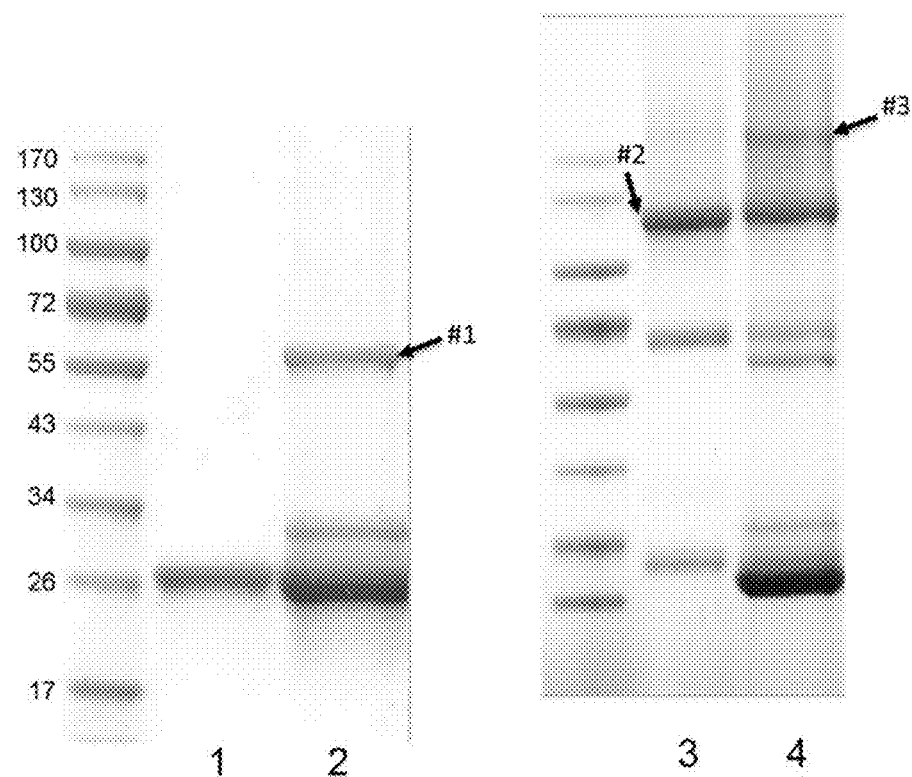
FIG. 34 shows the SDS-PAGE analysis of the reaction mixtures containing a linker unit of tetrazine-peptide 2 with three scFvs specific for CD79b, a TCO-peptide 7 with two scFvs specific for CD20, and a drug bundle with five DM1.

Example 39: Preparation of Joint-Linker Molecular Construct Composed of Targeting Linker Unit 1 with Three scFvs Specific for CD79b, Targeting Linker Unit 2 with Two scFvs Specific for CD20, and Effector Linker Unit with Five DM1 Molecules In this example, the targeting linker unit (targeting linker unit 2) with two scFvs specific for CD20 from the preceding Example was used as the center linker unit, which was linked with the first targeting unit (targeting linker unit 1) via the via iEDDA reaction between the tetrazine group of the first targeting linker unit and the TCO group of the center linker unit. Also, the center linker unit and the effector linker unit were joined via CuAAC reaction between the alkyne group of the center linker unit and the azide group of the effector linker unit. FIG. 34 shows the analysis of the reactants and reaction mixture at different reaction points. The dense band in lane 1 was purified scFv of anti-CD20; arrow 1 in lane 2 was the linker unit with two scFvs of anti-CD20, one TCO group and one alkyne group (targeting linker unit 2); arrow #2 in lane 3 was the linker unit with three scFvs of anti-CD79b and one tetrazine group (targeting linker unit 1); arrow #3 was the joint-linker comprising the targeting linker units 1 and 2.

The present joint-linker molecular construct, as illustrated below, comprised three scFvs specific for CD79b (from the first targeting linker unit), two scFvs specific for CD20 (from the center or the second targeting linker unit), and five DM1 molecules (from the effector linker unit).

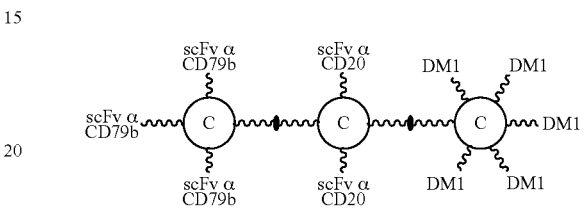

Example 40: Assay of Biological Activity of LPS Upon the Conjugation to Peptide Core Through Linking Arm To test the LPS biological activity of linker unit conjugated with LPS, TLR 4 stimulation cell-based assay was performed using HEK-blue™ detection kit (InvivoGen, San Diego, USA) according to manufacturer's instruction. HEK-blue™ hTLR4 cells express two human genes, TLR4 and MD-2/CD14 co-receptor genes, and contain the secreted embryonic alkaline phosphatase (SEAP) reporter gene for monitoring nuclear factor (NF)-κB activation. Upon interaction with the TLR4 agonist, TLR4 transduces a signal to trigger the activation of NF-κB and to express secreted alkaline phosphatase, which can be detected by using detection medium (HEK-blue™ detection, a medium used for the quantification of secreted alkaline phosphatase; InvivoGen) and measured with a spectrophotometer.

Briefly, HEK-hTLR4 cells were cultured at a density of $2.5 \times 10^4$ cells in 96-well plates and maintained in complete DMEM with selective antibiotics, normocin. Cells were stimulated with different concentrations (2-fold dilutions from 100 μg/ml) of crude LPS, purified LPS, dansyl hydrazine modified LPS, and the LPS conjugated to peptide core for 18 hours. The activation of TLR4 was analyzed by measuring SEAP from the culture medium using a spectrophotometer at 620 nm.

Figure 35:
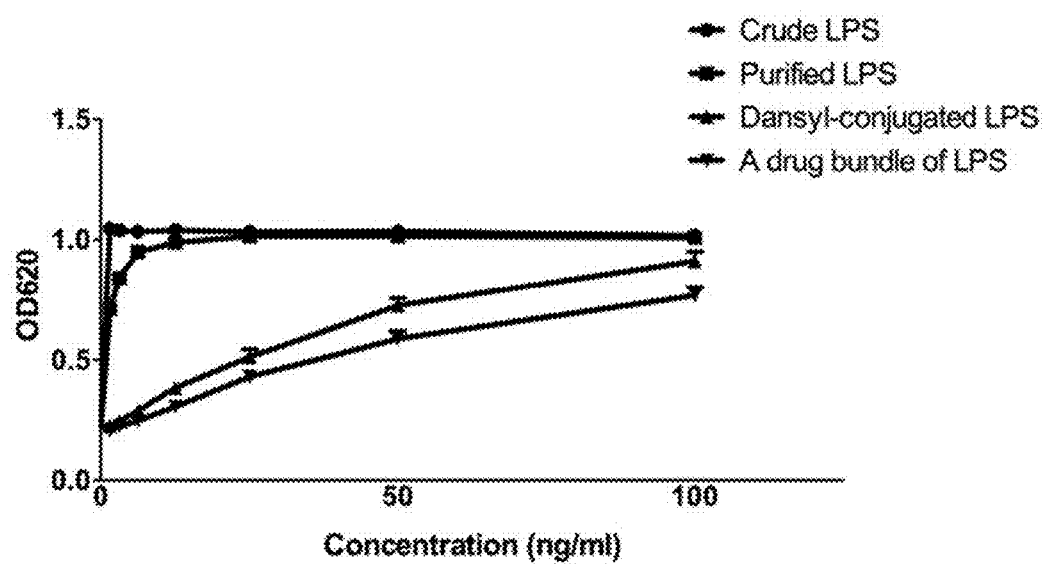
FIG. 35 shows the assay results of the biological activity of LPS, before and after modification with dansyl hydrazine.

FIG. 35 shows the assay results of the biological activity of LPS, before and after modification. The LPS fraction suitable for the modification with dansyl hydrazine was purified, which had a biological activity that was similar to the crude LPS. Dansyl hydrazine-modified LPS and the LPS conjugated to peptide core had comparable partial activities.

Example 41: Assay of Biological Activity Imiquimod Upon the Conjugation to Peptide Core Through Linking Arm To test the biological activity of $PEG_5$-NHS conjugated with imiquimod, TLR 7 stimulation cell-based assay was performed using HEK-blue™ detection kit (InvivoGen, San Diego, USA) per the manufacturer's instruction. HEK-blue™ hTLR7 cells express two human genes, TLR7 receptor gene and an secreted embryonic alkaline phosphatase (SEAP) reporter gene. Upon interaction with the TLR7 agonist, TLR7 transduces a signal to trigger the activation of NF-κB and to express secreted alkaline phosphatase, which can be detected by using detection medium (HEK-blue™ detection, a medium used for the quantification of secreted alkaline phosphatase; InvivoGen) and measured with a spectrophotometer.

Briefly, HEK-hTLR7 cells were cultured at a density of $4 \times 10^4$ cells in 96-well plates and maintained in complete DMEM with selective antibiotics, normocin. Cells were stimulated with different concentrations (2-fold dilutions from 20 μg/ml) of imiquimod and the $PEG_5$-NHS conjugated with imiquimod for 18 hours. The activation of TLR7 was analyzed by measuring SEAP from the culture medium using a spectrophotometer at 620 nm.

Figure 36:
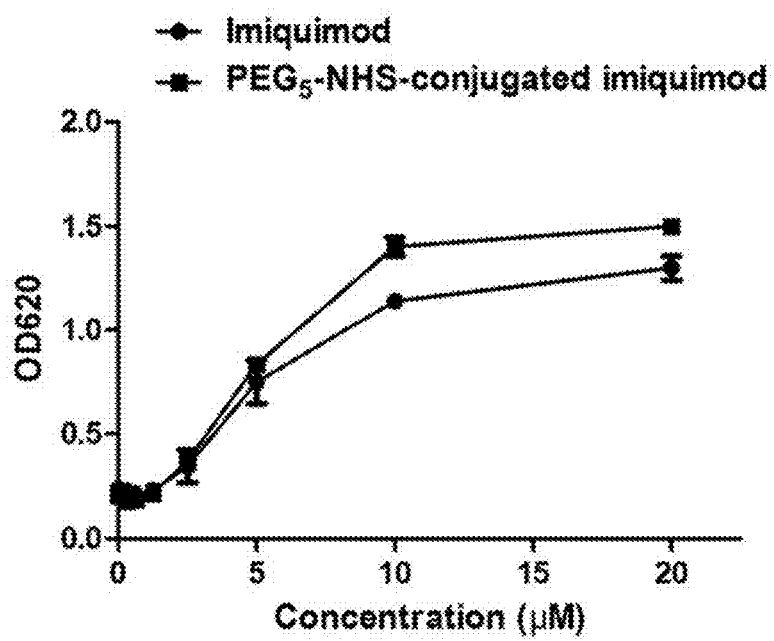
FIG. 36 shows the assay results of the biological activity of imiquimod upon the conjugation with PEG linking arm.

FIG. 36 shows the assay results of the biological activity of imiquimod upon the conjugation with linking arm, indicating that the imiquimod molecule conjugated with a linking arm had similar biological activity as the unmodified imiquimod.

Example 42: Cytotoxic Activities of Joint-Linker Molecular Construct with 3 Anti-CD79b scFvs and Five DM1 Molecules on Ramos Cells Ramos cells ($2 \times 10^4$/well) were seeded into wells of 96-well plates in RPMI1640 medium containing 10% fetal bovine serum. After 2 hours, cells were treated with different concentrations (2-fold dilutions from 20 nM) of scFv of anti-CD79, a linker unit with three scFvs of anti-CD79b (without a drug bundle), a linker unit with five DM1 molecules (a drug bundle), and a molecular construct with three scFvs of anti-CD79b and five DM1 molecules. After being incubated for 6 hours, the culture medium was removed by centrifuging at 300 g for 5 minutes and replaced by a fresh medium, and the cells were further incubated for another 24 hours. Cell viability was then determined by alamarBlue cell viability reagent kit (Invitrogen) in accordance with the manufacturer's instruction.

Figure 37:
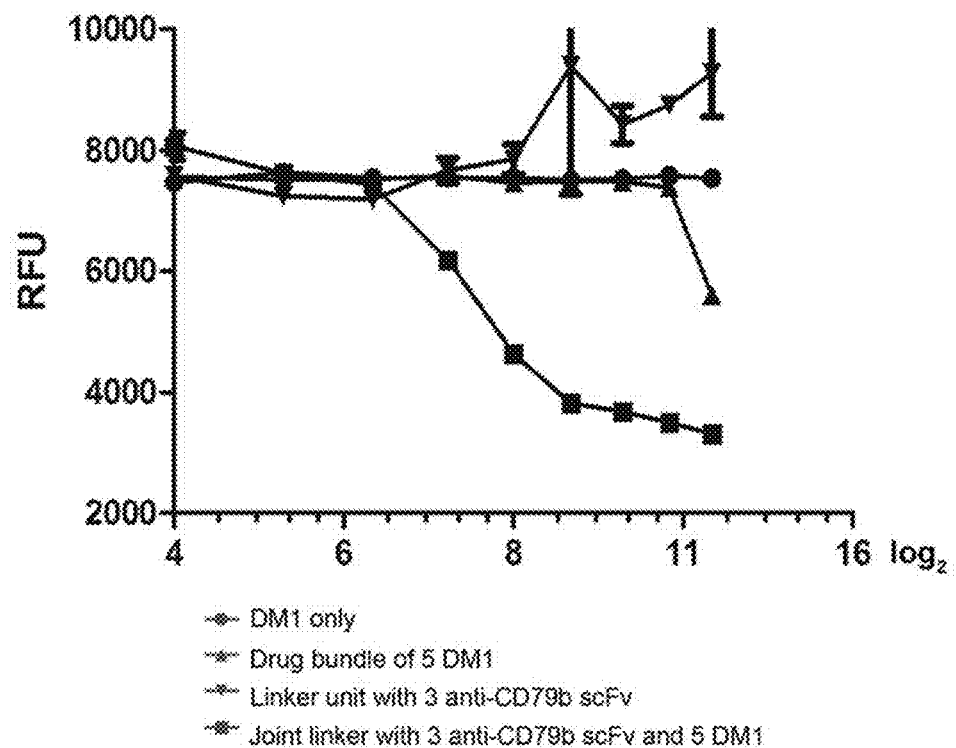
FIG. 37 shows the cytotoxicity assay results of the molecular construct with three scFvs specific for CD79b and a drug bundle of five DM1.

FIG. 37 shows the results of the viability of Ramos cells of the four treatments groups. The molecular construct with three scFvs specific for CD79b and a drug bundle of five DM1 molecules caused approximately 50% of cytolysis of RAMOS cells.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A molecular construct comprising a first linker unit and a second linker unit, wherein,
the first linker unit comprises a first center core comprising a plurality of amine groups, and a first linking arm and optionally a first coupling arm that are respectively linked to the amine groups of the first center core; and
the second linker unit comprises a second center core comprising a plurality of amine groups, and a second linking arm and optionally a second coupling arm that are respectively linked to the amine groups of the second center core; wherein
the first and second center cores are independently a polypeptide comprising a plurality of lysine (K) residues or a compound selected from the group consisting of, benzene-1,3,5-triamine, 2-(aminomethyl)-2-methylpropane-1,3-diamine, tris(2-aminoethyl)amine, benzene-1,2,4, 5-tetraamine, 3,3',5,5'-tetraamine-1,1'-biphenyl, tetrakis(2-aminoethyl)methane, tetrakis(ethylamine)hydrazine, N,N,N',N',-tetrakis(aminoethyl)ethylenediamine, benzene-1,2,3,4, 5,6-hexaamine, 1-N,1-N,3-N,3-N,5-N,5-N-hexakis(methylamine)-benzene-1,3,5-triamine, 1-N,1-N,2-N,2-N,4-N,4-N,5-N,5-N,-octakis(methylamine)-benzene-1,2,4,5-triamine, and N,N-bis[(1-amino-3,3-diaminoethyl)pentyl] methanediamine; and
the first and second linker units are coupled to each other via copper catalyzed azide-alkyne cycloaddition (CuAAC) reaction, strained-promoted azide-alkyne click chemistry (SPAAC) reaction or inverse electron demand Diels-Alder (iEDDA) reaction occurred between any of the followings: the first and second center cores, the first coupling arm and the second center core, the first and second coupling arms, or the first center core and the second coupling arm.

2. The molecular construct of claim 1, wherein the first and second linker units respectively comprise a plurality of the first and second linking arms linked thereto.

3. The molecular construct of claim 1, wherein each of the first and second linking arms has a maleimide group at the free terminus thereof.

4. The molecular construct of claim 3, further comprising a first targeting element and a first effector element respectively linked to the first and second linking arms via thiol-maleimide reaction.

5. The molecular construct of claim 1, wherein,
each of the first and second linking arms is a PEG chain having 2-20 repeats of ethylene glycol (EG) units; and
each of the first and second coupling arms is a PEG chain having 2-12 repeats of EG units.

6. The molecular construct of claim 1, wherein,
one of the first and second coupling arms has an azide group at the free-terminus thereof, and the other of the first and second coupling arms has an alkyne or a strained alkyne group at the free-terminus thereof; and
the first and second center cores are coupled to each other via copper catalyzed azide-alkyne cycloaddition (CuAAC) reaction or strained-promoted azide-alkyne click chemistry (SPAAC) reaction occurred between the first and second coupling arms.

7. The molecular construct of claim 6, wherein the strained alkyne group is dibenzocyclooctyne (DBCO), difluorinated cyclooctyne (DIFO), bicyclononyne (BCN), or dibenzocyclooctyne (DICO).

8. The molecular construct of claim 1, wherein,
one of the first and second coupling arms has a tetrazine group at the free-terminus thereof, and the other of the first and second coupling arms has a trans-cyclooctene (TCO) at the free-terminus thereof; and
the first and second center cores are coupled to each other via iEDDA reaction occurred between the first and second coupling arms.

9. The molecular construct of claim 8, wherein the tetrazine group is 1,2,3,4-tetrazine, 1,2,3,5-tetrazine or 1,2,4,5-tetrazine, or derivatives thereof.

10. The molecular construct of claim 1, wherein one or both of the first and the second center cores is the compound, wherein the coupling arm is linked to one of the plurality of amine groups of the center core via forming an amide bond therebetween, and the coupling arm has an azide, an alkyne, a strained alkyne or a tetrazine group at the free-terminus thereof.

11. The molecular construct of claim 10, wherein
one of the first and the second center cores is the compound, and the coupling arm is linked to one of the plurality of amine groups of the center core via forming an amide bond therebetween, wherein the coupling arm has a DBCO, a DIFO, a BCN, or a DICO group at the free-terminus thereof;
the other of the first and the second center cores is the polypeptide having, at its N or C-terminal, an amino acid residue of L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, or 6-azido-D-lysine; and
the first and second center cores are coupled to each other via SPAAC reaction occurred between the coupling arm and the amino acid residue.

12. The molecular construct of claim 1, wherein the number of K residues ranges from 2 to 15, and each K residue and its next K residue are separated by a filler sequence comprising glycine (G) and serine (S) residues.

13. The molecular construct of claim 12, wherein the filler sequence has the sequence of GS, GGS, GSG, or SEQ ID NOs: 1-16.

14. The molecular construct of claim 12, wherein the polypeptide comprises 2-15 units of the sequence of $G_{1-5}SK$.

15. The molecular construct of claim 14, wherein the polypeptide comprises the sequence of $(GSK)_{2-15}$.

16. The molecular construct of claim 1, wherein the polypeptide comprises the sequence of $(X_{aa}-K)_n$, where $X_{aa}$ is a PEGylated amino acid having 2 to 12 repeats of ethylene glycol (EG) unit, and n is an integral from 2 to 15.

17. The molecular construct of claim 1, wherein both the first and second center cores are the polypeptides.

18. The molecular construct of claim 17, wherein the N-terminus of each of the first and second center cores is modified with an acetyl group.

19. The molecular construct of claim 17, wherein,
the first amino acid residue at the N- or C-terminus of one of the first and second center cores is AHA, 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, or 6-azido-D-lysine;
the first amino acid residue at the N- or C-terminus of the other of the first and second center cores is L-homopropargylglycine (L-HPG), D-homopropargylglycine (D-HPG), or beta-homopropargylglycine (β-HPG); and the first and second cores are coupled to each other via copper catalyzed azide-alkyne cycloaddition (CuAAC) reaction occurred between the first amino acid residues.

20. The molecular construct of claim 17, wherein each of the first and second center cores comprises a cysteine residue at the N- or C-terminus thereof; and the first and second coupling arms are respectively linked to the cysteine residues of the first and second center cores via thio-maleimide reaction.

21. The molecular construct of claim 17, wherein,
one of the first and second center cores has, at its N or C-terminal, an amino acid reside of L-azidohomoalanine (AHA), 4-azido-L-phenylalanine, 4-azido-D-phenylalanine, 3-azido-L-alanine, 3-azido-D-alanine, 4-azido-L-homoalanine, 4-azido-D-homoalanine, 5-azido-L-ornithine, 5-azido-d-ornithine, 6-azido-L-lysine, or 6-azido-D-lysine;
the other of the first and second center cores has, at its N- or C-terminus, a cysteine residue, and the first or the second coupling arm is linked to the cysteine residue via thio-maleimide reaction, wherein the first or the second coupling arm has a DBCO, a DIFO, a BCN, or a DICO group at the free-terminus thereof; and
the first and second center cores are coupled to each other via SPAAC reaction occurred between the first center core and the second coupling arm, or between the second center core and the first coupling arm.

22. The molecular construct of claim 1, further comprising a third linking arm linked to the first or the second linker unit.

23. The molecular construct of claim 22, further comprising a long PEG chain having a molecular weight of about 20,000 to 50,000 daltons linked to the third linking arm via thiol-maleimide reaction.

24. The molecular construct of claim 4, further comprising a third linker unit comprising a third center core and a third linking arm and a third coupling arm that are respectively linked to the third center core, wherein the third linker unit is linked to the first or the second linker unit via CuAAC reaction, iEDDA reaction, or SPAAC reaction occurred between any of the followings: the first or the second coupling arm and the third coupling arm, the first or the second center core and the third coupling arm, the first or the second coupling arm and the third center core, or the first or the second center core and the third center core.

25. The molecular construct of claim 24, wherein the first, second, and third center cores are different.

26. The molecular construct of claim 24, wherein the third linking arm has a maleimide group at the free terminus thereof, and a second targeting element or a second effector element is linked to the third linking arm via thio-maleimide reaction.

27. The molecular construct of claim 26, wherein the second targeting element and the second effector element are respectively different from the first targeting element and the first effector element.

28. The molecular construct of claim 4, wherein,
the first targeting element is a first single-chain variable fragment (scFv) specific for a tissue-associated extracellular matrix protein; and
the first effector element is a second scFv specific for a cytokine or a receptor of the cytokine; or a soluble receptor of the cytokine.

29. The molecular construct of claim 28, wherein the tissue-associated extracellular matrix protein is selected from the group consisting of α-aggrecan, collagen I, collagen II, collagen III, collagen V, collagen VII, collagen IX, and collagen XI.

30. The molecular construct of claim 28, wherein the cytokine is selected from the group consisting of tumor necrosis factor-α (TNF-α), interleukin-17 (IL-17), IL-1, IL-6, shared protein of IL-12 and IL-23, and B cell activating factor (BAFF).

31. The molecular construct of claim 28, wherein the receptor of the cytokine is a receptor specific for IL-6 (IL-6R) or a receptor specific for IL-17 (IL-17R).

32. The molecular construct of claim 28, wherein the soluble receptor of the cytokine is specific for TNF-α or IL-1.

33. The molecular construct of claim 4, wherein,
the first targeting element is a first scFv specific for a first cell surface antigen; and
the first effector element is a cytotoxic drug or a second scFv specific for a second cell surface antigen.

34. The molecular construct of claim 33, wherein the first cell surface antigen is selected from the group consisting of, CD5, CD19, CD20, CD22, CD23, CD27, CD30, CD33, CD34, CD37, CD38, CD43, CD72a, CD78, CD79a, CD79b, CD86, CD134, CD137, CD138, and CD319.

35. The molecular construct of claim 33, wherein the cytotoxic drug is selected from the group consisting of auristatin, maytansine, doxorubicin, calicheamicin, and camptothecin.

36. The molecular construct of claim 33, wherein the second cell surface antigen is CD3 or CD16a.

37. The molecular construct of claim 33, wherein,
one of the first and second cell surface antigens is CD79a; and
the other one of the first and second cell surface antigens is CD79b.

38. The molecular construct of claim 4, wherein,
the first targeting element is a peptide hormone, a first growth factor, or a first scFv specific for a tumor-associated antigen; and
the first effector element is a cytotoxic drug, a toll-like receptor agonist, a chelator complexed with a radioactive nuclide, a cytokine, or a second scFv specific for a second growth factor, a cell surface antigen, a hapten, or the cytokine.

39. The molecular construct of claim 38, wherein the peptide hormone is secretin, cholecystokinin (CCK), somatostatin, or thyroid-stimulating hormone (TSH).

40. The molecular construct of claim 38, wherein the first growth factor is selected from the group consisting of epidermal growth factor (EGF), mutant EGF, epiregulin, heparin-binding epidermal growth factor (HB-EGF), vascular endothelial growth factor A (VEGF-A), basic fibroblast growth factor (bFGF), and hepatocyte growth factor (HGF).

41. The molecular construct of claim 38, wherein the tumor-associated antigen is selected from the group consisting of human epidermal growth factor receptor (HER1), HER2, HER3, HER4, carbohydrate antigen 19-9 (CA 19-9), carbohydrate antigen 125 (CA 125), carcinoembryonic antigen (CEA), mucin 1 (MUC 1), ganglioside GD2, melanoma-associated antigen (MAGE), prostate-specific membrane antigen (PSMA), prostate stem cell antigen (PSCA), mesothelin, mucine-related Tn, Sialyl Tn, Globo H, stage-specific embryonic antigen-4 (SSEA-4), and epithelial cell adhesion molecule (EpCAM).

42. The molecular construct of claim 38, wherein the cytotoxic drug is selected from the group consisting of auristatin, maytansine, doxorubicin, calicheamicin, and camptothecin.

43. The molecular construct of claim 38, wherein the toll-like receptor agonist is selected from the group consisting of lipopolysaccharide (LPS), monophosphoryl lipid A, motolimod, imiquimod, resiquimod, gardiquimod, CpG oligodeoxynucleotide (CpG DON), lipoteichoic acid, β-glucan, and zymosan.

44. The molecular construct of claim 38, wherein the chelator is selected from the group consisting of 1,4,7,10-tetraazacyclododecane-1,4,7,10-tetraacetic acid (DOTA), 1,4,7-triazacyclononane-1,4,7-triacetic acid (NOTA), 1,4,7-triazacyclononane-1,4-diacetic acid (NODA), and diethylenetriaminepentaacetic acid (DTPA).

45. The molecular construct of claim 38, wherein the radioactive nuclide is $^{111}$In, $^{131}$I, or $^{177}$Lu.

46. The molecular construct of claim 38, wherein the cytokine is selected from the group consisting of IL-2, IFN-α, IFN-γ, and TNF-α.

47. The molecular construct of claim 38, wherein the second growth factor is EGF, mutant EGF, VEGF-A, bFGF, or HGF.

48. The molecular construct of claim 38, wherein the cell surface antigen is selected from the group consisting of CD3, CD16a, CD28, CD134, cytotoxic T-lymphocyte-associated protein 4 (CTLA-4), programmed cell death 1 (PD-1), and programmed cell death 1 ligand 1 (PD-L1).

49. The molecular construct of claim 38, wherein the hapten is selected from the group consisting of dinitrophenol (DNP), trinitrophenol (TNP), and a short peptide having an amino acid sequence of SEQ ID NO: 20.

50. The molecular construct of claim 38, wherein the second scFv is a non-neutralizing scFv specific for the cytokine selected from the group consisting of IL-2, IFN-α, IFN-γ, and TNF-α.

51. The molecular construct of claim 4, wherein,
the first targeting element is an scfv specific for collagen I or osteonectin; and
the first effector element is an scfv specific for ligand receptor activator of nuclear factor κB (RANKL).

* * * * *

```
                        SEQUENCE LISTING

<160> NUMBER OF SEQ ID NOS: 50

<210> SEQ ID NO 1
<211> LENGTH: 4
<212> TYPE: PRT
<213> ORGANISM: Artificial Sequence
<220> FEATURE:
<223> OTHER INFORMATION: filler sequence-1

<400> SEQUENCE: 1

Gly Gly Gly Ser
1

<210> SEQ ID NO 2
<211> LENGTH: 4
<212> TYPE: PRT
<213> ORGANISM: Artificial Sequence
<220> FEATURE:
<223> OTHER INFORMATION: filler sequence-2

<400> SEQUENCE: 2

Gly Ser Gly Ser
1

<210> SEQ ID NO 3
<211> LENGTH: 4
<212> TYPE: PRT
<213> ORGANISM: Artificial Sequence
<220> FEATURE:
<223> OTHER INFORMATION: filler sequence-3

<400> SEQUENCE: 3

Gly Gly Ser Gly
1
```

```
<210> SEQ ID NO 4
<211> LENGTH: 5
<212> TYPE: PRT
<213> ORGANISM: Artificial Sequence
<220> FEATURE:
<223> OTHER INFORMATION: filler sequence-4

<400> SEQUENCE: 4

Gly Ser Gly Gly Ser
1               5

<210> SEQ ID NO 5
<211> LENGTH: 5
<212> TYPE: PRT
<213> ORGANISM: Artificial Sequence
<220> FEATURE:
<223> OTHER INFORMATION: filler sequence-5

<400> SEQUENCE: 5

Ser Gly Gly Ser Gly
1               5

<210> SEQ ID NO 6
<211> LENGTH: 5
<212> TYPE: PRT
<213> ORGANISM: Artificial Sequence
<220> FEATURE:
<223> OTHER INFORMATION: filler sequence-6

<400> SEQUENCE: 6

Gly Gly Gly Gly Ser
1               5

<210> SEQ ID NO 7
<211> LENGTH: 6
<212> TYPE: PRT
<213> ORGANISM: Artificial Sequence
<220> FEATURE:
<223> OTHER INFORMATION: filler sequence-7

<400> SEQUENCE: 7

Gly Gly Ser Gly Gly Ser
1               5

<210> SEQ ID NO 8
<211> LENGTH: 7
<212> TYPE: PRT
<213> ORGANISM: Artificial Sequence
<220> FEATURE:
<223> OTHER INFORMATION: filler sequence-8

<400> SEQUENCE: 8

Gly Gly Ser Gly Gly Ser Gly
1               5

<210> SEQ ID NO 9
<211> LENGTH: 8
<212> TYPE: PRT
<213> ORGANISM: Artificial Sequence
<220> FEATURE:
<223> OTHER INFORMATION: filler sequence-9

<400> SEQUENCE: 9

Ser Gly Ser Gly Gly Ser Gly Ser
1               5
```

-continued

```
<210> SEQ ID NO 10
<211> LENGTH: 9
<212> TYPE: PRT
<213> ORGANISM: Artificial Sequence
<220> FEATURE:
<223> OTHER INFORMATION: filler sequence-10

<400> SEQUENCE: 10

Gly Ser Gly Gly Ser Gly Ser Gly Ser
1               5

<210> SEQ ID NO 11
<211> LENGTH: 10
<212> TYPE: PRT
<213> ORGANISM: Artificial Sequence
<220> FEATURE:
<223> OTHER INFORMATION: filler sequence-11

<400> SEQUENCE: 11

Ser Gly Gly Ser Gly Gly Ser Gly Ser Gly
1               5                   10

<210> SEQ ID NO 12
<211> LENGTH: 11
<212> TYPE: PRT
<213> ORGANISM: Artificial Sequence
<220> FEATURE:
<223> OTHER INFORMATION: filler sequence-12

<400> SEQUENCE: 12

Gly Gly Ser Gly Gly Ser Gly Gly Ser Gly Ser
1               5                   10

<210> SEQ ID NO 13
<211> LENGTH: 12
<212> TYPE: PRT
<213> ORGANISM: Artificial Sequence
<220> FEATURE:
<223> OTHER INFORMATION: filler sequence-13

<400> SEQUENCE: 13

Ser Gly Gly Ser Gly Gly Ser Gly Ser Gly Gly Ser
1               5                   10

<210> SEQ ID NO 14
<211> LENGTH: 13
<212> TYPE: PRT
<213> ORGANISM: Artificial Sequence
<220> FEATURE:
<223> OTHER INFORMATION: filler sequence-14

<400> SEQUENCE: 14

Gly Gly Gly Gly Ser Gly Gly Ser Gly Gly Gly Gly Ser
1               5                   10

<210> SEQ ID NO 15
<211> LENGTH: 14
<212> TYPE: PRT
<213> ORGANISM: Artificial Sequence
<220> FEATURE:
<223> OTHER INFORMATION: filler sequence-15

<400> SEQUENCE: 15

Gly Gly Gly Ser Gly Ser Gly Ser Gly Ser Gly Gly Gly Ser
1               5                   10
```

```
<210> SEQ ID NO 16
<211> LENGTH: 15
<212> TYPE: PRT
<213> ORGANISM: Artificial Sequence
<220> FEATURE:
<223> OTHER INFORMATION: filler sequence-16

<400> SEQUENCE: 16

Ser Gly Ser Gly Gly Gly Gly Gly Ser Gly Gly Ser Gly Ser Gly
1               5                   10                  15

<210> SEQ ID NO 17
<211> LENGTH: 16
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-1

<400> SEQUENCE: 17

Cys Gly Gly Ser Gly Gly Ser Gly Gly Ser Lys Gly Ser Gly Ser Lys
1               5                   10                  15

<210> SEQ ID NO 18
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptitde core-2

<400> SEQUENCE: 18

Cys Gly Gly Ser Gly Gly Ser Gly Gly Ser Lys Gly Ser Gly Ser Lys
1               5                   10                  15
Gly Ser Lys

<210> SEQ ID NO 19
<211> LENGTH: 31
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide-3

<400> SEQUENCE: 19

Cys Gly Ser Lys Gly Ser Lys Gly Ser Lys Gly Ser Lys Gly Ser Lys
1               5                   10                  15
Gly Ser Lys Gly Ser Lys Gly Ser Lys Gly Ser Lys Gly Ser Lys
            20                  25                  30

<210> SEQ ID NO 20
<211> LENGTH: 8
<212> TYPE: PRT
<213> ORGANISM: Artificial Sequence
<220> FEATURE:
<223> OTHER INFORMATION: hapten
```

<400> SEQUENCE: 20

Trp Ala Asp Trp Pro Gly Pro Pro
1               5

<210> SEQ ID NO 21
<211> LENGTH: 16
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-4

<400> SEQUENCE: 21

Xaa Gly Gly Ser Gly Gly Ser Gly Gly Ser Lys Gly Ser Gly Ser Lys
1               5                   10                  15

<210> SEQ ID NO 22
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-5

<400> SEQUENCE: 22

Xaa Gly Gly Ser Gly Gly Ser Gly Gly Ser Lys Gly Ser Gly Ser Lys
1               5                   10                  15

Gly Ser Lys

<210> SEQ ID NO 23
<211> LENGTH: 19
<212> TYPE: PRT
<213> ORGANISM: Artificial Sequence
<220> FEATURE:
<221> NAME/KEY: MOD_RES
<222> LOCATION: 1
<223> OTHER INFORMATION: Xaa is L-azidohomoalanine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-6

<400> SEQUENCE: 23

Xaa Gly Gly Ser Gly Gly Ser Gly Gly Ser Lys Gly Ser Gly Ser Lys
1               5                   10                  15

Gly Ser Lys

<210> SEQ ID NO 24
<211> LENGTH: 21
<212> TYPE: PRT
<213> ORGANISM: Artificial Sequence

```
<220> FEATURE:
<221> NAME/KEY: MOD_RES
<222> LOCATION: 1
<223> OTHER INFORMATION: Xaa is homopropargylglycine
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-7

<400> SEQUENCE: 24

Xaa Gly Gly Ser Gly Gly Ser Gly Gly Ser Lys Gly Ser Gly Ser Lys
1               5                   10                  15

Gly Ser Gly Ser Cys
            20

<210> SEQ ID NO 25
<211> LENGTH: 7
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-8
<220> FEATURE:
<221> NAME/KEY: MOD_RES
<222> LOCATION: 2
<223> OTHER INFORMATION: Xaa is PEGylated amino acid with two EG units
<220> FEATURE:
<221> NAME/KEY: MOD_RES
<222> LOCATION: 4
<223> OTHER INFORMATION: Xaa is PEGylated amino acid with two EG units
<220> FEATURE:
<221> NAME/KEY: MOD_RES
<222> LOCATION: 6
<223> OTHER INFORMATION: Xaa is PEGylated amino acid with two EG units

<400> SEQUENCE: 25

Cys Xaa Lys Xaa Lys Xaa Lys
1               5

<210> SEQ ID NO 26
<211> LENGTH: 11
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: polypeptide core-9
<220> FEATURE:
<221> NAME/KEY: MOD_RES
<222> LOCATION: 2
<223> OTHER INFORMATION: Xaa is PEGylated amino acid with six EG units
<220> FEATURE:
<221> NAME/KEY: MOD_RES
<222> LOCATION: 4
<223> OTHER INFORMATION: Xaa is PEGylated amino acid with six EG units
<220> FEATURE:
<221> NAME/KEY: MOD_RES
<222> LOCATION: 6
<223> OTHER INFORMATION: Xaa is PEGylated amino acid with six EG units
<220> FEATURE:
<221> NAME/KEY: MOD_RES
<222> LOCATION: 8
<223> OTHER INFORMATION: Xaa is PEGylated amino acid with six EG units
<220> FEATURE:
<221> NAME/KEY: MOD_RES
<222> LOCATION: 10
<223> OTHER INFORMATION: Xaa is PEGylated amino acid with six EG units
```

```
<400> SEQUENCE: 26

Cys Xaa Lys Xaa Lys Xaa Lys Xaa Lys
1               5                   10

<210> SEQ ID NO 27
<211> LENGTH: 121
<212> TYPE: PRT
<213> ORGANISM: Artificial Sequence
<220> FEATURE:
<223> OTHER INFORMATION: 24C10-VH

<400> SEQUENCE: 27

Gln Val Gln Leu Gln Gln Ser Gly Pro Glu Leu Val Lys Pro Gly Ala
1               5                   10                  15

Ser Val Lys Ile Ser Cys Lys Thr Ser Gly Tyr Ala Phe Ser Phe Ser
            20                  25                  30

Trp Met Asn Trp Val Lys Trp Gly Pro Gly Gln Gly Leu Glu Trp Ile
        35                  40                  45

Gly Arg Ile Tyr Pro Gly Asn Gly Asp Thr Asn Tyr Asn Gly Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Val Asp Ser Ala Val Tyr Phe Cys
                85                  90                  95

Ala Arg Trp Val Tyr Ser Gly Asn Asn Tyr Ala Val Asp Tyr Trp Gly
            100                 105                 110

Gln Gly Thr Ser Val Thr Val Ser Ser
        115                 120

<210> SEQ ID NO 28
<211> LENGTH: 113
<212> TYPE: PRT
<213> ORGANISM: Artificial Sequence
<220> FEATURE:
<223> OTHER INFORMATION: 24C10-VL

<400> SEQUENCE: 28

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Tyr Thr Phe Gly Gly Gly Thr Lys Leu Glu Ile
            100                 105                 110

Lys

<210> SEQ ID NO 29
<211> LENGTH: 112
<212> TYPE: PRT
<213> ORGANISM: Artificial Sequence
<220> FEATURE:
<223> OTHER INFORMATION: 1F10-VH
```

-continued

<400> SEQUENCE: 29

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Glu Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Tyr Tyr Gly Ser Tyr Trp Gly Gln Gly Thr Leu Val Thr Val Ser Ala
            100                 105                 110

<210> SEQ ID NO 30
<211> LENGTH: 111
<212> TYPE: PRT
<213> ORGANISM: Artificial Sequence
<220> FEATURE:
<223> OTHER INFORMATION: 1F10-VL

<400> SEQUENCE: 30

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Gly Tyr Met Asp Trp Tyr Gln Gln Lys Pro Gly Gln Pro Pro
        35                  40                  45

Lys Leu Leu Ile Phe Ala Ala Ser Asn Leu Lys Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Thr Asn
                85                  90                  95

Glu Tyr Pro Trp Thr Phe Gly Gly Gly Thr Lys Leu Glu Ile Lys
            100                 105                 110

<210> SEQ ID NO 31
<211> LENGTH: 123
<212> TYPE: PRT
<213> ORGANISM: Artificial Sequence
<220> FEATURE:
<223> OTHER INFORMATION: LH7.2-VH

<400> SEQUENCE: 31

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Thr Ser Gly Gly Asp Tyr Thr Phe Tyr Pro Asp Ser Val
    50                  55                  60

Lys Gly Arg Phe Thr Ile Ser Arg Asp Asn Ala Lys Asn Thr Leu Tyr
65                  70                  75                  80

```
Leu Gln Met Ser Ser Arg Arg Ser Glu Asp Thr Ala Met Tyr Tyr Cys
                85                  90                  95

Ala Arg His Gly Glu Ile Gly Tyr Gly Ser Ser Ala Trp Phe Ala Tyr
            100                 105                 110

Trp Gly Gln Gly Thr Leu Val Thr Val Ser Ala
        115                 120

<210> SEQ ID NO 32
<211> LENGTH: 108
<212> TYPE: PRT
<213> ORGANISM: Artificial Sequence
<220> FEATURE:
<223> OTHER INFORMATION: LH7.2-VL

<400> SEQUENCE: 32

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Gly Gly Thr Lys Leu Glu Ile Lys Arg
            100                 105

<210> SEQ ID NO 33
<211> LENGTH: 252
<212> TYPE: PRT
<213> ORGANISM: Artificial Sequence
<220> FEATURE:
<223> OTHER INFORMATION: 1F10 scFv

<400> SEQUENCE: 33

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Gly Tyr Met Asp Trp Tyr Gln Gln Lys Pro Gly Gln Pro Pro
        35                  40                  45

Lys Leu Leu Ile Phe Ala Ala Ser Asn Leu Lys Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Thr Asn
                85                  90                  95

Glu Tyr Pro Trp Thr Phe Gly Gly Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
    130                 135                 140

Glu Thr Val Lys Ile Ser Cys Lys Ala Ser Gly Tyr Thr Phe Thr Asp
145                 150                 155                 160
```

```
Tyr Ser Met His Trp Val Lys Gln Ala Pro Gly Glu Gly Leu Lys Trp
            165                 170                 175

Met Gly Trp Ile Asn Thr Glu Thr Gly Glu Pro Thr Tyr Ala Asp Asp
        180                 185                 190

Phe Lys Gly Arg Phe Ala Phe Ser Leu Glu Thr Ser Ala Ser Thr Ala
    195                 200                 205

Tyr Leu Gln Ile Asn Asn Leu Lys Asn Glu Asp Thr Ala Thr Tyr Phe
        210                 215                 220

Cys Tyr Tyr Gly Ser Tyr Trp Gly Gln Gly Thr Leu Val Thr Val Ser
225                 230                 235                 240

Ala Gly Gly Gly Ser Gly Gly Gly Ser Cys
            245                 250

<210> SEQ ID NO 34
<211> LENGTH: 260
<212> TYPE: PRT
<213> ORGANISM: Artificial Sequence
<220> FEATURE:
<223> OTHER INFORMATION: CVII scFv

<400> SEQUENCE: 34

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Tyr
                85                  90                  95

Thr Phe Gly Gly Gly Thr Lys Leu Glu Ile Lys Arg Gly Ser Thr Ser
            100                 105                 110

Gly Ser Gly Lys Pro Gly Ser Gly Glu Gly Ser Thr Lys Gly Glu Val
        115                 120                 125

Met Leu Val Glu Ser Gly Gly Gly Leu Val Lys Pro Gly Gly Ser Leu
    130                 135                 140

Lys Leu Ser Cys Ala Ala Ser Gly Phe Thr Phe Ser Ser Tyr Ala Met
145                 150                 155                 160

Ser Trp Val Arg Gln Thr Pro Glu Lys Arg Leu Glu Trp Val Ala Thr
                165                 170                 175

Ile Thr Ser Gly Gly Asp Tyr Thr Phe Tyr Pro Asp Ser Val Lys Gly
            180                 185                 190

Arg Phe Thr Ile Ser Arg Asp Asn Ala Lys Asn Thr Leu Tyr Leu Gln
        195                 200                 205

Met Ser Ser Arg Arg Ser Glu Asp Thr Ala Met Tyr Tyr Cys Ala Arg
    210                 215                 220

His Gly Glu Ile Gly Tyr Gly Ser Ser Ala Trp Phe Ala Tyr Trp Gly
225                 230                 235                 240

Gln Gly Thr Leu Val Thr Val Ser Ala Gly Gly Gly Ser Gly Gly
                245                 250                 255

Gly Gly Ser Cys
            260
```

```
<210> SEQ ID NO 35
<211> LENGTH: 257
<212> TYPE: PRT
<213> ORGANISM: Artificial Sequence
<220> FEATURE:
<223> OTHER INFORMATION: Trastuzumab scFv

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Glu Val
        115                 120                 125

Gln Leu Val Glu Ser Gly Gly Gly Leu Val Gln Pro Gly Gly Ser Leu
    130                 135                 140

Arg Leu Ser Cys Ala Ala Ser Gly Phe Asn Ile Lys Asp Thr Tyr Ile
145                 150                 155                 160

His Trp Val Arg Gln Ala Pro Gly Lys Gly Leu Glu Trp Val Ala Arg
                165                 170                 175

Ile Tyr Pro Thr Asn Gly Tyr Thr Arg Tyr Ala Asp Ser Val Lys Gly
            180                 185                 190

Arg Phe Thr Ile Ser Ala Asp Thr Ser Lys Asn Thr Ala Tyr Leu Gln
        195                 200                 205

Met Asn Ser Leu Arg Ala Glu Asp Thr Ala Val Tyr Tyr Cys Ser Arg
    210                 215                 220

Trp Gly Gly Asp Gly Phe Tyr Ala Met Asp Tyr Trp Gly Gln Gly Thr
225                 230                 235                 240

Leu Val Thr Val Ser Ser Gly Gly Gly Ser Gly Gly Gly Gly Ser
                245                 250                 255

Cys

<210> SEQ ID NO 36
<211> LENGTH: 257
<212> TYPE: PRT
<213> ORGANISM: Artificial Sequence
<220> FEATURE:
<223> OTHER INFORMATION: Rituximab scFv

<400> SEQUENCE: 36

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45
```

```
Ala Thr Ser Asn Leu Ala Ser Gly Val Pro Val Arg Phe Ser Gly Ser
     50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys Arg Gly Ser Thr Ser Gly
            100                 105                 110

Ser Gly Lys Pro Gly Ser Gly Glu Gly Ser Thr Lys Gly Gln Val Gln
            115                 120                 125

Leu Gln Gln Pro Gly Ala Glu Leu Val Lys Pro Gly Ala Ser Val Lys
130                 135                 140

Met Ser Cys Lys Ala Ser Gly Tyr Thr Phe Thr Ser Tyr Asn Met His
145                 150                 155                 160

Trp Val Lys Gln Thr Pro Gly Arg Gly Leu Glu Trp Ile Gly Ala Ile
                165                 170                 175

Tyr Pro Gly Asn Gly Asp Thr Ser Tyr Asn Gln Lys Phe Lys Gly Lys
            180                 185                 190

Ala Thr Leu Thr Ala Asp Lys Ser Ser Ser Thr Ala Tyr Met Gln Leu
            195                 200                 205

Ser Ser Leu Thr Ser Glu Asp Ser Ala Val Tyr Tyr Cys Ala Arg Ser
    210                 215                 220

Thr Tyr Tyr Gly Gly Asp Trp Tyr Phe Asn Val Trp Gly Ala Gly Thr
225                 230                 235                 240

Thr Val Thr Val Ser Ala Gly Gly Gly Ser Gly Gly Gly Gly Ser
                245                 250                 255

Cys

<210> SEQ ID NO 37
<211> LENGTH: 256
<212> TYPE: PRT
<213> ORGANISM: Artificial Sequence
<220> FEATURE:
<223> OTHER INFORMATION: Centuxiamb scFv

<400> SEQUENCE: 37

Asp Ile Leu Leu Thr Gln Ser Pro Val Ile Leu Ser Val Ser Pro Gly
 1               5                  10                  15

Glu Arg Val Ser Phe Ser Cys Arg Ala Ser Gln Ser Ile Gly Thr Asn
                 20                  25                  30

Ile His Trp Tyr Gln Gln Arg Thr Asn Gly Ser Pro Arg Leu Leu Ile
             35                  40                  45

Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Gly Ser Thr Ser
            100                 105                 110

Gly Ser Gly Lys Pro Gly Ser Gly Glu Gly Ser Thr Lys Gly Gln Val
            115                 120                 125

Gln Leu Lys Gln Ser Gly Pro Gly Leu Val Gln Pro Ser Gln Ser Leu
130                 135                 140
```

```
Ser Ile Thr Cys Thr Val Ser Gly Phe Ser Leu Thr Asn Tyr Gly Val
145                 150                 155                 160

His Trp Val Arg Gln Ser Pro Gly Lys Gly Leu Glu Trp Leu Gly Val
                165                 170                 175

Ile Trp Ser Gly Gly Asn Thr Asp Tyr Asn Thr Pro Phe Thr Ser Arg
            180                 185                 190

Leu Ser Ile Asn Lys Asp Asn Ser Lys Ser Gln Val Phe Phe Lys Met
        195                 200                 205

Asn Ser Leu Gln Ser Asn Asp Thr Ala Ile Tyr Tyr Cys Ala Arg Ala
    210                 215                 220

Leu Thr Tyr Tyr Asp Tyr Glu Phe Ala Tyr Trp Gly Gln Gly Thr Leu
225                 230                 235                 240

Val Thr Val Ser Ala Gly Gly Gly Ser Gly Gly Gly Ser Cys
                245                 250                 255

<210> SEQ ID NO 38
<211> LENGTH: 252
<212> TYPE: PRT
<213> ORGANISM: Artificial Sequence
<220> FEATURE:
<223> OTHER INFORMATION: Nivolumab scFv

<400> SEQUENCE: 38

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Gln Val
        115                 120                 125

Gln Leu Val Glu Ser Gly Gly Gly Val Val Gln Pro Gly Arg Ser Leu
    130                 135                 140

Arg Leu Asp Cys Lys Ala Ser Gly Ile Thr Phe Ser Asn Ser Gly Met
145                 150                 155                 160

His Trp Val Arg Gln Ala Pro Gly Lys Gly Leu Glu Trp Val Ala Val
                165                 170                 175

Ile Trp Tyr Asp Gly Ser Lys Arg Tyr Tyr Ala Asp Ser Val Lys Gly
            180                 185                 190

Arg Phe Thr Ile Ser Arg Asp Asn Ser Lys Asn Thr Leu Phe Leu Gln
        195                 200                 205

Met Asn Ser Leu Arg Ala Glu Asp Thr Ala Val Tyr Tyr Cys Ala Thr
    210                 215                 220

Asn Asp Asp Tyr Trp Gly Gln Gly Thr Leu Val Thr Val Ser Ser Ser
225                 230                 235                 240

Ser Gly Gly Gly Gly Ser Gly Gly Gly Cys
                245                 250
```

```
<210> SEQ ID NO 39
<211> LENGTH: 255
<212> TYPE: PRT
<213> ORGANISM: Artificial Sequence
<220> FEATURE:
<223> OTHER INFORMATION: Ipilimumab scFv

<400> SEQUENCE: 39

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Gly Ser Thr Ser
            100                 105                 110

Gly Ser Gly Lys Pro Gly Ser Gly Glu Gly Ser Thr Lys Gly Gln Val
        115                 120                 125

Gln Leu Val Glu Ser Gly Gly Gly Val Val Gln Pro Gly Arg Ser Leu
    130                 135                 140

Arg Leu Ser Cys Ala Ala Ser Gly Phe Thr Phe Ser Ser Tyr Thr Met
145                 150                 155                 160

His Trp Val Arg Gln Ala Pro Gly Lys Gly Leu Glu Trp Val Thr Phe
                165                 170                 175

Ile Ser Tyr Asp Gly Asn Asn Lys Tyr Tyr Ala Asp Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Ile Tyr Tyr Cys Ala Arg
    210                 215                 220

Thr Gly Trp Leu Gly Pro Phe Asp Tyr Trp Gly Gln Gly Thr Leu Val
225                 230                 235                 240

Thr Val Ser Ser Gly Gly Gly Gly Ser Gly Gly Gly Ser Cys
                245                 250                 255

<210> SEQ ID NO 40
<211> LENGTH: 260
<212> TYPE: PRT
<213> ORGANISM: Artificial Sequence
<220> FEATURE:
<223> OTHER INFORMATION: Ranibizuman scFv

<400> SEQUENCE: 40

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Glu Val
            115                 120                 125

Gln Leu Val Glu Ser Gly Gly Leu Val Gln Pro Gly Gly Ser Leu
        130                 135                 140

Arg Leu Ser Cys Ala Ala Ser Gly Tyr Asp Phe Thr His Tyr Gly Met
145                 150                 155                 160

Asn Trp Val Arg Gln Ala Pro Gly Lys Gly Leu Glu Trp Val Gly Trp
                165                 170                 175

Ile Asn Thr Tyr Thr Gly Glu Pro Thr Tyr Ala Ala Asp Phe Lys Arg
                180                 185                 190

Arg Phe Thr Phe Ser Leu Asp Thr Ser Lys Ser Thr Ala Tyr Leu Gln
            195                 200                 205

Met Asn Ser Leu Arg Ala Glu Asp Thr Ala Val Tyr Tyr Cys Ala Lys
210                 215                 220

Tyr Pro Tyr Tyr Tyr Gly Thr Ser His Trp Tyr Phe Asp Val Trp Gly
225                 230                 235                 240

Gln Gly Thr Leu Val Thr Val Ser Ser Gly Gly Gly Ser Gly Gly
                245                 250                 255

Gly Gly Ser Cys
            260

<210> SEQ ID NO 41
<211> LENGTH: 258
<212> TYPE: PRT
<213> ORGANISM: Artificial Sequence
<220> FEATURE:
<223> OTHER INFORMATION: Adalimumab scFv

<400> SEQUENCE: 41

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Tyr
                 20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                 85                  90                  95

Thr Phe Gly Gln Gly Thr Lys Val Glu Ile Lys Arg Gly Ser Thr Ser
            100                 105                 110

Gly Ser Gly Lys Pro Gly Ser Gly Glu Gly Ser Thr Lys Gly Glu Val
            115                 120                 125

Gln Leu Val Glu Ser Gly Gly Gly Leu Val Gln Pro Gly Arg Ser Leu
        130                 135                 140

Arg Leu Ser Cys Ala Ala Ser Gly Phe Thr Phe Asp Asp Tyr Ala Met
145                 150                 155                 160
```

His Trp Val Arg Gln Ala Pro Gly Lys Gly Leu Glu Trp Val Ser Ala
            165                 170                 175

Ile Thr Trp Asn Ser Gly His Ile Asp Tyr Ala Asp Ser Val Glu Gly
        180                 185                 190

Arg Phe Thr Ile Ser Arg Asp Asn Ala Lys Asn Ser Leu Tyr Leu Gln
        195                 200                 205

Met Asn Ser Leu Arg Ala Glu Asp Thr Ala Val Tyr Tyr Cys Ala Lys
    210                 215                 220

Val Ser Tyr Leu Ser Thr Ala Ser Ser Leu Asp Tyr Trp Gly Gln Gly
225                 230                 235                 240

Thr Leu Val Thr Val Ser Ser Gly Gly Gly Gly Ser Gly Gly Gly Gly
            245                 250                 255

Ser Cys

<210> SEQ ID NO 42
<211> LENGTH: 255
<212> TYPE: PRT
<213> ORGANISM: Artificial Sequence
<220> FEATURE:
<223> OTHER INFORMATION: mutated teplizumab scFv

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr Arg Gly Ser Thr Ser Gly
            100                 105                 110

Ser Gly Lys Pro Gly Ser Gly Glu Gly Ser Thr Lys Gly Gln Val Gln
        115                 120                 125

Leu Val Gln Ser Gly Gly Gly Val Val Gln Pro Gly Arg Ser Leu Arg
    130                 135                 140

Leu Ser Cys Lys Ala Ser Gly Tyr Thr Phe Thr Arg Tyr Thr Met His
145                 150                 155                 160

Trp Val Arg Gln Ala Pro Gly Lys Gly Leu Glu Trp Ile Gly Tyr Ile
                165                 170                 175

Asn Pro Ser Arg Gly Tyr Thr Asn Tyr Asn Gln Lys Val Lys Asp Arg
            180                 185                 190

Phe Thr Ile Ser Arg Asp Asn Ser Lys Asn Thr Ala Phe Leu Gln Met
        195                 200                 205

Asp Ser Leu Arg Pro Glu Asp Thr Gly Val Tyr Phe Cys Ala Arg Tyr
    210                 215                 220

Tyr Asp Asp His Tyr Ser Leu Asp Tyr Trp Gly Gln Gly Thr Pro Val
225                 230                 235                 240

Thr Val Ser Ser Gly Gly Gly Gly Ser Gly Gly Gly Gly Ser Cys
                245                 250                 255

```
<210> SEQ ID NO 43
<211> LENGTH: 41
<212> TYPE: DNA
<213> ORGANISM: Artificial Sequence
<220> FEATURE:
<223> OTHER INFORMATION: scFv of adalimumab- forward primer

<400> SEQUENCE: 43
gtatctctcg agaaaagaga tattcagatg acgcaatccc c                           41

<210> SEQ ID NO 44
<211> LENGTH: 34
<212> TYPE: DNA
<213> ORGANISM: Artificial Sequence
<220> FEATURE:
<223> OTHER INFORMATION: scFv of adalimumab- reverse primer

<400> SEQUENCE: 44
gtatctgcgg ccgcttaaca ggagccaccg ccac                                   34

<210> SEQ ID NO 45
<211> LENGTH: 14
<212> TYPE: PRT
<213> ORGANISM: Artificial Sequence
<220> FEATURE:
<223> OTHER INFORMATION: CCK analogue
<220> FEATURE:
<221> NAME/KEY: MOD_RES
<222> LOCATION: 8
<223> OTHER INFORMATION: SO4H modification SULFATATION
<220> FEATURE:
<221> NAME/KEY: MOD_RES
<222> LOCATION: 9
<223> OTHER INFORMATION: Xaa is NOR-leucine
<220> FEATURE:
<221> NAME/KEY: MOD_RES
<222> LOCATION: 12
<223> OTHER INFORMATION: Xaa is NOR-leucine

<400> SEQUENCE: 45

Cys Gly Gly Gly Gly Ser Asp Tyr Xaa Gly Trp Xaa Asp Phe
1               5                   10

<210> SEQ ID NO 46
<211> LENGTH: 20
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<223> OTHER INFORMATION: Synthetic
<220> FEATURE:
<221> NAME/KEY: MOD_RES
<222> LOCATION: 20
<223> OTHER INFORMATION: Xaa is azidohomoalanine or alanine

<400> SEQUENCE: 46

Gly Ser Lys Gly Ser Lys Gly Ser Lys Gly Gly Gly Gly Ser Gly Gly
1               5                   10                  15

Gly Gly Ser Xaa
            20

<210> SEQ ID NO 47
<211> LENGTH: 26
<212> TYPE: PRT
<213> ORGANISM: Artificial Sequence
```

```
<220> FEATURE:
<221> NAME/KEY: MOD_RES
<222> LOCATION: 1
<223> OTHER INFORMATION: ACETYLATION
<220> FEATURE:
<223> OTHER INFORMATION: Synthesized
<220> FEATURE:
<221> NAME/KEY: MOD_RES
<222> LOCATION: 26
<223> OTHER INFORMATION: Xaa is glycine or homopropargylglycine

<400> SEQUENCE: 47

Gly Ser Lys Gly Ser Lys Gly Ser Lys Gly Ser Lys Gly Ser Lys Gly
1               5                   10                  15

Gly Gly Gly Ser Gly Gly Gly Gly Ser Xaa
            20                  25

<210> SEQ ID NO 48
<211> LENGTH: 26
<212> TYPE: PRT
<213> ORGANISM: Artificial Sequence
<220> FEATURE:
<221> NAME/KEY: MOD_RES
<222> LOCATION: 1
<223> OTHER INFORMATION: ACETYLATION
<220> FEATURE:
<221> NAME/KEY: MOD_RES
<222> LOCATION: 1
<223> OTHER INFORMATION: Xaa is L-azidohomoalanine
<220> FEATURE:
<223> OTHER INFORMATION: Synthesized

<400> SEQUENCE: 48

Xaa Ser Gly Gly Gly Gly Ser Gly Gly Gly Gly Ser Lys Gly Ser
1               5                   10                  15

Lys Gly Ser Lys Gly Ser Lys Gly Ser Lys
            20                  25

<210> SEQ ID NO 49
<211> LENGTH: 8
<212> TYPE: PRT
<213> ORGANISM: Artificial Sequence
<220> FEATURE:
<223> OTHER INFORMATION: Synthesized

<400> SEQUENCE: 49

Trp Ala Asp Trp Pro Gly Pro Pro
1               5

<210> SEQ ID NO 50
<211> LENGTH: 18
<212> TYPE: PRT
<213> ORGANISM: Artificial Sequence
<220> FEATURE:
<223> OTHER INFORMATION: Synthesized

<400> SEQUENCE: 50

Gly Ser Thr Ser Gly Ser Gly Lys Pro Gly Ser Gly Glu Gly Ser Thr
1               5                   10                  15

Lys Gly
```